US007449567B2

(12) United States Patent
Zhang et al.

(10) Patent No.: US 7,449,567 B2
(45) Date of Patent: Nov. 11, 2008

(54) ISOLATION AND IDENTIFICATION OF MOUSE AND HUMAN TRANSCRIPTION CONTROL ELEMENTS ASSOCIATED WITH CYTOCHROME EXPRESSION

(75) Inventors: Weisheng Zhang, Fremont, CA (US); Pamela Contag, San Jose, CA (US); Anthony Purchio, Alameda, CA (US); Sandy Hashima, San Diego, CA (US); Shirley Ma, Fremont, CA (US); Kevin Nawotka, Alameda, CA (US)

(73) Assignee: Xenogen Corporation, Alameda, CA (US)

( * ) Notice: Subject to any disclaimer, the term of this patent is extended or adjusted under 35 U.S.C. 154(b) by 0 days.

(21) Appl. No.: 10/121,960

(22) Filed: Apr. 11, 2002

(65) Prior Publication Data

US 2003/0145341 A1 Jul. 31, 2003

Related U.S. Application Data

(60) Provisional application No. 60/283,534, filed on Apr. 12, 2001.

(51) Int. Cl.
*C07H 21/04* (2006.01)
*C07H 21/02* (2006.01)
*G01N 33/00* (2006.01)
*G01N 33/567* (2006.01)
*C12N 5/06* (2006.01)
*C12N 5/10* (2006.01)

(52) U.S. Cl. ......................... 536/24.1; 536/23.1; 800/3; 435/354; 435/7.21

(58) Field of Classification Search ................ 536/23.1; 435/325; 800/14, 18, 3
See application file for complete search history.

(56) References Cited

U.S. PATENT DOCUMENTS

| | | | |
|---|---|---|---|
| 4,997,757 | A | 3/1991 | Schiestl |
| 6,432,639 | B1 | 8/2002 | Lichter et al. |
| 2002/0150915 | A1 | 10/2002 | Berkenstam et al. |

FOREIGN PATENT DOCUMENTS

| | | | |
|---|---|---|---|
| EP | 1 206 906 | A1 | 5/2002 |
| WO | WO 99/61622 | | 12/1999 |
| WO | WO 01/20025 | A2 | 3/2001 |
| WO | WO 01/20026 | A2 | 3/2001 |
| WO | WO 02/25270 | A1 | 3/2001 |
| WO | WO 02/008451 | A3 | 1/2002 |
| WO | WO 02/36784 | A1 | 5/2002 |
| WO | WO 02/083897 | A1 | 10/2002 |
| WO | WO 02/088305 | A2 | 11/2002 |

OTHER PUBLICATIONS

Huang, 1998, PNAS, vol. 95, pp. 14669-14674.*

Mullins, 1993, Hypertension, vol. 22, pp. 630-633.*

Mullins, 1990, Nature, Fulminant hypertension in transgenic rats harbouring the mose Ren-2 gene, vol. 344, pp. 541-544.*

Hammer, 1990, Spontaneous inflammatory disease in transgenic rats expressing HLA-B27 and human beta-2m: An animal model of HLA-B27-associated human disorders, Cell, vol. 63, pp. 1099.*

Mullins, 1989, Expression of the DBA/2J Ren-2 gene in the adrenal gland of transgenic mice, EMBO J. vol. 8, pp. 4065-4072.*

Mullins, 1996, J. Clin. Invest., vol. 98, pp. S37-S40.*

Eck, Goodman and Gilman's The Pharmacological Basis of Therapeutics, 1996, McGraw-Hill, pp. 77-101.*

Verma, 1997, Nature, vol. 389, pp. 239-242.*

Romano, G. 2000, Stem Cells, vol. 18, pp. 19-39.*

Genes V, Oxford University Press, 1994, editor Ben Lewin, pp. 860-864.*

Zhang et al., High Levels of Foreign Gene Expression in Hepatocytes after Tail Vein Injections of Naked Plasmid DNA, Human Gene Therapy, 10:1735-1737, 1999.*

Herrmann, J et al, 2004, Arch Virol, 149:1611-1617.*

Goodwin et al., "The orphan human pregnane X receptor mediates the transcriptional activation of CYP3A4 by rifampicin through a distal enhancer module," *Molecular Pharmacology* 56:1329-1339, 1999.

Finta et al., "The human cytochrome P450 3A locus. Gene evolution by capture of downstram exons," *Gene* 260(1-2):13-23, 2000.

Gellner et al., "Genomic organization of the human CYP3A locus: identification of a new, inducible CYP3A gene," *Pharmacogenetics* 11(2):111-121, 2001.

Itoh et al., "Isolation of a promoter region in mouse cytochrome P450 3A (Cyp3A16) gene and its transcriptional control," *Biochim Biophys Acta* 1350(2):155-158, 1997.

Macgregor et al., "New molecular endpoints and methods for routine toxicity testing," *Fundamental and Applied Toxicology* 26:156-173, 1995.

Martinez et al., "Expression of paclitaxel-inactivating CYP3A activity in human colorectal cancer: implications for drug therapy," *Br. J. Cancer* 87(6):681-686, 2002.

Quattrochi et al., "CYP3A regulation: from pharmacology to nuclear receptors," *Drug Metabolism and Disposition* 29(5):615-622, 2001.

Reid et al., "Rat and human liver cytochrome P-450 isoform metabolism of ecteinascidin 743 does not predict gender-dependent toxicity in humans," *Clin. Cancer Res.* 8(9):2952-2962, 2002.

Smith et al., "Molecular genetics of the human cytochrome P450 monooxygenase superfamily," *Xenobiotica* 28(12):1129-1165, 1998.

Toide et al., "Gene Structure of mouse Cyp3a11: evidence for an enhancer element within its 5' flanking sequences," *Arch Biochem. and Biophysics* 338:43-49, 1997.

(Continued)

*Primary Examiner*—Valarie Bertoglio
(74) *Attorney, Agent, or Firm*—Robins & Pasternak LLP

(57) ABSTRACT

The present invention relates to transcription control elements derived from mouse and human genes associated with cytochrome expression, e.g., Cyp3A11 and CYP3A4, respectively. Isolated polynucleotides, expression cassettes, vectors, recombinant cells, and transgenic animals, may comprise such transcription control elements as described herein.

12 Claims, 60 Drawing Sheets

OTHER PUBLICATIONS

Yanagimoto et al., "Mouse liver cytochrome P-450 (P-450IIIAMI): its cDNA cloning and inducibility by dexamethasone," *Biochim. Biophs. Acta* 1130(3):329-332, 1992.

Barwick, et al., "Trans-species Gene Transfer for Analysis of Glucocorticoid-Inducible Transcriptional Activation of Transiently Expressed Human CYP3A$ and Rabbit CYP3A6 in Primary Cultures of Adult Rat and Rabbit Hepatocytes," Molecular Pharmacology 50:10-16 (1996).

Hashimoto, et al., "Gene Structure of CYP3A4, an Adult-specific Form of Cytochrome P450 in Human Livers, and Its Transcrptional Control," Eur. J. Biochem 218:585-595 (1993).

Ogg, et al., "Development of an In Vitro Reporter Gene Assay to Assess Xenobiotic Induction of the Human CYP3A4 Gene," Eur. J. Drug Metab. Pharmacokinet 22(4):311-313 (1997).

Zhang et al., "Differential Regulation of the Human CYP34A Promoter in Transgenic Mice and Rats," Drug Metabolism and Disposition 32(2):163-167 (2004).

* cited by examiner

FIGURE 1A (Page 1 of 12)

GGTACCTGGT ATCTGTCCAG AAATTCATCC ATTTCATCCA GGTTTTCCAG TTTTGTTGAG 60

TATAGCTTTT TGTAGAAGGA TCTGATGGTG TTTTGGATTT CTTCAGGATC TGTTGTTATG 120

TCTCCCTTTT CATTTCTGAT TTTGTTAATT AGGATGTTGT CCCTGTGCCC TCTAGTGAGT 180

CTAGCTAAGG GTTTATCTAT CTTGTTGATT TTCTCAAAGA ACCAACTCCT CGTTTGGTTA 240

ATTCTTTTAA TAGTTCTTCT TGTTTCCACT TGGTTGATTT CACCCCTGAG TTTGATTATT 300

TCCTGCTGTC TACTCCTCTT GGGTGAATTT TCTTCCTTTT TTTTCTAGAG CTTTTAGATG 360

TGTTGTCAAG CTGCTAGTGT ATGCCCTCTC CAGTTTCTTC TTGGAGGCAC TCAGAGCTAT 420

GAGTTTCCCT CTTAGAAATG CTTTCATTGT GTCCCATAGG TTTGGGTATG TTGTGGCTTC 480

GTTTTCATTA AACTCTAAAA AGTCTTTAAT TTCTTTCTTT ATTCCTTCCT TGACCAAGGT 540

ATCATTGAGA AGAGTGTTGT TCAGTTTCCA TTTGAATGTT TGCTTTCCAT TATTTAATGT 600

TGCCTTAGTC CATGGTGGTC TGTGTCTTAG TCAGGGTTTC TTTTCCTGCA CAAACATCAT 660

GACCAAGAAA CAAGTTGGGG ATGAAAGGGT TTATTCAGCT TACACTTCCA TGCTGCTGTT 720

CATCACCAAA GGAAGTCAGG ACTGGAACTC AAACAGATCA GGGAGCAGGA GCTGATGCAG 780

AGGCCATGGA GGGATGTTCT TTACTGGCTT GCCTTCCCTG GCTTGCTCAG CCTGCTCTCT 840

TATAGAATCC AAGACTACCA GCCCAGAGAT GGCACCACCC ACAAGGGGCC TTTCCCCCTT 900

GATCACTAAT TGAGAAAATG CCTTACAGTT GGATCTCATG GAGGCATTTC CTCAACTGAA 960

GCTCCTTTCT CTGTGATATC TCCAGCTGTG TCAAGTTGAC ACAAAACTAG CCAGTACAAT 1020

TGACCCCTTG TCAACTTGAC ACACAAACAC ATCACTAGTA ACCCTCAACC CTTACATTCT 1080

FIGURE 1A (Page 2 of 12)

TATTCATCCC CAAGATCTAA ATAACTTTAA AAGTCCCACA GTCTTTACAT ATTCTTAAAA 1140

TTTCAATCTC TTTAAAATAT CCATCTCTTT TAAAATCCAA AGTCTTTTTA CAATTAAAAC 1200

TCTCTTAACT ATGGCCTCCA CTAAAACAGT TTCTTCCTTC AAGAGGGAAA ATATCAGGGC 1260

ACAGTCAAAG CAAAAATCAA TCTCCAACCA TCCAATGTCT GGGATCCAAC TCACAATCTT 1320

CTGGACTCCT CCAAGGGCTT GTGTCACTTC TCCAGCCATG CCCTTTGTAG CACAGGTGTC 1380

ATCCTCTAGG TTCCAGATGC CTGTACTCCA CTGATGCTGC TGCTCTTGGT GGTCATCTCA 1440

TGGTACTGGC ATCTCCAAAA CACTGCATGG CCCCTTCAGT CCTGGGCCTT CAATTGCAAC 1500

TGAGGCTGCA CCGTCACCAA TGGCCTTCCA TGCCCTCTCA CAGTGCCGAG CCTCAGCTGC 1560

TGTGCATGAC CCCTTCATGC CTTCAAAACC AGTACCACCT GGGTGACCCT TATACATTAC 1620

CAAGTCCCAC TGCAGCAGGA GTACAACCTT GGCTATCTCT GGAACACAGC CTCTTTGTGC 1680

TTTCAGAAAA CACTTCCCAG AAGATGTCAC CTCAACGACG CTGGTCTCTT CTTAATCACC 1740

GATAATTTCT TAGCTCCAGC TAACCAGCAT CAATAGTCAT AGTAATGCAA GGTTTTGCTT 1800

TAGTAGTTCT GGTATCTTGT TAATCACAGT TGATTCTTCA GCCCCAGCTA ACCAGAACTA 1860

CAGAATTTTC ACAATCAAAA CAGCAATGGC CCTGAAAAGA GTCTTTAATT TTCCCTCTGA 1920

AATTTCACAA GCCAGACCTC CATCTTCTGC ACTGTTCTCA ACATTATCTT CTAAGCTCCT 1980

ACACAACATC TGACAGAGCT CTTAACAATG AACGGATCTT CAAGCCGAAA GTTCCAAAGT 2040

CCTTCCACAG TCCTCCCCAA AACATGGTCA GGTTGTCACA GGAATACCCC ACTCCTGGTA 2100

CCAATTTGTC TTAGTCAGGG TTTCTATTCC TGCACAAACA TCATGGCCAA GAAACAAGTT 2160

FIGURE 1A (Page 3 of 12)

GGGGAGGAAA GGGTTTATTT AGCTTACACT TCCATGCTGC TGTTCATCAC CAAAGGAAGT 2220

CAGGACTGGA ACTCAAACAG GTCAGGGAGC AGGAGCTGAT GCAGAGGCCA TGGAGGGATG 2280

TTCTTTACTG GCTTGCCTTC CCTGGCTTGC TCAGCCTGCA CTCTTATAGA ATCCAAGACT 2340

ACCAGCCCAG AGATGGCACC ACCCACAAGG GGCCTTTCCC CCTTGATCAC TAATTGAGAA 2400

AATGCCTTAC AGTTGGATCT CATGGAGGCA TTTCCTCAAC TGAAGCTCCT TTCTCTGTGA 2460

TATCTCCAGC TGTGTCAAGT TGACACAAAA CTAGCCAGTA CAGTCTGATA GGATGCATGG 2520

GACAATTTCA ATATTTTTGT ATCTGTTGAG GCCTGTTTTG TGACCAATTA TATGGTTAAT 2580

TTTGGAGAAG GTTCCGTGAG GTGCTGAGAA GTATATCATT TTGTTTTAGG ATAAAATGTT 2640

CTGTAGATAT CTGTCAAATC CATTTGTTTC ATCACTTCTG TTAGTTTCAC TGTGTCCTGT 2700

TTAGTTTCTG TTTTCATGAT CTGTCCACTG ATGAAAGTGG TGTGTTGAAG TCTCCCACTA 2760

TTATTGTGTG AGGTGCAATG TGTGCTTTGA GCTTTACTAA AGTGTCTTTA ATGAATGTGG 2820

CTGCCCTTGC ATTTGGAGCA TAGATATTCA AAATTGAGAG TTCCTCTTGG AGGATTTTAC 2880

CTTTGATGAG TATGAAGTGT CCCTCCTTGT CTTTTTTGAT AACTTTGGTT TGGAAGTTGA 2940

TTTTATTTGA TATTAGAATG GCTACCCCAG CTTGTTTCTT CAGACCATTT GCTTGGAAAA 3000

TTGTTTTCCA GCCTTTCACT CTGAGGTAGT GTCTGTCTTT TTCCCTGAGA TGGGTTTCCT 3060

GTAAGCAGCA GAATGTTGGG TCCTGTTTGT GTAGCCAGTC TGTTAGTCTA TGTCTTTTTA 3120

TTGGGGAATT GAGTCCATTG ATATTAAGAG ATATTAAGGA AAAGTAATTG TTGCTTCCTA 3180

TTATTTTTGT TGTTAGAGTT GGCATTCTGT TCTTTTGGCT GTCTTCTTTT TGGCTTGTTG 3240

FIGURE 1A (Page 4 of 12)

AGGAATTACT TTCTTGCTTT TTCTAGGGCG TGATATCTGT CCTTGTATTT TTTTTTCTGT 3300

TATTATCCTT TGAAGGGCTG GATTCTGGAA AGATAATGTG TGAATTTGGT TTTGTCATGG 3360

AATACTTTGG TTTCTCCATC TATGGTAATT GAGAGTTTGG CCGGGTATAG TAGCCTGGGC 3420

TGGCTTTTTT TTGTTCTCTT AGTGTCTGTA TAACATCTGT CCAGGCTCTT CTGGCTTTCA 3480

TAGTCTCTGG TGAAAAGTCT GGTGTAATTC TGATAGGCCT GCCTTTATAT GTTACTTGAC 3540

CTTTCTCCCG TACTGCTTTT AATATTCTCT CTTTATTTAG TGCATTTGTT GTTCTGATTA 3600

TTGTGTGTTG GGAGGAATCT CTTTTCTGGT CCAGTCTATA TGGAGTTCTG TAGGCTTCTT 3660

GTATGTTCAT GGGCATGTCA TTCTTTAGGT TCGGGAAGTT TTCTTCTATA ATTTTGTTGA 3720

AAATATTTGC TGGCCCTTTA AGTTGAAAAT CTTCATTCTC ATCAACTCCT ATTATCTGTA 3780

GGTTTGGTCT TCTCATTGTG TCCTGGATTT CCTGGATGTT TTGAGTTAGG ACCTTTTTGT 3840

GTTTTGTATT ATCTTTGATT GTTGTCCTGA TGTTCTCTAT GGAATCTTCT GCACCTGAGA 3900

TTCTCTCTTC CATCTTTTGT ATCCTGTTGC TGATGCTCAC GTCTATGGTT CCAGATTTCT 3960

TTCCTAGAGT TTCTATCTCC AGCGTTGCCT CACTTTGGGT TTTCTTTATT GTGTCTACTT 4020

CCCTTTTTAG GTCTAGTATG GCTTTGTTCA TTTCCATCAC CTGTTTGGAT GTGTTTGCCT 4080

GTTTTTCTAT GAGGACTTCT ACCTGTTTGG TTGTGTTTTC CTGCTATTCT TTAAGGATTT 4140

GTAACTCTTT AGCAGTGGTC TCCTGTATTT CTTTAAGTGA GTTATTAAAG TCCTTCTTGA 4200

TGTCCTCTAC CATCATCATG AGATATGCTT TTAAATACAG GTCTACCTTT ACGGTTGTGT 4260

TGGGGTGCCC AGGACTAGGT GGGGTGGGAG TGCTGCATTC TGATGATGGT GAGTGGTCTT 4320

FIGURE 1A (Page 5 of 12)

GATTTCTGTT AGTAGGATTC TTACGTTTTC CTTTTGCCAT CTGGTAATCT CTGGAGTTAT 4380

TTGTTATAGT AGTCTCTGGT TAGAGCTTGT TCCTCAGGTG ATTCTGTTAT GCTCTATCAG 4440

CAGACCTGGG AGACTAGCTC TATCCTTAGT TTCAGTGGTC AGAGTACTCT CTGCAGGCAA 4500

GCTCTCCTCT TGCAGGGAAG GTGCCCAGAT ATCTGGTGTT TGAACCTGCC TCCTGGCAGA 4560

AGTTGTGTTC TACTCACCAT AGGTCTTAAG ATCCCATGGT TGGTCCTGTG TGGTTCCTTG 4620

CGTGTGTCCG GAGACTCCCC GGGCCAGGGT CCCTGGTGAT TGGAAGGGAC TTGTGCACCG 4680

GATCAGGCCA GGTTATCTGA TTCCTTAATT AATGCAGTCT CAGGTCCCGT GCGATTGAAT 4740

TGGAGCAGGC GCTGTGTTCC ACTCACCAGA GGTCTTAGGA TCCTGTGGAG GATCCTGTGT 4800

GGGTCCTTGC GGGTGTCTGC AGACTCCCCG GGCCAGGGAC CATGGTGCTG CAGTGGGCCG 4860

GAAGGGACTT GAGCCCTGGA TCATGCCGGA TTATCTGCTT CCTTAATTAA TGCAGTCTCA 4920

GGTCCTGGCG ATTGGATTGG AGCAGGCGCT GTGTTCCACT CACCAGAGGC CTTAGAATCC 4980

CGTGGCGGAT CCTGTGTGGG TCCTTATGGG TGTCCGCAGA CTCCCCGGGG CTAGGGACCA 5040

CGGTGCTCCA GTGGGCCGGA AGGGACTTGA GCCCCGGATC AGGCCGGATT ATCTGCTTCC 5100

TTAATTCCTG ATAGTCTTTT AAAAGTAAAC TTATAGTTAG ACACTGTACA CAGGTATATA 5160

ATACATTTTA AATATTCTCT CACTATGCCA GGTGGTATCA TATAAGAACT TTTGAATATA 5220

TTTCTTAAAG ATTAATTTTA ATATTTTATG CTCTTATACT ATGCTTAATT CCCAAAGAAT 5280

ATTTTGTATG TTTTGAAACA ATTTACTCTT CAACATTANA TATAGGATTC ACAGTTATAG 5340

ATAGTATTAA ATGTCCATTA ATGATATTTT TAGGGTATAA AAGGATATGA ATATAAAAGT 5400

FIGURE 1A (Page 6 of 12)

TGAACAAAAA AGAGGGGATG GGCCATAAAG AATATATTCA TATGTATATA TATATGTGAA 5460

TAATTCAAAG AATAAATAAA TATAATTTTA AAAAGCAGCA GGTATCCCCC CCAAAATACA 5520

GTTGTTGAAG TGCCTTGTGA TAGAACCTTG TCAAATGATA AACCAAAGAA ATACCAACTA 5580

CCCACCCAGC CACCCAAGAG ATGGATTAGA GTCAGTGGAT TATTCAGGGT GTGGGAGCCT 5640

GAGGATAAAA AATCAGAACC CCAGACCCCC TAAAAAAGGT ATGCAGACCG TACAGCCATT 5700

TTATAGTTTT GTGTTGAGCT TCATTCAGCG GGACTCTGGG TACACATGGC TTGTGTGGGG 5760

GTGTGTTGAC AACCTGCAAG TGTTCATTCC TAAGCTGATA TACACACAAG CACATAAGTA 5820

GCACTAAATG GTCTGTGACC TTGCTTTGGG TGGGGGACAA GTATGTTTGG CAGGGGCTAA 5880

ATGATAGAAC CACTAAGTTT AGGGCTGTGG GAGAGACAGA GATAATAAAT NGATAGGGCC 5940

CACATTTCAG GCAGTATACA TTTGTGCCAA GCAGTGTGAA TAGAGGCAAG TTCTAATGGT 6000

ATTGGCGAAG TGCTTGCATA TTTTATCCAT GGATTCGAAA GTGTTGGGAG TGGGATGGTA 6060

ACTTGATCCC TCCAGGAGCA AAGGAGGGTA GAAAAGGAGA CCAGGAGTGG GATGGTTGTG 6120

ACAGATCCCA GGGAAAAGCC AGGTGGAACA GAAGGGAGCT GGGAGAGGTC AGAGTCCGTG 6180

CAATAGCTCC TGGGCAAGGC AGAATGTGCT TATAAAACTA CAGAGACAAA GTTTGGAGCT 6240

GTGACGAAAG GATGGACCAT CTAGAGACTG CCATATCCAG GGGATCCATC CCATAATCAG 6300

CTTCTAAACG CTGACACCAT TGCATACACT AGCAAGATTT TGCTGAAAGG ACCCAGATAT 6360

AGTTGTCTCT ATATGTGAGA CTATGCTGGG GCCTAGCAAA CACAGAAGTG GATGCTCACA 6420

GTCAGCTATT GGATGGATCA CAGGGCTCCC AATGGAGGAG CTAGAGATAG TACCCAAGGA 6480

FIGURE 1A (Page 7 of 12)

GCTAAAGGGA TCTGCAATCC TATAGGTGGA ACAACATTAT GAACTAACCA GTACCCCGGA 6540

GCTCTTGACT CTAGCTGCAT ATGTATCAAA AGATGGCCTA GTAGACCATC ACTGGAAAGA 6600

GAGGCCCATT GGACACGCAA ACTTTATATT CCCCAGTACA GGGGAACGCC AGGGCCAAAA 6660

AAACAAAAAA CAAAAAAAAA TGGGAATGGG TGGGTAGGGA AGTGTGGGGG AGGGTATGGG 6720

GGACTTTTGG GATAGCATTG GAAATGTAAT TGAGGAAAAT ACGTAATAAA AAATATTAAA 6780

AAAAAACCTA CATAGGACAG ACAGGCAACC ATTTTAGGAC AACCCTTGCT CCAGTTGTTA 6840

GGGGACCCAT ATGAAGATAT ACCTTTATAT TTGTTACATA TCTGTGGGTG TTGGAGGATC 6900

TAAGTCCAGC CCATCTATTC TCTTTGGTTG GTGGCTCCAT GAGAGCTCCC ACGGTTCTAG 6960

GTTATTTGAC TGTTGGTCTC CCTGTGGAGT TCCTACCCAG TTTGGGGCCC TCAAAATTTT 7020

TCTCAGTTTT CTTCTCANAG CTTCTGAACT CCATCCAGTT TTTGGCTGTG AATATCTGCA 7080

TCTTCCTGAG TAAGCTTTTG GATAGAGCCT CTTAGAGGAC AACCATACTA GGCTCTTGTC 7140

TCCAAGTTTA AATGTATCAT TAATAGTGTC AGAGATTGAT GCTTGCCCAT GGGATTGGTG 7200

TCAAGTTGGA CCAGTTAATG GTTGATCATT CCCTCAGTCT CTGCTTCATC TTTGTCCCTG 7260

CATTTCTTAT AAACAGACCA ATTTTTGTTT CAAAAGTTTT ATGAGTGGGT TGGTGTTTTT 7320

ATACCTCCAT TGGGGATCCT GCCTGATCCT GGGGAGATGG CCTCTTCAGG TTCCATATCC 7380

CCTTTACTAT GATTCTCTAC TAAGGTCATT TACATTGATA TCGGAGGTCT TTCTTTATTC 7440

TGGGTCTCTG GCTTCTCCTA GAGATGCCCC AATCCCTCAC TCCTAGCAGC TGTAGATTTC 7500

TATTCACTCT CCTGGCCCTC TGGCTTTCAC TCCTGTCTCT TCCCTCACCA CATCCTGAAC 7560

FIGURE 1A (Page 8 of 12)

CCCCATACTC CCTTCCTCCA CATTCATGGG TACATTTTTT AAATCCCAGA ACACAGAAGG 7620

CAGAAGCAGG CAGATCTCTA CAAGTTTTAG GCAAGCCTGG TCTATAGAGC AAATTTCAGG 7680

ATGGCCAGGG CTACACAGTG AAACTCTATC TTAAAAAACA AAAAAACAAA ATAAGTTATT 7740

TATTACATAT TTACTTGTTT ATATGTAAGC ATATATGTGT GGGGGCTGAA GAGACCAGAA 7800

GACAAGTTGT GGAAATTCAT TCTTCTGTTC CATCACATAG ATGCTGGGAA TTAAAATCAG 7860

GTTGTCGGGT TTGGAGACAG GTGACTTTGT TGTCTGAGCT TCCTTGAGAG CCTATAAGTT 7920

TTTCTTTCAT TGTTAGTGTG CTAGCTGATA TCCACATTGT TTTCTGTGCT AGGTATCCTG 7980

AATTCCAGTT GAGTCCACAT GTCATGGAAT GTCCTCTTAC AACCTCTGCC ACTGGGTTTT 8040

GTTTCCTACT ATTTAACTTA GGACTTTTTT TTTGGTAGTG ATTCTTACAA GAAAGGTACA 8100

CATACATTTT TCTTTTTTGA GTTTGATTTG GATCAAGTTA TAATCGTGCA AGTCATGGTG 8160

CCCTTCTTAC TAAGTCTCTA GGTTGCTATG GCTTTGTGAA AACTTTTGGA TTTTATCCTA 8220

AAAAAATAAT AATTAAAAAA AAATCCAGTA ACAATCACTT TGTGCACATT TATTCCTAAG 8280

CTATAAGTTT CCACTTCTGT AACGTAGGTA TTTGAGATTG AAGAAGAAAT CTTTATGTGT 8340

ATGGGTGTCT TGCTGGCATG CATATCCTTG CACTATGTGT ATATCTGGGT GCCTGTGAAG 8400

GCCAAATTAT GACTACAAAA ACCCAGGAGC TGGAGCTAAA GACCATTGTG AGCCACCAGA 8460

AGGGTACTGG GAATTGAATC CAGGTCCTTT ACAGCAGTGG ACAATAGATG TTAACTGCTG 8520

AGCCATATCT TTAGCTCTAA CATGGGGACA ATAGCTTACT TATCCCTAGG ACTTATCATG 8580

AGGACCCCAA AGAGAGTGAA AAGTACTTAT AAGATATGAT GTCTTATCCT CTAGAGCAAG 8640

FIGURE 1A (Page 9 of 12)

AAAGCCAGAG AGGAAATCCT GCTTTATTTT TTTTTTAGTA CTCATTGTCA GCTTGCTGGT 8700

CTCCCTTACT TTGTCCCTGC TTAGAGGGAT GAGTGTGGGG TTTTTATTAC CCATTGGGGG 8760

AACATCCCAA TTGGAATGAG GTGCTGGTTT CTCGACTAAT CCTGTATGAC ACCAAAGAAG 8820

TATGAATCTG TTAAAGGTGA AAATTTTGCC ATCAACAACC CAACCTTCAT ACTTAAGTCT 8880

CAGAGAATAC AGAGGAAGAG GGCCAGTAAT ATATTAAGAG TTAGAGGACT AGGAATTCTG 8940

CTCTCAGATG GTGTCTCCAA GAAATGGAGG CAGGACCAGA CACATTAAAT ATCAACAATC 9000

TATACAAGAT ACAATGAAAT CTCAAATAGG CATGGTAAAG AATATATATA TATATAACAC 9060

AATAATAATA ATCGCAAAGA AGCCATGAAT TTGATAGGGA GTTGCGAGAT GGGAAGAACT 9120

GGAGGGAGGA GATGAAAGAA GATGATCTAA TTTCATTGTA GTTAATAATT TTAAAAGATG 9180

AAGAACTTGA ACTTTAGAAC AACATGGTCT CTTGGATCCT GGTTTCATTA AGGATTTATT 9240

ATGTAACCTT GATTGAATCA GTTATCATTT GGGGTATGGT TTGTTCACTT GTGACAGAGT 9300

TATCCCTCAC AACATTGCAG GGTAGATGAT ATCAGCTAAT GAGGGCAAAG TTCTCAGGAC 9360

TGTAAATATT AGCAATCATT CTGTGATGTA ATCTTGGTGG GTATGTGGTG CTTGTGTATG 9420

CATACACCTG TGGTTGTATG GCACTTTGTA CTCTGGAGTT TCAGTTGAGA AACAATGAAT 9480

TTTTAGACTT CAAGGCCACA GTGTTGTTTT CTAAAATCCA TCTTCTTTTT TTTTCAGTAT 9540

TCTGTCCTAC ACTCAGTAAC CATTGCATCC TGGTTGGGCT TGGAGACTTT GTTGTTTTTT 9600

TCTACTTAAT CTTTTTTTCA AAAAAAAAAA TATATTTGGT AGCAGCAACA CCTGCCTCCT 9660

ATCCTCCCAG TCCCAGCCTC ACAAATCCCT CTCCCATTAC TCTCTCCCAT TCTTTTCAGA 9720

FIGURE 1A (Page 10 of 12)

GAAGGTGAAG CCCCTCTTTG AGTATCTTTC CTGGGACACC AAGTCTCAGC AGAACTAGGT 9780

ATATCCTCTC CCACTGAGGC CATCCTGGGT AGTCCAGATA TGGGAAGGGG ATCTTATGGC 9840

ATGCAAAAGT CAGAGACAGT CCCTGCTTCA ATTGTTGGGG GACCATTATG AAGACCAAGC 9900

TGTGCATCTG TTATATAAGT TTAGGGGCCC TAGGTCCAGC CCCTTCATAC TGTTTGGTTG 9960

GTGGTTCAGT TTTTGTCAGT CCCATAGTTT CAGGTTTGTT GACTGTAGAT TTTCCTGTGG 10020

TGTCCTTGAC CCCTCTGGCT CACTCAATCC TATCTGTCAC CGTTCCACAA GAATCCTTGG 10080

GCTTCCTGTG AAGTTTGACT GTGGCTGGCT ACATTCCATA GCTAATTTTT AAATTCAATC 10140

TCTCTCTCTC TCTCTCTCTC TCTCTCTCTC TCTCTCTCTC TCTCTCTCTC TCTGTGTGTG 10200

TGTGTGTGTG TCTGACAACT GTATGTGTGT ATAGAATGCA TTCTGATTAA ATTTTCCCCA 10260

CTCTCTTACC CTATCCCTAT CAGCCTCTGT CCTTCCCATA TTCATGACTT GTTTTGTGTT 10320

CTGAAGACTT TAGTGCCATC TGTGTGACTG TGGGTTTGGA ACTATCCACT AGAGCCTGTG 10380

GGTCACCAGT CACCAGGGGA TCACAACTGA GTACAATACC TCCTTCTTTC TCAGCAGTGA 10440

GTGGCAGGGC TTGTTTCTTC CTCACTGACA CAATTGTCAA GGGATGGCAG GTGTTGGATT 10500

TTTGTGGATA GATGTAGTAG AGTATTTTTT GAGACATGTA CTCCCTTATC CAATGCTTGT 10560

CTCAAACACT ATTTTGCTTT GAACTTTGTC TGTGAACTTC TGATTCCCCT GCTTCTACTG 10620

TCTGAGTGTA TTTTTGAATG AAGCCAGCCT TGGTGAGAGG GTATTTGTTG TTGAATTTGC 10680

TTGAATTTCT TATAAAAACC AAGAACTTTT ACCCATCTGG CACTGTTGTT TACTGATGCC 10740

ACACAGAATG TTAGCTCAAA GTAGGTCAAG TTGGGCTGTG GATGAACTAT ACGAACTGCC 10800

FIGURE 1A (Page 11 of 12)

TAGAGAAGAG AGTACCAAAG TCCAGTGATG CAAAGGTGAT CCATCTACTG GCTTGATCCC 10860

TGGTGCCGCC CATTCTCCCA GCATATAATT ACTGCAGGCT GTCCTCAGTG CAGCAGAGTG 10920

GGCAGAGGGA AGCATTGAGG AGGATCACAC ACACAGTTGT AGGGAGAACA CAGAGAAGTA 10980

AATTGCTGAC AAACAAGCAG GGATGGACCT GGTTTCAGCT CTCTCACTGG AAACCTGGGT 11040

GCTCCTAGCA ATCAGCTTGG TGCTCCTCTA CCGGTAAGTG ATCTTTACAT TTCCTTCCCA 11100

TACCATGTCT TGAGGATCAG GGTGATACTC AGACATCTAT TCTGTTATTA TTGGGAGGCT 11160

CAAAATGATT ATCAGAACCA GCAGCTGGAG AGCCGATGGC TCAGTGGTTA AGGTCACTTG 11220

CTGCTCTTTC AGAGTACTCA AGTTTTAAGC CCAACATCCA CAAGCAGCTC AGAATCATCT 11280

GTAACTATAG CTCCAGGGAA TCTGACACCT TCCACAGGCA TAGTTAGTAT GGTATTTAAT 11340

GGTGGTAGCT TTTGTAACCT GGCTAGCTCC TAAATAATTG GGACAGAGAC CTATTAAGTT 11400

TATTAGCAAT TTTTAAGCAC TATGATTGGG CAGGTTCAAA GCTGTTTTAG CCCACAAAGC 11460

TATCTACATC CCAGCTATAG GCTCAGTTTT ACTTGCACTG TGACTGTTTC CCTGGCTTGC 11520

TCTGCTCCAT GTGTGTCCTC ATGGTGAGCT CCTTTGATGA CTCCTTCCCA TGTCTGACCT 11580

CATGGGAACC TTCTTCTTCC TCCACCTTCT TCTGGCCCTT CTGCTCCTAG ACCCTCATGG 11640

GCCTTGTGGC CAACAACTTC TCTTCTGCCC AGTCATTTGA TCTTCAGTTT ATTATCCACC 11700

AATCAGAGAT AATTGGGGAA CATTCTTTAT ACCACATTGA TATAGGAGAT TCCTCATTAG 11760

TCATGACAAT ACAGTCCAGA CTGTATCGAT GTCTCAGGTT ACAGAAACCA GCATCTGAAT 11820

ACACAGAGTG AAAGACCCTC CTCCAACAGA GAGCAGAAGT TGAAATTAAG TCTTGCAAAA 11880

FIGURE 1A (Page 12 of 12)

AGTTTTCGAA ATTTCATGTT TTTATTTATT GTGGTTAGGG ACAGCGCATG TGAGTGTGTG 11940

TGTGTGTGTG TGTGTGTGTG TGTGTGTGTG TGTGTGTATT TGTGTATGCA GGTCAGAGGA 12000

CAACTTTTCA GAGAGTTCTC TCCTCTCATG TTGGTCCTGA AGACCAAACT CAGATTATCA 12060

ACATTATCCA TCAATGCCTT TACTTGTGGA GTCATCTCAA AGGTCCAAGA TGAAATGAGG 12120

ACTGAGTTAA TTTTGCATTT TAATGTTTTG GCAGTATGGA GGATCAAGTC AGAGTTTATA 12180

TATGCTAGGC ACACTCTTCA CTTCTTAGCT ATATTCCCAG TGGTACTAAC TCTTATTAAA 12240

GCTCATACTG ATGTTCTGCA GATCTTTTGG GTACC 12275

FIGURE 1B (Page 1 of 9)

GGTACCTGGT ATCTGTCCAG AAATTCATCC ATTTCATCCA GGTTTTCCAG TTTTGTTGAG 60

TATAGCTTTT TGTAGAAGGA TCTGATGGTG TTTTGGATTT CTTCAGGATC TGTTGTTATG 120

TCTCCCTTTT CATTTCTGAT TTTGTTAATT AGGATGTTGT CCCTGTGCCC TCTAGTGAGT 180

CTAGCTAAGG GTTTATCTAT CTTGTTGATT TTCTCAAAGA ACCAACTCCT CGTTTGGTTA 240

ATTCTTTTAA TAGTTCTTCT TGTTTCCACT TGGTTGATTT CACCCCTGAG TTTGATTATT 300

TCCTGCTGTC TACTCCTCTT GGGTGAATTT TCTTCCTTTT TTTTCTAGAG CTTTTAGATG 360

TGTTGTCAAG CTGCTAGTGT ATGCCCTCTC CAGTTTCTTC TTGGAGGCAC TCAGAGCTAT 420

GAGTTTCCCT CTTAGAAATG CTTTCATTGT GTCCCATAGG TTTGGGTATG TTGTGGCTTC 480

GTTTTCATTA AACTCTAAAA AGTCTTTAAT TTCTTTCTTT ATTCCTTCCT TGACCAAGGT 540

ATCATTGAGA AGAGTGTTGT TCAGTTTCCA TTTGAATGTT TGCTTTCCAT TATTTAATGT 600

TGCCTTAGTC CATGGTGGTC TGTGTCTTAG TCAGGGTTTC TTTTCCTGCA CAAACATCAT 660

GACCAAGAAA CAAGTTGGGG ATGAAAGGGT TTATTCAGCT TACACTTCCA TGCTGCTGTT 720

CATCACCAAA GGAAGTCAGG ACTGGAACTC AAACAGATCA GGGAGCAGGA GCTGATGCAG 780

AGGCCATGGA GGGATGTTCT TTACTGGCTT GCCTTCCCTG GCTTGCTCAG CCTGCTCTCT 840

TATAGAATCC AAGACTACCA GCCCAGAGAT GGCACCACCC ACAAGGGGCC TTTCCCCCTT 900

GATCACTAAT TGAGAAAATG CCTTACAGTT GGATCTCATG GAGGCATTTC CTCAACTGAA 960

GCTCCTTTCT CTGTGATATC TCCAGCTGTG TCAAGTTGAC ACAAAACTAG CCAGTACAAT 1020

TGACCCCTTG TCAACTTGAC ACACAAACAC ATCACTAGTA ACCCTCAACC CTTACATTCT 1080

FIGURE 1B (Page 2 of 9)

TATTCATCCC CAAGATCTAA ATAACTTTAA AAGTCCCACA GTCTTTACAT ATTCTTAAAA 1140

TTTCAATCTC TTTAAAATAT CCATCTCTTT TAAAATCCAA AGTCTTTTTA CAATTAAAAC 1200

TCTCTTAACT ATGGCCTCCA CTAAAACAGT TTCTTCCTTC AAGAGGGAAA ATATCAGGGC 1260

ACAGTCAAAG CAAAAATCAA TCTCCAACCA TCCAATGTCT GGGATCCAAC TCACAATCTT 1320

CTGGACTCCT CCAAGGGCTT GTGTCACTTC TCCAGCCATG CCCTTTGTAG CACAGGTGTC 1380

ATCCTCTAGG TTCCAGATGC CTGTACTCCA CTGATGCTGC TGCTCTTGGT GGTCATCTCA 1440

TGGTACTGGC ATCTCCAAAA CACTGCATGG CCCCTTCAGT CCTGGGCCTT CAATTGCAAC 1500

TGAGGCTGCA CCGTCACCAA TGGCCTTCCA TGCCCTCTCA CAGTGCCGAG CCTCAGCTGC 1560

TGTGCATGAC CCCTTCATGC CTTCAAAACC AGTACCACCT GGGTGACCCT TATACATTAC 1620

CAAGTCCCAC TGCAGCAGGA GTACAACCTT GGCTATCTCT GGAACACAGC CTCTTTGTGC 1680

TTTCAGAAAA CACTTCCCAG AAGATGTCAC CTCAACGACG CTGGTCTCTT CTTAATCACC 1740

GATAATTTCT TAGCTCCAGC TAACCAGCAT CAATAGTCAT AGTAATGCAA GGTTTTGCTT 1800

TAGTAGTTCT GGTATCTTGT TAATCACAGT TGATTCTTCA GCCCCAGCTA ACCAGAACTA 1860

CAGAATTTTC ACAATCAAAA CAGCAATGGC CCTGAAAAGA GTCTTTAATT TTCCCTCTGA 1920

AATTTCACAA GCCAGACCTC CATCTTCTGC ACTGTTCTCA ACATTATCTT CTAAGCTCCT 1980

ACACAACATC TGACAGAGCT CTTAACAATG AACGGATCTT CAAGCCGAAA GTTCCAAAGT 2040

CCTTCCACAG TCCTCCCCAA AACATGGTCA GGTTGTCACA GGAATACCCC ACTCCTGGTA 2100

CCAATTTGTC TTAGTCAGGG TTTCTATTCC TGCACAAACA TCATGGCCAA GAAACAAGTT 2160

FIGURE 1B (Page 3 of 9)

GGGGAGGAAA GGGTTTATTT AGCTTACACT TCCATGCTGC TGTTCATCAC CAAAGGAAGT 2220

CAGGACTGGA ACTCAAACAG GTCAGGGAGC AGGAGCTGAT GCAGAGGCCA TGGAGGGATG 2280

TTCTTTACTG GCTTGCCTTC CCTGGCTTGC TCAGCCTGCA CTCTTATAGA ATCCAAGACT 2340

ACCAGCCCAG AGATGGCACC ACCCACAAGG GGCCTTTCCC CCTTGATCAC TAATTGAGAA 2400

AATGCCTTAC AGTTGGATCT CATGGAGGCA TTTCCTCAAC TGAAGCTCCT TTCTCTGTGA 2460

TATCTCCAGC TGTGTCAAGT TGACACAAAA CTAGCCAGTA CAGTCTGATA GGATGCATGG 2520

GACAATTTCA ATATTTTTGT ATCTGTTGAG GCCTGTTTTG TGACCAATTA TATGGTTAAT 2580

TTTGGAGAAG GTTCCGTGAG GTGCTGAGAA GTATATCATT TTGTTTTAGG ATAAAATGTT 2640

CTGTAGATAT CTGTCAAATC CATTTGTTTC ATCACTTCTG TTAGTTTCAC TGTGTCCTGT 2700

TTAGTTTCTG TTTTCATGAT CTGTCCACTG ATGAAAGTGG TGTGTTGAAG TCTCCCACTA 2760

TTATTGTGTG AGGTGCAATG TGTGCTTTGA GCTTTACTAA AGTGTCTTTA ATGAATGTGG 2820

CTGCCCTTGC ATTTGGAGCA TAGATATTCA AAATTGAGAG TTCCTCTTGG AGGATTTTAC 2880

CTTTGATGAG TATGAAGTGT CCCTCCTTGT CTTTTTTGAT AACTTTGGTT TGGAAGTTGA 2940

TTTTATTTGA TATTAGAATG GCTACCCCAG CTTGTTTCTT CAGACCATTT GCTTGGAAAA 3000

TTGTTTTCCA GCCTTTCACT CTGAGGTAGT GTCTGTCTTT TTCCCTGAGA TGGGTTTCCT 3060

GTAAGCAGCA GAATGTTGGG TCCTGTTTGT GTAGCCAGTC TGTTAGTCTA TGTCTTTTTA 3120

TTGGGGAATT GAGTCCATTG ATATTAAGAG ATATTAAGGA AAAGTAATTG TTGCTTCCTA 3180

TTATTTTTGT TGTTAGAGTT GGCATTCTGT TCTTTTGGCT GTCTTCTTTT TGGCTTGTTG 3240

FIGURE 1B (Page 4 of 9)

AGGAATTACT TTCTTGCTTT TTCTAGGGCG TGATATCTGT CCTTGTATTT TTTTTTCTGT 3300

TATTATCCTT TGAAGGGCTG GATTCTGGAA AGATAATGTG TGAATTTGGT TTTGTCATGG 3360

AATACTTTGG TTTCTCCATC TATGGTAATT GAGAGTTTGG CCGGGTATAG TAGCCTGGGC 3420

TGGCTTTTTT TTGTTCTCTT AGTGTCTGTA TAACATCTGT CCAGGCTCTT CTGGCTTTCA 3480

TAGTCTCTGG TGAAAAGTCT GGTGTAATTC TGATAGGCCT GCCTTTATAT GTTACTTGAC 3540

CTTTCTCCCG TACTGCTTTT AATATTCTCT CTTTATTTAG TGCATTTGTT GTTCTGATTA 3600

TTGTGTGTTG GGAGGAATCT CTTTTCTGGT CCAGTCTATA TGGAGTTCTG TAGGCTTCTT 3660

GTATGTTCAT GGGCATGTCA TTCTTTAGGT TCGGGAAGTT TTCTTCTATA ATTTTGTTGA 3720

AAATATTTGC TGGCCCTTTA AGTTGAAAAT CTTCATTCTC ATCAACTCCT ATTATCTGTA 3780

GGTTTGGTCT TCTCATTGTG TCCTGGATTT CCTGGATGTT TTGAGTTAGG ACCTTTTTGT 3840

GTTTTGTATT ATCTTTGATT GTTGTCCTGA TGTTCTCTAT GGAATCTTCT GCACCTGAGA 3900

TTCTCTCTTC CATCTTTTGT ATCCTGTTGC TGATGCTCAC GTCTATGGTT CCAGATTTCT 3960

TTCCTAGAGT TTCTATCTCC AGCGTTGCCT CACTTTGGGT TTTCTTTATT GTGTCTACTT 4020

CCCTTTTTAG GTCTAGTATG GCTTTGTTCA TTTCCATCAC CTGTTTGGAT GTGTTTGCCT 4080

GTTTTTCTAT GAGGACTTCT ACCTGTTTGG TTGTGTTTTC CTGCTATTCT TTAAGGATTT 4140

GTAACTCTTT AGCAGTGGTC TCCTGTATTT CTTTAAGTGA GTTATTAAAG TCCTTCTTGA 4200

TGTCCTCTAC CATCATCATG AGATATGCTT TTAAATACAG GTCTACCTTT ACGGTTGTGT 4260

TGGGGTGCCC AGGACTAGGT GGGGTGGGAG TGCTGCATTC TGATGATGGT GAGTGGTCTT 4320

FIGURE 1B (Page 5 of 9)

```
GATTTCTGTT AGTAGGATTC TTACGTTTTC CTTTTGCCAT CTGGTAATCT CTGGAGTTAT 4380
TTGTTATAGT AGTCTCTGGT TAGAGCTTGT TCCTCAGGTG ATTCTGTTAT GCTCTATCAG 4440
CAGACCTGGG AGACTAGCTC TATCCTTAGT TTCAGTGGTC AGAGTACTCT CTGCAGGCAA 4500
GCTCTCCTCT TGCAGGGAAG GTGCCCAGAT ATCTGGTGTT TGAACCTGCC TCCTGGCAGA 4560
AGTTGTGTTC TACTCACCAT AGGTCTTAAG ATCCCATGGT TGGTCCTGTG TGGTTCCTTG 4620
CGTGTGTCCG GAGACTCCCC GGGCCAGGGT CCCTGGTGAT TGGAAGGGAC TTGTGCACCG 4680
GATCAGGCCA GGTTATCTGA TTCCTTAATT AATGCAGTCT CAGGTCCCGT GCGATTGAAT 4740
TGGAGCAGGC GCTGTGTTCC ACTCACCAGA GGTCTTAGGA TCCTGTGGAG GATCCTGTGT 4800
GGGTCCTTGC GGGTGTCTGC AGACTCCCCG GGCCAGGGAC CATGGTGCTG CAGTGGGCCG 4860
GAAGGGACTT GAGCCCTGGA TCATGCCGGA TTATCTGCTT CCTTAATTAA TGCAGTCTCA 4920
GGTCCTGGCG ATTGGATTGG AGCAGGCGCT GTGTTCCACT CACCAGAGGC CTTAGAATCC 4980
CGTGGCGGAT CCTGTGTGGG TCCTTATGGG TGTCCGCAGA CTCCCCGGGG CTAGGGACCA 5040
CGGTGCTCCA GTGGGCCGGA AGGGACTTGA GCCCCGGATC AGGCCGGATT ATCTGCTTCC 5100
TTAATTCCTG ATAGTCTTTT AAAAGTAAAC TTATAGTTAG ACACTGTACA CAGGTATATA 5160
ATACATTTTA AATATTCTCT CACTATGCCA GGTGGTATCA TATAAGAACT TTTGAATATA 5220
TTTCTTAAAG ATTAATTTTA ATATTTTATG CTCTTATACT ATGCTTAATT CCCAAAGAAT 5280
ATTTTGTATG TTTTGAAACA ATTTACTCTT CAACATTANA TATAGGATTC ACAGTTATAG 5340
ATAGTATTAA ATGTCCATTA ATGATATTTT TAGGGTATAA AAGGATATGA ATATAAAAGT 5400
```

FIGURE 1B (Page 6 of 9)

TGAACAAAAA AGAGGGGATG GGCCATAAAG AATATATTCA TATGTATATA TATATGTGAA 5460

TAATTCAAAG AATAAATAAA TATAATTTTA AAAAGCAGCA GGTATCCCCC CCAAAATACA 5520

GTTGTTGAAG TGCCTTGTGA TAGAACCTTG TCAAATGATA AACCAAAGAA ATACCAACTA 5580

CCCACCCAGC CACCCAAGAG ATGGATTAGA GTCAGTGGAT TATTCAGGGT GTGGGAGCCT 5640

GAGGATAAAA AATCAGAACC CCAGACCCCC TAAAAAAGGT ATGCAGACCG TACAGCCATT 5700

TTATAGTTTT GTGTTGAGCT TCATTCAGCG GGACTCTGGG TACACATGGC TTGTGTGGGG 5760

GTGTGTTGAC AACCTGCAAG TGTTCATTCC TAAGCTGATA TACACACAAG CACATAAGTA 5820

GCACTAAATG GTCTGTGACC TTGCTTTGGG TGGGGGACAA GTATGTTTGG CAGGGGCTAA 5880

ATGATAGAAC CACTAAGTTT AGGGCTGTGG GAGAGACAGA GATAATAAAT NGATAGGGCC 5940

CACATTTCAG GCAGTATACA TTTGTGCCAA GCAGTGTGAA TAGAGGCAAG TTCTAATGGT 6000

ATTGGCGAAG TGCTTGCATA TTTTATCCAT GGATTCGAAA GTGTTGGGAG TGGGATGGTA 6060

ACTTGATCCC TCCAGGAGCA AAGGAGGGTA GAAAAGGAGA CCAGGAGTGG GATGGTTGTG 6120

ACAGATCCCA GGGAAAAGCC AGGTGGAACA GAAGGGAGCT GGGAGAGGTC AGAGTCCGTG 6180

CAATAGCTCC TGGGCAAGGC AGAATGTGCT TATAAAACTA CAGAGACAAA GTTTGGAGCT 6240

GTGACGAAAG GATGGACCAT CTAGAGACTG CCATATCCAG GGGATCCATC CCATAATCAG 6300

CTTCTAAACG CTGACACCAT TGCATACACT AGCAAGATTT TGCTGAAAGG ACCCAGATAT 6360

AGTTGTCTCT ATATGTGAGA CTATGCTGGG GCCTAGCAAA CACAGAAGTG GATGCTCACA 6420

GTCAGCTATT GGATGGATCA CAGGGCTCCC AATGGAGGAG CTAGAGATAG TACCCAAGGA 6480

FIGURE 1B (Page 7 of 9)

GCTAAAGGGA TCTGCAATCC TATAGGTGGA ACAACATTAT GAACTAACCA GTACCCCGGA 6540

GCTCTTGACT CTAGCTGCAT ATGTATCAAA AGATGGCCTA GTAGACCATC ACTGGAAAGA 6600

GAGGCCCATT GGACACGCAA ACTTTATATT CCCCAGTACA GGGGAACGCC AGGGCCAAAA 6660

AAACAAAAAA CAAAAAAAAA TGGGAATGGG TGGGTAGGGA AGTGTGGGGG AGGGTATGGG 6720

GGACTTTTGG GATAGCATTG GAAATGTAAT TGAGGAAAAT ACGTAATAAA AAATATTAAA 6780

AAAAAACCTA CATAGGACAG ACAGGCAACC ATTTTAGGAC AACCCTTGCT CCAGTTGTTA 6840

GGGGACCCAT ATGAAGATAT ACCTTTATAT TTGTTACATA TCTGTGGGTG TTGGAGGATC 6900

TAAGTCCAGC CCATCTATTC TCTTTGGTTG GTGGCTCCAT GAGAGCTCCC ACGGTTCTAG 6960

GTTATTTGAC TGTTGGTCTC CCTGTGGAGT TCCTACCCAG TTTGGGGCCC TCAAAATTTT 7020

TCTCAGTTTT CTTCTCANAG CTTCTGAACT CCATCCAGTT TTTGGCTGTG AATATCTGCA 7080

TCTTCCTGAG TAAGCTTTTG GATAGAGCCT CTTAGAGGAC AACCATACTA GGCTCTTGTC 7140

TCCAAGTTTA AATGTATCAT TAATAGTGTC AGAGATTGAT GCTTGCCCAT GGGATTGGTG 7200

TCAAGTTGGA CCAGTTAATG GTTGATCATT CCCTCAGTCT CTGCTTCATC TTTGTCCCTG 7260

CATTTCTTAT AAACAGACCA ATTTTTGTTT CAAAAGTTTT ATGAGTGGGT TGGTGTTTTT 7320

ATACCTCCAT TGGGGATCCT GCCTGATCCT GGGGAGATGG CCTCTTCAGG TTCCATATCC 7380

CCTTTACTAT GATTCTCTAC TAAGGTCATT TACATTGATA TCGGAGGTCT TTCTTTATTC 7440

TGGGTCTCTG GCTTCTCCTA GAGATGCCCC AATCCCTCAC TCCTAGCAGC TGTAGATTTC 7500

TATTCACTCT CCTGGCCCTC TGGCTTTCAC TCCTGTCTCT TCCCTCACCA CATCCTGAAC 7560

FIGURE 1B (Page 8 of 9)

CCCCATACTC CCTTCCTCCA CATTCATGGG TACATTTTTT AAATCCCAGA ACACAGAAGG 7620

CAGAAGCAGG CAGATCTCTA CAAGTTTTAG GCAAGCCTGG TCTATAGAGC AAATTTCAGG 7680

ATGGCCAGGG CTACACAGTG AAACTCTATC TTAAAAAACA AAAAAACAAA ATAAGTTATT 7740

TATTACATAT TTACTTGTTT ATATGTAAGC ATATATGTGT GGGGGCTGAA GAGACCAGAA 7800

GACAAGTTGT GGAAATTCAT TCTTCTGTTC CATCACATAG ATGCTGGGAA TTAAAATCAG 7860

GTTGTCGGGT TTGGAGACAG GTGACTTTGT TGTCTGAGCT TCCTTGAGAG CCTATAAGTT 7920

TTTCTTTCAT TGTTAGTGTG CTAGCTGATA TCCACATTGT TTTCTGTGCT AGGTATCCTG 7980

AATTCCAGTT GAGTCCACAT GTCATGGAAT GTCCTCTTAC AACCTCTGCC ACTGGGTTTT 8040

GTTTCCTACT ATTTAACTTA GGACTTTTTT TTTGGTAGTG ATTCTTACAA GAAAGGTACA 8100

CATACATTTT TCTTTTTTGA GTTTGATTTG GATCAAGTTA TAATCGTGCA AGTCATGGTG 8160

CCCTTCTTAC TAAGTCTCTA GGTTGCTATG GCTTTGTGAA AACTTTTGGA TTTTATCCTA 8220

AAAAAATAAT AATTAAAAAA AAATCCAGTA ACAATCACTT TGTGCACATT TATTCCTAAG 8280

CTATAAGTTT CCACTTCTGT AACGTAGGTA TTTGAGATTG AAGAAGAAAT CTTTATGTGT 8340

ATGGGTGTCT TGCTGGCATG CATATCCTTG CACTATGTGT ATATCTGGGT GCCTGTGAAG 8400

GCCAAATTAT GACTACAAAA ACCCAGGAGC TGGAGCTAAA GACCATTGTG AGCCACCAGA 8460

AGGGTACTGG GAATTGAATC CAGGTCCTTT ACAGCAGTGG ACAATAGATG TTAACTGCTG 8520

AGCCATATCT TTAGCTCTAA CATGGGGACA ATAGCTTACT TATCCCTAGG ACTTATCATG 8580

AGGACCCCAA AGAGAGTGAA AAGTACTTAT AAGATATGAT GTCTTATCCT CTAGAGCAAG 8640

FIGURE 1B (Page 9 of 9)

```
AAAGCCAGAG AGGAAATCCT GCTTTATTTT TTTTTTAGTA CTCATTGTCA GCTTGCTGGT 8700

CTCCCTTACT TTGTCCCTGC TTAGAGGGAT GAGTGTGGGG TTTTTATTAC CCATTGGGGG 8760

AACATCCCAA TTGGAATGAG GTGCTGGTTT CTCGACTAAT CCTGTATGAC ACCAAAGAAG 8820

TATGAATCTG TTAAAGGTGA AAATTTTGCC ATCAACAACC CAACCTTCAT ACTTAAGTCT 8880

CAGAGAATAC AGAGGAAGAG GGCCAGTAAT ATATTAAGAG TTAGAGGACT AGGAATTCTG 8940

CTCTCAGATG GTGTCTCCAA GAAATGGAGG CAGGACCAGA CACATTAAAT ATCAACAATC 9000

TATACAAGAT ACAATGAAAT CTCAAATAGG CATGGTAAAG AATATATATA TATATAACAC 9060

AATAATAATA ATCGCAAAGA AGCCATGAAT TTGATAGGGA GTTGCGAGAT GGGAAGAACT 9120

GGAGGGAGGA GATGAAAGAA GATGATCTAA TTTCATTGTA GTTAATAATT TTAAAAGATG 9180

AAGAACTTGA ACTTTAGAAC AACATGGTCT CTTGGATCCT GGTTTCATTA AGGATTTATT 9240

ATGTAACCTT GATTGAATCA GTTATCATTT GGGGTATGGT TTGTTCACTT GTGACAGAGT 9300

TATCCCTCAC AACATTGCAG GGTAGATGAT                                  9330
```

FIG. 16A
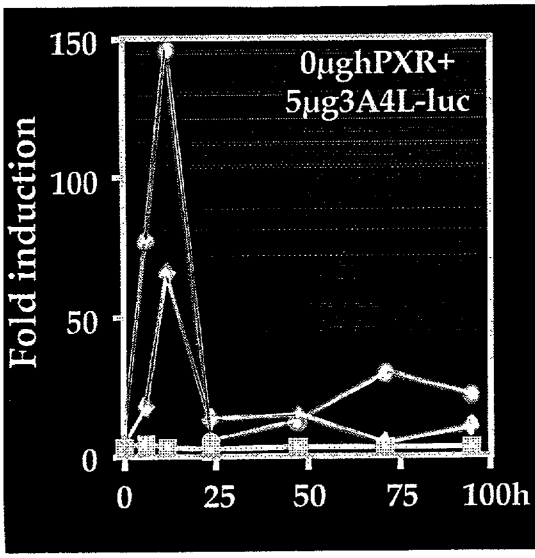
FIG. 16B
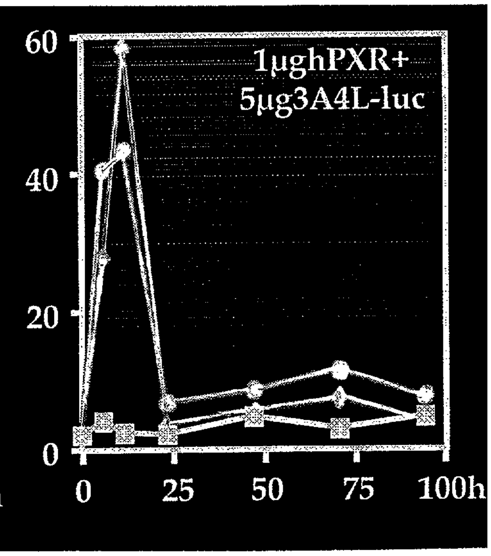
FIG. 16C
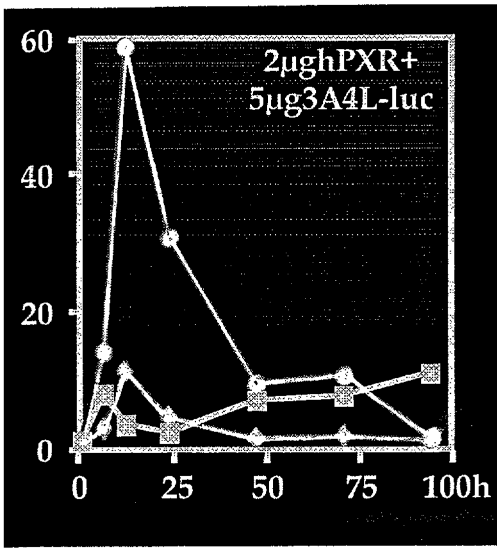
FIG. 16D
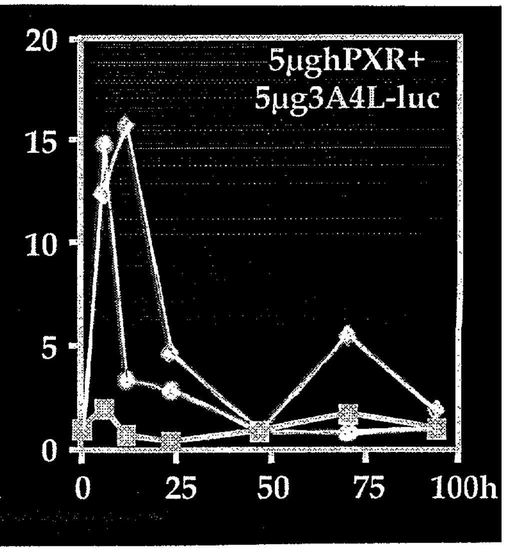

FIGURE 17A (Page 1 of 12)

GGTACCTGGT TATCTATTGG GACTGGTTGG ACAAGAGGGT GCAGCCCACG GAGGGTGAGC 60

CAAGCAGGGT GGGGCGTCGC CTCACCTGGG AAGCACAAGG GGTCGTGGAA TTTTCTCCCC 120

TACCCAAGGA AAGCCATAAG GGACTGAGCC TGAGGAACTG TGCACTCTGG CCCAGATACT 180

GCACTTTTCC CATGGTCTTT GCAACCCGCA GACCAGGAGA TTCCCTCCGG TGCCTATGCC 240

ACCAGGGCCC TGGGTTTCAA GCACAAAACT GGGCAGCCAT TTGGGCAGAC ACCGAACTAG 300

CTGCAGGAGT TTTTTTTTTT TTTTTCCATA CCCCATTGGC ACCTGGAACG CCAGTGAGAC 360

AGAACCGTTC ACTCCCCTGG AAAGGGGGCT GAAACCAGGG ATCCAAGTGG TCTGGCTCGG 420

TGGGCCCCAC CCCCATGGAG CCCAGCAAAC AAAGATTCAC TTGGCTTGAA ATTCTTGCTG 480

CCAGCACAGC AGCAGTCTGA GATTGACCTG GGACCCTCGA ACTTGGTTGG GTGCTGTGGG 540

GGGGCATCTT CCATTGCTGA GGCTTGAGTA GGTGGTTTTA CCTTCGCGGT GTAAACAAAG 600

CTGCTGGGAA GTTTGAACTG GGTGGAGCTC ACCACAGCTC AGTAAGGCCA CTGTGGCCAG 660

ACTGCCTCTC TGGATTTCTC CTCTCTGGGA AGGATATCTC TGAAAAAAAG GCAGCAGCCC 720

CAGTCAGGGA CTTATAGATG AAACCCCCAT CTCCCTGGGA CAGAGCCCCT CGGGGAAGAG 780

GTGGCTTCCA CCATTGTGGA AGACTGTGTG GCAATTCCTC ACGGATTTAG AACTAGAGAT 840

ACCATTTGAC CCAGCAATCC CATTACTGGG TGTATACCCA TAGGATTATA AATCATTCTA 900

CTATAAAGAC ACATGCACAC TTATGTTTAT TGTAACACTA TTTACAATAG CAATGACCTG 960

GAACCAATCC AAAAGCCCAT CAATGATAGA CTGAATAAAG AAAATGTGGC ACATATACAC 1020

TGTGGAATAC TATGCAGCCA TAAAAAAGGA TGAGTTCATG TCCTTTGCAG AGACATGGAT 1080

GAAGCTGGAA ACCATCATTC TCAGCAAACT AGCACAATAA CAGAAAACCA AACACTGCAT 1140

FIGURE 17A (Page 2 of 12)

GTTGTCACTC ATAAGTGGGA GTTAAACAAT GAGAACACAT GGACACAGGG AGGGGAACGT 1200

CACACACTGG GGCATGTCGG GGAGTGGGGG CCTACGGGAG GGATAGCATT AGCAGAAATA 1260

CCTAATGTAG GTGACGGGTT GATGGGTGCA GCAAACCACC ATGGCACATA TACACCTATG 1320

TAATAAAACT GCACGTTCTG CACATGTACC CCAGAACTTA AAGTATAATT AATAATAATA 1380

ATAATTTCTG GGCATGTAAG TAGCTGTCTT TCAGGTTCTA CTTTGATACA TATTCTGAGA 1440

GAATTAAACC TGTCAAAGAA ACCTTGACTT TCAATGGCAG GCACTGGAAT TGACCCTAAT 1500

AATGTGTTTT GGGGTAAGCC TACTCATATT CTCAACCTGT CTGCAGTAGT CGTTAGAATC 1560

TGAACTTCCT GAAGTTCATG TGCAAAGTTG AGTTAATTGT TTAATATTCA ACAAGGATTA 1620

TGCCAGTAAG ATGGTAGGAA AATATTAGAT ATGTGTCATC ACTGCTGGTA TTATTTAAAC 1680

TGCAACATAT TTTAGCTGGC TGCTGATCTC AGCCACCATG CCTGCATTTT ATCTCTGTCT 1740

CGTGGTCTGC AACCTTGGAA GCTTTGAACT TAGCTCATAG AATCCTGGGC ATCAAGAACA 1800

TGTGGTTCTA ATGGCTAGAT AGGGAATGAG AGTAAAAGGA TTTTGCCCAC GGTCACGTGA 1860

GTAAACAACA GATTTGGAGG GGTCTGGACT ACTGTGATGA CTTCATTCTG ACAATATGTT 1920

CCAGTTGTCC TTTCATTTCC TCCTAATCAC ATGTTTGGTC TGATTTGGCT GTTTCCCACC 1980

TTCCAATTCC TGCCTTCTCC AATGCTCCCT TCCGTAGGTC ACTCTGTGGC TCAGAGACCC 2040

TGCTTAGCAA GCGCCCAACC TTTCAATTAT TTGTTCAGTA AAACTTGAAC TCATGTCTCC 2100

CCTTCTTGAT AAAAAGAAAA TACGTTATGT AATGTCGGGT TACTCTATAA CTCTTGTCCT 2160

GTCTCTCGGC AACTAGTGAA CTAACTGTTT TCATATTGAG CAAACGTTTA TGGAAGGACT 2220

FIGURE 17A (Page 3 of 12)

GCCAAGAGTC AGGTACTAGG CTTGGTAATA TTCCCCGTTC TCTCTAGTCA AAGCCAACAC 2280

CAGCCAGACT TGCAGATCTA GGTCCCAAGC CCACTGCAGA TCACAGGCCA GGGTCTGGTC 2340

TCCTCTGAGC TCCTTTGGGA GGGAAAGACA GAATTATTAA CACCCATTTT GTAGATTAGG 2400

CAACTGAGGC TGAGGAAGTT TAAATAACTC AGACAGGGCC TGCACGTCAG TCATATTCCA 2460

AGGATCCCTA CTCACTGTCT TCTCTCTACA GAACGAGATG TCTCTGGAGT CCATAGAAAG 2520

CCCAGGAGCC TGGCTGGGCA CGGTGGCTCC TGCCTGTAAT CCCAGCACTT TGGGAGGCCG 2580

AGGCAGGCAG ATCACCTGAG CTCAGGAGTT CAAGACCAGC CTGGGCAACA TGGCAAAACC 2640

CCATCTCTAC TAAAAATACA AAAAATTAGC TGGGCGTGGT GGTGCATGCC TCTAATCCCA 2700

GCTACTTGGG AGGCTGAGGC ACAAGAATTG CTTGAGCCCA GGAGGCAGCA GTTGCAGTGA 2760

GCTGAGATTG TGCCAGTGCA CTCCAGCCTG GGCAACAGAG CAAGATTCCA TTTCAAAAAC 2820

AAAAACAAAC ACAAACAAAC AAACAAAAAT AGAAAGCCCA GGGACCACCT GCGTCAGGTT 2880

CCCAGCCACA CCTTTTTCTT GTCCTCCTCT GTCTCTGGCA TCTTCTCACA GGTTCCTAAT 2940

TGTTTGTGGT TGCACAAATT CAAAATCCCA GAAAAATTAC CACTTCACAC CCACTCAGAT 3000

GGCTATTTTT TTTTTGAAGG AAGATAACAA GTGTTGACAA GAACATGGAG AAATTGGAAT 3060

TCTCACCCAT TGCTGGTGAG AATGTAATAC GGTGCTGCTG CTATGGAAAA CAGCTTGGAG 3120

TTTCCTCAAA AAGTTCAACA GAATTTCAAT GTGACCCAGC AATTCCCCTC TAAGTTATAG 3180

ATCTGAGAGG ATTAAAAACA GTTACTAAAA TACACGGACT CACATATTTC TAACAGTCCA 3240

ATTCACAAGG GCCAAAAGGT GCTAATAGCC CACATGTCCA TCGATGGATG GATAAATAAA 3300

FIGURE 17A (Page 4 of 12)

TTGTGGTCTA TCCATACAAT GGAATATTAT TCGGCCATAA ATGGAATGAA GTACTGACGC 3360

ATGCTACAGA ATGGATGAAC CGCAAAAAAA ATGGATGAAC ACATGCTACA GAATGGATAG 3420

CCTCACTTTA CTATGAAGTG AAGGCCAGAA ACGAAGTCCA TATATTGCAT CATACAAAAT 3480

ATCCAGAAGA GGGAAGCCCA CAGAGACAGA ATGTGCAATG GTGGATGCCA GGGTCTGGGG 3540

AGAGGGGAGA GTGGGGAGAA ACTGCTCAAC TGGTACAGGC TTTATTTTGG AATGATGGGA 3600

ACATTTTGCA ACTAGATAGA GGTAGTGATT GCAGAACACA GAATGTACTG AATTCCACTG 3660

ATTTTTTTCA CCTTAAAATG GTTAATTTTC AGTCCTGAGA TTGGATAATC ATAAAAAAAT 3720

GGTTAATTTT ATGTTATGTG AATTTCATCC CTATACATAT TTTAAACCTC AGAAATATAC 3780

ACTAGCAGGC ATGGAACAGG TCACTGTGGT GCCTGCCAAG CCCGGTGATG TTATCTGGGG 3840

TCCCCGGCCA GCCTTAAGCC TCTTGCTGAC CGGTGGAGGG CAGAACCTTT GCCCTAAAAG 3900

TATAATATCC ACATGCTGGC ATGATTCCTG GCCAGATGGC TTCTTTATTA GCAGTAATTG 3960

AAACTGCCTC GATACAGACA CTGTACCTTG CAACCAAAAA ATGACTCAAC AATGATAATA 4020

AGGGTTAAGC TGGGCCTTTC TCTCTTTGCC AGTTAAATTA TATTTATTAT AGCTTGACAT 4080

GAAAAACAAA GCAACTCCAA CAGGTATCAC AAGGGCAAAG GACATGAACA TTTTATCAAA 4140

GAAGAAATGC AGCTGTCAAA AATACAGAAA TATTCAACCT TGTTCATAAT AAAGTGGCTG 4200

GGCTCAGTGG TTCATGCCTG TAATCCCAGT GCTTTGCAAG GCTGAGACAG GAGGATCATT 4260

TGAAGCCAGA AGTTCAAGAC CATCCTAGGC AAGTCAGTTC AATACCAGAC TTCATGTCTA 4320

CAAAACATCA AAAAATTAGC CAGGCATGGT GATGCATGCC TGTTGTCCCA GCTACTCAGG 4380

AGGCTGAGGC AGGAGAATTG CTTGAGCCTG GGAGGCTGCG GTGGCGGTGA GCCATGATTG 4440

FIGURE 17A (Page 5 of 12)

TGCCATTGTA CTCCAGCCTG GGCAATGCAG CAAGACTGTC TAAATAACAA AAATAATAGT 4500

AAAGAAAAGG ATTGGGATGC CATTTACTTG CGTATTCAAT ACACAGAGTT AAAAGTAATT 4560

TCTACGTTTT CTATTTTTTT ATTACTAAAA AAAGCTGGAC CATTCTCACA GCCTGAAATG 4620

CTTCTCACTT TCCCTTCTTC TGTCCAAACA CTTCTCTATG ATAATGCAAA CAGTCACTCC 4680

TTTAGGAAGA CTTCACCCCA GGTAGTTCCA GATCCCCTTA TCTCTGCCTT CCCAGAACTC 4740

CTGGTGTCTC TCCAGTTCCC TCCGTGTGGT GAAGTACCCT ACCTAGGGTT TCAGTATGGC 4800

TCTGTCTGCA AAGGTCTTGT TCACACCTTC CCTTATGGTT CTGTTGCCCT GTGTTGTGTC 4860

ATAGCACAGG GCACAGTGGA GAACCCATTC ACACTGATAG AGAGGGCCCC ATGGTCCTGG 4920

AGATAACCAT GTAACCGATC AGAATAAGGC ATTGAGGGCT GGGTGTCAGG CGTGGGCTGC 4980

ACTTGGGTGG GCAGGTCCCC TGGAAAGTCA CTGGGTTTGG CAAGCTTCCT AGTAACATGT 5040

CTCTCTGGGG TCCCCCTTGG AACTTCATGC AAAAATGCTG GTTGCTGGTT TATTCTAGAG 5100

AGATGGTTCA TTCCTTTCAT TTGATTATCA AAGAAACTCA TGTCCCAATT AAAGGTCATA 5160

AAGCCCAGTT TGTAAACTGA GATGATCTCA GCTGAATGAA CTTGCTGACC CTCTGCTTTC 5220

CTCCAGCCTC TCGGTGCCCT TGAAATCATG TCGGTTCAAG CAGCCTCATG AGGCATTACA 5280

AAGTTTAATT ATTTCAGTGA TTATTAAACC TTGTCCTGTG TTGACCCCAG GTGAATCACA 5340

AGCTGAACTT CTGACAAGAA CAAGCTATCA TATTCTTTTC AATTACAGAA AAAAGTAAGT 5400

TAATTGATAG GATTTTTTTT GTTTAAAAAA AATGTTACTA GTTTTGAAAA GGTAATATGT 5460

GCACATGGTA AACACTAAGA AGGTATAAGA GCATAATGCT TTTATACTAC TAAGAATAAT 5520

FIGURE 17A (Page 6 of 12)

GTTTTCTCTA AGTTTTTTTT GGTAGATGCT TTCATCAGAT TAAGAAAATT CCCTGCTATT 5580

AGTTGTTGAA GGTTTTTATA TCATAAATGA AAGTTGAATA TTATTATCAT ATATTATTAA 5640

TATATTGTTA TTGAACTATC AAAGCCTTTT CCTAAAACCA TTGAGATGAT CTTATAACCA 5700

TTCTCCTTTA ACCTGTTGAC GAGATCATTG GTATTTATAC TATTTCTCTG TTAACCATTC 5760

TTGAGTCTCA GGTTTAAATT CAACTTGGTC ATGGTGTGTC ATCTTTGATC ATTGCTGTCT 5820

GTGGCTTGCT ACTGTTTTGT TTAGGATTTT TGCACTGATG CTCATCAATG AGACTGGCAT 5880

GCCATCTTCC TTTGCAGTCC TGATTTTTTT CTGATTTGGA TCATGTGGTT ATGGCCCTCA 5940

TGGAATGAGT TGGGCATGAT GCCTTTTTTT CATGTCTCTG GATTGATGGG ACACTTTGGA 6000

TTCTCTCCAG ATGGCCCTCA ATGGTCCCTG CCTCCTCATT GTTAGGCCCC TGGGCAAGCC 6060

CTTCTCATTT CTGGTAGGCC CAGGAACCTG TGGGGGTTTT GTTTGTTTGT TTGTTTCTTG 6120

AGTCGGAGTC TCACTCTGTC ACCCAGGCTG GAGTTGGAGT GCAATGGCCC GATCTTGGCT 6180

CACTGCAACC TCCACCTCCC AGATTCAAGC AATTCTCCTG CCTCAGCCTC CTGAGTAGCT 6240

GGAATTACAG GCACCCACCG ACACACCCTG CTAATTTTTG TATTTTTAGT ACAGATGGGG 6300

TTTCACAATA TTGGCCAAGC TGGTCTCGAA CTCCTGATCT CATGATCTGC CCGGCTTGGC 6360

CTCCCAAAGT GTTGAGATTA CAAGCATGAG CCACCACACC CAGTGAACCT GTGGTTTTTA 6420

GAAGCTCCCC ATGCATGTGA ATGCTGTGAG CATCCCAGGA TGACAGCCAC TGTGTGTTCA 6480

GCTGTTGGAA CTGTGAGAAA GCACCAGTGG GACCTTCTCC AGCACCTGCC TGCTGAGTTC 6540

ATGGAAGAGG CTTGTTGGGG AGATGATGCC CTGGCTGACT CCTGAAGGAT GGTTAGGAAT 6600

FIGURE 17A (Page 7 of 12)

GCACCAGATG GAAGCTGGGT TGGACCCACT CTATGCTGAA GAACAGCTTG TGTGGACACA 6660

AGGAGACACG GATATGTCAT TTTTGTAGAG CCTGAGGAGT GTCCAATCAC ACCATTTGCT 6720

TAAAACATCA TGCACACTTG GAAAAGTGGA CTGAGACCGA ATGAAGAAGC TAACAGTGGC 6780

CAGATCAGAA AGGGTCTTGT GTTACTTCCT AGAGATACTT AGATTTTATC CTGTGGGTGA 6840

TAGGAGCAGT TGGAGGGACT GAAGACAAGG AAAGAAACAT GTTTCAAGAT CTATGTTTTT 6900

CAAGACGCTT TTCTGGTGGC TGAGTAGGGA ATTCCCTGGA TAAGTCCTGC CCAGGGTCAG 6960

GCAAAACAAG TTAGGGGGTT ACTGAAATAA GGAGTATGAG AAATGGTGTA GGTTGTGCTG 7020

ACGTTTTGTA ACACATCTCA TGATGATCTT CATTTCCTTC ACTAATTTCC TGTTTCATTA 7080

ATTCCCTTCC ACGTGCTCTT CTGAAATTTG CCTCACATTC TCTGATTTCT CTTTTACCTG 7140

TTGGTTTCAT CACCTTTTAC TTTTTGCTTT CCTGGAAACA CAAATGATTC TGATTGTGAC 7200

ATGTCAGAAT TATTTGCAAC ATTTGCCTTT CTGCTGAAAC CATGAGTTCA CTGAATACAC 7260

AATTTAGTAA AGTGTAGGAT GCACATGTCG TTTTCGTGGT CACAACCAGC TCTGTAGCAT 7320

TTTATAACTA CACTGGCAGT GTGCTGGGAG GTGTAGAGAG AAATATTTAT CACATGTGTG 7380

GCTGACACAA CCTGCCAAGT TATTTTAGGA GCCTCCTTGG AATCCCAGCA AGAATGCTAC 7440

CGGCACAATT TGTAATCACA GCATCCTGCT CCATGCCTTG GCTTCATGGC ATAGTCACTT 7500

CTGCAAGTCT CTTTCCAGCT GTCTGTTCCC ATGTCTATAA AGTATGAGTT AAATCATCCT 7560

AACACTACTC ATCTTACAAA GTTTTCTTGC TGATGTTAAG AGAGTTGGGA AAGAACTGTA 7620

TAAACTGTGA AGTGCCATGG AGATGTTAGT GGTTACTTTA TCAAGAAATA GACACTCTAG 7680

AATGGAGTAG AAAGCCAACA GTTATGATTG AGTCCTCCTC CTCTTCTTCT TTTTATTAAT 7740

FIGURE 17A (Page 8 of 12)

TTATAAAGAA AAGAGGTTTA ATTGACTCAC AGTTCCATAT GGCTGGGGAG GCCTCGGGAA 7800

ACTCTCAGTC ATAGCAGGAG GCAAAGGGGA AGAAGGCACC TTCTTCACAA GGCGGCAGGA 7860

GAGAGAGAGC TCCTGTTCTT TTTTGTCATA AAGTCTACAG AAGTGCTTAT ACTTCAGGAC 7920

AAGGGCAGGC AGAGAGAAGG AAGGACATTG CTTCACCCCA GCCCTCACTG ACGAGTTTGC 7980

TAGGGGACCT CACTTTGTCC CAGAGTAGGG CAGAACTCTG GCCACTACCC ATTCAGAAGG 8040

CCTGGGCTGC ACTGCTAGTT CCTCACTAAC TCTGTGTGGC CTTGGGCAAG GTTGGGCCTG 8100

TGTTAACAGA TTATGACCCT GGGCTCTCAA GCTAGAGGAT CTAAATTTGA ATCCTGGCTC 8160

TGCTAAAGCA ATTAGTGATG TAAACTTTAA TGGGTCAGTT AACCTTCCTG TGGCTTAGTT 8220

TGCTCATCTG TAAAATAGGG ATCATAACAG TATCAATACC ACATGATTGT TGGACAGATT 8280

GAATCAGTTA ATGCAGGGGA AGTACTTAGC ATGACACGTA TTCACTATCA TTTCCTGGAG 8340

TAAGAGCTGT GTGTGAGTGG GTGTGAGCAT GTGTGAAACC TTTTCTCTGC AATCTCAGTT 8400

AAGAAACCAA TCCAGAATTT AAAGTTCAGG GCCTAAATGG GTGGTTATCT TCTCCCAGTT 8460

CCATCCTATC CCACCTTTGC TCTTCCTCCC GCCCACAGGA GCTGTTGGTC CTTGATTGGG 8520

CTGGAAGACC TGGTGGACCC TAAGTGATCT ATAAGAGGAG AATAGAGAAC AGGGAATGTC 8580

TTCAAAAATC TAGAGGGACA CAGAGGCTGA GAGGCAGGCA GTCCTGCAGG GTCTTCTGAT 8640

TGGGACAAGG AGAACCTTGG TCTTCACAGG CCAATTCTGG TCAGTTTCCC CCATGGACAG 8700

ATGAGGAAAC AGGCCCAGGA ATATCCAAGG TCTCACACTT CCCATCTGTC AAGTCTTGTT 8760

GATTCTGTTG TATTCATGTC TCTCAAAGGG AGATAGAGTT TAGGGAAGAA AGAAGGATCA 8820

FIGURE 17A (Page 9 of 12)

ACTGTGTCTG ATACCACTGG GAGCTTAAGT AAAGGGTTCT TTTACTTCAT AGCATTTATC 8880

CCAATTTGTA ATTCAGTATT ATTTGTGTGG CTGTTTGGTG TCTCTTTCTC CTATATGAGT 8940

GCTAGCTTCA TAAGGGCAAG GATTTTGATT CTTTAATATT TAGTGCTTGC CACATGCCCT 9000

GAACACAGCA GGCATACAGG CTAACCAACA TACAGTGGCA TGAAAGTCAT GAAAGTGAGA 9060

CACCTACCTC CTCCAGTGCC AAGAGAGCAT AACCATGCAC CTGTCACTCT CCTCAACACC 9120

ACCCCCAAGC ATGAGGCCCA AAAGCATTAG CTAATCCCCT CCTCCAGCCA CTAAAACTTA 9180

AAGGCCAGGT GTGGTGGCTC CCATCTGAAA TCCCAGAACT TCAGGAGACA GCAGCAGGAG 9240

GATCACTTGA GGCCAGGAGT TTGAGATCAG CCTGGGCAAC ATAGCTAGGT CCCATCTGTA 9300

CTAAAAATTA GCTGGGCGTT GTTGCATGCC TGTAGTCCCA GCTACTAAGG AGGCTGAGGT 9360

GGGAGGATCA CTTGAGCCCA GGAGGTGGAA ACAACAGTAA GCTATAATCA CAGCACTGAA 9420

CTCTAGCCTG GGCAACAGAG TGACACCCTG CCTCAAAACA ATTTTAAAAA TAAATAAGAG 9480

CAAAACTTAG ATACCACGTG GTCACCCCAA CATGCAAAAT CAAGTTTTCC CCTACTGAGA 9540

AGAATGGGGA CTTGACAGCT GAGTTACAGA GAGATAATCT TCTTCTTCTT TTTTTTTTTT 9600

TGGTTTACAT CCTCAAGATC ATGACTTGTG AAATTTGAAT CGAATACACA TGTAATTCCA 9660

GAGCAATGTT GCCTCCGCAT ACCATCAGCA ATTCACTTGG CTACTGGAAG TCAGGATAAG 9720

CTTCCCAGAA GAGAGGTACC ACTTGGGCTA CCAATATAAA AGGATGAAAA TATCAGAGTG 9780

ATGGTGTTCT TTACAACGTT GAGTCCCTGG ACAGCCTGTC CACTGATGCT GATATCTGAG 9840

CCTAATGCTT CTCTGAATGT TGAGATTGAA CTTTGATCCA ATGAAACTAG AACGAGAAAG 9900

FIGURE 17A (Page 10 of 12)

AAGATAAGTC TTTCATTGTT GATAAGGACA TTATGTTTCT CATACTTGTA TGATTATTTT 9960

TCCTTAGCTG TACTATAATT ATCTGCTTAT TTGTCTCTGC TCTATGTGCT TAGGGTACAA 10020

AGTTGACCAA GACCAACTTT GGTTGGAAGC ATAGTACTAA GAGCACAGTA CTGAGAGCAC 10080

AGTATTGAGA GCACAGCTTT AAAAAACATG ATGAAGGCTT TAATACAGGA AATGAGCAGG 10140

GGAGAGGCAT GTGGTGGTTG GATGTATCTT CCTTGACACA GTCAGTGCAG CTCTCAGTAG 10200

TCAAGTCCCT ACATGTTAGA AGATGTTACC TTCTGTGGAA TTAAGTGGCA GAACTTGCCT 10260

TCAATTATTT TCCTTTGCAG AACAACACCA ACTGCATTAG TTAGGACACA GTGCTGGCTG 10320

CATTTAAGTC CCAAGCGATG ATTAGTCTCT CACTGTTGGT ATAGATTCAA ACCAATCAGA 10380

CCACCTCCTA AAGTTTGTAG GGCAGGTAAA TCCTCATCTT AGAATAAAAA TCATCTTACC 10440

AAGTATGTGT TTTAGAGGCA AGAAGAAAAC ATATTTGTTT CTGTAAGAGT TTTGTTTAAA 10500

AAAAATATAA GAAAGGCTCT CGGTTTAGGT GAGGTAATGA AGTTGTTGAT AGTTATCAGA 10560

TGACACTGGA ATCTTTACTT CTCTGAACGT GTTCTGTGCA TCTCTCAGTG TGGGAACATA 10620

GAGAGGGAGA TCCTCCAGCA ATGCCACTGA TATGGTCAGA AACTGCATCT TTCTTTCTCC 10680

CTGCTGAGAT GAGATGGAGT CCTTTGTTCT AGAAGACCCA TGGTGGTGCC GCTGGGAGTA 10740

ACCCTTGAGA CAGGAACACA AATCCCAACC AATTTGTGGT TGCAGCCTTG AGTCTCACTA 10800

TTTCCCATAG TGATGCGTAG CAGGGAATGG CAGGTGCACC AGAGCAGGAG AGGACCTAAT 10860

ATCTCCCTTC CTGTTAGCTT TTTATAAAGT TTTATTGTGA TCAGTAGCAG TTGGGAAGCT 10920

ACTTGCAGTC ACTGAGCCTC AGTTTCTACA TCTGTAAACT GGGGATAGTA GCATGGCCCC 10980

TACTTAATGT GCTCAGCAAA GCCACTGAAA GGAGACAGAA ATGTATCTAA ATTACCCTGG 11040

FIGURE 17A (Page 11 of 12)

ACTTTTATCC TACCTCTCTT GGGGATTGTC ACCACCTTCC CATGTTTGTC CTTTTTGGTT 11100

TGATGCTTGC TGTCACTTCT TTCCTTAGGT GCCTCTCTGT ACGGCTCTTT TATCCCAGGG 11160

ATTCCAGAGT TACAGCACAT GCATACCACC ATCCAAGCAT GTTTATTTGT CTCCTGCTTC 11220

ACTAGGCTGT CCCCAAGGAA CATGTGGCTC CCGGCACACA CCTGGCACAA CACTGCACAT 11280

GACATTCACC CACTTGGCCT TGAATCTGAC AAGGAATCTG GCATGATGTT CACCCACTCA 11340

GGCCAGGTGC CGAGCAGCCC TGGAGGCTTA GGGGCCAGAG GGATGGGAAA AGGTGTCTTT 11400

CTGGGGTGAG TATCAGTTTC TGCAGGAGGG CTGAATGTGA GAAAGAATAA AGAGAGAAGG 11460

AAGCGAACAA GCACAGCTTA AACATCGCCT ATTTCTATTG AGTTTTAAGA ACGCTGTGAT 11520

TTTGTTTGTC ATGCAATCCA TTCATCAGGC CAGGCAGACA CAGAACTTGG GTGTGAGTGA 11580

CGATAATGAG CTGATATAAT TTTCACACCC TCATCACTGA GATCTCTCCC ATCAGGAATG 11640

GGTCAGGGAG CTCACAGGTG GCAGCAACTG CTATTACAGG CCTCATCTCT ACCAGCTCCT 11700

GGGGCCTGCC CTCCTCCCAT TAGAAAATCC TCCACTTGTC AAAAAGGAAG CCATTTGCTT 11760

TGAACTCCAA TTCCACCCCC AAGAGGCTGG GACCATCTTA CTGGAGTCCT TGATGCTGTG 11820

TGACCTGCAG TGACCACTGC CCCATCATTG CTGGCTGAGG TGGTTGGGGT CCATCTGGCT 11880

ATCTGGGCAG CTGTTCTCTT CTCTCCTTTC TCTCCTGTTT CCAGACATGC AGTATTTCCA 11940

GAGAGAAGGG GCCACTCTTT GGCAAAGAAC CTGTCTAACT TGCTATCTAT GGCAGGACCT 12000

TTGAAGGGTT CACAGGAAGC AGCACAAATT GATACTATTC CACCAAGCCA TCAGCTCCAT 12060

CTCATCCATG CCCTGTCTCT CCTTTAGGGG TCCCCTTGCC AACAGAATCA CAGAGGACCA 12120

FIGURE 17A (Page 12 of 12)

GCCTGAAAGT GCAGAGACAG CAGCTGAGGC ACAGCCAAGA GCTCTGGCTG TATTAATGAC 12180

CTAAGAAGTC ACCAGAAAGT CAGAAGGGAT GACATGCAGA GGCCCAGCAA TCTCAGCTAA 12240

GTCAACTCCA CCAGCCTTTC TAGTTGCCCA CTGTGTGTAC AGCACCCTGG TAGGGACCAG 12300

AGCCATGACA GGGAATAAGA CTAGACTATG CCCTTGAGGA GCTCACCTCT GTTCAGGGAA 12360

ACAGGCGTGG AAACACAATG GTGGTAAAGA GGAAAGAGGA CAATAGGATT GCATGAAGGG 12420

GATGGAAGGT GCCCAGGGGA GGAAATGGTT ACATCTGTGT GAGGAGTTTG GTGAGGAAAG 12480

ACTCTAAGAG AAGGCTCTGT CTGTCTGGGT TTGGAAGGAT GTGTAGGAGT CTTCTAGGGG 12540

GCACAGGCAC ACTCCAGGCA TAGGTAAAGA TCTGTAGGTG TGGCTTGTTG GGATGAATTT 12600

CAAGTATTTT GGAATGAGGA CAGCCATAGA GACAAGGGCA AGAGAGAGGC GATTTAATAG 12660

ATTTTATGCC AATGGCTCCA CTTGAGTTTC TGATAAGAAC CCAGAACCCT TGGACTCCCC 12720

AGTAACATTG ATTGAGTTGT TTATGATACC TCATAGAATA TGAACTCAAA GGAGGTCAGT 12780

GAGTGGTGTG TGTGTGATTC TTTGCCAACT TCCAAGGTGG AGAAGCCTCT TCCAACTGCA 12840

GGCAGAGCAC AGGTGGCCCT GCTACTGGCT GCAGCTCCAG CCCTGCCTCC TTCTCTAGCA 12900

TATAAACAAT CCAACAGCCT CACTGAATCA CTGCTGTGCA GGGCAGGAAA GCTCCATGCA 12960

CATAGCCCAG CAAAGAGCAA CACAGAGCTG AAAGGAAGAC TCAGAGGAGA GAGATAAGTA 13020

AGGAAAGTAG TGATG 13035

FIGURE 17B (Page 1 of 3)

GGTACCTGGT TATCTATTGG GACTGGTTGG ACAAGAGGGT GCAGCCCACG GAGGGTGAGC 60

CAAGCAGGGT GGGGCGTCGC CTCACCTGGG AAGCACAAGG GGTCGTGGAA TTTTCTCCCC 120

TACCCAAGGA AAGCCATAAG GGACTGAGCC TGAGGAACTG TGCACTCTGG CCCAGATACT 180

GCACTTTTCC CATGGTCTTT GCAACCCGCA GACCAGGAGA TTCCCTCCGG TGCCTATGCC 240

ACCAGGGCCC TGGGTTTCAA GCACAAAACT GGGCAGCCAT TTGGGCAGAC ACCGAACTAG 300

CTGCAGGAGT TTTTTTTTTT TTTTTCCATA CCCCATTGGC ACCTGGAACG CCAGTGAGAC 360

AGAACCGTTC ACTCCCCTGG AAAGGGGGCT GAAACCAGGG ATCCAAGTGG TCTGGCTCGG 420

TGGGCCCCAC CCCCATGGAG CCCAGCAAAC AAAGATTCAC TTGGCTTGAA ATTCTTGCTG 480

CCAGCACAGC AGCAGTCTGA GATTGACCTG GGACCCTCGA ACTTGGTTGG GTGCTGTGGG 540

GGGGCATCTT CCATTGCTGA GGCTTGAGTA GGTGGTTTTA CCTTCGCGGT GTAAACAAAG 600

CTGCTGGGAA GTTTGAACTG GGTGGAGCTC ACCACAGCTC AGTAAGGCCA CTGTGGCCAG 660

ACTGCCTCTC TGGATTTCTC CTCTCTGGGA AGGATATCTC TGAAAAAAAG GCAGCAGCCC 720

CAGTCAGGGA CTTATAGATG AAACCCCCAT CTCCCTGGGA CAGAGCCCCT CGGGGAAGAG 780

GTGGCTTCCA CCATTGTGGA AGACTGTGTG GCAATTCCTC ACGGATTTAG AACTAGAGAT 840

ACCATTTGAC CCAGCAATCC CATTACTGGG TGTATACCCA TAGGATTATA AATCATTCTA 900

CTATAAAGAC ACATGCACAC TTATGTTTAT TGTAACACTA TTTACAATAG CAATGACCTG 960

GAACCAATCC AAAAGCCCAT CAATGATAGA CTGAATAAAG AAAATGTGGC ACATATACAC 1020

TGTGGAATAC TATGCAGCCA TAAAAAAGGA TGAGTTCATG TCCTTTGCAG AGACATGGAT 1080

FIGURE 17B (Page 2 of 3)

```
GAAGCTGGAA ACCATCATTC TCAGCAAACT AGCACAATAA CAGAAAACCA AACACTGCAT 1140
GTTGTCACTC ATAAGTGGGA GTTAAACAAT GAGAACACAT GGACACAGGG AGGGGAACGT 1200
CACACACTGG GGCATGTCGG GGAGTGGGGG CCTACGGGAG GGATAGCATT AGCAGAAATA 1260
CCTAATGTAG GTGACGGGTT GATGGGTGCA GCAAACCACC ATGGCACATA TACACCTATG 1320
TAATAAAACT GCACGTTCTG CACATGTACC CCAGAACTTA AAGTATAATT AATAATAATA 1380
ATAATTTCTG GGCATGTAAG TAGCTGTCTT TCAGGTTCTA CTTTGATACA TATTCTGAGA 1440
GAATTAAACC TGTCAAAGAA ACCTTGACTT TCAATGGCAG GCACTGGAAT TGACCCTAAT 1500
AATGTGTTTT GGGGTAAGCC TACTCATATT CTCAACCTGT CTGCAGTAGT CGTTAGAATC 1560
TGAACTTCCT GAAGTTCATG TGCAAAGTTG AGTTAATTGT TTAATATTCA ACAAGGATTA 1620
TGCCAGTAAG ATGGTAGGAA AATATTAGAT ATGTGTCATC ACTGCTGGTA TTATTTAAAC 1680
TGCAACATAT TTTAGCTGGC TGCTGATCTC AGCCACCATG CCTGCATTTT ATCTCTGTCT 1740
CGTGGTCTGC AACCTTGGAA GCTTTGAACT TAGCTCATAG AATCCTGGGC ATCAAGAACA 1800
TGTGGTTCTA ATGGCTAGAT AGGGAATGAG AGTAAAAGGA TTTTGCCCAC GGTCACGTGA 1860
GTAAACAACA GATTTGGAGG GGTCTGGACT ACTGTGATGA CTTCATTCTG ACAATATGTT 1920
CCAGTTGTCC TTTCATTTCC TCCTAATCAC ATGTTTGGTC TGATTTGGCT GTTTCCCACC 1980
TTCCAATTCC TGCCTTCTCC AATGCTCCCT TCCGTAGGTC ACTCTGTGGC TCAGAGACCC 2040
TGCTTAGCAA GCGCCCAACC TTTCAATTAT TTGTTCAGTA AAACTTGAAC TCATGTCTCC 2100
CCTTCTTGAT AAAAAGAAAA TACGTTATGT AATGTCGGGT TACTCTATAA CTCTTGTCCT 2160
```

FIGURE 17B (Page 3 of 3)

GTCTCTCGGC AACTAGTGAA CTAACTGTTT TCATATTGAG CAAACGTTTA TGGAAGGACT 2220

GCCAAGAGTC AGGTACTAGG CTTGGTAATA TTCCCCGTTC TCTCTAGTCA AAGCCAACAC 2280

CAGCCAGACT TGCAGATCTA GGTCCCAAGC CCACTGCAGA TCACAGGCCA GGGTCTGGTC 2340

TCCTCTGAGC TCCTTTGGGA GGGAAAGACA GAATTATTAA CACCCATTTT GTAGATTAGG 2400

CAACTGAGGC TGAGGAAGTT TAAATAACTC AGACAGGGCC TGCACGTCAG TCATATTCCA 2460

A 2461

Figure 17C (page 1 of 7)

GGTACCTGGTTATCTATTGGGACTGGTTGGACAAGAGGGTGCAGCCCACG
GAGGGTGAGCCAAGCAGGGTGGGGCGTCGCCTCACCTGGGAAGCACAAG
GGGTCGTGGAATTTTCTCCCCTACCCAAGGAAAGCCATAAGGGACTGAGC
CTGAGGAACTGTGCACTCTGGCCCAGATACTGCACTTTTCCCATGGTCTTT
GCAACCCGCAGACCAGGAGATTCCCTCCGGTGCCTATGCCACCAGGGCCC
TGGGTTTCAAGCACAAAACTGGGCAGCCATTTGGGCAGACACCGAACTAG
CTGCAGGAGTTTTTTTTTTTTTTTCCATACCCCATTGGCACCTGGAACGCC
AGTGAGACAGAACCGTTCACTCCCCTGGAAAGGGGGCTGAAACCAGGGA
TCCAAGTGGTCTGGCTCGGTGGGCCCCACCCCCATGGAGCCCAGCAAACA
AAGATTCACTTGGCTTGAAATTCTTGCTGCCAGCACAGCAGCAGTCTGAG
ATTGACCTGGGACCCTCGAACTTGGTTGGGTGCTGTGGGGGGGCATCTTCC
ATTGCTGAGGCTTGAGTAGGTGGTTTTACCTTCGCGGTGTAAACAAAGCTG
CTGGGAAGTTTGAACTGGGTGGAGCTCACCACAGCTCAGTAAGGCCACTG
TGGCCAGACTGCCTCTCTGGATTTCTCCTCTCTGGGAAGGATATCTCTGAA
AAAAAGGCAGCAGCCCCAGTCAGGGACTTATAGATGAAACCCCCATCTCC
CTGGGACAGAGCCCCTCGGGGAAGAGGTGGCTTCCACCATTGTGGAAGAC
TGTGTGGCAATTCCTCACGGATTTAGAACTAGAGATACCATTTGACCCAGC
AATCCCATTACTGGGTGTATACCCATAGGATTATAAATCATTCTACTATAA
AGACACATGCACACTTATGTTTATTGTAACACTATTTACAATAGCAATGAC
CTGGAACCAATCCAAAAGCCCATCAATGATAGACTGAATAAAGAAAATGT
GGCACATATACACTGTGGAATACTATGCAGCCATAAAAAAGGATGAGTTC
ATGTCCTTTGCAGAGACATGGATGAAGCTGGAAACCATCATTCTCAGCAA
ACTAGCACAATAACAGAAAACCAAACACTGCATGTTGTCACTCATAAGTG
GGAGTTAAACAATGAGAACACATGGACACAGGGAGGGGAACGTCACACA
CTGGGGCATGTCGGGGAGTGGGGGCCTACGGGAGGGATAGCATTAGCAG
AAATACCTAATGTAGGTGACGGGTTGATGGGTGCAGCAAACCACCATGGC
ACATATACACCTATGTAATAAAACTGCACGTTCTGCACATGTACCCCAGA
ACTTAAAGTATAATTAATAATAATAATAATTTCTGGGCATGTAAGTAGCTG
TCTTTCAGGTTCTACTTTGATACATATTCTGAGAGAATTAAACCTGTCAAA
GAAACCTTGACTTTCAATGGCAGGCACTGGAATTGACCCTAATAATGTGTT
TTGGGGTAAGCCTACTCATATTCTCAACCTGTCTGCAGTAGTCGTTAGAAT
CTGAACTTCCTGAAGTTCATGTGCAAAGTTGAGTTAATTGTTTAATATTCA
ACAAGGATTATGCCAGTAAGATGGTAGGAAAATATTAGATATGTGTCATC
ACTGCTGGTATTATTTAAACTGCAACATATTTTAGCTGGCTGCTGATCTCA
GCCACCATGCCTGCATTTTATCTCTGTCTCGTGGTCTGCAACCTTGGAAGC
TTTGAACTTAGCTCATAGAATCCTGGGCATCAAGAACATGTGGTTCTAATG
GCTAGATAGGGAATGAGAGTAAAAGGATTTTGCCCACGGTCACGTGAGTA
AACAACAGATTTGGAGGGGTCTGGACTACTGTGATGACTTCATTCTGACA
ATATGTTCCAGTTGTCCTTTCATTTCCTCCTAATCACATGTTTGGTCTGATT
TGGCTGTTTCCCACCTTCCAATTCCTGCCTTCTCCAATGCTCCCTTCCGTAG
GTCACTCTGTGGCTCAGAGACCCTGCTTAGCAAGCGCCCAACCTTTCAATT
ATTTGTTCAGTAAAACTTGAACTCATGTCTCCCCTTCTTGATAAAAAGAAA
ATACGTTATGTAATGTCGGGTTACTCTATAACTCTTGTCCTGTCTCTCGGC
AACTAGTGAACTAACTGTTTTCATATTGAGCAAACGTTTATGGAAGGACT
GCCAAGAGTCAGGTACTAGGCTTGGTAATATTCCCCGTTCTCTCTAGTCAA
AGCCAACACCAGCCAGACTTGCAGATCTAGGTCCCAAGCCCACTGCAGAT
CACAGGCCAGGGTCTGGTCTCCTCTGAGCTCCTTTGGGAGGGAAAGACAG

Figure 17C (page 2 of 7)

AATTATTAACACCCATTTTGTAGATTAGGCAACTGAGGCTGAGGAAGTTT
AAATAACTCAGACAGGGCCTGCACGTCAGTCATATTCCAAGGATCCCTAC
TCACTGTCTTCTCTCTACAGAACGAGATGTCTCTGGAGTCCATAGAAAGCC
CAGGAGCCTGGCTGGGCACGGTGGCTCCTGCCTGTAATCCCAGCACTTTG
GGAGGCCGAGGCAGGCAGATCACCTGAGCTCAGGAGTTCAAGACCAGCC
TGGGCAACATGGCAAAACCCCATCTCTACTAAAAATACAAAAAATTAGCT
GGGCGTGGTGGTGCATGCCTCTAATCCCAGCTACTTGGGAGGCTGAGGCA
CAAGAATTGCTTGAGCCCAGGAGGCAGCAGTTGCAGTGAGCTGAGATTGT
GCCAGTGCACTCCAGCCTGGGCAACAGAGCAAGATTCCATTTCAAAAACA
AAAACAAACACAAACAAACAAACAAAAATAGAAAGCCCAGGGACCACCT
GCGTCAGGTTCCCAGCCACACCTTTTTCTTGTCCTCCTCTGTCTCTGGCATC
TTCTCACAGGTTCCTAATTGTTTGTGGTTGCACAAATTCAAAATCCCAGAA
AAATTACCACTTCACACCCACTCAGATGGCTATTTTTTTTTTGAAGGAAGA
TAACAAGTGTTGACAAGAACATGGAGAAATTGGAATTCTCACCCATTGCT
GGTGAGAATGTAATACGGTGCTGCTGCTATGGAAAACAGCTTGGAGTTTC
CTCAAAAAGTTCAACAGAATTTCAATGTGACCCAGCAATTCCCCTCTAAGT
TATAGATCTGAGAGGATTAAAAACAGTTACTAAAATACACGGACTCACAT
ATTTCTAACAGTCCAATTCACAAGGGCCAAAAGGTGCTAATAGCCCACAT
GTCCATCGATGGATGGATAAATAAATTGTGGTCTATCCATACAATGGAAT
ATTATTCGGCCATAAATGGAATGAAGTACTGACGCATGCTACAGAATGGA
TGAACCGCAAAAAAAATGGATGAACACATGCTACAGAATGGATAGCCTC
ACTTTACTATGAAGTGAAGGCCAGAAACGAAGTCCATATATTGCATCATA
CAAAATATCCAGAAGAGGGAAGCCCACAGAGACAGAATGTGCAATGGTG
GATGCCAGGGTCTGGGGAGAGGGGAGAGTGGGGAGAAACTGCTCAACTG
GTACAGGCTTTATTTTGGAATGATGGGAACATTTTGCAACTAGATAGAGG
TAGTGATTGCAGAACACAGAATGTACTGAATTCCACTGATTTTTTTCACCT
TAAAATGGTTAATTTTCAGTCCTGAGATTGGATAATCATAAAAAAATGGTT
AATTTTATGTTATGTGAATTTCATCCCTATACATATTTTAAACCTCAGAAA
TATACACTAGCAGGCATGGAACAGGTCACTGTGGTGCCTGCCAAGCCCGG
TGATGTTATCTGGGGTCCCCGGCCAGCCTTAAGCCTCTTGCTGACCGGTGG
AGGGCAGAACCTTTGCCCTAAAAGTATAATATCCACATGCTGGCATGATT
CCTGGCCAGATGGCTTCTTTATTAGCAGTAATTGAAACTGCCTCGATACAG
ACACTGTACCTTGCAACCAAAAAATGACTCAACAATGATAATAAGGGTTA
AGCTGGGCCTTTCTCTCTTTGCCAGTTAAATTATATTTATTATAGCTTGACA
TGAAAAACAAAGCAACTCCAACAGGTATCACAAGGGCAAAGGACATGAA
CATTTTATCAAAGAAGAAATGCAGCTGTCAAAAATACAGAAATATTCAAC
CTTGTTCATAATAAAGTGGCTGGGCTCAGTGGTTCATGCCTGTAATCCCAG
TGCTTTGCAAGGCTGAGACAGGAGGATCATTTGAAGCCAGAAGTTCAAGA
CCATCCTAGGCAAGTCAGTTCAATACCAGACTTCATGTCTACAAAACATC
AAAAAATTAGCCAGGCATGGTGATGCATGCCTGTTGTCCCAGCTACTCAG
GAGGCTGAGGCAGGAGAATTGCTTGAGCCTGGGAGGCTGCGGTGGCGGT
GAGCCATGATTGTGCCATTGTACTCCAGCCTGGGCAATGCAGCAAGACTG
TCTAAATAACAAAAATAATAGTAAAGAAAAGGATTGGGATGCCATTTACT
TGCGTATTCAATACACAGAGTTAAAAGTAATTTCTACGTTTTCTATTTTTTT
ATTACTAAAAAAAGCTGGACCATTCTCACAGCCTGAAATGCTTCTCACTTT
CCCTTCTTCTGTCCAAACACTTCTCTATGATAATGCAAACAGTCACTCCTTT
AGGAAGACTTCACCCCAGGTAGTTCCAGATCCCCTTATCTCTGCCTTCCCA
GAACTCCTGGTGTCTCTCCAGTTCCCTCCGTGTGGTGAAGTACCCTACCTA

Figure 17C (page 3 of 7)

GGGTTTCAGTATGGCTCTGTCTGCAAAGGTCTTGTTCACACCTTCCCTTAT
GGTTCTGTTGCCCTGTGTTGTGTCATAGCACAGGGCACAGTGGAGAACCC
ATTCACACTGATAGAGAGGGCCCCATGGTCCTGGAGATAACCATGTAACC
GATCAGAATAAGGCATTGAGGGCTGGGTGTCAGGCGTGGGCTGCACTTGG
GTGGGCAGGTCCCCTGGAAAGTCACTGGGTTTGGCAAGCTTCCTAGTAAC
ATGTCTCTCTGGGGTCCCCCTTGGAACTTCATGCAAAAATGCTGGTTGCTG
GTTTATTCTAGAGAGATGGTTCATTCCTTTCATTTGATTATCAAAGAAACT
CATGTCCCAATTAAAGGTCATAAAGCCCAGTTTGTAAACTGAGATGATCT
CAGCTGAATGAACTTGCTGACCCTCTGCTTTCCTCCAGCCTCTCGGTGCCC
TTGAAATCATGTCGGTTCAAGCAGCCTCATGAGGCATTACAAAGTTTAATT
ATTTCAGTGATTATTAAACCTTGTCCTGTGTTGACCCCAGGTGAATCACAA
GCTGAACTTCTGACAAGAACAAGCTATCATATTCTTTTCAATTACAGAAAA
AAGTAAGTTAATTGATAGGATTTTTTTTGTTTAAAAAAAATGTTACTAGTT
TTGAAAAGGTAATATGTGCACATGGTAAACACTAAGAAGGTATAAGAGCA
TAATGCTTTTATACTACTAAGAATAATGTTTTCTCTAAGTTTTTTTGGTAG
ATGCTTTCATCAGATTAAGAAAATTCCCTGCTATTAGTTGTTGAAGGTTTT
TATATCATAAATGAAAGTTGAATATTATTATCATATATTATTAATATATTG
TTATTGAACTATCAAAGCCTTTTCCTAAAACCATTGAGATGATCTTATAAC
CATTCTCCTTTAACCTGTTGACGAGATCATTGGTATTTATACTATTTCTCTG
TTAACCATTCTTGAGTCTCAGGTTTAAATTCAACTTGGTCATGGTGTGTCA
TCTTTGATCATTGCTGTCTGTGGCTTGCTACTGTTTTGTTTAGGATTTTTGC
ACTGATGCTCATCAATGAGACTGGCATGCCATCTTCCTTTGCAGTCCTGAT
TTTTTTCTGATTTGGATCATGTGGTTATGGCCCTCATGGAATGAGTTGGGC
ATGATGCCTTTTTTTCATGTCTCTGGATTGATGGGACACTTTGGATTCTCTC
CAGATGGCCCTCAATGGTCCCTGCCTCCTCATTGTTAGGCCCCTGGGCAAG
CCCTTCTCATTTCTGGTAGGCCCAGGAACCTGTGGGGGTTTTGTTTGTTTGT
TTGTTTCTTGAGTCGGAGTCTCACTCTGTCACCCAGGCTGGAGTTGGAGTG
CAATGGCCCGATCTTGGCTCACTGCAACCTCCACCTCCCAGATTCAAGCAA
TTCTCCTGCCTCAGCCTCCTGAGTAGCTGGAATTACAGGCACCCACCGACA
CACCCTGCTAATTTTTGTATTTTTAGTACAGATGGGGTTTCACAATATTGG
CCAAGCTGGTCTCGAACTCCTGATCTCATGATCTGCCCGGCTTGGCCTCCC
AAAGTGTTGAGATTACAAGCATGAGCCACCACACCCAGTGAACCTGTGGT
TTTTAGAAGCTCCCCATGCATGTGAATGCTGTGAGCATCCCAGGATGACA
GCCACTGTGTGTTCAGCTGTTGGAACTGTGAGAAAGCACCAGTGGGACCT
TCTCCAGCACCTGCCTGCTGAGTTCATGGAAGAGGCTTGTTGGGGAGATG
ATGCCCTGGCTGACTCCTGAAGGATGGTTAGGAATGCACCAGATGGAAGC
TGGGTTGGACCCACTCTATGCTGAAGAACAGCTTGTGTGGACACAAGGAG
ACACGGATATGTCATTTTTGTAGAGCCTGAGGAGTGTCCAATCACACCATT
TGCTTAAAACATCATGCACACTTGGAAAAGTGGACTGAGACCGAATGAAG
AAGCTAACAGTGGCCAGATCAGAAAGGGTCTTGTGTTACTTCCTAGAGAT
ACTTAGATTTTATCCTGTGGGTGATAGGAGCAGTTGGAGGGACTGAAGAC
AAGGAAAGAAACATGTTTCAAGATCTATGTTTTTCAAGACGCTTTTCTGGT
GGCTGAGTAGGGAATTCCCTGGATAAGTCCTGCCCAGGGTCAGGCAAAAC
AAGTTAGGGGGTTACTGAAATAAGGAGTATGAGAAATGGTGTAGGTTGTG
CTGACGTTTTGTAACACATCTCATGATGATCTTCATTTCCTTCACTAATTTC
CTGTTTCATTAATTCCCTTCCACGTGCTCTTCTGAAATTTGCCTCACATTCT
CTGATTTCTCTTTTACCTGTTGGTTTCATCACCTTTTACTTTTTGCTTTCCTG
GAAACACAAATGATTCTGATTGTGACATGTCAGAATTATTTGCAACATTTG

Figure 17C (page 4 of 7)

CCTTTCTGCTGAAACCATGAGTTCACTGAATACACAATTTAGTAAAGTGTA
GGATGCACATGTCGTTTTCGTGGTCACAACCAGCTCTGTAGCATTTTATAA
CTACACTGGCAGTGTGCTGGGAGGTGTAGAGAGAAATATTTATCACATGT
GTGGCTGACACAACCTGCCAAGTTATTTAGGAGCCTCCTTGGAATCCCAG
CAAGAATGCTACCGGCACAATTTGTAATCACAGCATCCTGCTCCATGCCTT
GGCTTCATGGCATAGTCACTTCTGCAAGTCTCTTTCCAGCTGTCTGTTCCC
ATGTCTATAAAGTATGAGTTAAATCATCCTAACACTACTCATCTTACAAAG
TTTTCTTGCTGATGTTAAGAGAGTTGGGAAAGAACTGTATAAACTGTGAA
GTGCCATGGAGATGTTAGTGGTTACTTTATCAAGAAATAGACACTCTAGA
ATGGAGTAGAAAGCCAACAGTTATGATTGAGTCCTCCTCCTCTTCTTCTTT
TTATTAATTTATAAAGAAAAGAGGTTTAATTGACTCACAGTTCCATATGGC
TGGGGAGGCCTCGGGAAACTCTCAGTCATAGCAGGAGGCAAAGGGGAAG
AAGGCACCTTCTTCACAAGGCGGCAGGAGAGAGAGAGCTCCTGTTCTTTT
TTGTCATAAAGTCTACAGAAGTGCTTATACTTCAGGACAAGGGCAGGCAG
AGAGAAGGAAGGACATTGCTTCACCCCAGCCCTCACTGACGAGTTTGCTA
GGGGACCTCACTTTGTCCCAGAGTAGGGCAGAACTCTGGCCACTACCCAT
TCAGAAGGCCTGGGCTGCACTGCTAGTTCCTCACTAACTCTGTGTGGCCTT
GGGCAAGGTTGGGCCTGTGTTAACAGATTATGACCCTGGGCTCTCAAGCT
AGAGGATCTAAATTTGAATCCTGGCTCTGCTAAAGCAATTAGTGATGTAA
ACTTTAATGGGTCAGTTAACCTTCCTGTGGCTTAGTTTGCTCATCTGTAAA
ATAGGGATCATAACAGTATCAATACCACATGATTGTTGGACAGATTGAAT
CAGTTAATGCAGGGGAAGTACTTAGCATGACACGTATTCACTATCATTTCC
TGGAGTAAGAGCTGTGTGTGAGTGGGTGTGAGCATGTGTGAAACCTTTTC
TCTGCAATCTCAGTTAAGAAACCAATCCAGAATTTAAAGTTCAGGGCCTA
AATGGGTGGTTATCTTCTCCCAGTTCCATCCTATCCCACCTTTGCTCTTCCT
CCCGCCCACAGGAGCTGTTGGTCCTTGATTGGGCTGGAAGACCTGGTGGA
CCCTAAGTGATCTATAAGAGGAGAATAGAGAACAGGGAATGTCTTCAAAA
ATCTAGAGGGACACAGAGGCTGAGAGGCAGGCAGTCCTGCAGGGTCTTCT
GATTGGGACAAGGAGAACCTTGGTCTTCACAGGCCAATTCTGGTCAGTTT
CCCCCATGGACAGATGAGGAAACAGGCCCAGGAATATCCAAGGTCTCACA
CTTCCCATCTGTCAAGTCTTGTTGATTCTGTTGTATTCATGTCTCTCAAAGG
GAGATAGAGTTTAGGGAAGAAAGAAGGATCAACTGTGTCTGATACCACTG
GGAGCTTAAGTAAAGGGTTCTTTTACTTCATAGCATTTATCCCAATTTGTA
ATTCAGTATTATTTGTGTGGCTGTTTGGTGTCTCTTTCTCCTATATGAGTGC
TAGCTTCATAAGGGCAAGGATTTTGATTCTTTAATATTTAGTGCTTGCCAC
ATGCCCTGAACACAGCAGGCATACAGGCTAACCAACATACAGTGGCATGA
AAGTCATGAAAGTGAGACACCTACCTCCTCCAGTGCCAAGAGAGCATAAC
CATGCACCTGTCACTCTCCTCAACACCACCCCCAAGCATGAGGCCCAAAA
GCATTAGCTAATCCCCTCCTCCAGCCACTAAAACTTAAAGGCCAGGTGTG
GTGGCTCCCATCTGAAATCCCAGAACTTCAGGAGACAGCAGCAGGAGGAT
CACTTGAGGCCAGGAGTTTGAGATCAGCCTGGGCAACATAGCTAGGTCCC
ATCTGTACTAAAAATTAGCTGGGCGTTGTTGCATGCCTGTAGTCCCAGCTA
CTAAGGAGGCTGAGGTGGGAGGATCACTTGAGCCCAGGAGGTGGAAACA
ACAGTAAGCTATAATCACAGCACTGAACTCTAGCCTGGGCAACAGAGTGA
CACCCTGCCTCAAAACAATTTTAAAAATAAATAAGAGCAAAACTTAGATA
CCACGTGGTCACCCCAACATGCAAAATCAAGTTTTCCCCTACTGAGAAGA
ATGGGGACTTGACAGCTGAGTTACAGAGAGATAATCTTCTTCTTCTTTTT
TTTTTTTGGTTTACATCCTCAAGATCATGACTTGTGAAATTTGAATCGAAT

Figure 17C (page 5 of 7)

ACACATGTAATTCCAGAGCAATGTTGCCTCCGCATACCATCAGCAATTCAC
TTGGCTACTGGAAGTCAGGATAAGCTTCCCAGAAGAGAGGTACCACTTGG
GCTACCAATATAAAAGGATGAAAATATCAGAGTGATGGTGTTCTTTACAA
CGTTGAGTCCCTGGACAGCCTGTCCACTGATGCTGATATCTGAGCCTAATG
CTTCTCTGAATGTTGAGATTGAACTTTGATCCAATGAAACTAGAACGAGA
AAGAAGATAAGTCTTTCATTGTTGATAAGGACATTATGTTTCTCATACTTG
TATGATTATTTTTCCTTAGCTGTACTATAATTATCTGCTTATTTGTCTCTGC
TCTATGTGCTTAGGGTACAAAGTTGACCAAGACCAACTTTGGTTGGAAGC
ATAGTACTAAGAGCACAGTACTGAGAGCACAGTATTGAGAGCACAGCTTT
AAAAAACATGATGAAGGCTTTAATACAGGAAATGAGCAGGGGAGAGGCA
TGTGGTGGTTGGATGTATCTTCCTTGACACAGTCAGTGCAGCTCTCAGTAG
TCAAGTCCCTACATGTTAGAAGATGTTACCTTCTGTGGAATTAAGTGGCAG
AACTTGCCTTCAATTATTTTCCTTTGCAGAACAACACCAACTGCATTAGTT
AGGACACAGTGCTGGCTGCATTTAAGTCCCAAGCGATGATTAGTCTCTCA
CTGTTGGTATAGATTCAAACCAATCAGACCACCTCCTAAAGTTTGTAGGGC
AGGTAAATCCTCATCTTAGAATAAAAATCATCTTACCAAGTATGTGTTTTA
GAGGCAAGAAGAAAACATATTTGTTTCTGTAAGAGTTTTGTTTAAAAAAA
ATATAAGAAAGGCTCTCGGTTTAGGTGAGGTAATGAAGTTGTTGATAGTT
ATCAGATGACACTGGAATCTTTACTTCTCTGAACGTGTTCTGTGCATCTCT
CAGTGTGGGAACATAGAGAGGGAGATCCTCCAGCAATGCCACTGATATGG
TCAGAAACTGCATCTTTCTTTCTCCCTGCTGAGATGAGATGGAGTCCTTTG
TTCTAGAAGACCCATGGTGGTGCCGCTGGGAGTAACCCTTGAGACAGGAA
CACAAATCCCAACCAATTTGTGGTTGCAGCCTTGAGTCTCACTATTTCCCA
TAGTGATGCGTAGCAGGGAATGGCAGGTGCACCAGAGCAGGAGAGGACC
TAATATCTCCCTTCCTGTTAGCTTTTTATAAAGTTTTATTGTGATCAGTAGC
AGTTGGGAAGCTACTTGCAGTCACTGAGCCTCAGTTTCTACATCTGTAAAC
TGGGGATAGTAGCATGGCCCCTACTTAATGTGCTCAGCAAAGCCACTGAA
AGGAGACAGAAATGTATCTAAATTACCCTGGACTTTTATCCTACCTCTCTT
GGGGATTGTCACCACCTTCCCATGTTTGTCCTTTTTGGTTTGATGCTTGCTG
TCACTTCTTTCCTTAGGTGCCTCTCTGTACGGCTCTTTTATCCCAGGGATTC
CAGAGTTACAGCACATGCATACCACCATCCAAGCATGTTTATTTGTCTCCT
GCTTCACTAGGCTGTCCCCAAGGAACATGTGGCTCCCGGCACACACCTGG
CACAACACTGCACATGACATTCACCCACTTGGCCTTGAATCTGACAAGGA
ATCTGGCATGATGTTCACCCACTCAGGCCAGGTGCCGAGCAGCCCTGGAG
GCTTAGGGGCCAGAGGGATGGAAAAGGTGTCTTTCTGGGGTGAGTATCA
GTTTCTGCAGGAGGGCTGAATGTGAGAAAGAATAAAGAGAGAAGGAAGC
GAACAAGCACAGCTTAAACATCGCCTATTTCTATTGAGTTTTAAGAACGCT
GTGATTTTGTTTGTCATGCAATCCATTCATCAGGCCAGGCAGACACAGAAC
TTGGGTGTGAGTGACGATAATGAGCTGATATAATTTTCACACCCTCATCAC
TGAGATCTCTCCCATCAGGAATGGGTCAGGGAGCTCACAGGTGGCAGCAA
CTGCTATTACAGGCCTCATCTCTACCAGCTCCTGGGGCCTGCCCTCCTCCC
ATTAGAAAATCCTCCACTTGTCAAAAAGGAAGCCATTTGCTTTGAACTCCA
ATTCCACCCCCAAGAGGCTGGGACCATCTTACTGGAGTCCTTGATGCTGTG
TGACCTGCAGTGACCACTGCCCCATCATTGCTGGCTGAGGTGGTTGGGGTC
CATCTGGCTATCTGGGCAGCTGTTCTCTTCTCTCCTTTCTCTCCTGTTTCCA
GACATGCAGTATTTCCAGAGAGAAGGGGCCACTCTTTGGCAAAGAACCTG
TCTAACTTGCTATCTATGGCAGGACCTTTGAAGGGTTCACAGGAAGCAGC
ACAAATTGATACTATTCCACCAAGCCATCAGCTCCATCTCATCCATGCCCT

Figure 17C (page 6 of 7)

GTCTCTCCTTTAGGGGTCCCCTTGCCAACAGAATCACAGAGGACCAGCCT
GAAAGTGCAGAGACAGCAGCTGAGGCACAGCCAAGAGCTCTGGCTGTATT
AATGACCTAAGAAGTCACCAGAAAGTCAGAAGGGATGACATGCAGAGGC
CCAGCAATCTCAGCTAAGTCAACTCCACCAGCCTTTCTAGTTGCCCACTGT
GTGTACAGCACCCTGGTAGGGACCAGAGCCATGACAGGGAATAAGACTA
GACTATGCCCTTGAGGAGCTCACCTCTGTTCAGGGAAACAGGCGTGGAAA
CACAATGGTGGTAAAGAGGAAAGAGGACAATAGGATTGCATGAAGGGGA
TGGAAGGTGCCCAGGGGAGGAAATGGTTACATCTGTGTGAGGAGTTTGGT
GAGGAAAGACTCTAAGAGAAGGCTCTGTCTGTCTGGGTTTGGAAGGATGT
GTAGGAGTCTTCTAGGGGGCACAGGCACACTCCAGGCATAGGTAAAGATC
TGTAGGTGTGGCTTGTTGGGATGAATTTCAAGTATTTTGGAATGAGGACA
GCCATAGAGACAAGGGCAAGAGAGAGGCGATTTAATAGATTTTATGCCAA
TGGCTCCACTTGAGTTTCTGATAAGAACCCAGAACCCTTGGACTCCCCAGT
AACATTGATTGAGTTGTTTATGATACCTCATAGAATATGAACTCAAAGGA
GGTCAGTGAGTGGTGTGTGTGTGATTCTTTGCCAACTTCCAAGGTGGAGA
AGCCTCTTCCAACTGCAGGCAGAGCACAGGTGGCCCTGCTACTGGCTGCA
GCTCCAGCCCTGCCTCCTTCTCTAGCATATAAACAATCCAACAGCCTCACT
GAATCACTGCTGTGCAGGGCAGGAAAGCTCCATGCACATAGCCCAGCAAA
GAGCAACACAGAGCTGAAAGGAAGCTTGCGGCCGCTTAACTGCAGAAGTT
GGTCGTGAGGCACTGGGCAGGTAAGTATCAAGGTTACAAGACAGGTTTAA
GGAGACCAATAGAAACTGGGCTTGTCGAGACAGAGAAGACTCTTGCGTTT
CTGATAGGCACCTATTGGTCTTACTGACATCCACTTTGCCTTTCTCTCCACA
GGTGTCCACTCCCAGGTTCAATTACAGCTCTTAAGCGGCCGCAAGCTTGGC
ATTCCGGTACTGTTGGTAAAGCCACCATGGAAGACGCCAAAAACATAAAG
AAAGGCCCGGCGCCATTCTATCCGCTGGAAGATGGAACCGCTGGAGAGCA
ACTGCATAAGGCTATGAAGAGATACGCCCTGGTTCCTGGAACAATTGCTT
TTACAGATGCACATATCGAGGTGGACATCACTTACGCTGAGTACTTCGAA
ATGTCCGTTCGGTTGGCAGAAGCTATGAAACGATATGGGCTGAATACAAA
TCACAGAATCGTCGTATGCAGTGAAAACTCTCTTCAATTCTTTATGCCGGT
GTTGGGCGCGTTATTTATCGGAGTTGCAGTTGCGCCCGCGAACGACATTTA
TAATGAACGTGAATTGCTCAACAGTATGGGCATTTCGCAGCCTACCGTGG
TGTTCGTTTCCAAAAAGGGGTTGCAAAAAATTTTGAACGTGCAAAAAAAG
CTCCCAATCATCCAAAAAATTATTATCATGGATTCTAAAACGGATTACCAG
GGATTTCAGTCGATGTACACGTTCGTCACATCTCATCTACCTCCCGGTTTT
AATGAATACGATTTTGTGCCAGAGTCCTTCGATAGGGACAAGACAATTGC
ACTGATCATGAACTCCTCTGGATCTACTGGTCTGCCTAAAGGTGTCGCTCT
GCCTCATAGAACTGCCTGCGTGAGATTCTCGCATGCCAGAGATCCTATTTT
TGGCAATCAAATCATTCCGGATACTGCGATTTTAAGTGTTGTTCCATTCCA
TCACGGTTTTGGAATGTTTACTACACTCGGATATTTGATATGTGGATTTCG
AGTCGTCTTAATGTATAGATTTGAAGAAGAGCTGTTTCTGAGGAGCCTTCA
GGATTACAAGATTCAAAGTGCGCTGCTGGTGCCAACCCTATTCTCCTTCTT
CGCCAAAAGCACTCTGATTGACAAATACGATTTATCTAATTTACACGAAA
TTGCTTCTGGTGGCGCTCCCCTCTCTAAGGAAGTCGGGGAAGCGGTTGCCA
AGAGGTTCCATCTGCCAGGTATCAGGCAAGGATATGGGCTCACTGAGACT
ACATCAGCTATTCTGATTACACCCGAGGGGGATGATAAACCGGGCGCGGT
CGGTAAAGTTGTTCCATTTTTTGAAGCGAAGGTTGTGGATCTGGATACCGG
GAAAACGCTGGGCGTTAATCAAAGAGGCGAACTGTGTGTGAGAGGTCCTA
TGATTATGTCCGGTTATGTAAACAATCCGGAAGCGACCAACGCCTTGATT

Figure 17C (page 7 of 7)

GACAAGGATGGATGGCTACATTCTGGAGACATAGCTTACTGGGACGAAGA
CGAACACTTCTTCATCGTTGACCGCCTGAAGTCTCTGATTAAGTACAAAGG
CTATCAGGTGGCTCCCGCTGAATTGGAATCCATCTTGCTCCAACACCCCAA
CATCTTCGACGCAGGTGTCGCAGGTCTTCCCGACGATGACGCCGGTGAAC
TTCCCGCCGCCGTTGTTGTTTTGGAGCACGGAAAGACGATGACGGAAAAA
GAGATCGTGGATTACGTCGCCAGTCAAGTAACAACCGCGAAAAAGTTGCG
CGGAGGAGTTGTGTTTGTGGACGAAGTACCGAAAGGTCTTACCGGAAAAC
TCGACGCAAGAAAAATCAGAGAGATCCTCATAAAGGCCAAGAAGGGCGG
AAAGATCGCCGTGTAATTCTAGAGTCGGGGCGGCCGGCCGCTTCGAGCAG
ACATGATAAGATACATTGATGAGTTTGGACAAACCACAACTAGAATGCAG
TGAAAAAAATGCTTTATTTGTGAAATTTGTGATGCTATTGCTTTATTTGTA
ACCATTATAAGCTGCAATAAACAAGTTAACAACAACAATTGCATTCATTTT
ATGTTTCAGGTTCAGGGGGAGGTGTGGGAGGTTTTTTAAAGCAAGTAAAA
CCTCTACAAATGTGGTAAAATCGATAAGGATCGATCCGTCGAC

Effects of Xenobiotics on Expression of CYP3A4-*luc* in Tg FvB Mice
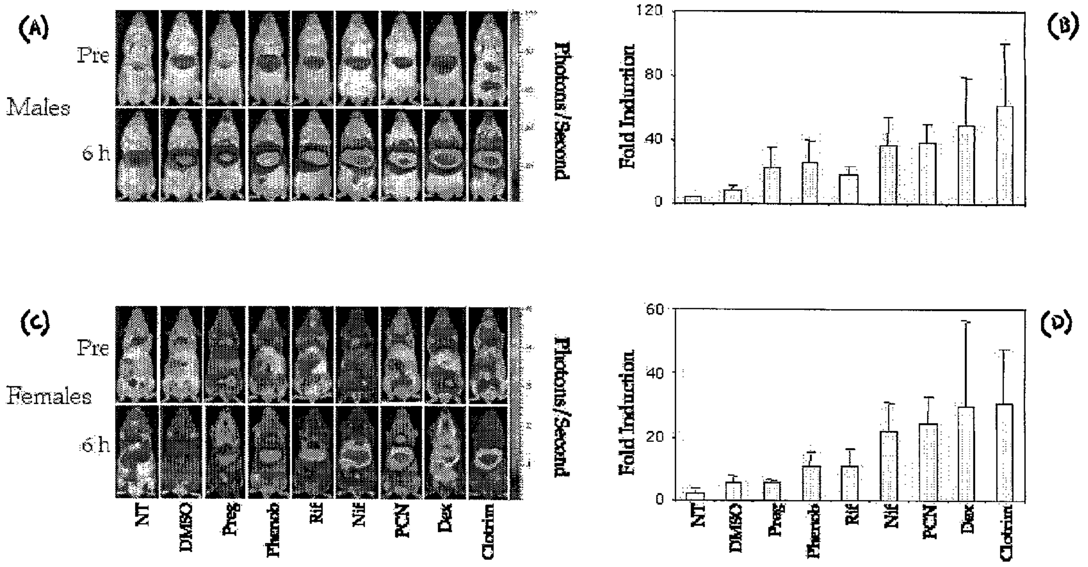
Figure 22 (panels A-D)

ISOLATION AND IDENTIFICATION OF MOUSE AND HUMAN TRANSCRIPTION CONTROL ELEMENTS ASSOCIATED WITH CYTOCHROME EXPRESSION

CROSS-REFERENCE TO RELATED APPLICATIONS

This application is related to U.S. Provisional Patent Application Ser. No. 60/283,534, filed Apr. 12, 2001, from which priority is claimed under 35 USC §119(e)(1), and which application is incorporated herein by reference in its entirety.

FIELD OF THE INVENTION

The present invention relates generally to the field of molecular biology and medicine. In particular, the invention relates to transcription control elements derived from genomic locii of the murine Cyp3A11 gene and the human CYP3A4 gene, as well as methods of using the same. The invention further relates to isolated polynucleotides derived from regulatory regions of the murine Cyp3A11 gene and the human CYP3A4 gene, reporter constructs comprising those isolated polynucleotides, cells transformed with those reporter constructs, transgenic animals comprising those reporter constructs, and methods of use of such cells and transgenic animals for identifying compounds that modulate expression mediated by the murine Cyp3A11 gene and the human CYP3A4 gene derived transcription control elements. The invention further relates to in vivo assay methods which employ animals transfected with such reporter constructs.

BACKGROUND OF THE INVENTION

Toxicology studies of substances have traditionally relied on unicellular organisms (for example, the Ames test or the yeast carcinogenic assay described in U.S. Pat. No. 4,997,757) or in vitro systems for toxicity testing and the prediction of human risk. However, there are many factors that make it difficult to extrapolate from such data to human risk including cellular affinity of the substance, uptake and distribution differences between single cells and whole animals, metabolism of the substance, and cascade effects where the effect of the substance is mediated through a cellular process. These same factors can affect the progress of pharmaceutical research and development as well when attempting to determining and/or predicting the effects of an analyte in an animal system.

Further, the end-point of traditional animal based toxicology studies is typically determination of an LD50 (the dose at which 50% of the test animals die). Dead animals may be subjected to further analysis, for example, histopathology, but such analysis is generally labor intensive and relatively insensitive. MacGregor, et al (*Fundamental and Applied Toxicology,* 26:156-173, 1995) have reviewed molecular end-points and methods of routine toxicity testing including the following: damage-inducible genes in individual cells; bacterial models of toxicity; screening of stress-gene expression using hybridization or polymerase chain reaction; hybridization probes for detection of chromosomal aberrations; single cell electrophoresis assays; and in vivo animal studies involving animal sacrifice and subsequent analysis of tissue/cellular damage.

P450 enzymes have been shown to be involved in the biosynthesis of steroids and cholesterols and in metabolizing drugs or xenobiotics. P450 enzyme induction is a result of fluctuations in levels of steroids and cholesterols, or of repeated exposure to drugs or xenobiotics. Changes in P450 enzyme levels result in changes in plasma and/or tissue levels of the drugs they metabolize, which in turn affects the stability, efficacy and toxicity of those drugs. Among P450 superfamilies, the Cyp3A family typically accounts for 14-31% of total P450 present in human liver microsomes and for 50-60% of the drug metabolic activity. (Toide et al. (1997) *Arch. Biochem. and Biophysics* 338:43-49). Clones encoding distinct Cyp3A forms have been isolated from human, rat, guinea pig and mice, including Cyp3A11 in mice and CYP3A4 in humans. Therefore, P450 enzyme expression, particularly the Cyp3A family of genes, is a vital pharmacological parameter of bioavailability of pharmaceutical agents, as well as of drug-to-drug interactions.

Currently, conventional assays for P450 gene regulation are laborious and time-consuming, for example Northern blots, Western blots, RT-PCR or reporter assays ex vivo. In addition, expression of P450 genes in cell line has proven difficult. Thus, there remains a need to directly monitor P450 gene regulation in real-time in live animals.

BRIEF DESCRIPTION OF THE DRAWINGS

FIG. 1A (SEQ ID NO:12) comprises the nucleotide sequence of a transcriptional control element from the mouse Cyp3A11 gene locus. In the figure, the sequence represents 12,275 nucleotides in total, the translational start codon (ATG) is located at positions 11,003-11,005, a TATA box is located at positions 10,884 to 10,887, a major transcription start site begins with the C at position 10,914. An approximately 9.3 kb region of the Cyp3A11 gene is from nucleotide position 1 to 9,330 of FIG. 1A and the approximately 9.3 kb sequence is presented alone in FIG. 1B (SEQ ID NO:13).

FIG. 16, panels A-D, depict the results of hPXR titration experiments performed in order to optimize the amount of hPXR plasmid co-administered with 5 μg of pGL3-I-3A4L. Panel A, 0 μg hPXR+5 μg 3A4L-luc. Panel B, 1 μg hPXR+5 μg 3A4L-luc. Panel C, 2 μg hPXR+5 μg 3A4L-luc. Panel D, 5 μg hPXR+5 μg 3A4L-luc.

FIG. 17A (SEQ ID NO:14) comprises the nucleotide sequence of a transcriptional control element from the human CYP3A4 gene locus. In the figure, the sequence represents 13,035 nucleotides in total, the translational start codon (ATG) is located at positions 13,033 to 13,035, a TATA box is located at positions 12,901 to 12,904, a major transcription start site begins with the A at position 12,930. An approximately 2.5 kb region of the CYP3A4 gene, useful to facilitate expression as described herein, is from nucleotide position 1 to 2,461 of FIG. 17A and the approximately 2.5 kb sequence is presented alone in FIG. 17B (SEQ ID NO:15). FIG. 17C (SEQ ID NO:17) presents the entire sequence of CYP3A4-luc transgene used to generate FVB/N-TgN(CYP3A4-luc) mice.

FIG. 22, panel A, B, C, and D, present exemplary results of the effects of xenobiotics on expression of CYP3A4-luc in the #82 line of Tg FvB mice.

SUMMARY OF THE INVENTION

Figure 2:
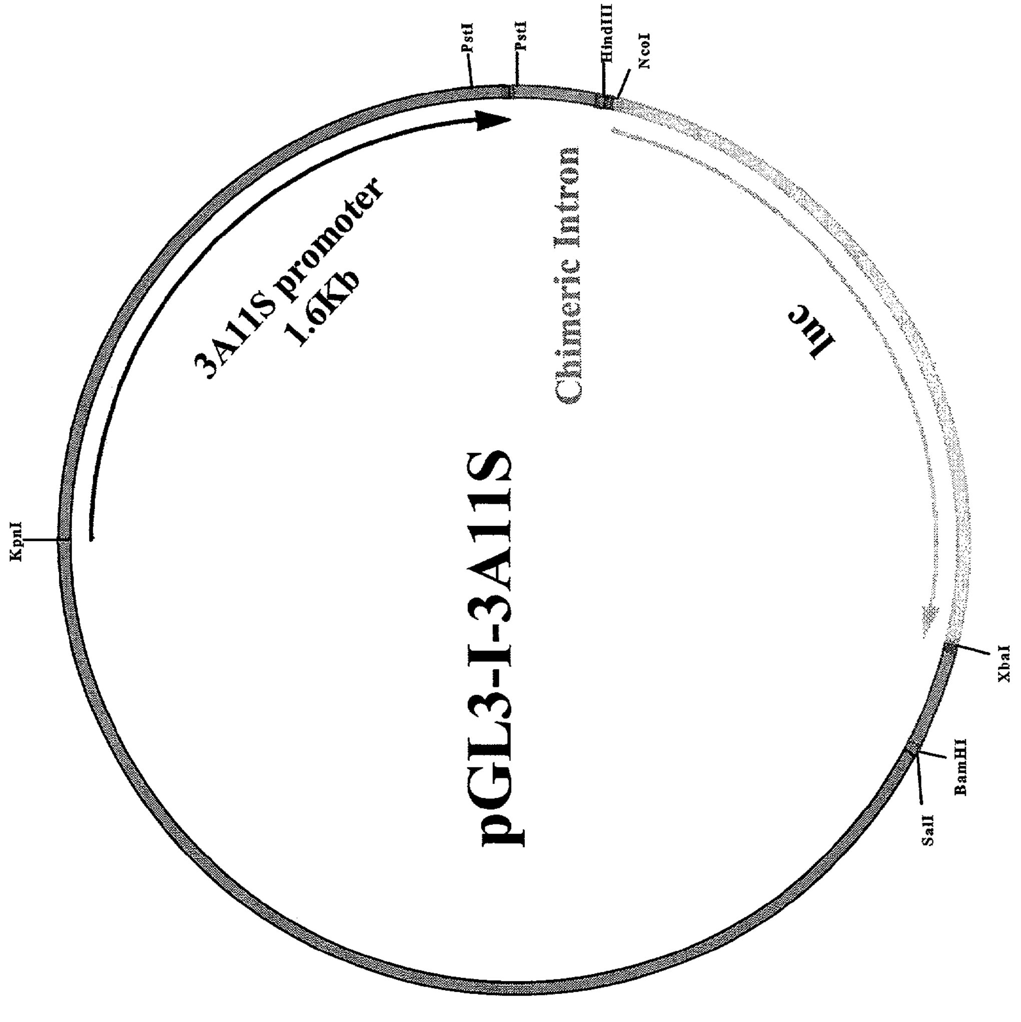
FIG. 2 is a schematic of the pGL3-I-3A11S vector construct containing the 1.6 kb Cyp3A11 promoter sequence.

The present invention relates to transcription control elements derived from mouse and human genes associated with cytochrome expression, e.g., Cyp3A11 and CYP3A4, respectively. The present invention comprises isolated polynucleotides, expression cassettes, vectors, recombinant cells, liver-push non-human animals and transgenic, non-human animals that comprise the transcription control elements described herein.

In one aspect, the present invention relates to transcription control elements derived from cytochrome P450 genes (e.g., Cyp3A11 and CYP3A4), expression cassettes which include those control elements, vector constructs, cells and transgenic animals containing the expression cassettes, and methods of using the cells and transgenic animals containing the expression cassettes, for example, as modeling, screening and/or test systems. Methods of using the control elements, expression cassettes, cells, and transgenic animals of the present invention include, but are not limited to, studies involving toxicity and drug metabolism, and methods for screening drug metabolism, safety and/or possible toxicity. Exemplary transcription control elements useful in the practice of the present invention include those derived from mouse Cyp3A11 locus and those derived from the human CYP3A4 locus.

In particular, the invention relates to transcription control elements derived from genomic locii of the murine Cyp3A11 gene and the human CYP3A4 gene, wherein these transcription control elements are associated with a reporter sequence. In particular, recombinant nucleic acid molecules comprising SEQ ID NO:12, SEQ ID NO:13, SEQ ID NO:14, and SEQ ID NO:15, as well as fragments thereof, are described. The invention further relates to in vivo assay methods which employ animals transfected with such reporter constructs.

In one aspect, the present invention comprises a polynucleotide, or fragments thereof typically greater than 100 contiguous nucleotides, derived from the mouse Cyp3A11 gene, the polynucleotide (or fragments thereof) having at least 95% identity to nucleotides 1-11,002 of SEQ ID NO:12 (or corresponding fragments thereof). The polynucleotide (or fragments thereof) may be operably linked to a coding sequence of interest. The polynucleotide (or fragments thereof) typically comprises at least one transcriptional control element. An expression cassette may comprise the polynucleotide and coding sequence of interest.

In another aspect, the present invention comprises a polynucleotide, or fragments thereof typically greater than 100 contiguous nucleotides, derived from the mouse Cyp3A11 gene, the polynucleotide (or fragments thereof) having at least 95% identity to the sequence of SEQ ID NO:13 (or fragments thereof at least about 100 contiguous nucleotides of SEQ ID NO:13). The polynucleotide (or framents thereof) may be operably linked to a coding sequence of interest. The polynucleotide (or fragments thereof) typically comprises at least one transcriptional control element. An expression cassette may comprise the polynucleotide and coding sequence of interest. In one embodiment, the polynucleotide comprises a first polynucleotide having 95% identity or greater to nucleotides 5104-6218 of SEQ ID NO:13 and a second polynucleotide having 95% identity or greater to nucleotides 6792-9330 of SEQ ID NO:13.

In one aspect, the present invention includes isolated polynucleotides and/or expression cassettes comprising a polynucleotide having at least about 95% identity to the sequence of SEQ ID NO:13, or fragments thereof, operably linked to a coding sequence of interest, wherein the polynucleotide or fragments thereof comprise at least one transcriptional control element.

In another aspect, the present invention includes isolated polynucleotides and/or expression cassettes comprising a polynucleotide having at least about 95% identity to the sequence of SEQ ID NO:15, or fragments thereof, operably linked to a coding sequence of interest, wherein the polynucleotide or fragments thereof comprise at least one transcriptional control element.

In some embodiments the coding sequence of interest is a reporter sequence, for example, a light-generating protein. Such light-generating proteins comprise bioluminescent proteins (including but not limited to, procaryotic or eucaryotic luciferase) and fluorescent proteins (including but not limited to, blue fluorescent protein, cyan fluorescent protein, green fluorescent protein, yellow fluorescent protein, and red fluorescent protein, as well as, enhanced and/or destabilized variants thereof).

The present invention also includes vectors comprising the isolated polynucleotides and/or expression cassettes of the present invention. Such vectors typically include a vector backbone, and may be linear or circular, comprise one or more origins of replication (e.g., a shuttle vector), be site-specifically or randomly integrating, and comprise one or more selectable or screenable markers.

In one embodiment the present invention includes cells comprising the expression cassettes and/or vectors of the present invention. In another embodiment, transgenic non-human, animals (e.g., rodents, including, but not limited to, mice, rats, hamsters, gerbils, and guinea pigs) may comprise the expression cassettes and/or vectors or the present invention. In a further embodiment, the present invention includes non-human animals that comprise a subset of cells comprising the expression cassettes and/or vectors of the present invention, for example, non-human animals whose livers comprise cells transfected with the constructs of the present invention. Such non-human animals may be generated, for example, by administration of the expression cassettes and/or vectors of the present invention via intravenous injection.

In yet another aspect, the present invention includes methods of using the expression cassettes, vectors, cells, and non-human animals of the present invention. In one embodiment, the invention includes a method for identifying an analyte that modulates expression (for example, of a reporter sequence) mediated by mouse Cyp3A11 gene-derived transcription control elements and/or a human CYP3A4 gene-derived transcription control elements in a transgenic, living, non-human animal. Such a method typically comprises administering to the animal an analyte (e.g., a drug). The animal comprises one or more of the expression cassettes or vectors of the present invention typically including a reporter sequence. Expression of the reporter sequence is monitored. An effect on the level of expression of the reporter sequence indicates that the analyte affects expression of the gene corresponding to the transcriptional control elements which comprise the expression cassettes and/or vectors employed in the method.

Another method comprises identifying an analyte that modulates expression (for example, of a reporter sequence) mediated by mouse Cyp3A11 gene-derived transcription control elements and/or a human CYP3A4 gene-derived transcription control elements in a transgenic, living, non-human animal. In this method a vector mixture, comprising an expression cassette of the present invention, is administered to the animal concomitant with, before, or after administration of an analyte. The vector mixture comprises one or more of the expression cassettes of the present invention typically including a reporter sequence. Expression of the reporter sequence is monitored. An effect on the expression of the reporter sequence indicates that the analyte affects expression mediated by the transcriptional control elements that comprise the expression cassettes and/or vectors employed in the method. In one embodiment the vector mixture is administered by intravenous injection.

In a further embodiment of the present invention, the expression cassettes comprising the transcription control elements of the present invention and a reporter, are used to monitor the expression of the mouse Cyp3A11 gene or the human CYP3A4 gene in a cell. In this embodiment expression of a reporter sequence is monitored in the cell and expression of the reporter sequence corresponds to expression of gene corresponding to the transcriptional control elements which comprise the expression cassettes and/or vectors employed in the method. Further, analytes may be screened such cells wherein an effect on the expression of the reporter sequence indicates that the analyte affects expression mediated by the transcriptional control elements that comprise the expression cassettes and/or vectors employed in the method.

In another aspect, the present invention comprises, a transgenic, non-human animal, e.g., rodent. The transgenic, non-human animal typically comprises, an expression cassette comprising a polynucleotide derived from the human CYP3A4 gene, the polynucleotide having at least 95% or greater identity to nucleotides 1-13,032 of SEQ ID NO:14 (or fragments thereof), wherein (i) the polynucleotide (or fragments thereof) is operably linked to a coding sequence of interest, (ii) the polynucleotide (or fragments thereof) comprises at least one transcriptional control element, and (iii) expression of the coding sequence of interest is induced in the liver of the living, transgenic, non-human animal by dexamethasone or rifampicin.

In one embodiment, expression of the coding sequence of interest is induced in the living, transgenic animal by dexamethasone administered at 50 mg/kg body weight, and/or expression of the coding sequence of interest is induced in the living, transgenic animal by rifampicin administered at 50 mg/kg body weight. Further, induction of expression of the coding sequence of interest may be greater than or equal to 10-fold induction by dexamethasone over basal levels, and/or, induction of expression of the coding sequence of interest is greater than or equal to two-fold induction by rifampicin over basal levels.

In one embodiment, basal expression of the coding sequence in the liver region of the living, transgenic, non-human animal is greater than or equal to that in other regions of the body of the living, transgenic non-human animal.

In another embodiment, the transgenic, non-human animal does not have sequences encoding a functional hPXR (a human rifampicin co-receptor). That is, the animal does not express a function human PXR gene product.

In a further embodiment, expression of the coding sequence of interest is induced in the living, transgenic, non-human animal by at least one compound selected from the group consisting of phenobarbitol, nifedipine, 5-pregnene-3b-OL-20-ONE-16a-Carbonitrile and clotrimazole, wherein induction of expression is seen in the liver region of the living, transgenic animal.

In the transgenic, non-human animal the coding sequence of interest may, for example, be a reporter sequence. Such a reporter sequence may, for example, encode a light-generating protein (e.g., a bioluminescent protein or a fluorescent protein). One exemplary bioluminescent protein is luciferase. In one embodiment of the invention, the transgenic, non-human animal may include an expression cassette comprising SEQ ID NO:17 (an exemplary CYP3A4/luc transgene). Exemplary fluorescent proteins include, but are not limited to, blue fluorescent protein, cyan fluorescent protein, green fluorescent protein, yellow fluorescent protein, and red fluorescent protein.

The transgenic, non-human animal may be a rodent, including, but not limited to, mouse, rat, hamster, gerbil, or guinea pig.

The present invention also includes a method for identifying an analyte that modulates expression of a reporter sequence, wherein expression of the reporter sequence is mediated by transcription control elements derived from, for example, a human CYP3A4 gene, in a transgenic, living rodent. In the method the analyte is administered to the transgenic, living, non-human transgenic animal described above. Expression of the reporter sequence is monitored. An effect on the level of expression of the reporter sequence indicates that the analyte affects mediated by transcription control elements, e.g., derived from the human CYP3A4 gene.

These and other embodiments of the present invention will readily occur to those of ordinary skill in the art in view of the disclosure herein.

DETAILED DESCRIPTION OF THE INVENTION

The practice of the present invention will employ, unless otherwise indicated, conventional techniques of molecular biology, microbiology, cell biology, transgenic animal manipulation, and recombinant DNA, which are within the skill of the art. See, e.g., Sambrook, Fritsch, and Maniatis, MOLECULAR CLONING: A LABORATORY MANUAL, 2nd edition (1989); CURRENT PROTOCOLS IN MOLECULAR BIOLOGY, (F. M. Ausubel et al. eds., 1987); the series METHODS IN ENZYMOLOGY (Academic Press, Inc.); PCR 2: A PRACTICAL APPROACH (M. J. McPherson, B. D. Hames and G. R. Taylor eds., 1995); ANIMAL CELL CULTURE (R. I. Freshney. Ed., 1987); "Transgenic Animal Technology: A Laboratory Handbook," by Carl A. Pinkert, (Editor) First Edition, Academic Press; ISBN: 0125571658; and "Manipulating the Mouse Embryo: A Laboratory Manual," Brigid Hogan, et al., ISBN: 0879693843, Publisher: Cold Spring Harbor Laboratory Press, Pub. Date: September 1999, Second Edition.

All publications, patents and patent applications cited herein, whether supra or infra, are hereby incorporated by reference in their entirety.

1. Definitions

In describing the present invention, the following terms will be employed, and are intended to be defined as indicated below. Unless otherwise indicated, all terms used herein have the same meaning as they would to one skilled in the art of the present invention.

The terms "nucleic acid molecule" and "polynucleotide" are used interchangeably to and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term polynucleotide sequence is the alphabetical representation of a polynucleotide molecule. This alphabetical representation can be input into databases in a computer having a central processing unit and used for bioinformatics applications such as functional genomics and homology searching.

A "coding sequence" or a sequence which "encodes" a selected polypeptide, is a nucleic acid molecule which is transcribed (in the case of DNA) and translated (in the case of mRNA) into a polypeptide, for example, in vivo when placed under the control of appropriate regulatory sequences (or "control elements"). The boundaries of the coding sequence are typically determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral or procaryotic DNA, and even synthetic DNA sequences. A transcription termination sequence may be located 3' to the coding sequence. Other "control elements" may also be associated with a coding sequence. A DNA sequence encoding a polypeptide can be optimized for expression in a selected cell by using the codons preferred by the selected cell to represent the DNA copy of the desired polypeptide coding sequence. "Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence. Also encompassed are polypeptide sequences, which are immunologically identifiable with a polypeptide encoded by the sequence.

A "transcription factor" typically refers to a protein (or polypeptide) which affects the transcription, and accordingly the expression, of a specified gene. A transcription factor may refer to a single polypeptide transcription factor, one or more polypeptides acting sequentially or in concert, or a complex of polypeptides.

Typical "control elements" include, but are not limited to, transcription promoters, transcription enhancer elements, cis-acting transcription regulating elements (transcription regulators, e.g., a cis-acting element that affects the transcription of a gene, for example, a region of a promoter with which a transcription factor interacts to induce or repress expression of a gene), transcription initiation signals (e.g., TATA box), basal promoters, transcription termination signals, as well as polyadenylation sequences (located 3' to the translation stop codon), sequences for optimization of initiation of translation (located 5' to the coding sequence), translation enhancing sequences, and translation termination sequences. Transcription promoters can include, for example, inducible promoters (where expression of a polynucleotide sequence operably linked to the promoter is induced by an analyte, cofactor, regulatory protein, etc.), repressible promoters (where expression of a polynucleotide sequence operably linked to the promoter is induced by an analyte, cofactor, regulatory protein, etc.), and constitutive promoters.

"Expression enhancing sequences," also referred to as "enhancer sequences" or "enhancers," typically refer to control elements that improve transcription or translation of a polynucleotide relative to the expression level in the absence of such control elements (for example, promoters, promoter enhancers, enhancer elements, and translational enhancers (e.g., Shine and Delagarno sequences)).

The term "modulation" refers to both inhibition, including partial inhibition, as well as stimulation. Thus, for example, a compound that modulates expression of a reporter sequence may either inhibit that expression, either partially or completely, or stimulate expression of the sequence.

"Purified polynucleotide" refers to a polynucleotide of interest or fragment thereof which is essentially free, e.g., contains less than about 50%, preferably less than about 70%, and more preferably less than about 90%, of the protein with which the polynucleotide is naturally associated. Techniques for purifying polynucleotides of interest are well known in the art and include, for example, disruption of the cell containing the polynucleotide with a chaotropic agent and separation of the polynucleotide(s) and proteins by ion-exchange chromatography, affinity chromatography and sedimentation according to density.

A "heterologous sequence" typically refers to either (i) a nucleic acid sequence that is not normally found in the cell or organism of interest, or (ii) a nucleic acid sequence introduced at a genomic site wherein the nucleic acid sequence does not normally occur in nature at that site. For example, a DNA sequence encoding a polypeptide can be obtained from yeast and introduced into a bacterial cell. In this case the yeast DNA sequence is "heterologous" to the native DNA of the bacterial cell. Alternatively, a promoter sequence from a Tie2 gene can be introduced into the genomic location of a fosB gene. In this case the Tie2 promoter sequence is "heterologous" to the native fosB genomic sequence.

A "polypeptide" is used in it broadest sense to refer to a compound of two or more subunit amino acids, amino acid analogs, or other peptidomimetics. The subunits may be linked by peptide bonds or by other bonds, for example ester, ether, etc. The term "amino acid" typically refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is typically called a polypeptide or a protein.

"Operably linked" refers to an arrangement of elements wherein the components so described are configured so as to perform their usual function. Thus, a given promoter that is operably linked to a coding sequence (e.g., a reporter expression cassette) is capable of effecting the expression of the coding sequence when the proper enzymes are present. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

"Recombinant" describes a nucleic acid molecule means a polynucleotide of genomic, cDNA, semisynthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide. "Recombinant host cells," "host cells," "cells," "cell lines," "cell cultures," and other such terms denoting, e.g., procaryotic microorganisms or eucaryotic cell lines cultured as unicellular entities, are used interchangeably, and refer to cells which can be, or have been, used as recipients for recombinant vectors or other transfer DNA, and include the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

An "isolated polynucleotide" molecule is a nucleic acid molecule separate and discrete from the whole organism with which the molecule is found in nature; or a nucleic acid molecule devoid, in whole or part, of sequences normally associated with it in nature; or a sequence, as it exists in nature, but having heterologous sequences (as defined below) in association therewith.

Techniques for determining nucleic acid and amino acid "sequence identity" also are known in the art. Typically, such techniques include determining the nucleotide sequence of the mRNA for a gene and/or determining the amino acid sequence encoded thereby, and comparing these sequences to a second nucleotide or amino acid sequence. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by HIGH SCORE; Databases:=non-redundant, GenBank+EMBL+DDBJ+PDB+GenBank CDS translations+Swiss protein+Spupdate+PIR. Details of these programs can be found on the internet.

One of skill in the art can readily determine the proper search parameters to use for a given sequence in the above programs. For example, the search parameters may vary based on the size of the sequence in question. Thus, for example, a representative embodiment of the present invention would include an isolated polynucleotide comprising X contiguous nucleotides, wherein (i) the X contiguous nucleotides have at least about 50% identity to Y contiguous nucleotides derived from any of the sequences described herein, (ii) X equals Y, and (iii) X is equal to from 6 up to the number of nucleotides present in a selected full-length sequence as described herein (e.g., see the Examples, Figures, Sequence Listing and claims), including all integer values falling within the above-described ranges. A "fragment" of a polynucleotide refers to any length polynucleotide molecule derived from a larger polynucleotide described herein (i.e., Y contiguous nucleotides, where X=Y as just described). Exemplary fragment lengths include, but are not limited to, at least about 6 contiguous nucleotides, at least about 50 contiguous nucleotides, about 100 contiguous nucleotides, about 200 contiguous nucleotides, about 250 contiguous nucleotides, about 500 contiguous nucleotides, or at least about 1000 contiguous nucleotides or more, wherein such contiguous nucleotides are derived from a larger sequence of contiguous nucleotides.

The purified polynucleotides and polynucleotides used in construction of expression cassettes of the present invention include the sequences disclosed herein as well as related polynucleotide sequences having sequence identity of approximately 80% to 100% and integer values therebetween. Typically the percent identities between the sequences disclosed herein and the claimed sequences are at least about 80-85%, preferably at least about 90-92%, more preferably at least about 95%, and most preferably at least about 98% sequence identity (including all integer values falling within these described ranges). These percent identities are, for example, relative to the claimed sequences, or other sequences of the present invention, when the sequences of the present invention are used as the query sequence.

Alternatively, the degree of sequence similarity between polynucleotides can be determined by hybridization of polynucleotides under conditions that form stable duplexes between homologous regions, followed by digestion with single-stranded-specific nuclease(s), and size determination of the digested fragments. Two DNA, or two polypeptide sequences are "substantially homologous" to each other when the sequences exhibit at least about 80-85%, preferably 85-90%, more preferably 90-95%, and most preferably 98-100% sequence identity to the reference sequence over a defined length of the molecules, as determined using the methods above. Substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

Two nucleic acid fragments are considered to "selectively hybridize" as described herein. The degree of sequence identity between two nucleic acid molecules affects the efficiency and strength of hybridization events between such molecules. A partially identical nucleic acid sequence will at least partially inhibit a completely identical sequence from hybridizing to a target molecule. Inhibition of hybridization of the completely identical sequence can be assessed using hybridization assays that are well known in the art (e.g., Southern blot, Northern blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a target nucleic acid sequence, and then by selection of appropriate conditions the probe and the target sequence "selectively hybridize," or bind, to each other to form a hybrid molecule. A nucleic acid molecule that is capable of hybridizing selectively to a target sequence under "moderately stringent" typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/target hybridization where the probe and target have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.).

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

"Nucleic acid expression vector" or "expression cassette" refers to an assembly that is capable of directing the expression of a sequence or gene of interest. The nucleic acid expression vector includes a promoter that is operably linked to the sequences or gene(s) of interest. Other control elements may be present as well. Expression cassettes described herein may be contained within a plasmid construct. In addition to the components of the expression cassette, the plasmid construct may also include a bacterial origin of replication, one or more selectable markers, a signal which allows the plasmid construct to exist as single-stranded DNA (e.g., a M13 origin of replication), a multiple cloning site, and a "mammalian" origin of replication (e.g., a SV40 or adenovirus origin of replication).

An "expression cassette" comprises any nucleic acid construct capable of directing the expression of a gene/coding sequence of interest. Such cassettes can be constructed into a "vector," "vector construct," "expression vector," or "gene transfer vector," in order to transfer the expression cassette into target cells. Thus, the term includes cloning and expression vehicles, as well as viral vectors.

A variety of "reporter genes" also referred to as "reporter sequences" and "marker sequences," i.e., genes or sequences the expression of which indicates the expression of polynucleotide sequences of interest to which the reporter gene or sequence is operably linked. Preferred are those reporter sequences that produce a protein product that is easily measured, preferably in a routine assay. Suitable reporter genes include, but are not limited to chloramphenicol acetyl transferase (CAT), light generating proteins (e.g., luc-encoded, lux-encoded, fluorescent proteins), and beta-galactosidase. Convenient assays include, but are not limited to calorimetric, fluorimetric and enzymatic assays. In one aspect, reporter genes may be employed that are expressed within the cell and whose extracellular products are directly measured in the intracellular medium, or in an extract of the intracellular medium of a cultured cell line. This provides advantages over using a reporter gene whose product is secreted, since the rate and efficiency of the secretion introduces additional variables that may complicate interpretation of the assay. In a preferred embodiment, the reporter gene is a light generating protein. When using the light generating reporter proteins described herein, expression can be evaluated accurately and non-invasively as described above (see, for example, Contag, P. R., et al., (1998) Nature Med. 4:245-7; Contag, C. H., et al., (1997) Photochem Photobiol. 66:523-31; Contag, C. H., et al., (1995) Mol Microbiol. 18:593-603).

A "light generating protein" or "light-emitting protein" is a bioluminescent or fluorescent protein capable of producing light typically in the range of 200 nm to 1100 nm, preferably in the visible spectrum (i.e., between approximately 350 nm and 800 nm). Bioluminescent proteins produce light through a chemical reaction (typically requiring a substrate, energy source, and oxygen). Fluorescent proteins produce light through the absorption and re-emission of radiation (such as with green fluorescent protein). Examples of bioluminescent proteins include, but are not limited to, the following: "luciferase," unless stated otherwise, includes procaryotic (e.g., bacterial lux-encoded) and eucaryotic (e.g., firefly luc-encoded) luciferases, as well as variants possessing varied or altered optical properties, such as luciferases that produce different colors of light (e.g., Kajiyama, N., and Nakano, E., *Protein Engineering* 4(6):691-693 (1991)); and "photoproteins," for example, calcium activated photoproteins (e.g., Lewis, J. C., et al., Fresenius *J. Anal. Chem.* 366(6-7):760-768 (2000)). Examples of fluorescent proteins include, but are not limited to, green, yellow, cyan, blue, and red fluorescent proteins (e.g., Hadjantonakis, A. K., et al., *Histochem. Cell Biol.* 115(1):49-58 (2001)).

"Bioluminescent protein substrate" describes a substrate of a light-generating protein, e.g., luciferase enzyme, that generates an energetically decayed substrate (e.g., luciferin) and a photon of light typically with the addition of an energy source, such as ATP or FMNH2, and oxygen. Examples of such substrates include, but are not limited to, decanal in the bacterial lux system, 4,5-dihydro-2-(6-hydroxy-2-benzothiazolyl)-4-thiazolecarboxylic acid (or simply called luciferin) in the Firefly luciferase (luc) system, "panal" in the bioluminescent fungus Panellus stipticus system (Tetrahedron 44:1597-1602, 1988) and N-iso-valeryl-3-aminopropanol in the earth worm Diplocardia longa system (Biochem. 15:1001-1004, 1976). In some systems, as described herein, aldehyde can be used as a substrate for the light-generating protein.

"Light" is defined herein, unless stated otherwise, as electromagnetic radiation having a wavelength of between about 200 nm (e.g., for UV-C) and about 1100 nm (e.g., infrared). The wavelength of visible light ranges between approximately 350 nm to approximately 800 nm (i.e., between about 3,500 angstroms and about 8,000 angstroms).

"Animal" typically refers to a non-human animal, including, without limitation, farm animals such as cattle, sheep, pigs, goats and horses; domestic mammals such as dogs and cats; laboratory animals including ferrets, hares and rabbits, rodents, such as mice, rats, hamsters, gerbils, and guinea pigs; non-human primates, including chimpanzees. The term "animal" may also include, without limitation; birds, including domestic, wild and game birds such as chickens, turkeys and other gallinaceous birds, ducks, geese, and the like, as well as amphibians, fish, insects, reptiles, etc. The term does not denote a particular age. Thus, adult, embryonic, fetal, and newborn individuals are intended to be covered.

A "transgenic animal" refers to a genetically engineered animal or offspring of genetically engineered animals. A transgenic animal usually contains material from at least one unrelated organism, such as from a virus, microorganism, plant, or other animal. The term "chimeric animal" is used to refer to animals in which the heterologous gene is found, or in which the heterologous gene is expressed in some but not all cells of the animal.

"Analyte" refers to any compound or substance whose effects (e.g., induction or repression of a specific promoter) can be evaluated using the test animals and methods of the present invention. Such analytes include, but are not limited to, chemical compounds, pharmaceutical compounds, polypeptides, peptides, polynucleotides, and polynucleotide analogs. Many organizations (e.g., the National Institutes of Health, pharmaceutical and chemical corporations) have large libraries of chemical or biological compounds from natural or synthetic processes, or fermentation broths or extracts. Such compounds/analytes can be employed in the practice of the present invention.

The term "positive selection marker" refers to a gene encoding a product that enables only the cells that carry the gene to survive and/or grow under certain conditions. For example, plant and animal cells that express the introduced neomycin resistance ($Neo^r$) gene are resistant to the compound G418. Cells that do not carry the $Neo^r$ gene marker are killed by G418. Other positive selection markers will be known to those of skill in the art. Typically, positive selection markers encode products that can be readily assayed. Thus, positive selection markers can be used to determine whether a particular DNA construct has been introduced into a cell, organ or tissue.

"Negative selection marker" refers to gene encoding a product that can be used to selectively kill and/or inhibit growth of cells under certain conditions. Non-limiting examples of negative selection inserts include a herpes simplex virus (HSV)-thymidine kinase (TK) gene. Cells containing an active HSV-TK gene are incapable of growing in the presence of gangcylovir or similar agents. Thus, depending on the substrate, some gene products can act as either positive or negative selection markers.

The term "homologous recombination" refers to the exchange of DNA fragments between two DNA molecules or chromatids at the site of essentially identical nucleotide sequences. It is understood that substantially homologous sequences can accommodate insertions, deletions, and substitutions in the nucleotide sequence. Thus, linear sequences of nucleotides can be essentially identical even if some of the nucleotide residues do not precisely correspond or align (see, above).

A "knock-out" mutation refers to partial or complete loss of expression of at least a portion the target gene. Examples of knock-out mutations include, but are not limited to, gene-replacement by heterologous sequences, gene disruption by heterologous sequences, and deletion of essential elements of the gene (e.g., promoter region, portions of a coding sequence). A "knock-out" mutation is typically identified by the phenotype generated by the mutation.

A "gene" as used in the context of the present invention is a sequence of nucleotides in a genetic nucleic acid (chromosome, plasmid, etc.) with which a genetic function is associated. A gene is a hereditary unit, for example of an organism, comprising a polynucleotide sequence (e.g., a DNA sequence for mammals) that occupies a specific physical location (a "locus", "gene locus" or "genetic locus") within the genome of an organism. A gene can encode an expressed product, such as a polypeptide or a polynucleotide (e.g., tRNA). Alternatively, a gene may define a genomic location for a particular event/function, such as the binding of proteins and/or nucleic acids (e.g., phage attachment sites), wherein the gene does not encode an expressed product. Typically, a gene includes coding sequences, such as, polypeptide encoding sequences, and non-coding sequences, such as, transcription control elements (e.g., promoter sequences), poly-adenlyation sequences, transcriptional regulatory sequences (e.g., enhancer sequences). Many eucaryotic genes have "exons" (coding sequences) interrupted by "introns" (non-coding sequences). In certain cases, a gene may share sequences with another gene(s) (e.g., overlapping genes).

The "native sequence" or "wild-type sequence" of a gene is the polynucleotide sequence that comprises the genetic locus corresponding to the gene, e.g., all regulatory and open-reading frame coding sequences required for expression of a completely functional gene product as they are present in the wild-type genome of an organism. The native sequence of a gene can include, for example, transcriptional promoter sequences, translation enhancing sequences, introns, exons, and poly-A processing signal sites. It is noted that in the general population, wild-type genes may include multiple prevalent versions that contain alterations in sequence relative to each other and yet do not cause a discernible pathological effect. These variations are designated "polymorphisms" or "allelic variations."

By "replacement sequence" is meant a polynucleotide sequence that is substituted for at least a portion of the native or wild-type sequence of a gene.

"Linear vector" or "linearized vector," is a vector having two ends. For example, circular vectors, such as plasmids, can be linearized by digestion with a restriction endonuclease that cuts at a single site in the plasmid. Preferably, the expression vectors described herein are linearized such that the ends are not within the sequences of interest.

Before describing the present invention in detail, it is to be understood that this invention is not limited to particular formulations or method parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

2. Modes of Carrying Out the Invention

Throughout this application, various publications, patents, and published patent applications are referred to by an identifying citation. The disclosures of these publications, patents, and published patent specifications referenced in this application are hereby incorporated by reference into the present disclosure to more fully describe the state of the art to which this invention pertains.

As used in this specification and the appended claims, the singular forms "a," "an" and "the" include plural references unless the content clearly dictates otherwise. Thus, for example, reference to "an expression construct" includes a mixture of two or more such agents.

2.1.0 General Overview

In one aspect, the present invention relates to transcription control elements derived from cytochrome P450 genes (e.g., Cyp3A11 and CYP3A4), expression cassettes which include those control elements, vector constructs, cells and transgenic animals containing the expression cassettes, and methods of using the cells and transgenic animals containing the expression cassettes, for example, as modeling, screening and/or test systems. Methods of using the control elements, expression cassettes, cells, and transgenic animals of the present invention include, but are not limited to, studies involving toxicity and drug metabolism, and methods for screening drug metabolism, safety and/or possible toxicity. Exemplary transcription control elements useful in the practice of the present invention include those derived from mouse Cyp3A11 locus and those derived from the human CYP3A4 locus. Experiments performed in support of the present invention demonstrate that the effects of a compound on modulation of expression mediated by Cyp3A11 or CYP3A4 transcriptional control elements can be directly monitored in live animals to provide information about the effects of the compound, e.g., toxicity.

In one embodiment, the present invention relates to (1) transcription control elements (e.g., promoters) derived from the mouse Cyp3A11 gene locus or from the human CYP3A4 gene locus; (2) expression cassettes comprising such transcription control elements operatively linked to genes encoding a gene product, such as, a reporter, a protein, polypeptide, hormone, ribozyme, or antisense RNA, (3) recombinant cells comprising such expression cassettes, (4) methods of screening for safety and/or possible toxicity using such cells (e.g., screening for toxicity or safety of compounds which modulated expression mediated by the transcription control elements of the present invention), (5) animals (e.g., transgenic or "liver push") comprising the aforementioned transcription control elements, expression cassettes, and/or vector constructs, (6) methods of monitoring safety and/or toxicity using such animals, and (7) methods of screening for safety and/or toxicity of compounds using such animals.

A variety of transcription control elements are useful in the practice of the present invention, for example, transcription control elements derived from genes or gene loci associated with drug metabolism. Specific locations of selected transcriptional control elements within a defined polynucleotide sequence can be identified by methods known to those of skill in the art, e.g., sequence comparison, deletion analysis, and/or linker-insertion mutagenesis, in view of the teachings of the present specification. An exemplary transcription control element can be one that is associated with oxidative metabolism of drug, for instance the P450 superfamily of hemoproteins that metabolize a wide variety of endogenous and xenobiotics. Particular embodiments of such transcription control elements include those associated with the mouse Cyp3A11 gene and the human CYP3A4 gene. In this way, expression of the reporter sequence is induced in the transgenic animals of the present invention when, for example, after administration of a candidate drug, and safety and/or toxicity of the drug can be evaluated by non-invasive imaging methods using the whole animal. Various forms of the different embodiments of the invention, described herein, may be combined.

Non-invasive imaging and/or detecting of light-emitting conjugates in mammalian subjects was described in U.S. Pat. Nos. 5,650,135, and 6,217,847, by Contag, et al., issued Jul. 22, 1997, and Apr. 17, 2001, respectively, and herein incorporated by reference in their entireties. This imaging technology can be used in the practice of the present invention in view of the teachings of the present specification. In the imaging method, the conjugates contain a biocompatible entity and a light-generating moiety. Biocompatible entities include, but are not limited to, small molecules such as cyclic organic molecules; macromolecules such as proteins; microorganisms such as viruses, bacteria, yeast and fungi; eucaryotic cells; all types of pathogens and pathogenic substances; and particles such as beads and liposomes. In another aspect, biocompatible entities may be all or some of the cells that constitute the mammalian subject being imaged, for example, cells carrying the expression cassettes of the present invention expressing a reporter sequence.

Light-emitting capability is conferred on the biocompatible entities by the conjugation of a light-generating moiety. Such moieties include fluorescent molecules, fluorescent proteins, enzymatic reactions which give off photons, and luminescent substances, such as bioluminescent proteins. In the context of the present invention, light emitting capability is typically conferred on target cells by having at least one copy of a light-generating protein, e.g., a luciferase, present. In preferred embodiments, luciferase is operably linked to appropriate control elements that can facilitate expression of a polypeptide having luciferase activity. Substrates of luciferase can be endogenous to the cell or applied to the cell or system (e.g., injection into a transgenic mouse, having cells carrying a luciferase construct, of a suitable substrate for the luciferase, for example, luciferin). The conjugation may involve a chemical coupling step, genetic engineering of a fusion protein, or the transformation of a cell, microorganism or animal to express a light-generating protein.

Thus, in one aspect, the present invention relates to animal test systems and methods for toxicology studies of an analyte of interest. In the practice of the present invention, transgenic mammals or liver pushed animals are constructed where control elements, for example, a promoter or transcriptional regulatory sequence, of two or more stress-induced genes are operably linked to reporter gene coding sequences (for example, luciferase). An appropriate substrate for the reporter gene product is administered to the animal in addition to an analyte of interest. The order of administration of these two substances can be empirically determined for each analyte of interest. Induction of expression mediated by any of the control elements is then evaluated by non-invasive imaging methods using the whole animal.

Thus, in one aspect of the present invention, animals described herein can be used to evaluate the in vivo effects of high production volume (HPV) chemicals, for example, by examining the effects of HPVs on expression of toxicity related genes such as P450. To date there are approximately 3,000 HPV chemicals within the set of non-polymeric chemicals (polymeric chemicals tend to be poorly absorbed by organisms and thus generally have low toxicity). Before the present invention there has been no routine, effective way to evaluate toxicity of these chemicals in vivo, which takes into account toxicity of not only the chemical itself, but of metabolites thereof (e.g., breakdown products).

Chemical producers and importers have been invited by the United States Environmental Protection Agency (EPA) to provide basic toxicity information on their high production volume (HPV) chemicals. HPV chemicals are chemicals produced in or imported to the United States in amounts over 1 million pounds per year. Each chemical companies participating in the voluntary program will make a commitment to identify chemicals that the company will adopt for testing. Following the guidelines established by EPA, participating companies will perform the following tasks: assessment of the adequacy of existing data; design and submission of test plans; provide test results as generated; and prepare summaries of the data characterizing each chemical. Currently, the voluntary program uses the same tests, testing protocols, and basic information summary formats employed by the Screening Information Data Set (SIDS) program. SIDS is a cooperative, international effort to secure basic toxicity information on HPV chemicals worldwide. Accordingly, information prepared for the U.S. domestic program will be acceptable in the international effort.

Of the approximately 3,000 chemicals that the U.S. imports or produces at more than 1 million lbs./yr., a recent EPA analysis finds that 43% of these high production volume chemicals have no testing data on basic toxicity and only seven percent have a full set of basic test data. This lack of test data compromises the public's right to know about the chemicals that are found in the environment, homes, workplaces, and products.

There are six basic tests which have been internationally agreed to for screening high production volume (HPV) chemicals for toxicity. The tests agreed to under the Organization for Economic Cooperation and Development's Screening Information Data Set (OECD/SIDS) program include the following: acute toxicity; chronic toxicity; developmental/reproductive toxicity; mutagenicity; ecotoxicity and environmental fate. Several of these tests rely on animal models where the animal must be sacrificed to obtain toxicity data. The transgenic animals described herein are useful for toxicity testing and avoid the need for a "death as the end-point" model. Accordingly, use of the transgenic animals of the present invention to evaluate toxicity will provide for a more humane means of toxicity testing. Further, because "death as the end-point" is not always necessary using transgenic animals carrying the reporter expression cassettes of the present invention, costs associated with toxicity testing in live animals can likely be reduced.

The EPA's Chemical Hazard Data Availability Study found major gaps in the basic information that is readily available to the public. Most consumers assume that basic toxicity testing is available and that all chemicals in commerce today are safe. A recent EPA study has found that this is not a prudent assumption. The EPA has reviewed the publicly available data on these chemicals and has learned that most of them may have never been tested to determine how toxic they are to humans or the environment. The EPA cannot begin to judge the hazards and risks of HPV consumer chemicals without basic information, and, in fact, substantially more detailed and exhaustive testing is needed to assess these high exposure chemicals. It is clear that companies need to do more to address this problem.

SIDS tests do not fully measure a chemical's toxicity. The tests only provide a minimum set of information that can be used to determine the relative hazards of chemicals and to judge if additional testing is necessary. However, the transgenic animals of the present invention provide models for in vivo toxicity testing that can greatly expand the information available about the hazards of these chemicals and their metabolites.

OSHA sets Permissible Exposure Limits (PELs) for hazardous chemicals in the workplace. It seems reasonable to expect that chemicals with PELs have been thoroughly tested at least for human health effects. However, even the high volume chemicals with PELs have significant data gaps from the human health portion of the basic screening test set. Only 53% of these high volume chemicals with PELs have basic screening tests for all four of the human health endpoints. In contrast, only 5% of the non-PEL HPV chemicals had all four health effects tests and 49% had no health test data available. Thus, the bulk of HPV chemicals without PELs lack even the minimal data needed to support development of a PEL value to protect workers. The transgenic animals of the present invention provide means for testing toxicity that provide specific, in vivo data concerning toxicity not only of the chemicals themselves, but of metabolites of these chemicals as well.

Finally, chemicals contained in consumer products are a major concern due to the likelihood of their exposure to children, as well as other sensitive populations (e.g., pregnant women and health-compromised individuals). Although the chemical industry has completed basic testing for more of these chemicals than is the case for other HPV chemicals, a more complete evaluation of in vivo toxicity using the transgenic animals of the present invention would be desirable. Given the great exposure potential of consumer products, significantly greater amounts of testing are needed to assess the risks of such chemicals. The transgenic animals described herein help to meet this need.

In a related aspect of the present invention, the transgenic animals described herein can be used to evaluate the in vivo effects of endocrine disruptors (ED). EDs are typically chemicals that interfere with the normal functioning of the endocrine system (including, for example, many pesticides and fertilizers). The increasing need for evaluation of HPV and potential endocrine disruptors, both in view of public interest and mandates for testing from the U.S. Federal Government, are likely to be met by the transgenic animals and accompanying compound screening methods of the present invention.

Several classes of stress-related genes, and the promoters/control elements thereof, are described in more detail below.

2.2.0 Promoters

The expression cassettes, vectors, cells and transgenic animals described herein contain a sequence encoding a detectable gene product, e.g., a luciferase gene, operably linked to a transcription control element, e.g., a promoter. The promoter may be from the same species as the transgenic animal (e.g., mouse promoter used in construct to make transgenic mouse) or from a different species (e.g., human promoter used in construct to make transgenic mouse). The promoter can be derived from any gene of interest. In one embodiment of the present invention, the promoter is derived from a gene whose expression is induced during oxidative metabolism, for example clearing of a drug via the liver. Thus, when a drug is administered to a transgenic animal carrying a vector construct of the present invention, the promoter is induced and the animal expresses luciferase, which can then be monitored in vivo.

Exemplary transcription control elements (e.g., promoters) for use in the present invention include, but are not limited to, promoters derived from the P450-related genes and gene families. In humans, 40 different P450 genes (designated "CYP" genes) and 13 pseudogenes are currently known. Those genes are classified into 16 families based on amino acid sequence similarity. Families 1, 2 and 3 are involved in drug metabolism, and over 90% of drug oxidation in humans is attributed to only 6 CYP genes (1A2, 2C9, 2C19, 2D6, 2E1 and 3A4). 1A2, 2C9, 2D6 and 3A4 contribute the most, with CYP3A4 accounting for 50-60% of the activity. Mouse Cyp3A11 is described, for example, in Yanagimoto T. et al. (1997) Archives of Biochemistry and Biophysics 340(2):215-8 and Toide K. et al. (1997) Archives of Biochemistry and Biophysics 338(1):43-49. Human CYP3A4 is described, for example, in Hashimoto H. et al. (1993). Eur J Biochem. 218(2):585-95; Goodwin B. et al. (1999).Mol Pharmacol. 56(6):1329-39; and Bertilsson G. et al. (1998) Proc Natl Acad Sci USA. 95(21):12208-13. Exemplified herein are transcription control elements derived mouse Cyp3A11 as well as transcription elements derived from human CYP3A4.

As one of skill in the art will appreciate in view of the teachings of the present specification, transcription control element sequences can be derived and isolated from, e.g., genomic sequences, using method known in the art in view of the teachings herein. For example, the transcription control element sequences of Cyp3A11 were isolated and sequenced as described in Example 1 below.

Similarly, a sequence that confers liver-specific expression was obtained from the CYP3A4 gene. It has been suggested that HIF4, COUP-TF/HIF4, GRE, Rifampicin, Dex responsive elements are located in the 10.5 kb promoter region of CYP3A4 (Goodwin et al., supra). However, prior to the present application, no regulatory elements had been described in the distal 2.5 Kb region of this locus. As described herein, when the activity of the 10.5 Kb and the 13 Kb promoters were compared in liver-push experiments and transgenic animals, the 13 Kb promoter was found to mediate much higher expression in the livers than the 10.5 Kb promoter. Indeed, liver-push experiments showed that the 13 Kb promoter activity was 25 fold higher than activity observed using the 10.5 Kb promoter. Furthermore, luciferase expression in transgenic mice containing the 13 Kb promoter showed luciferase reporter is highest in liver, while luciferase expression in 10.4 kb-transgenic animals is high in intestines. Thus, data obtained from liver push experiments and transgenic animals demonstrate that the ~2.5 Kb distal fragment of the CYP3A4 promoter dramatically enhances liver-specific gene expression. Potential transcription factor binding sites in this 2.5 Kb include: four potential HNF-3b sites (in opposite orientation) and two HNF-3b sites (in direct orientation).

Another exemplary method of isolating promoter sequences employs a GenomeWalker® kit, commercially available from Clontech (Palo Alto, Calif.), and described on page 27 of the 1997-1998 Clontech catalog.

2.2.1 Mouse Cyp3A11 and Human CYP3A4 Transcription Control Elements Sequences

The subject nucleic acids of the present invention (e.g., as described in Example 1) find a wide variety of applications including use as hybridization probes, PCR primers, expression cassettes useful for compound screening, detecting the presence of Cyp3A11 or CYP3A4 genes or variants thereof, detecting the presence of gene transcripts, detecting or amplifying nucleic acids encoding additional Cyp3A11 or CYP3A4 promoter sequences or homologues thereof (as well as, structural analogs), and in a variety of screening assays.

The present invention provides efficient methods for determining the toxicity of pharmacological agents which are active at the level of Cyp3A11 or CYP3A4 gene transcription. A wide variety of assays for transcriptional expression can be used based on the teaching of the present specification, including, but not limited to, cell-based transcription assays, screening in vivo in transgenic animals, and promoter-protein binding assays. For example, the disclosed luciferase reporter constructs are used to transfect cells for cell-based transcription assays. For example, primary endothelial cells are plated onto microtiter plates and used to screen libraries of candidate agents for compounds which modulate the transcriptional regulation of the Cyp3A11 or CYP3A4 gene promoters, as monitored by luciferase expression (See Examples below).

As noted above, the present invention relates to a recombinant nucleic acid molecule comprising transcription control elements derived from a mouse Cyp3A11 gene locus or from a human CYP3A4 locus. In particular, recombinant nucleic acid molecules comprising SEQ ID NO:12, SEQ ID NO:13, SEQ ID NO:14 and SEQ ID NO:15, as well as fragments thereof, are described. The fragments have approximately 80% to 100%, and integer values therebetween, sequence identity to sequences disclosed, at least 80-85%, preferably 85-90%, more preferably 90-95%, and most preferably 98-100% sequence identity to the reference sequence (i.e., the sequences of the present invention). The present invention may also include a nucleic acid sequence substantially complementary to said polynucleotide sequences, or fragments thereof, as well as, a nucleic acid sequence that specifically hybridizes to said polynucleotide sequences or fragments thereof.

The invention includes further transcription control element sequences (e.g., promoter sequences) identified based on the teachings of the present specification (including, but not limited to, sequence information and isolation methods, e.g., Example 1).

The nucleic acid molecules of this invention are useful for producing transfected cells, liver push animals and transgenic animals that are themselves useful in a variety of applications, and for screening for safety and/or possible toxicity of compounds that modulate P450-mediated metabolism (see Examples 2-4).

Those skilled in the art can practice the invention by following the guidance of the specification supplemented with standard procedures of molecular biology for the isolation and characterization of the Cyp3A11 and CYP3A4 transcription control elements, their transfection into host cells, and expression of heterologous DNA operably linked to said Cyp3A11 or CYP3A4 promoters. For example, DNA is commonly transferred or introduced into recipient mammal cells by calcium phosphate-mediated gene transfer, electroporation, lipofection, viral infection, and the like. General methods and vectors for gene transfer and expression may be found, for example, in M. Kriegler, Gene Transfer and Expression: A Laboratory Manual, Stockton Press (1990). Direct gene transfer to cells in vivo can be achieved, for example, by the use of modified viral vectors, including, but not limited to, retroviruses, adenoviruses, adeno-associated viruses and herpes viruses, liposomes, and direct injection of DNA into certain cell types. In this manner, recombinant expression vectors and recombinant cells containing the Cyp3A11 and CYP3A4 transcription control elements of the present invention operably linked to a desired heterologous gene can be delivered to specific target cells in vivo. See, e.g., Wilson, Nature, 365: 691-692 (1993); Plautz et al, Annals NY Acad. Sci., 716: 144-153 (1994); Farhood et al, Annals NY Acad. Sci., 716: 23-34 (1994) and Hyde et al Nature, 362: 250-255 (1993). Furthermore, cells may be transformed ex vivo and introduced directly at localized sites by injection, e.g., intra-articular, intracutaneous, intramuscular and the like. In addition, recombinant expression vectors can be delivered via a liver push to animals, for example by intravenous injection (see, also, Experimental Materials and Methods, below).

Cloning and characterization of the Cyp3A11-locus-derived transcription control elements and the CYP3A4-locus-derived transcription control elements are described in Example 1, below. Cloning and characterization of transcription control elements derived from the CYP3A4 locus are also described in the Examples below. Characterization of some regions of the 5' non-coding regions of the mouse Cyp3A11 locus and the human CYP3A4 locus is presented in Example 5 (see also, FIGS. 18 and 19).

The present invention includes a polynucleotide effective to promote transcription of an operably linked heterologous sequence, said polynucleotide derived from the 5' non-coding region of the mouse Cyp3A11 gene. One aspect of the present invention comprises the approximately 13 kb sequence (SEQ ID NO:12) and fragments thereof, in particular, fragments capable of functioning as transcription promoters and/or transcription regulatory sequences.

In one embodiment, a transcription control element of the present invention includes a polynucleotide derived from the mouse Cyp3A11 gene comprising a polynucleotide sequence having 90% or greater identity to nucleotides 1-11,002 of SEQ ID NO:12. One aspect of the present invention comprises the approximately 9.3 kb sequence (SEQ ID NO:13) and fragments thereof, in particular, fragments capable of functioning as transcription promoters and/or transcription regulatory sequences. In one embodiment, a transcription control element of the present invention includes a polynucleotide derived from the mouse Cyp3A11 gene comprising a polynucleotide sequence having 90% or greater identity to SEQ ID NO:13. In another embodiment, a transcription control element of the present invention includes a polynucleotide derived from the mouse Cyp3A11 gene, said polynucleotide comprising a polynucleotide having 90% identity or greater to nucleotides 5104-6218 of SEQ ID NO:13. In another embodiment, a transcription control element of the present invention includes a polynucleotide derived from the mouse Cyp3A11 gene, said polynucleotide comprising a polynucleotide having 90% identity or greater to nucleotides 6792-9330 of SEQ ID NO:13. In yet another embodiment, a transcription control element of the present invention includes a polynucleotide derived from the mouse Cyp3A11 gene, said polynucleotide comprising a first polynucleotide having 90% identity or greater to nucleotides 5104-6218 of SEQ ID NO:13 and a second polynucleotide having 90% identity or greater to nucleotides 6792-9330 of SEQ ID NO:13.

The polynucleotides of the present invention, e.g., a polynucleotide comprising the 9.3 kb sequence (SEQ ID NO:13), or polynucleotides comprising fragments thereof may also be associated with a basal promoter in order to confer certain regulatory characteristics on the basal promoter (a basal promoter may, for example, comprise a minimum unit necessary to promote transcription, e.g., a TATA box).

The present invention includes, but is not limited to, isolated polynucleotides (for example, those just described), methods of use of such polynucleotides, vectors comprising such polynucleotides, expression cassettes comprising such polynucleotides, vectors comprising such polynucleotides, recombinant cells comprising such polynucleotides, liver-push non-human animals comprising such polynucleotides, and transgenic, non-human animals comprising such polynucleotides. In one embodiment the present invention includes a transgenic, non-human animal (e.g., a rat or a mouse), comprising a 3A11-derived polynucleotide operably linked to a reporter gene (e.g., a light-generating protein).

The present invention includes a polynucleotide effective to promote transcription of an operably linked heterologous sequence, said polynucleotide derived from the 5' non-coding region of the human CYP3A4 gene. One aspect of the present invention comprises the approximately 13 kb sequence (SEQ ID NO:14) and fragments thereof, in particular, fragments capable of functioning as transcription promoters and/or transcription regulatory sequences. One such exemplary fragment is identified by SEQ ID NO:15. In one embodiment, a transcription control element of the present invention includes a polynucleotide derived from the human CYP3A4 gene comprising a polynucleotide sequence having 90% or greater identity to nucleotides 1-13,032 of SEQ ID NO:14.

In one embodiment, a transcription control element of the present invention includes a polynucleotide derived from the human CYP3A4 gene comprising a polynucleotide sequence having 90% or greater identity to SEQ ID NO:14. In another embodiment, a transcription control element of the present invention includes a polynucleotide derived from the human CYP3A4 gene, said polynucleotide comprising a polynucleotide having 90% identity or greater to nucleotides 1290-2446 of SEQ ID NO:14. In another embodiment, a transcription control element of the present invention includes a polynucleotide derived from the human CYP3A4 gene, said polynucleotide comprising a polynucleotide having 90% identity or greater to nucleotides 2758-4111 of SEQ ID NO:14. In another embodiment, a transcription control element of the present invention includes a polynucleotide derived from the human CYP3A4 gene, said polynucleotide comprising a polynucleotide having 90% identity or greater to nucleotides 4424-6010 of SEQ ID NO:14. In another embodiment, a transcription control element of the present invention includes a polynucleotide derived from the human CYP3A4 gene, said polynucleotide comprising a polynucleotide having 90% identity or greater to nucleotides 6317-9099 of SEQ ID NO:14. In another embodiment, a transcription control element of the present invention includes a polynucleotide derived from the human CYP3A4 gene, said polynucleotide comprising a polynucleotide having 90% identity or greater to nucleotides 9401-12998 of SEQ ID NO:14. In yet another embodiment, a transcription control element of the present invention includes a polynucleotide derived from the human CYP3A4 gene, said polynucleotide comprising a first polynucleotide having 90% identity or greater to nucleotides 1290-2446 of SEQ ID NO:14, a second polynucleotide having 90% identity or greater to nucleotides 2758-4111 of SEQ ID NO:14, a third polynucleotide having 90% identity or greater to nucleotides 4424-6010 of SEQ ID NO:14, a fourth polynucleotide having 90% identity or greater to nucleotides 6317-9099 of SEQ ID NO:14, and a fifth polynucleotide having 90% identity or greater to nucleotides 9401-12998 of SEQ ID NO:14.

The polynucleotides of the present invention, e.g., a polynucleotide comprising the approximately 13 kb sequence (SEQ ID NO:14), or polynucleotides comprising fragments thereof may also be associated with a basal promoter in order to confer certain regulatory characteristics on the basal promoter (a basal promoter may, for example, comprise a minimum unit necessary to promote transcription, e.g., a TATA box).

The present invention includes, but is not limited to, isolated polynucleotides (for example, those just described), methods of use of such polynucleotides, vectors comprising such polynucleotides, expression cassettes comprising such polynucleotides, vectors comprising such polynucleotides, recombinant cells comprising such polynucleotides, liver-push non-human animals comprising such polynucleotides, and transgenic, non-human animals comprising such polynucleotides.

A preferred embodiment of one aspect of the present invention, includes a transgenic, non-human animal that comprises a transcription control element derived from the human CYP3A4 gene (e.g., a polynucleotide sequence having 90% or greater identity to nucleotides 1-13,032 of SEQ ID NO:14) operably linked to a heterologous sequence (e.g., encoding a light-generating protein, for example, luciferase). In one embodiment, the transgenic, non-human animal does not comprise a polynucleotide encoding hPXR (a human rifampicin co-receptor), that is, the transgenic, non-human animal does not express a functional human PXR protein. For example, a transgenic rodent (e.g., a mouse or rat) has been generated that comprises a transcription control element derived from the human CYP3A4 gene, but the animal does not express the human rifampicin co-receptor (see Example 6).

2.3.0 Expression Cassettes and Vectors

The expression cassettes described herein may typically include the following components: (1) a polynucleotide encoding a reporter gene, such as a sequence encoding a light generating protein, (2) a transcription control element operably linked to the reporter gene sequence, wherein the control element is heterologous to the coding sequences of the light generating protein (e.g., the Cyp3A11 and CYP3A4 sequences of the present invention). Transcription control elements derived from the sequences provided herein may be associated with, for example, a basal transcription promoter to confer regulation provided by such control elements on such a basal transcription promoter. Exemplary expression constructs are described in Example 1.

The present invention also includes providing such expression cassettes in vectors, comprising, for example, a suitable vector backbone and optionally a sequence encoding a selection marker e.g., a positive or negative selection marker. Suitable vector backbones generally include an F1 origin of replication; a colE1 plasmid-derived origin of replication; polyadenylation sequence(s); sequences encoding antibiotic resistance (e.g., ampicillin resistance) and other regulatory or control elements. Non-limiting examples of appropriate backbones include: pBluescriptSK (Stratagene, La Jolla, Calif.); pBluescriptKS (Stratagene, La Jolla, Calif.) and other commercially available vectors.

A variety of reporter genes may be used in the practice of the present invention. Preferred are those that produce a protein product which is easily measured in a routine assay. Suitable reporter genes include, but are not limited to chloramphenicol acetyl transferase (CAT), light generating proteins (e.g., luciferase), and beta-galactosidase. Convenient assays include, but are not limited to calorimetric, fluorimetric and enzymatic assays. In one aspect, reporter genes may be employed that are expressed within the cell and whose extracellular products are directly measured in the intracellular medium, or in an extract of the intracellular medium of a cultured cell line. This provides advantages over using a reporter gene whose product is secreted, since the rate and efficiency of the secretion introduces additional variables that may complicate interpretation of the assay. In a preferred embodiment, the reporter gene is a light generating protein. When using the light generating reporter proteins described herein, expression can be evaluated accurately and non-invasively as described above (see, for example, Contag, P. R., et al., (1998) Nature Med. 4:245-7; Contag, C. H., et al., (1997) Photochem Photobiol. 66:523-31; Contag, C. H., et al., (1995) Mol Microbiol. 18:593-603).

In one aspect of the invention, the light generating is luciferase. Luciferase coding sequences useful in the practice of the present invention include sequences obtained from lux genes (procaryotic genes encoding a luciferase activity) and luc genes (eucaryotic genes encoding a luciferase activity). A variety of luciferase encoding genes have been identified including, but not limited to, the following: B. A. Sherf and K. V. Wood, U.S. Pat. No. 5,670,356, issued 23, Sep. 1997; Kazami, J., et al., U.S. Pat. No. 5,604,123, issued 18, Feb. 1997; S. Zenno, et al, U.S. Pat. No. 5,618,722; K. V. Wood, U.S. Pat. No. 5,650,289, issued 22, Jul. 1997; K. V. Wood, U.S. Pat. No. 5,641,641, issued 24, Jun. 1997; N. Kajiyama and E. Nakano, U.S. Pat. No. 5,229,285, issued 20, Jul. 1993; M. J. Cormier and W. W. Lorenz, U.S. Pat. No. 5,292,658, issued 8, Mar. 1994; M. J. Cormier and W. W. Lorenz, U.S. Pat. No. 5,418,155, issued 23, May 1995; de Wet, J. R., et al,

*Molec. Cell. Biol.* 7:725-737, 1987; Tatsumi, H. N., et al, *Biochim. Biophys. Acta* 1131:161-165, 1992; and Wood, K. V., et al, *Science* 244:700-702, 1989; all herein incorporated by reference. Another group of bioluminescent proteins includes light-generating proteins of the aequorin family (Prasher, D. C., et al., Biochem. 26:1326-1332 (1987)). Luciferases, as well as aequorin-like molecules, require a source of energy, such as ATP, NAD(P)H, and the like, and a substrate, such as luciferin or coelentrizine and oxygen.

Wild-type firefly luciferases typically have emission maxima at about 550 nm. Numerous variants with distinct emission maxima have also been studied. For example, Kajiyama and Nakano (*Protein Eng.* 4(6):691-693, 1991; U.S. Pat. No. 5,330,906, issued 19, Jul. 1994, herein incorporated by reference) teach five variant firefly luciferases generated by single amino acid changes to the *Luciola cruciata* luciferase coding sequence. The variants have emission peaks of 558 nm, 595 nm, 607 nm, 609 nm and 612 nm. A yellow-green luciferase with an emission peak of about 540 nm is commercially available from Promega, Madison, Wis. under the name pGL3. A red luciferase with an emission peak of about 610 nm is described, for example, in Contag et al. (1998) *Nat. Med.* 4:245-247 and Kajiyama et al. (1991) *Port. Eng.* 4:691-693. The coding sequence of a luciferase derived from Renilla muelleri has also been described (mRNA, GENBANK Accession No. AY015988, protein Accession AAG54094).

In another aspect of the present invention, the light-generating protein is a fluorescent protein, for example, blue, cyan, green, yellow, and red fluorescent proteins.

Several light-generating protein coding sequences are commercially available, including, but not limited to, the following. Clontech (Palo Alto, Calif.) provides coding sequences for luciferase and a variety of fluorescent proteins, including, blue, cyan, green, yellow, and red fluorescent proteins. Enhanced green fluorescent protein (EGFP) variants are well expressed in mammalian systems and tend to exhibit brighter fluorescence than wild-type GFP. Enhanced fluorescent proteins include enhanced green fluorescent protein (EGFP), enhanced cyan fluorescent protein (ECFP), and enhanced yellow fluorescent protein (EYFP). Further, Clontech provides destabilized enhanced fluorescent proteins (dEFP) variants that feature rapid turn over rates. The shorter half life of the dEFP variants makes them useful in kinetic studies and as quantitative reporters. DsRed coding sequences are available from Clontech. DsRed is a red fluorescent protein useful in expression studies. Further, Fradkov, A. F., et. al., described a novel fluorescent protein from Discosoma coral and its mutants which possesses a unique far-red fluorescence (FEBS Lett. 479 (3), 127-130 (2000)) (mRNA sequence, GENBANK Accession No. AF2727 11, protein sequence, GENBANK Accession No. AAG16224). Promega (Madison, Wis.) also provides coding sequences for fire fly luciferase (for example, as contained in the pGL3 vectors). Further, coding sequences for a number of fluorescent proteins are available from GENBANK, for example, accession numbers AY015995, AF322221, AF080431, AF292560, AF292559, AF292558, AF292557, AF139645, U47298, U47297, AY015988, AY015994, and AF292556.

Modified lux coding sequences have also been described, e.g., WO 01/18195, published 15, Mar. 2001, Xenogen Corporation. In addition, further light generating systems may be employed, for example, when evaluating expression in cells. Such systems include, but are not limited to, Luminescent beta-galactosidase Genetic Reporter System (Clontech).

Positive selection markers include any gene which a product that can be readily assayed. Examples include, but are not limited to, an HPRT gene (Littlefield, J. W., Science 145:709-710 (1964), herein incorporated by reference), a xanthine-guanine phosphoribosyltransferase (GPT) gene, or an adenosine phosphoribosyltransferase (APRT) gene (Sambrook et al., supra), a thymidine kinase gene (i.e. "TK") and especially the TK gene of the herpes simplex virus (Giphart-Gassler, M. et al., Mutat. Res. 214:223-232 (1989) herein incorporated by reference), a nptII gene (Thomas, K. R. et al., Cell 51:503-512 (1987); Mansour, S. L. et al., Nature 336:348-352 (1988), both references herein incorporated by reference), or other genes which confer resistance to amino acid or nucleoside analogues, or antibiotics, etc., for example, gene sequences which encode enzymes such as dihydrofolate reductase (DHFR) enzyme, adenosine deaminase (ADA), asparagine synthetase (AS), hygromycin B phosphotransferase, or a CAD enzyme (carbamyl phosphate synthetase, aspartate transcarbamylase, and dihydroorotase). Addition of the appropriate substrate of the positive selection marker can be used to determine if the product of the positive selection marker is expressed, for example cells which do not express the positive selection marker nptII, are killed when exposed to the substrate G418 (Gibco BRL Life Technology, Gaithersburg, Md.).

The vector typically contains insertion sites for inserting polynucleotide sequences of interest, e.g., the Cyp3A11 and CYP3A4 sequences of the present invention. These insertion sites are preferably included such that there are two sites, one site on either side of the sequences encoding the positive selection marker, luciferase and the promoter. Insertion sites are, for example, restriction endonuclease recognition sites, and can, for example, represent unique restriction sites. In this way, the vector can be digested with the appropriate enzymes and the sequences of interest ligated into the vector.

Optionally, the vector construct can contain a polynucleotide encoding a negative selection marker. Suitable negative selection markers include, but are not limited to, HSV-tk (see, e.g., Majzoub et al. (1996) *New Engl. J. Med.* 334:904-907 and U.S. Pat. No. 5,464,764), as well as genes encoding various toxins including the diphtheria toxin, the tetanus toxin, the cholera toxin and the pertussis toxin. A further negative selection marker gene is the hypoxanthine-guanine phosphoribosyl transferase (HPRT) gene for negative selection in 6-thioguanine.

Exemplary promoters for use in the practice of the present invention are described above.

Vector Construction: The vectors described herein can be constructed utilizing methodologies known in the art of molecular biology (see, for example, Ausubel or Maniatis) in view of the teachings of the specification. As described above, the vector constructs containing the expression cassettes are assembled by inserting the desired components into a suitable vector backbone, for example, (1) polynucleotides encoding a reporter protein, such as a light-generating protein, e.g., a luciferase gene, operably linked to a transcription control element(s) of interest; (2) a sequence encoding a positive selection marker; and, optionally (3) a sequence encoding a negative selection marker. In addition, the vector construct contains insertion sites such that additional sequences of interest can be readily inserted to flank the sequence encoding positive selection marker and luciferase-encoding sequence.

A preferred method of obtaining polynucleotides, suitable regulatory sequences (e.g., promoters) is PCR. General procedures for PCR as taught in MacPherson et al., PCR: A Practical Approach, (IRL Press at Oxford University Press, (1991)). PCR conditions for each application reaction may be empirically determined. A number of parameters influence the success of a reaction. Among these parameters are annealing temperature and time, extension time, Mg2+ and ATP concentration, pH, and the relative concentration of primers, templates and deoxyribonucleotides. Exemplary primers are described below in the Examples. After amplification, the resulting fragments can be detected by agarose gel electrophoresis followed by visualization with ethidium bromide staining and ultraviolet illumination.

In one embodiment, PCR can be used to amplify fragments from genomic libraries. Many genomic libraries are commercially available. Alternatively, libraries can be produced by any method known in the art. Preferably, the organism(s) from which the DNA is has no discernible disease or phenotypic effects. This isolated DNA may be obtained from any cell source or body fluid (e.g., ES cells, liver, kidney, blood cells, buccal cells, cerviovaginal cells, epithelial cells from urine, fetal cells, or any cells present in tissue obtained by biopsy, urine, blood, cerebrospinal fluid (CSF), and tissue exudates at the site of infection or inflammation). DNA is extracted from the cells or body fluid using known methods of cell lysis and DNA purification. The purified DNA is then introduced into a suitable expression system, for example a lambda phage. Another method for obtaining polynucleotides, for example, short, random nucleotide sequences, is by enzymatic digestion.

Polynucleotides are inserted into vector backbones using methods known in the art. For example, insert and vector DNA can be contacted, under suitable conditions, with a restriction enzyme to create complementary or blunt ends on each molecule that can pair with each other and be joined with a ligase. Alternatively, synthetic nucleic acid linkers can be ligated to the termini of a polynucleotide. These synthetic linkers can contain nucleic acid sequences that correspond to a particular restriction site in the vector DNA. Other means are known and, in view of the teachings herein, can be used.

The vector backbone may comprise components functional in more than one selected organism in order to provide a shuttle vector, for example, a bacterial origin of replication and a eucaryotic promoter. Alternately, the vector backbone may comprise an integrating vector, i.e., a vector that is used for random or site-directed integration into a target genome.

The final constructs can be used immediately (e.g., for introduction into ES cells or for liver-push assays), or stored frozen (e.g., at −20° C.) until use. In some embodiments, the constructs are linearized prior to use, for example by digestion with suitable restriction endonucleases.

2.4.0 Liver Push Animals

The expression cassettes of the present invention may be introduced (extra-genomically) into an animal in order to practice the methods described herein. High levels of foreign gene expression have been obtained in muscle and liver via direct injection of naked plasmid DNA. In addition, high levels of expression can also be achieved by direct, intravascular adminstration of naked plasmid DNA into the vessels supplying the liver or muscle. See, Wolff et al. (1990) *Science* 247:1465-1468; Budker et al. (1996) *Gene Ther* 3:593-598; Budker et al. (1998) *Gene Ther* 5:272-276; Zhang et al. (1997) *Human Gene Ther* 8:1763-1772. Recently, Zhang et al. (1999) *Human Gene Ther* 10:1735-1737 reported that high levels of foreign gene expression was seen in hepatocytes following tail vein injections of naked plasmid DNA.

Thus, in a preferred embodiment, the expression cassettes described herein are injected intravenously (e.g., into the tail vein of a mouse) in amounts, volumes and durations that are sufficient to achieve expression in hepatocytes. Determining such amounts and volumes is within the purview of one of skill in the art. For example, the volume of DNA injection is preferably relatively large, for example between about 1 to 10 mL, more preferably between about 1 to 5 mL, even more preferably between about 1 to 3 mL, and most preferably around 2.5 mL. The DNA may be administered in an aqueous solution or in any pharmaceutically acceptable vehicle such as Ringer's Solution. Other acceptable vehicles are known to those of skill in the art and are described, for example, in Remington's, supra. The amount of DNA can be similarly determined and is preferably between about 5-1000 μg, more preferably between about 10 and 500 μg and even more preferably between about 10 and 300 μg. Furthermore, the injections are preferably relatively rapid, e.g., the entire volume is injected over a period less than 2 minutes, more preferably less than 1 minutes and even more preferably less than 30 seconds.

2.5.0 Transgenic Animals

The expression cassettes of the present invention may be introduced into the genome of an animal in order to produce transgenic animals for purposes of practicing the methods of the present invention. In a preferred embodiment of the present invention, the transgenic animal is a transgenic rodent, for example, a mouse, rat, or guinea pig. When a light-generating protein is used as a reporter, imaging is typically carried out using an intact, living, non-human transgenic animal, for example, a living, transgenic rodent (e.g., a mouse or rat). A variety of transformation techniques are well known in the art. Those methods include the following.

(i) Direct microinjection into nuclei: Expression cassettes can be microinjected directly into animal cell nuclei using micropipettes to mechanically transfer the recombinant DNA. This method has the advantage of not exposing the DNA to cellular compartments other than the nucleus and of yielding stable recombinants at high frequency. See, Capecchi, M., Cell 22:479-488 (1980).

For example, the expression cassettes of the present invention may be microinjected into the early male pronucleus of a zygote as early as possible after the formation of the male pronucleus membrane, and prior to its being processed by the zygote female pronucleus. Thus, microinjection according to this method should be undertaken when the male and female pronuclei are well separated and both are located close to the cell membrane. See, e.g., U.S. Pat. No. 4,873,191 to Wagner, et al. (issued Oct. 10, 1989); and Richa, J., (2001) "Production of Transgenic Mice," Molecular Biotechnology, March 2001 vol. 17:261-8.

(ii) ES Cell Transfection: The DNA containing the expression cassettes of the present invention can also be introduced into embryonic stem ("ES") cells. ES cell clones which undergo homologous recombination with a targeting vector are identified, and ES cell-mouse chimeras are then produced. Homozygous animals are produced by mating of hemizygous chimera animals. Procedures are described in, e.g., Koller, B. H. and Smithies, O., (1992) "Altering genes in animals by gene targeting", Annual review of immunology 10:705-30.

(iii) Electroporation: The DNA containing the expression cassettes of the present invention can also be introduced into the animal cells by electroporation. In this technique, animal cells are electroporated in the presence of DNA containing the expression cassette. Electrical impulses of high field strength reversibly permeabilize biomembranes allowing the introduction of the DNA. The pores created during electroporation permit the uptake of macromolecules such as DNA. Procedures are described in, e.g., Potter, H., et al., Proc. Nat'l. Acad. Sci. U.S.A. 81:7161-7165 (1984); and Sambrook, ch. 16.

(iv) Calcium phosphate precipitation: The expression cassettes may also be transferred into cells by other methods of direct uptake, for example, using calcium phosphate. See, e.g., Graham, F., and A. Van der Eb, Virology 52:456-467 (1973); and Sambrook, ch.16.

(v) Liposomes: Encapsulation of DNA within artificial membrane vesicles (liposomes) followed by fusion of the liposomes with the target cell membrane can also be used to introduce DNA into animal cells. See Mannino, R. and S. Gould-Fogerite, BioTechniques, 6:682 (1988).

(vi) Viral capsids: Viruses and empty viral capsids can also be used to incorporate DNA and transfer the DNA to animal cells. For example, DNA can be incorporated into empty polyoma viral capsids and then delivered to polyoma-susceptible cells. See, e.g., Slilaty, S. and H. Aposhian, Science 220:725 (1983).

(vii) Transfection using polybrene or DEAE-dextran: These techniques are described in Sambrook, ch.16.

(viii) Protoplast fusion: Protoplast fusion typically involves the fusion of bacterial protoplasts carrying high numbers of a plasmid of interest with cultured animal cells, usually mediated by treatment with polyethylene glycol. Rassoulzadegan, M., et al., Nature, 295:257 (1982).

(ix) Ballistic penetration: Another method of introduction of nucleic acid segments is high velocity ballistic penetration by small particles with the nucleic acid either within the matrix of small beads or particles, or on the surface, Klein, et al., Nature, 327, 70-73, 1987.

Any technique that can be used to introduce DNA into the animal cells of choice can be employed (e.g., "Transgenic Animal Technology: A Laboratory Handbook," by Carl A. Pinkert, (Editor) First Edition, Academic Press; ISBN: 0125571658; "Manipulating the Mouse Embryo: A Laboratory Manual," Brigid Hogan, et al., ISBN: 0879693843, Publisher: Cold Spring Harbor Laboratory Press, Pub. Date: September 1999, Second Edition.). Electroporation has the advantage of ease and has been found to be broadly applicable, but a substantial fraction of the targeted cells may be killed during electroporation. Therefore, for sensitive cells or cells which are only obtainable in small numbers, microinjection directly into nuclei may be preferable. Also, where a high efficiency of DNA incorporation is especially important, such as transformation without the use of a selectable marker (as discussed above), direct microinjection into nuclei is an advantageous method because typically 5-25% of targeted cells will have stably incorporated the microinjected DNA. Retroviral vectors are also highly efficient but in some cases they are subject to other shortcomings, as described by Ellis, J., and A. Bernstein, Molec. Cell. Biol. 9:1621-1627 (1989). Where lower efficiency techniques are used, such as electroporation, calcium phosphate precipitation or liposome fusion, it is preferable to have a selectable marker in the expression cassette so that stable transformants can be readily selected, as discussed above.

In some situations, introduction of the heterologous DNA will itself result in a selectable phenotype, in which case the targeted cells can be screened directly for homologous recombination. For example, disrupting the gene hart results in resistance to 6-thioguanine. In many cases, however, the transformation will not result in such an easily selectable phenotype and, if a low efficiency transformation technique such as calcium phosphate precipitation is being used, it is preferable to include in the expression cassette a selectable marker such that the stable integration of the expression cassette in the genome will lead to a selectable phenotype. For example, if the introduced DNA contains a neo gene, then selection for integrants can be achieved by selecting cells able to grow on G418.

Transgenic animals prepared as above are useful for practicing the methods of the present invention. Operably linking a promoter of interest to a reporter sequence enables persons of skill in the art to monitor a wide variety of biological processes involving expression of the gene from which the promoter is derived. The transgenic animals of the present invention that comprise the expression cassettes of the present invention provide a means for skilled artisans to observe those processes as they occur in vivo, as well as to elucidate the mechanisms underlying those processes.

With respect to transgenic animals carrying expression cassettes that employ a light-generating protein as a reporter sequence, the monitoring of expression of luciferase reporter expression cassettes using non-invasive whole animal imaging has been described (Contag, C. et al, U.S. Pat. Nos. 5,650,135, and 6,217,847, issued 22, Jul. 1997, and Apr. 17, 2001, respectively, herein incorporated by reference in their entireties; Contag, P., et al, *Nature Medicine* 4(2):245-247, 1998; Contag, C., et al, *OSA TOPS on Biomedical Optical Spectroscopy and Diagnostics* 3:220-224, 1996; Contag, C. H., et al, *Photochemistry and Photobiology* 66(4):523-531, 1997; Contag, C. H., et al, *Molecular Microbiology* 18(4): 593-603, 1995). Such imaging typically uses at least one photo detector device element, for example, a charge-coupled device (CCD) camera.

Thus, in one exemplary embodiment, transgenic mice carrying expression cassettes comprising control elements derived from Cyp3A11 or CYP3A4 operably linked to a luciferase-encoding reporter sequence may be used to monitor Cyp3A11- or CYP3A4-mediated drug metabolism. The transgenic animals of the present invention that comprise the expression cassettes of the present invention also provide a means for screening analytes that may be capable of modulating such toxicity and metabolic processes and thereby identifying and characterizing compounds for safety, possible toxicity and pharmaceutical applications.

Methods of administration of the analyte include, but are not limited to, injection (subcutaneously, epidermally, intradermally), intramucosal (such as nasal, rectal and vaginal), intraperitoneal, intravenous, oral or intramuscular. Other modes of administration include oral and pulmonary administration, suppositories, and transdermal applications. Dosage treatment may be a single dose schedule or a multiple dose schedule. For example, the analyte of interest can be administered over a range of concentration to determine a dose/response curve. The analyte may be administered to a series of test animals or to a single test animal (given that response to the analyte can be cleared from the transgenic animal).

Thus, in one exemplary embodiment, transgenic mice carrying expression cassettes comprising the Cyp3A11 or CYP3A4 promoter operably linked to a luciferase-encoding reporter sequence may be used to monitor the effects of a candidate compound on Cyp3A11 or CYP3A4 expression. The results of those experiments demonstrate that the transgenic mice of the present invention may be used to screen compounds which may be effective pharmaceutical agents.

The creation and phenotypic characterization of transgenic animals comprising a CYP3A4 transgene is described in Example 6 (see also FIG. 22). The characterization methods described in Example 6 may also be applied to the characterization of transgenic animals comprising Cyp3A11 transgenes.

Criteria for selecting a transgenic animal, e.g., rodent, useful in a model for screening compounds affecting the expression of, for example, the human CYP3A4 gene are generally as follows:

Criterion 1. An increase in reporter gene expression, e.g., luciferase gene expression measured by output of light from the liver region, in response to treatment with dex or rif High induction in liver (preferably greater than or equal to 10-fold induction over basal levels) by dexamethasone (e.g., administered at 50 mg/kg body weight) and/or induction in liver (preferably greater than or equal to two-fold induction over basal levels) by rifampicin (e.g., administered at 50 mg/kg body weight).

Criterion 2. Greater induction in the liver region relative to other body regions of the whole animal.

Criterion 3. Basal expression seen in the liver region is greater than or equal to basal expression in other regions of the animal's body. A lower level of intestinal expression, both basal and induced, relative to expression in liver is preferred.

Criterion 4 (may optionally be applied). An increase in reporter gene expression, e.g., luciferase as reporter and expression measured by output of light from the liver region, in response to treatment with at least one of compound selected from the following group: phenobarbitol (Phenob), nifedipine (Nif), 5-pregnene-3b-OL-20-ONE-16a-Carbonitrile (PCN), and clotrimazole (Clotrim). Additionally pregnenolone (Preg) may be employed.

It has been reported that hPXR is the xenobiotic receptor mediating CYP3A4 induction in cell cultures. The seven compounds described above have been shown to activate hPXR in cell culture to various degrees (Xie W et al. 2000; Genes Dev. 2000 Dec. 1,; 14(23):3014-23; Goodwin et al 1999; Mol Pharmacol. 1999 December; 56(6):1329-39). It appears that Rif, Clotrim, Nif and Phenob were relatively better inducers of CYP3A4 expression, while Dex, PCN and Preg were weaker inducers. However, a human hepatocyte study suggested Dex was a good CYP3A4 inducer (Ledirac et al. 2000; Drug Metab Dispos. 2000 December; 28(12):1391-3.). The results presented herein show that Clotrim, Dex, PCN, and Nif induced the transgene CYP3A4-luc better than other three compounds. However, all drugs except for Preg induced the transgene to various degrees, these data support that this animal model is useful for screening CYP3A4 inducers.

Experiments performed in support of the present invention indicate that the presence of a functional hPXR gene product is not essential to the use of a CYP3A4 (or Cyp3A11) transgene reporter in a transgenic, non-human, animal or in liver-push experiments (see, e.g., Examples 2 and 6).

Cytochrome P450 CYP3A4 is an important human gene that codes for an enzyme expressed in liver. The CYP3A4 gene product is believed to be pivotal to the metabolism of many exogenous chemicals (xenobiotics), including, but not limited to, therapeutic drugs, as well as endogenous substances such as steroid hormones. Changes in the level of expression of the CYP3A4 gene can dramatically affect a drug's elimination and, as such, have a large impact on the drug's effectiveness.

2.6.0 Monitoring Promoter Activity

Activity of the transcription control element sequences comprising the expression cassettes and vectors of the present invention may be monitored by detecting and/or quantifying the protein products encoded by the reporter sequences operably linked to those promoters. The particular method used to monitor promoter activity depends on the reporter sequence employed, and may include, for example, enzymatic assay methods, as well as, in the case of reporter sequences which encode light-generating proteins, in vitro or in vivo imaging.

For example, promoter activity in liver push or transgenic animals carrying the expression cassettes of the present invention may be monitored using in vivo bioluminescence imaging (see Contag et al., (see, for example, Contag, P. R., et al., (1998) Nature Med. 4:245-7; Contag, C. H., et al., (1997) Photochem Photobiol. 66:523-31; Contag, C. H., et al., (1995) Mol Microbiol. 18:593-603).

Monitoring promoter activity in turn enables one to monitor the biological processes with which that promoter is associated. It may further be employed in methods of screening analytes which modulate those processes at the promoter level (see discussion in the following section).

Thus, in one aspect of the invention, liver push or transgenic animals carrying expression cassettes comprising promoter sequences derived from P450-related gene loci such as those described above may be used to monitor drug metabolism and possible toxicity.

The effect of drugs on Cyp3A11 or CYP3A4 expression is still another embodiment of this aspect of the invention by in vivo imaging of Cyp3A11 or CYP3A4 promoter liver push or transgenic mice. The results of the liver push experiments demonstrate that animals carrying the expression constructs of the present invention may be used to investigate the possible toxicity and metabolism of drug by their effect on the Cyp3A11 or CYP3A4 promoter-mediated gene expression during the process of drug metabolism.

2.7.0 Screening Analytes

The methods of monitoring promoter activity discussed above may be employed for the purpose of screening analytes (e.g., candidate drugs) which modulate a variety of biological processes, the toxic and metabolic effects of which can be evaluated by determining expression at the promoter level. Screening may be accomplished by means of in vitro assays employing transiently or stably transfected cells, and may also be conducted using the liver push and/or transgenic animals of the present invention discussed above, either by themselves or in conjunction with other wild-type or transformed cells or tissues that have been introduced into those animals. The particular assay method used to measure the effects of various candidate compounds on promoter activity will be determined by the particular reporter sequence present in the expression cassette carried by the cells or animals employed. As discussed above, promoter activity in liver push or transgenic animals carrying constructs employing reporter sequences encoding light-generating proteins may be measured by means of ex vivo assay methods or by means of the in vivo imaging technique reference previously (employing, for example, a bioluminescent or fluorescent protein reporter).

Thus, one aspect of this invention is the use of the expression cassettes and vectors for use in screening for toxicity (via induction of P450 promoter activity) or pharmacologically active agents (or compounds) that modulate expression of P450 (e.g., Cyp3A11, CYP3A4, etc.) promoter activity, either by affecting signal transduction pathways that necessarily precede transcription or by directly affecting transcription of the P450 gene.

For screening purposes, appropriate host cells, preferably liver cells for monitoring Cyp3A11 promoter-mediated expression, are transformed with an expression vectors comprising a reporter gene (e.g., luciferase) operably linked to the P450 (e.g., either Cyp3A11 or CYP3A4) gene promoters of this invention. The transformed cells are next exposed to various test substances and then analyzed for expression of the reporter gene. The expression exhibited by these cells can be compared to expression from cells that were not exposed to the test substance. A compound that modulates the promoter activity of the P450 promoter will result in modulated reporter gene expression relative to the control. See, e.g. Examples, below.

Thus, one aspect of the invention is to screen for test compounds that regulate (i.e., stimulate or inhibit) gene expression levels mediated by the P450 (e.g., Cyp3A)-locus derived transcription control elements (e.g., promoters). Screening may be accomplished by, for example, (i) contacting host cells in which the P450 promoter disclosed herein is operably linked to a reporter gene with a test medium containing the test compound under conditions which allow for expression of the reporter gene; (ii) measuring the expression of the reporter gene in the presence of the test medium; (iii) contacting the host cells with a control medium which does not contain the test compound but is otherwise essentially identical to the test medium in (i), under conditions essentially identical to those used in (i); (iv) measuring the expression of reporter gene in the presence of the control medium; and (v) relating the difference in expression between (ii) and (iv) to the ability of the test compound to affect the activity of the promoter.

Alternatively, the transformed cells may be induced with a transcriptional inducer, such as IL-1 or TNF-alpha, forskolin, dibutyryl-cAMP, or a phorbol-type tumor promoter, e.g., PMA. Transcriptional activity is measured in the presence or absence of a pharmacologic agent of known activity (e.g., a standard compound) or putative toxicity (e.g., a test compound). A change in the level of expression of the reporter gene in the presence of the test compound is compared to that effected by the standard compound. In this way, the ability of a test compound to affect P450 (e.g., Cyp3A11 or CYP3A4) transcription and the relative toxicities of the test and standard compounds can be determined.

Thus in a further aspect, the present invention provides methods of measuring the ability of a test compound to modulate Cyp3A11 or CYP3A4 transcription by: (i) contacting a host cell in which the Cyp3A11 or CYP3A4 promoter, disclosed herein, is operably linked to a reporter gene with an inducer of the promoter activity under conditions which allow for expression of the reporter gene; (ii) measuring the expression of the reporter gene in the absence of the test compound; (iii) exposing the host cells to the test compound either prior to, simultaneously with, or after contacting, the host cells with the inducer; (iv) measuring the expression of the reporter gene in the presence of the test compound; and (iv) relating the difference in expression between (ii) and (iv) to the ability of the test compound to modulate Cyp3A11- or CYP3A4-mediated transcription.

Because different inducers are known to affect different modes of signal transduction, it is possible to identify, with greater specificity, compounds that affect a particular signal transduction pathway. Further, Cyp3A11 or CYP3A4 has been shown to be upregulated in processes of drug metabolism. Therefore, such assays provide a means of identifying the toxicity of compounds t by their effect on Cyp3A11 or CYP3A4.

This invention also provides transgenic animals useful as models for studying other physiological and pathological processes that involve P450 (e.g., Cyp3A11 or CYP3A4) gene expression.

Various forms of the different embodiments of the invention, described herein, may be combined.

Experimental

Below are examples of specific embodiments for carrying out the present invention. The examples are offered for illustrative purposes only, and are not intended to limit the scope of the present invention in any way.

Materials and Methods

Unless indicated otherwise, the experiments described herein were performed using standard methods.

A. PCR Amplification

For PCR amplifications, the reaction mix contained: 5 μl of 10× reaction buffer (no $MgCl_2$); 4 μl 25 mM $MgCl_2$; 0.4 μl of 25 mM dNTP mix; 0.5 μl of 10 pmoles/ul forward primer; 0.5 μl of 10 pmoles/μl reverse primer; 1 μl (0.2 μg) of DNA (BAC or genomic); 38.35 μl of $H_2O$; and 0.25 μl of Taq Polymerase (Life Technologies). The PCR was carried out as follows: 3 minutes at 94° C.; 30 cycles of 30 sec at 94° C.; 30 seconds at 57° C. and 1 min 30 sec at 72° C.; 7 minutes at 72° C.; and stored at 4° C.

B. Southern Blotting (i) Primers were designed and used to PCR screen a mouse 129/SvJ genomic DNA BAC (bacterial artificial chromosome) library (Genome Systems, Inc., St. Louis, Mo.) in order to isolate a Cyp3A11 promoter sequence.

A library containing, on average, contained inserts of 120 kb with sizes ranging between 50 kb to 240 kb was screened. A large genomic DNA fragment that contained Cyp3A11 promoter region was obtained. Similarly, a large DNA fragment that contained CYP3A4 promoter was obtained by screening a similarly-sized human library.

The Cyp3A11 and CYP3A4 BAC DNA were isolated by CsCl ultracentrifugation and digested with various restriction enzymes for 2 hours. Digested DNA fragments were separated on a 1% agarose gel. The gel was depurinated in 250 mM HCL for 10 minutes and then denatured twice in 20×SSC with 0.5M NaOH for 20 minutes. DNA was then transferred onto Hybond N+ membrane (Amersham, Piscataway N.J.) with 20×SSC for 1-2 hours using a vacuum blotting apparatus (Stratagene, La Jolla, Calif.). After transferring, the membrane was cross-linked according to the manufacturer's directions using UV Cross-Linker (Stratagene, La Jolla, Calif.) and rinsed with 5×SSC. The membrane was then prehybridized at 60° C. for 1-6 hours with prehybridization solution (Stratagene, La Jolla, Calif.).

Probes were prepared by labeling PCR fragments or isolated DNA. For example, the 1.6 kb promoter fragment amplified by PCR (as described in, e.g., Example 1) was labeled according to the manufacturer's instructions using Gene Image Random-Prime Labeling and Detection System (Amersham, Piscataway N.J.). Denatured probe was added to the prehybridization solution and the membrane hybridized overnight at 60° C.

After hybridization, the membrane was washed twice with pre-warmed 1×SSC, 0.1% SDS for 20 minutes at 60° C. each time. Subsequently, the membrane was washed twice with pre-warmed 0.5×SSC for 20 minutes at 60° C. each time. The membrane was blocked at RT for 1 hour using blocking solution (Stratagene, La Jolla, Calif.) and incubated with antibody conjugated to alkaline phosphatase for 1 hour. After three washed, substrate CDP-Star was added for 5 minutes. The membrane was exposed to X-ray film for between 1 minute and 3 hours.

(ii) Primers were designed and used to PCR screen a human genomic DNA BAC (bacterial artificial chromosome) library (Genome Systems, Inc., St. Louis, Mo.) in order to isolate CYP3A4 promoter sequence. The library, on average, contained inserts of 120 kb with sizes ranging between 50 kb to 240 kb. A large genomic DNA fragment that contained CYP3A4 promoter region was obtained. Southern analysis was performed essentially as described above with the exception that PCR fragment probes and isolated DNA probes were CYP3A4-sequence specific.

C. In Vivo Expression Assays: Liver Push Protocol

In vivo gene expression mediated by Cyp3A11 or CYP3A4 regulatory sequences were assayed by means of "liver push" assays.

Plasmids administered for liver push experiments were injected intravenously according to the method of Zhang et al., (1999) Human Gene Therapy 10:1735-1737. For example, 2.2 ml of a PBS solution containing the desired Cyp3A11 or CYP3A4 promoter constructs were injected into the tail vein over a period of less than 8 seconds.

For Cyp3A11 and CYP3A4, it was previously believed that a co-receptor is necessary for induction by rifampicin. Accordingly, a plasmid expressing hPXR (a human rifampicin co-receptor) was optionally co-administered with the Cyp3A11-luc or CYP3A4-luc constructs. PXR-expressing plasmids were obtained from Dr. Steven Kliewer at Glaxo-Wellcome.

D. Preparation of Transgenic Animals

The transgenic animals described below were prepared using the microinjection into single cell stage embryos (see, e.g., U.S. Pat. No. 4,873,191 to Wagner, et al. (issued Oct. 10, 1989); Richa, J., (2001) Molecular biotechnology 17:261-8). The embryos were implanted into pseudo-pregnant females and the offspring screener by PCR using primers lucF1 (GCCATTCTATCCGCTGGAAGATGG; SEQ ID NO:11) and lucR4 (CGATTTTACCACATTTGTAGAGGTTTTACTTGC; SEQ ID NO:16). Imaging of animals was done as described below.

E. In Vivo Imaging

In vivo imaging was performed as described previously (Contag, et al. (see e.g., Contag, P. R., et al., (1998) Nature Med. 4:245-7; Contag, C. H., et al., (1997) Photochem Photobiol. 66:523-31; Contag, C. H., et al., (1995) Mol Microbiol. 18:593-603); Zhang et al., (2001) Transgenic Res. 2001 October; 10(5):423-34) using either an intensified CCD camera (ICCD; model C2400-32, Hamamatsu, Japan) fitted with a 50 mm f 1.2 Nikkor lens (Nikon, Japan) and an image processor (Argus 20, Hamamatsu), or with a cryogenically cooled camera (Roper Scientific, Trenton, N.J.) fitted with a 50 mm f 0.95 Navitar lens (Buhl Optical, Pittsburgh, Pa.) available as an integrated imaging system (IVIS™ Imaging System, Xenogen, Corporation, Alameda, Calif.) controlled using LivingImage® software (Xenogen, Corporation, Alameda, Calif.).

The substrate luciferin was injected into the intraperitoneal cavity at a dose of 150 mg/kg body weight (30 mg/ml Luciferin stock) approximately five minutes prior to imaging. Mice were anesthetized with either Nembutal (25-50 mg/kg body weight) or in a gas chamber with an isoflurane/oxygen mixture and isoflurane tubing was placed on the animals' noses, and placed on the imaging stage under anesthesia. Mice were typically imaged from the ventral side for 1 minute. Relative photon emission over the liver region was quantified using LivingImage® software (Xenogen, Alameda, Calif.).

These imaging method can be used to track events in a test subject over time. For example, a compound may be administered to a subject (comprising a light-generating reporter), and photon emission from the subject after administration of the compound may be measured. Such measuring may be repeated at selected time intervals which is typically effective to track an effect of the compound on a level of reporter expression in the subject over time.

F. Western Blot Analysis

Following final imaging, animals were sacrificed, and their livers excised and immediately frozen in liquid nitrogen. The liver tissue from each animal was then homogenized separately in 4 volumes of PBS buffer using a Sonic Dismembrator (Fisher Scientific, Pa.). The protein concentration of each of the homogenates was measured using the Bradford Reagent (Sigma Chemical Co., St. Louis, Mo.) according to the manufacturer's recommendations. Proteins in the tissue homogenates were separated by size on a denaturing 10% polyacrylamide gel according to the method of Laemmli, U.K. (1970) and then transferred to a nitrocellulose membrane (BioRad, Emeryville, Calif.).

Cyp3A11 protein was detected using primary Goat-anti-Rat Cyp3A2 antibody (GenTest, Woburn, Mass., 01801). The secondary antibody was anti-goat-IgG-peroxidase conjugated antibody (Sigma, St. Louis, Mo.).

EXAMPLE 1

Vector Construction

A. Mouse Cyp3A11

Figure 5:
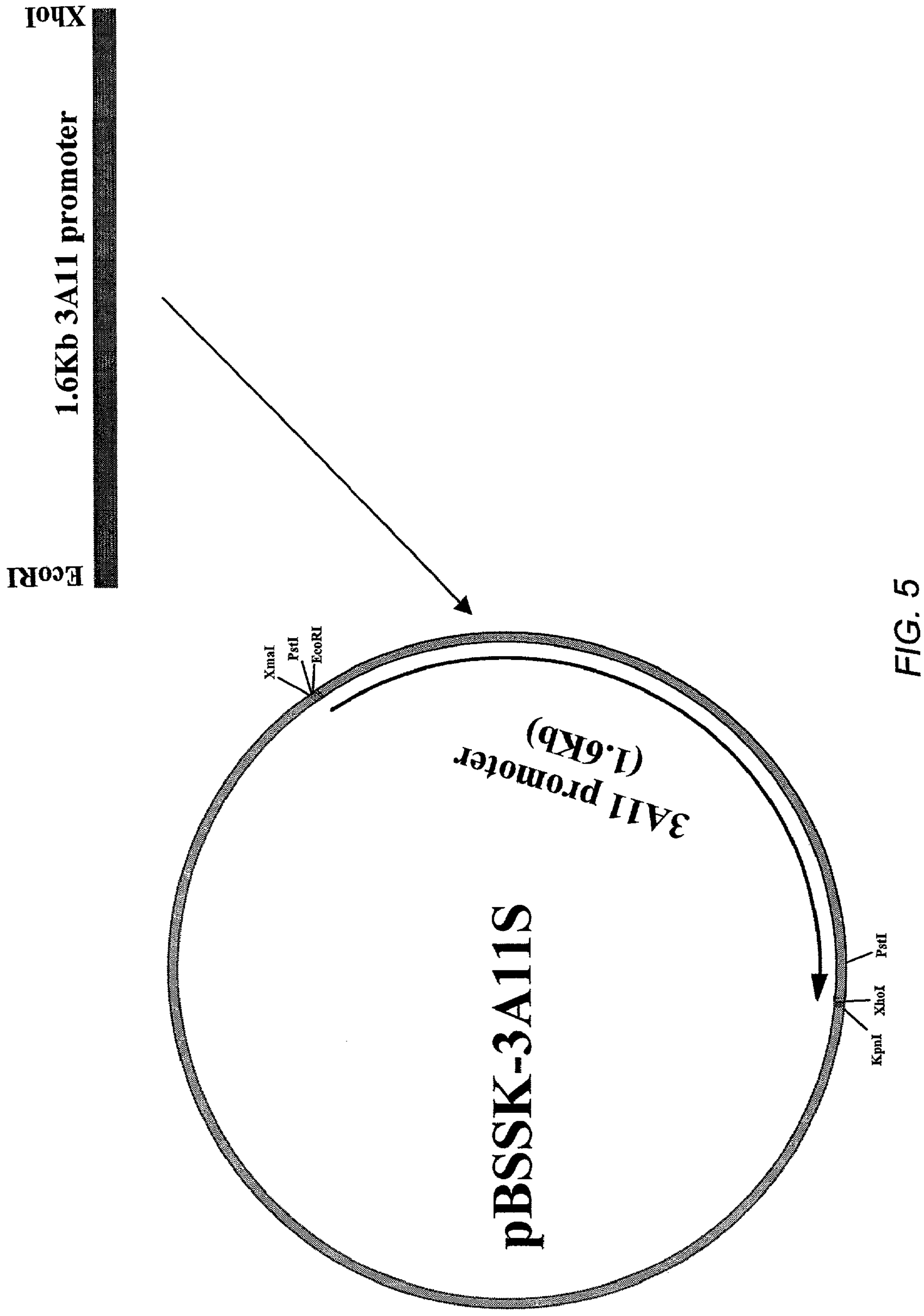
FIG. 5 is a schematic of the pBSSK-3A11S vector construct containing the 1.6 kb Cyp3A11 promoter sequence.

Cyp3A11 and other expression constructs were constructed as described below.

pBSSK-Cyp3A11S: FIG. 5 shows a schematic of the construct designated pBSSK-Cyp3A11S. Briefly, the construct was made as follows. A 1.6 kb fragment of the Cyp3A11 promoter (extending from −1.6 kb to +65 bp) was PCR amplified from mouse genomic DNA using Cyp3A11TopEcoRI.primer (GTTGAATTCCAGCTAATGAGGGCAAAGTTCTCAG, SEQ ID NO:1) and Cyp3A11Bot XhoI.primer (ATCCTCGAGCTTCTCTGTGTTCTCCCTACAACTG, SEQ ID NO:2). (See, also, Toide et al. (1997) *Arch. Biochem. and Biophysics* 338:43-49). pBlueScriptSK (Stratagene, La Jolla, Calif.) was digested with EcoRI and XhoI and the 1.6 kb Cyp3A11 promoter fragment ligated into the vector.

pBSSK-Cyp3A11M: This construct contains a 6 kb fragment of the mouse Cyp3A11 promoter and was constructed as follows. Primers designated Cyp3A11F1.primer (GGTATGTGGTGCTTGTGTATGCATAC, SEQ ID NO:3) and Cyp3A11R2.primer (CAGATAGGATTGAGTGAGCCAGAGG, SEQ ID NO:4) were used to screen BAC clones of mouse genomic DNA (see, also, Materials and Methods above). One positive BAC clone was selected and analyzed by restriction digests and Southern blotting, as described above, using the 1.6 kb promoter fragment as the probe.

Figure 3:
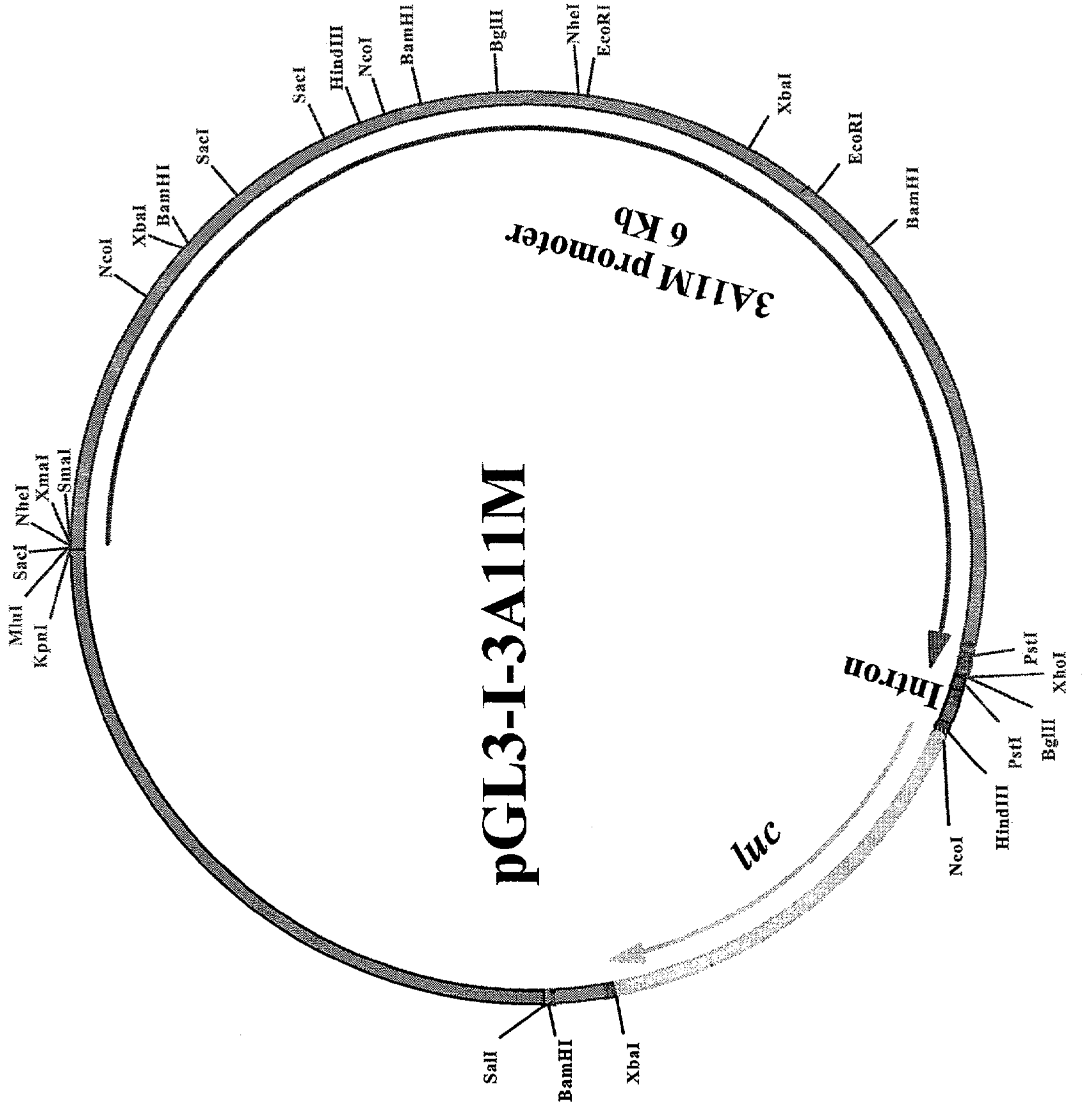
FIG. 3 is a schematic of the pGL3-I-3A11M vector construct containing the 6.0 kb Cyp3A11 promoter sequence.
Figure 4:
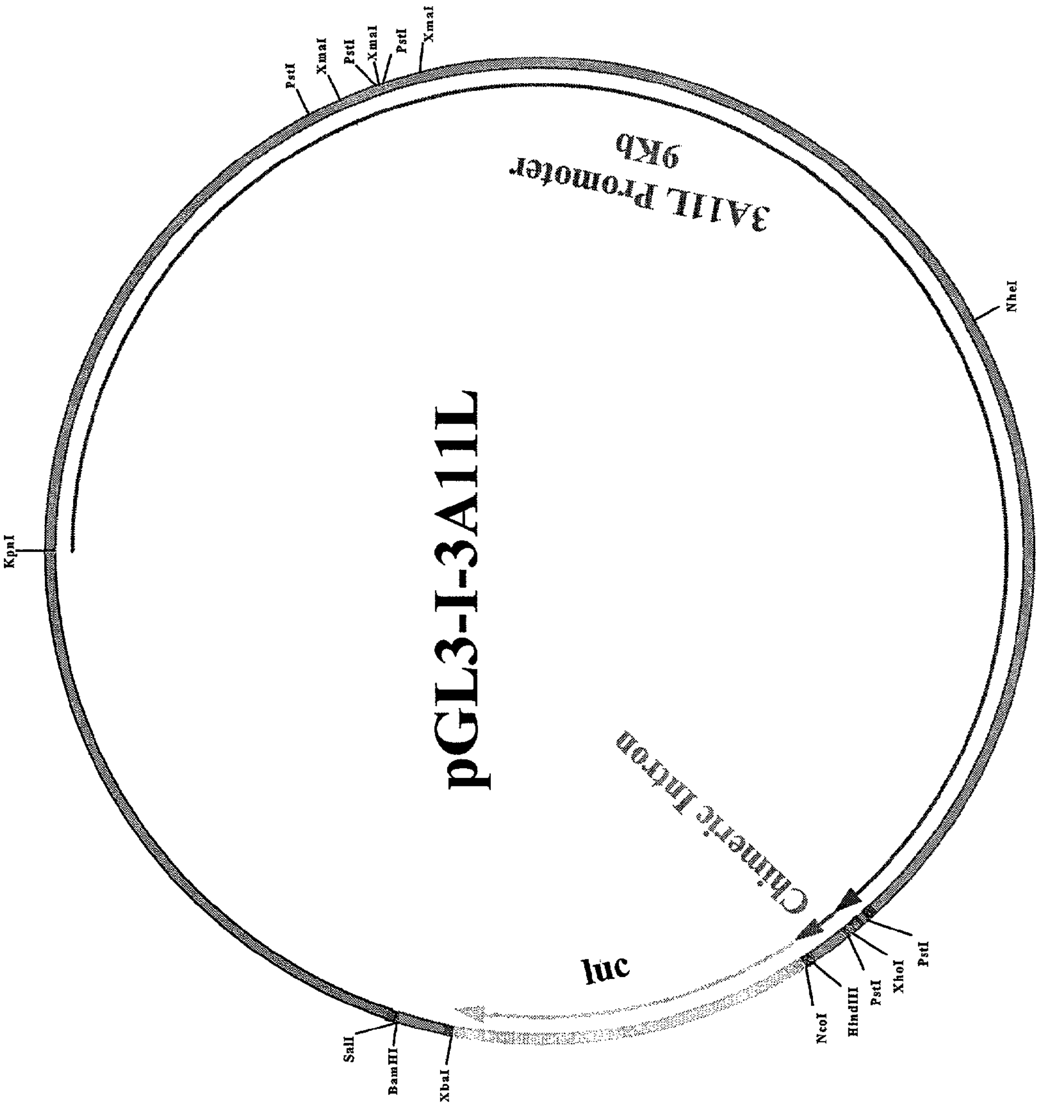
FIG. 4 is a schematic of the pGL3-I-3A11L vector construct containing the 9.0 kb Cyp3A11 promoter sequence.
Figure 6:
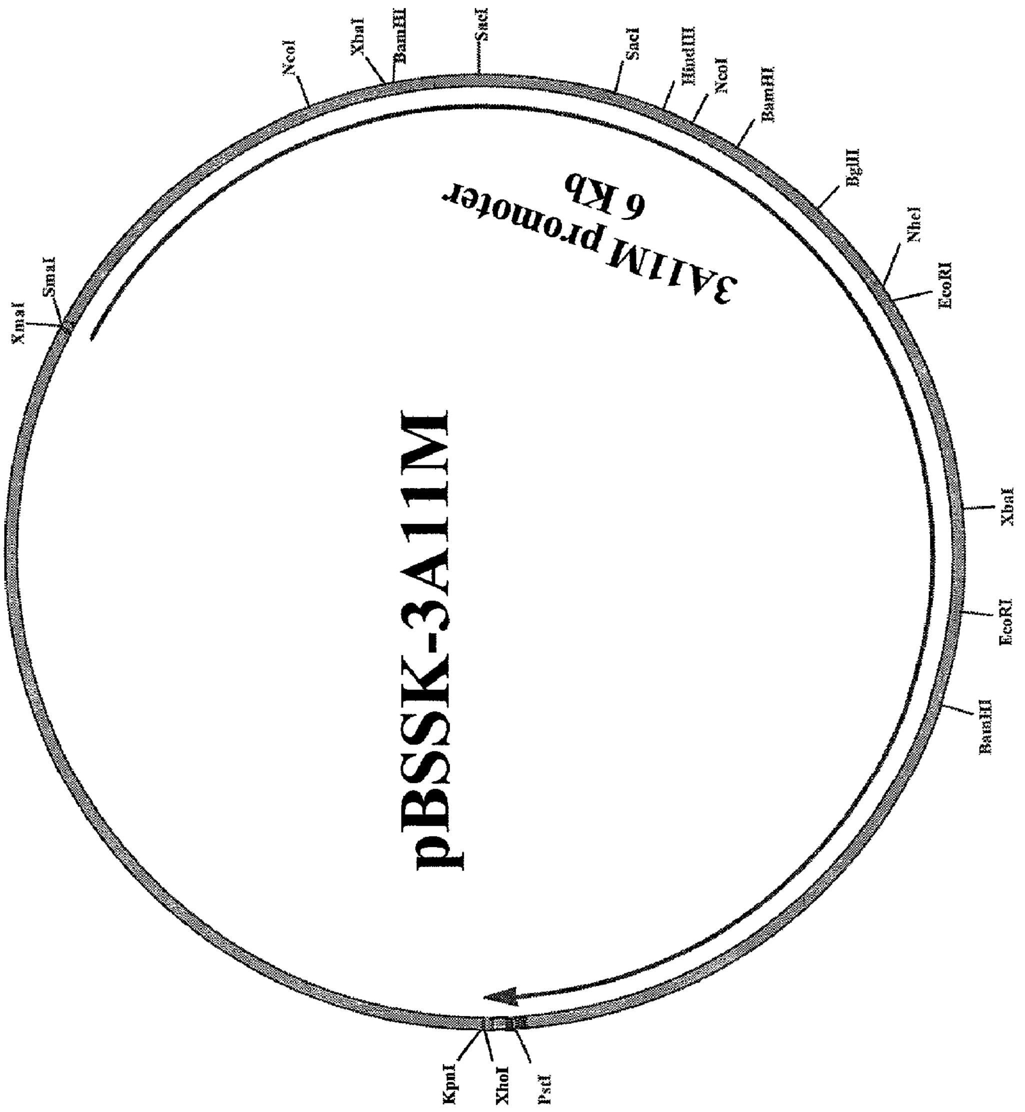
FIG. 6 is a schematic of the pBSSK-3A11M vector construct containing the 6 kb Cyp3A11 promoter sequence.
Figure 7:
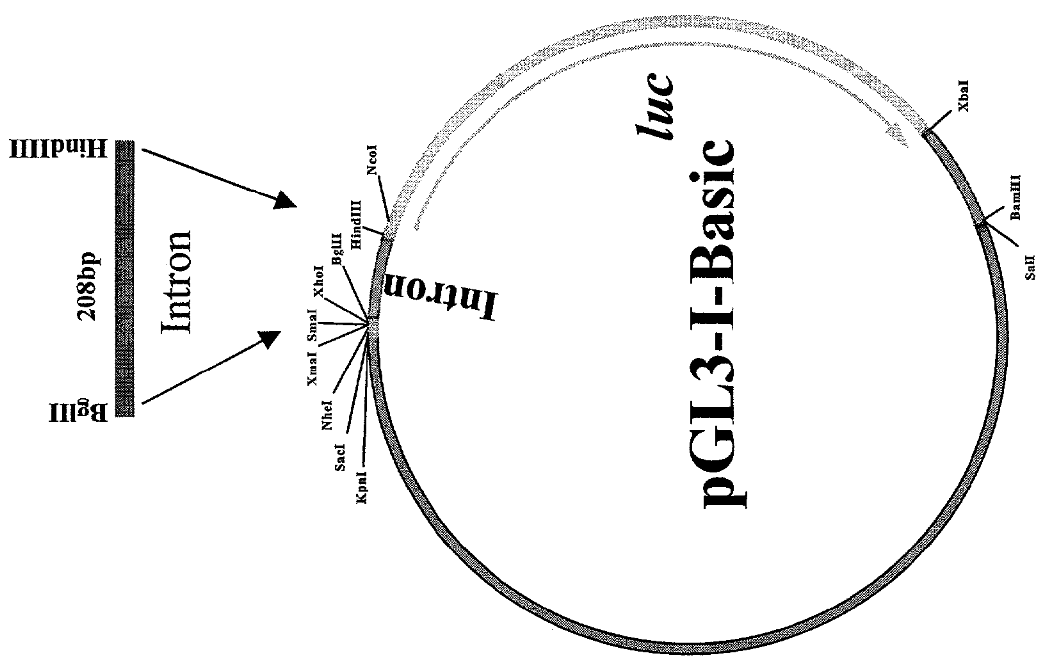
FIG. 7 is a schematic of the pGL3-I-Basic vector construct.

Based on these Southern blots of the selected BAC clone, the PstI fragment of the BAC clone was isolated, subdloned into a sequencing vector and sequenced. Subsequently, the PstI subclone was digested with SmaI/PstI and the resulting 5.9 kb XmaI/PstI fragment isolated. pBSSK-Cyp3A11S was digested with XmaI/PstI and the backbone (including the downstream promoter region extending from the 3' PstI site to the XhoI site was isolated. The 5.9 XmaI/PstI fragment was cloned into XmaI/PstI-digested pBSSK-Cyp3A11S backbone. Thus, after ligation, the resulting pBSSK-Cyp3A11M (FIG. 6) contained the 5.9 kb SmaI/Pst BAC fragment and, additional downstream promoter sequences extending from the 3' PstI to the XhoI site of pBSSK-Cyp3A11S.

pGL3-I-Basic: A 208 base pair intron fragment was amplified from pCAT-Basic (Promega, Madison, Wis.) using Intron Top BglII.primer (TCGAGATCTTGCGGCCGCTTAACTGCAGAAGTTG, SEQ ID NO:5) and Intron Bot HindIII.Primer (GCCAAGCTTGCGGCCGCTTAAGAGCTG, SEQ ID NO:6). A yellow-green luciferase with an emission peak of about 540 nm is commercially available in a plasmid vector from Promega, Madison, Wis. under the name pGL3 and this plasmid was digested with BglII and HindIII. The PCR intron fragment was then ligated into the BglII-HindIII cut pGL3 vector. The resulting vector, designated pGL3-I-Basic is shown in FIG. 7.

pGL3-I-Cyp3A11S: The 1.6 kb Cyp3A11S promoter was amplified from the Cyp3A11-BAC clone using Cyp3A11TopKpnI.primer (GTTGGTACCCAGCTAATGAGGGCAAAGTTCTCAG, SEQ ID NO:7) and Cyp3A11Bot HindIII.primer (ATCAAGCTTCTTCTCTGTGTTCTCCCTACAACTG, SEQ ID NO:8). The PCR product was cloned in to the pGL3-I-Basic vector which had been digested with KpnI and HindIII. The resulting construct, pGL3-I-Cyp3A11S, is shown in FIG. 2.

pGL3-I-Cyp3A11M: pBSSK-Cyp3A11M was digested with XmaI and XhoI and the resulting 6 kb fragment ligated into pGL3-I-Basic which had been previously digested with XmaI and XhoI. The resulting construct is shown in FIG. 3.

pGL3-I-Cyp3A11L: As described above, Southern blotting was carried out on the selected BAC clone using the 1.6 kb promoter fragment as a probe. In addition to the 6 kb PstI fragment used to generate pBSSK-Cyp3A11M, a 10 kb KpnI fragment was also identified. The 10 kb KpnI fragment was sub-cloned, sequenced and restriction sites identified from the sequence. It was determined that the 10 kb fragment overlapped the 5.9 pBSSK-Cyp3A11M fragment and also contained additional upstream sequence. The overlapping portion included an NheI site (FIG. 6). Both pGL3-I-3A11M and the 10 kb KpnI subdlone were digested with NheI and KpnI. This resulted in a pGL3-I-Cyp3A11M backbone that included the upstream region of the promoter extending from NheI to XhoI in the vector backbone. After ligating the NheI/KpnI fragment of the 10 kp KpnI fragment into the pGL3-I -Cyp3A11M backbone, the resulting pGL3-I-Cyp3A11L contained approximately 9 kb of promoter sequences, including additional downstream sequence extending from the internal NheI to the flanking XhoI site of pGL3-I-Cyp3A11M. The resulting construct is shown in FIG. 4.

pGL3-I-Cyp3A11XL: In addition to 6 Kb PstI and 10 Kb KpnI subclones, an 11 Kb XmaI fragment was also subdloned from 3A11 BAC clone. Sequence data showed this 11 Kb XmaI fragment overlapped with the 10 Kb KpnI fragment. A 2.1 Kb KpnI fragment was cloned from the 11 Kb subclone in the KpnI site of pGL3-I-Cyp3A11L. The orientation of the 2.1 Kb KpnI fragment was confirmed by DNA sequencing. The resulting new construct was designated pGL3-I-Cyp3A11XL containing 11 Kb Cyp3A11 promoter region.

Experiments performed in support of the present invention have provided approximately 9,330 base pairs (FIG. 1B; SEQ ID NO:13) of sequence derived from the Cyp3A11 gene locus, upstream of the protein coding region. The sequence of the promoter region comprising transcription control elements is presented in FIG. 1A (SEQ ID NO:12). The figure includes genomic sequences including the initiation ATG codon. Table 1 indicates the sequences from the Cyp3A11 gene locus, upstream of the protein coding region, which comprise the above described constructs. The starting and ending positions in Table 1 are given relative to the sequence presented in FIG. 1A.

TABLE 1

| Vector Name | Approximate Size of Fragment from the Cyp3A11 gene locus | Starting Position of Cyp3A11 gene locus fragment relative to FIG. 1A | Ending Position of Cyp3A11 gene locus fragment relative to FIG. 1A |
|---|---|---|---|
| pGL3-I-Cyp3A11S | 1.6 kb | 9,334 | 10,978 |
| pGL3-I-Cyp3A11M | 6.0 kb | 5,024 | 10,978 |
| pGL3-I-Cyp3A11L | 8.9 kb | 2,096 | 10,978 |
| pGL3-I-Cyp3A11XL | 11 kb | 1 | 10,978 |

B. Human CYP3A4

Figure 8:
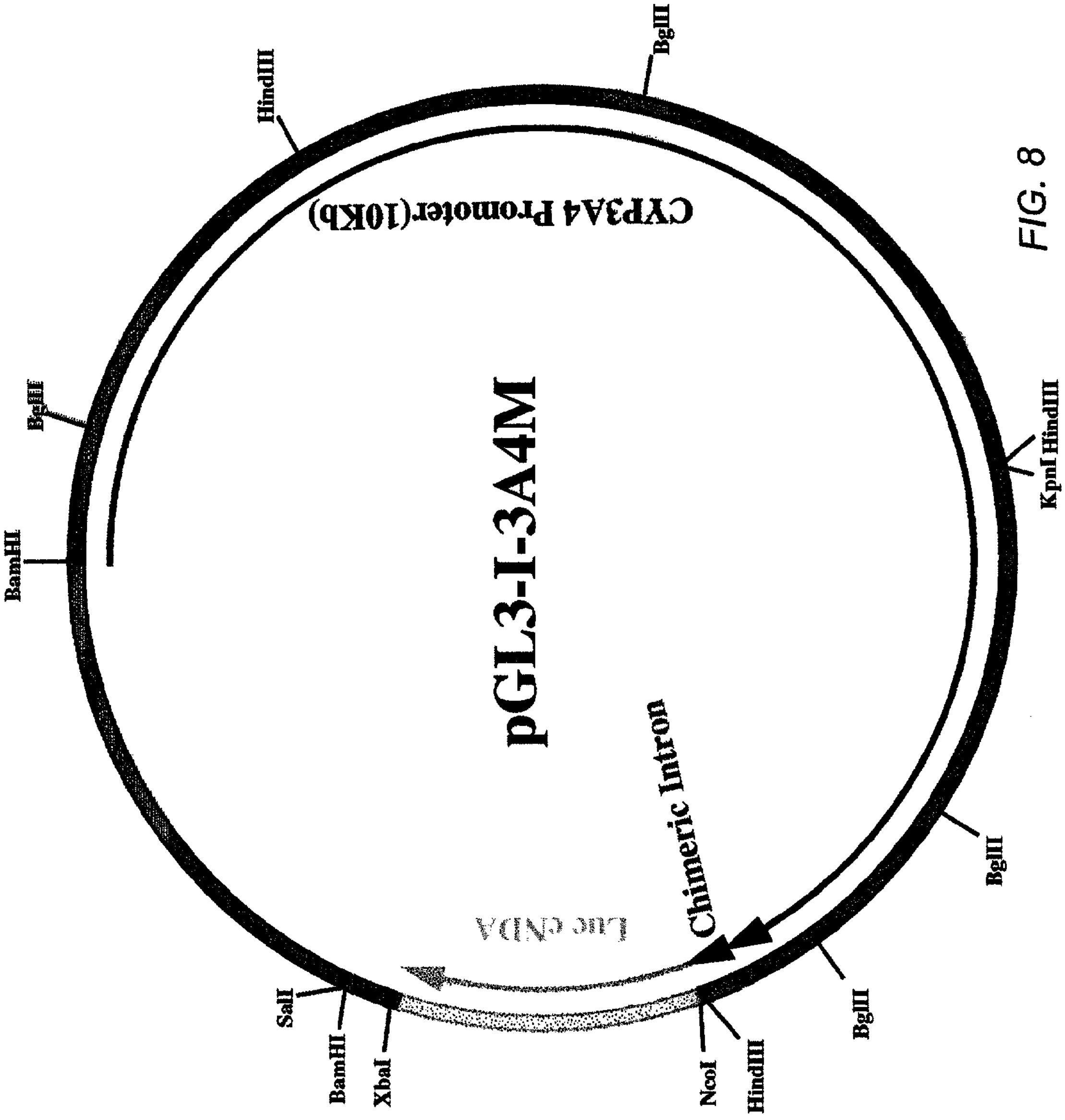
FIG. 8 is a schematic of the pGL3-I-3A4M vector construct containing the 10 kb CYP3A4 promoter sequence.
Figure 9:
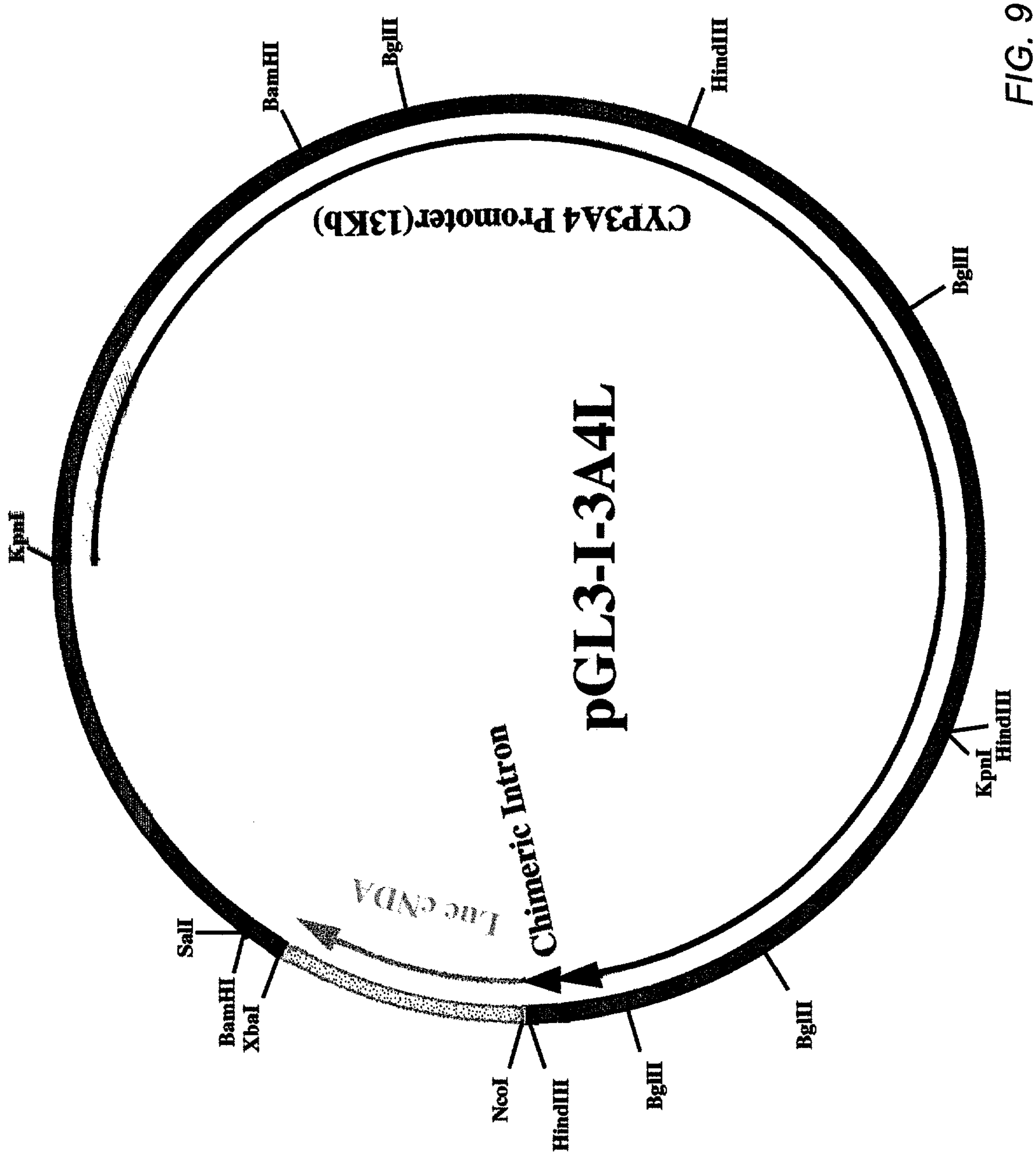
FIG. 9 is a schematic of the pGL3-I-3A4L vector construct containing the 13 kb CYP3A4 promoter sequence.

CYP3A4 and other expression constructs were constructed as described below.

pGL3-I-CYP3A4L: a 13 Kb human CYP3A4 promoter was constructed from a human BAC clone (Screened by Incyte Genomics, Inc. using primers 3A4Top (GTTGGTACCCTGCAGTGACCACTGCCCCATCATTG, SEQ ID NO:9) and 3A4Bot Primer (ATCAAGCTTCCTTTCAGCTCTGTGTTGCTCTTTGC, SEQ ID NO:10). Goodwin, et al., (WO 9961622 A1, published 2 Dec. 1999) published a 632 bp CYP3A4 promoter sequence from approximately 6 kb to approximately 5.4 kb of the 13 kb promoter sequence. Upstream (5') DNA sequences were obtained for the region corresponding to approximately −13 Kb to −10.5 Kb (KpnI site to BamHI site). Putative Hepatocyte nuclear factor 3b (HNF-3b) binding sites were identified in this region. The resulting construct is shown in FIG. 9.

pGL3-I-CYP3A4M: A 12.5 kb BamHI fragment from pGL3-I-CYP3A4L containing 10.5 kb promoter region was cloned into pBSSK (Stratagene, La Jolla, Calif.). The resulting plasmid was called pGL3-I-CYP3A4M. The resulting construct is shown in FIG. 8.

FIG. 17A (SEQ ID NO:14) presents approximately 13 kb of sequence derived from the human CYP3A4 gene locus, upstream of the protein coding region. The figure includes genomic sequences including the initiation ATG codon. A 2.5 kb fragment of the promoter region comprising transcription control elements, identified herein, that affect liver-specific basal expression in mouse liver is presented in FIG. 17B (SEQ ID NO:15).

Table 2 indicates the sequences from the CYP3A4 gene locus, upstream of the protein coding region, which comprise the above described constructs. The starting and ending positions in Table 2 are given relative to the sequence presented in FIG. 17A.

TABLE 2

| Vector Name | Approximate Size of Fragment from the CYP3A4 gene locus | Starting Position of CYP3A4 gene locus fragment relative to FIG. 17A | Ending Position of CYP3A4 gene locus fragment relative to FIG. 17A |
|---|---|---|---|
| pGL3-I-CYP3A4M | 10.5 kb | 2,461 | 12,998 |
| pGL3-I-CYP3A4L | 13 kb | 1 | 12,998 |

EXAMPLE 2

Liver Push Assays

Liver push assays were conducted as described above.

A. Mouse Cyp3A11 Constructs

Briefly, expression constructs described in Example 1A were intravenously injected into mice and imaged as described above two weeks later (pre-treatment group). For each expression construct, 3 mice were then treated with 100 μl of DMSO (solvent control); 3 mice were treated with 0.1 mg/g dexamethasone (100 μl ); and 3 mice were treated with 0.1 mg/g of Rifampicin (100 μl). Dexamethasone and rifampicin have been previously shown to induce Cyp3A11 expression Yanagimoto et al. (1997) *Arch Biochem Biophys* 340(2):215-8. In additional, mice were treated with a single dose of DMSO, rifampicin (Rif) and dexamethasone (Dex), at the same dosages. The mice were then imaged a various time points after drug administration.

Figure 10:
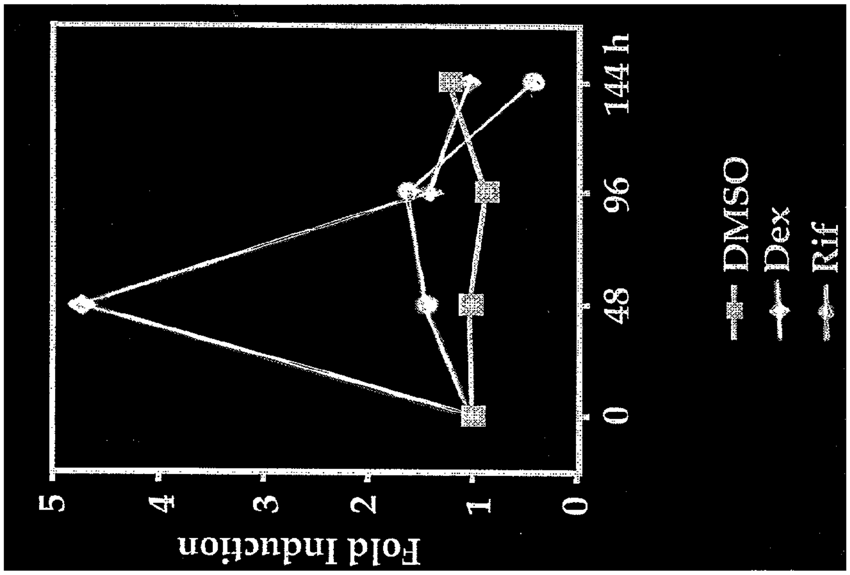
FIG. 10 depicts the results of liver push experiments wherein FVB mice were liver-pushed with 5 μg of the pGL3-I-3A11 M construct and 0 μg of hPXR plasmid.

As shown in FIG. 10, imaging mice subjected to liver push with 5 μg of Cyp3A11M and 0 μg of hPXR showed nearly 5 fold induction of luciferase activity approximately 48 hours after dexamethasone administration. DMSO-treated mice showed little or no induction, while rifampicin-treated mice showed some induction in luciferase approximately 48 to 96 hours after drug treatment.

Figure 12:
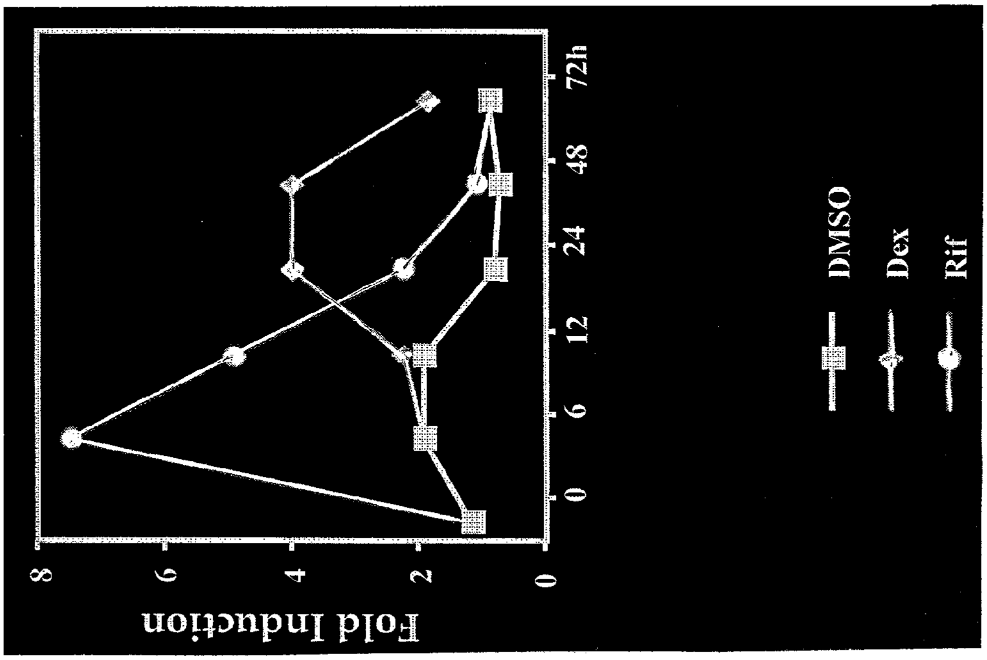
FIG. 12 depicts the results of liver push experiments wherein FVB mice were liver-pushed with 5 μg of the pGL3-I-3A11L construct and 1 μg of hPXR plasmid.

As shown in FIG. 12, imaging mice subjected to liver push with 5 μg of Cyp3A11L and 1 μg of hPXR showed nearly 8 fold induction of luciferase activity approximately 6 hours after rifampicin administration. DMSO-treated mice showed little or no induction, while dexamethasone-treated mice showed approximately 4 fold induction in luciferase approximately 24 to 48 hours after drug treatment.

Thus, modulation of expression mediated by Cyp3A11 transcriptional control elements can be directly monitored in live animals to provide information on toxicity of a compound.

B. Titration of hPXR

It was previously believed that rifampicin uptake required co-administration of a rifampicin co-receptor such as hPXR. In particular, hPXR has been shown to mediate induction of CYP3A4 expression in human hepatocytes by the drugs dexamethasone and rifampicin, see Pascussi J M, et al., *Mol Pharmacol* (2000 August) 58(2):361-72.

Figures 11A, 11B, 11C, 11D:
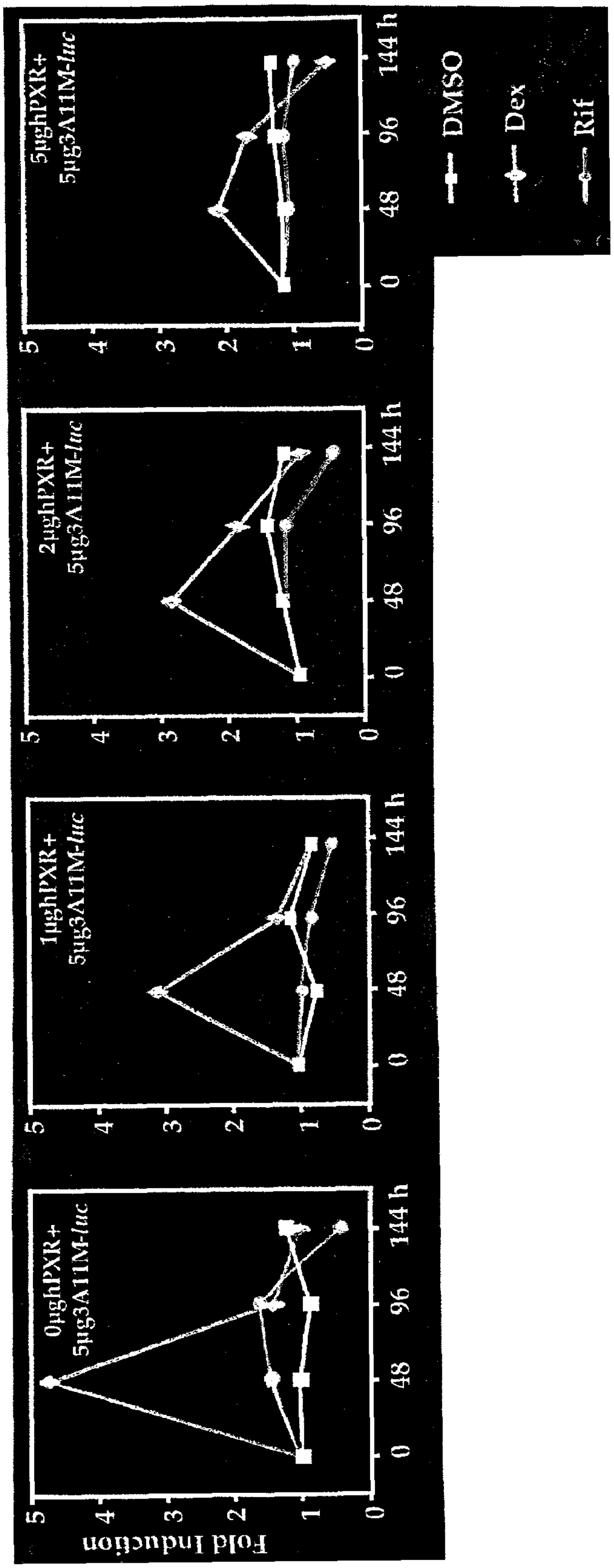
FIG. 11, panels A-D, depict the results of hPXR titration experiments performed in order to optimize the amount of hPXR plasmid co-administered with 5 μg of pGL3-I-3A11M. Panel A, 0 μg hPXR+5 μg 3A11M-luc. Panel B, 1 μg hPXR+5 μg 3A11M-luc. Panel C, 2 μg hPXR+5 μg 3A11M-luc. Panel D, 5 μg hPXR+5 μg 3A11M-luc.
Figures 13A, 13B, 13C, 13D:
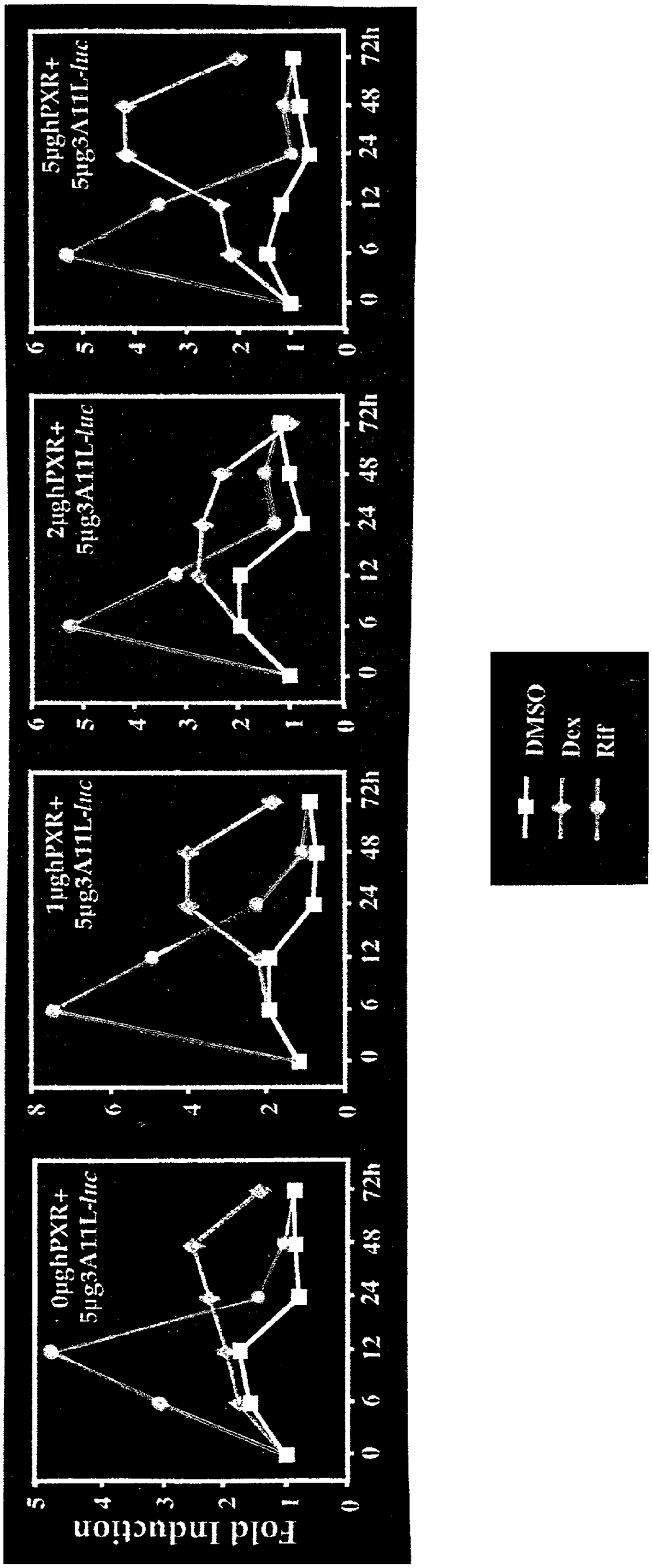
FIG. 13, panels A-D, depict the results of hPXR titration experiments performed in order to optimize the amount of HPXR plasmid co-administered with 5 μg of pGL3-I-3A11L. Panel A, 0 μg hPXR+5 μg 3A11L-luc. Panel B, 1 μg hPXR+5 μg 3A11L-luc. Panel C, 2 μg hPXR+5 μg 3A11L-luc. Panel D, 5 μg hPXR+5 μg 3A11L-luc.

To test this notion, we conducted liver push experiments with varying amounts of hPXR and the cyp-expression constructs described in Example 1. As shown in FIGS. 11, 13 and 16, PXR is not required for rifampicin uptake or induction of luciferase activity mediated by CYP3A4L or Cyp3A11M. Indeed, in certain cases, induction of luciferase expression actually decreased when higher dosages of PXR were used.

Thus, administration of a rifampicin co-receptor is not required for ripampicin uptake.

C. Human CYP3A4 Constructs

Briefly, expression constructs described in Example 1B were intravenously injected into mice and imaged as described above two weeks later (pre-treatment group). For each expression construct, a 2.2 ml volume of plasmid mixture (pGL3-I-CYP3A4M or pGL3-I-CYP3A4L) was intravenously injected into a 22 gram FVB female mouse over a period of less than 8 seconds. For imaging, the substrate luciferin was injected into the peritoneal cavity at a dose of 150 mg/kg body weight (15 mg/ml luciferin stock). Mice were then anesthetized in a gas chamber with isoflurane/oxygen. 5 minutes after luciferin injection, anesthetized mice with isoflurane tubing on noses were placed on the imaging stage and imaged from the inventral side for 1 minutes using Xenogen IVIS imaging system. Relative photon emission over the liver region was quantified using LivingImage software.

Figure 15:
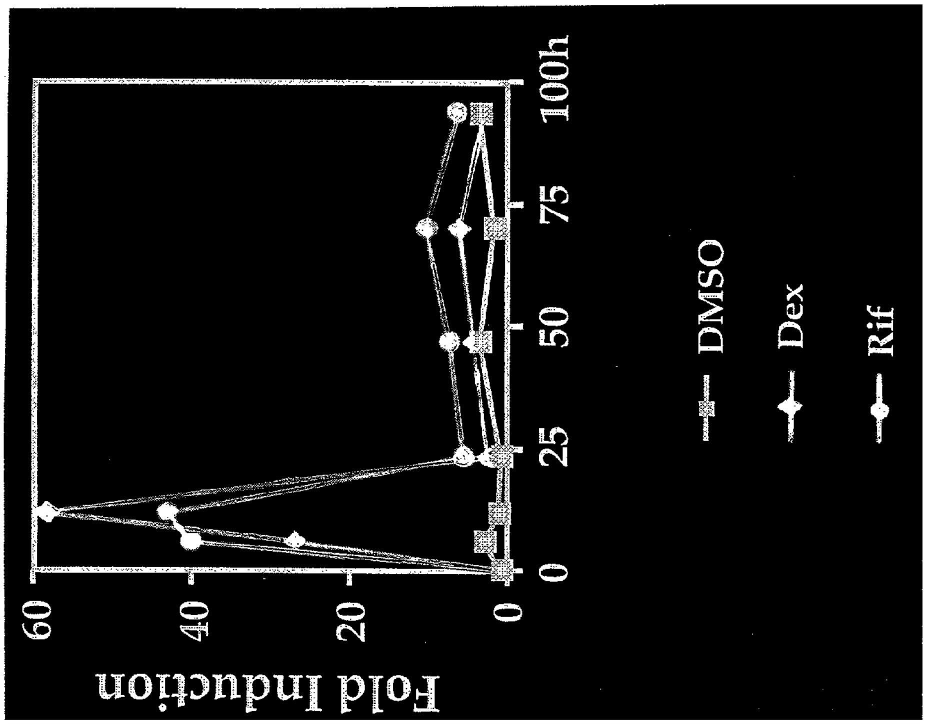
FIG. 15 depicts the results of liver push experiments wherein FVB mice were liver-pushed with 5 μg of the pGL3-I-3A4L construct and 1 μg of hPXR plasmid.
Figure 14:
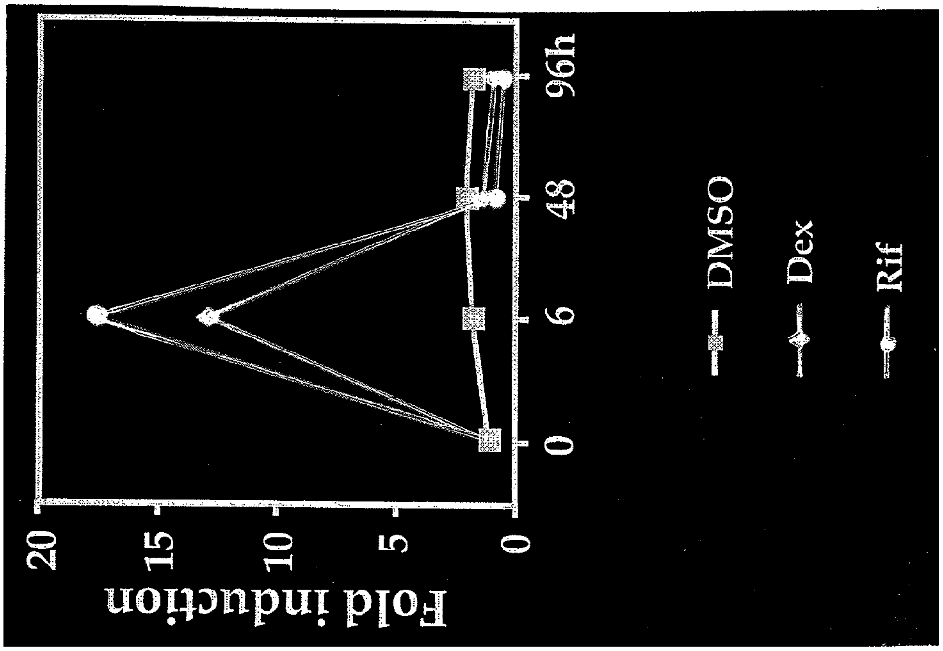
FIG. 14 depicts the results of liver push experiments wherein FVB mice were liver-pushed with 5 μg of the pGL3-I-3A4L construct and 0 μg of hPXR plasmid.

As shown in FIG. 14, mice subjected to liver push with 5 μg of pGL3-I-CYP3A4L and 0 μg of hPXR showed approximately 15-fold induction of luciferase activity approximately 6 hours after Rif administration; approximately 13-fold induction 6 hours after dexamethasone treatment and little or no induction at any time following DMSO administration. As shown in FIG. 15 (data shown for second dose; twelve days after first dosing, mice were treated with a second dose and imaged), mice subjected to liver push with 5 μg of pGL3-I-CYP3A4L and 1 μg of hPXR showed approximately 40-fold induction of luciferase activity approximately 12 hours after Rif administration; approximately 60-fold induction 12 hours after dexamethasone treatment and little or no induction at any time following DMSO administration.

Furthermore, the 13 Kb promoter (pGL3-I-CYP3A4L) mediated much higher expression in the livers than the 10.5 Kb promoter (pGL3-I-CYP3A4M) by approximately 25 fold.

EXAMPLE 3

High Through-Put Toxicity Screening Via the Cyp3A11/CYP3A4 Promoter Sequence Compounds can be screened for safety and/or possible toxicity by monitoring their ability to modulate Cyp3A11 or CYP3A4 promoter-mediated bioluminescence in transfected cells. Host cells (e.g., liver cells) are transfected, for example using lipofectamine (Promega, Madison, Wis.) with Cyp3A11-Luc or CYP3A4-Luc constructs and are plated into 96 well plates and used for high-through-put screening of a compound library. Transfections are carried out according to the manufacturer's instructions or standard protocols. After transfection, the cells are treated with selected compounds for approximately 36 hours and, subsequently, the cells are lysed with passive lysis buffer (Promega) and assayed with the Dual-Luciferase Reporter Assay System (Promega) for luciferase activity.

EXAMPLE 4

In Vivo Monitoring of Cyp3A11- or CYP3A4-Mediated Metabolism

A. Mouse Cyp3A11

Transgenic mice carrying the Cyp3A11 promoter-LucYG-expression cassette are obtained with known methods for generating transgenic mice (see the discussion above). These animals ("founders") were bred to non-transgenic mates to produce litters ("F1 animals").

F1 animals from the founders are imaged from the age of one to six weeks according to the methods described above. The observed signal intensities were quantified.

These experiments demonstrate that the expression cassettes and transgenic animals of the present invention may be used to monitor Cyp3A11 promoter-mediated expression of bioluminescence in vivo.

B. Human CYP3A4

Transgenic mice were generated using the pGL3-I-CYP3A4M-luc or pGL3-I-CYP3A4L constructs. For pGL3-I-CYP3A4M, the plasmid was digested with BamHI and the 12.5 kb fragment containing the 10.5 Kb CYP3A4 promoter, a chimeric intron, and firefly luciferase cDNA was purified from agarose gel by electroelution. For pGL3-I-CYP3A4L, the plasmid was digested with PvuI and the 15 kb containing 13 Kb CYP3A4 promoter, a chimeric intron, and firefly luciferase cDNA was purified from Agarose gel by electroelution.

The purified fragments were then each microinjected into single cell stage FVB embryos. The embryos were then implanted into pseudo-pregnant mice. The founders were screened by PCR and imaging and the resulting transgenic animals were imaged from the age of one to six weeks according to the methods described above. The observed signal intensities were quantified. Luciferase levels were highest in the livers of pGL3-I-CYP3A4L animals and in the intestines of pGL3-I-CYP3A4M animals.

EXAMPLE 5

Identification of Repeat Sequences and Promoter Regions

A. In The Cyp3A11 Promoter Region.

FIG. 1A (SEQ ID NO:12) comprises the nucleotide sequence of a transcriptional control element from the mouse Cyp3A11 gene locus. In the figure, the sequence represents 12,275 nucleotides in total, the translational start codon (ATG) is located at positions 11,003-11,005, a TATA box is located at positions 10,884 to 10,887, a major transcription start site begins with the C at position 10,914. An approximately 9.3 kb region of the Cyp3A11 gene is from nucleotide position 1 to 9,330 of FIG. 1A and the approximately 9.3 kb sequence is presented alone in FIG. 1B (SEQ ID NO:13). The present invention also includes a transcriptional control element sequence comprising a polynucleotide of nucleotides 1-11,002 of SEQ ID NO:12.

The approximately 9.3 kb sequence from the mouse Cyp3A11 promoter was used in a BLAST search of GenBank. In one search, a match to a mouse L1 element (LINE family of repeated sequences)(Locus MUSL1M9) was identified. There are three known families of L1 elements in the Mus genome (Mears, M. L., and Hutchison, C. A., J Mol Evol January 2001; 52(1):51-62). L1 elements are believed to be associated with a retrotransposon subfamily in mice (e.g., Goodier J. L., et al., Genome Res October 2001; 11(10): 1677-85). Aligning this sequence with the 3A11 sequence identified a region with approximately 91% identity (see FIG. 18).

Figure 18:
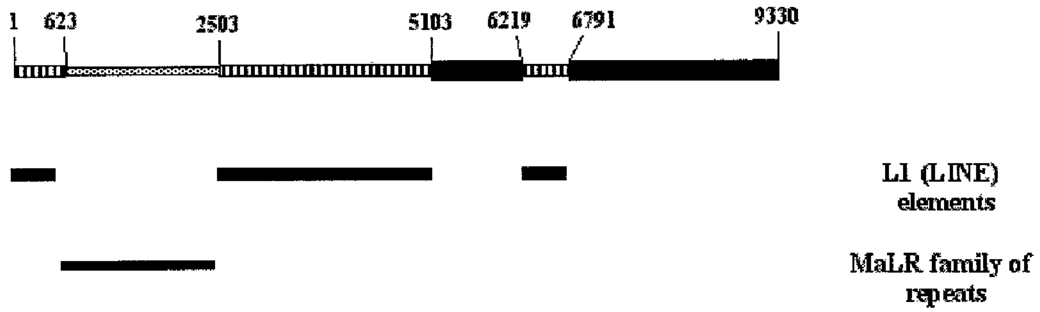
FIG. 18 presents a schematic diagram of an approximately 9.3 kb promoter region sequence, located 5' to the Cyp3A11 coding sequences in the mouse genome, where the diagram shows the approximate locations of repeat elements from two known families.
Figure 19:
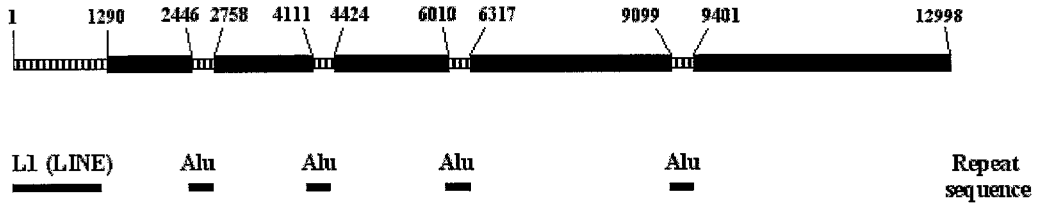
FIG. 19 presents a schematic diagram of an approximately 13 kb promoter region sequence, located 5' to the CYP3A4 coding sequences in the human genome, where the diagram shows the approximate locations of repeat elements from two known families.

In addition, the approximately 9.3 kb 3A11 sequence was analyzed using the RepeatMasker program which can identify regions that have high homology to known repeated sequences (e.g. LINES, SINES, and LTR elements). Three regions (approximately 1-623, 2503-5 103, and 6129-6791) were identified having high homology (91%) to L1 elements (FIG. 18). Another region (approximately 623-2503) was shown to be highly homologous to the mouse MaLR family of repeats (FIG. 18). The MaLR family of repeats is also thought to be associated with a mammalian retrotransposon-like super-family (Kelly, R. G., Genomics December 1994; 24(3): 509-15).

Two primary non-repeat regions of the approximately 9.3 kb 3A11 sequence were identified (approximately 5104-6218 and 6792-9330).

B. In The CYP3A4 Promoter Region.

FIG. 17A (SEQ ID NO:14) comprises the nucleotide sequence of a transcriptional control element from the human CYP3A4 gene locus. In the figure, the sequence represents 13,035 nucleotides in total, the translational start codon (ATG) is located at positions 13,033 to 13,035, a TATA box is located at positions 12,901 to 12,904, a major transcription start site begins with the A at position 12,930. An approximately 2.5 kb region of the CYP3A4 gene, useful to facilitate expression as described herein, is from nucleotide position 1 to 2,461 of FIG. 17A and the approximately 2.5 kb sequence is presented alone in FIG. 17B (SEQ ID NO:15).

Similar analyses to those described above were carried out on the approximately 13 kb CYP3A4 promoter region. A summary of the results of this analysis are presented in FIG. 19. Two different kinds of repeat sequences were identified: L1 elements and Alu repeats.

Five primary non-repeat regions of the approximately 13 kb CYP3A4 promoter region were identified (approximately 1290-2446, 2758-4111, 4424-6010, 6317-9099, and 9401-12998).

EXAMPLE 6

Generation of a CYP3A4-luc FvB Transgenic Mouse Line

A. Plasmid Construction

A CYP3A4-luc reporter was designed essentially as described in Example 1B, briefly as follows. A BAC clone containing the human CYP3A4 promoter region was screened by PCR using primers (5'-GTTGGTACCCTGCAGTGACCACTGCCCCATCATTG-3' (SEQ ID NO:9) corresponding to nt −1105 to −1080 and 5'-ATCAAGCTTCCTTTCAGCTCTGTGTTGCTCTTTGC-3' (SEQ ID NO:10) corresponding to nt +40 to 69 of CYP3A4 promoter region. The primers were also used to amplify a 1.2 kb promoter region of CYP3A4 from human genomic DNA using pfu DNA polymerase (Stratagene, La Jolla, Calif.). The PCR product was digested with KpnI/HindIII and purified from agarose gel using Geneclean Kit (Qbiogene, Carlsbad, Calif.). The 1.2 kb promoter region was cloned into pGL3-Basic vector (Promega, Madison, Wis.) containing the modified firefly luciferase cDNA sequences. A 233 bp HindIII fragment containing a chimeric intron from pCAT-3-Basic vector (Promega, Madison, Wis.) was then inserted between the CYP3A4 promoter region and the luciferase gene. A 1.88 kb KpnI/BglII fragment, a 950 bp BglII fragment, and a 10 kb KpnI fragment subcloned from the BAC clone were inserted sequentially into the previous construct. The final construct pGL3-I-CYP3A4 contains a 13 kb human CYP3A4 promoter region, 233 bp chimeric intron, and modified firefly luciferase cDNA. All the joints in the construct were confirmed by DNA sequencing (Stanford PAN Facility, Stanford, Calif.). The entire sequence of CYP3A4-luc transgene is shown in FIG. 17C (SEQ ID NO:17).

B. Generating CYP3A4-luc Transgenic (Tg) Mice

The transgenic lines were created by the microinjection method (see, e.g., U.S. Pat. No. 4,873,191 to Wagner, et al. (issued Oct. 10, 1989); and Richa, J., (2001) "Production of transgenic mice" Molecular biotechnology March 2001 vol. 17:261-8) using FVB donor embryos.

C. Screening Tg Mice

Eighteen founder mice were screened by PCR using luciferase primers LucF1 and LucR4 or primers Luc 3 primer (5'-GAAATGTCCGTTCGGTTGGCAGAAGC-3' (SEQ ID NO:18)) and Luc 4 primer (5'-CCAAAACCGTGATGGAATGGAACAACA-3' (SEQ ID NO:19)). These same primers were also used to screen Tg offspring.

(i) PCR Screening

Figure 20:
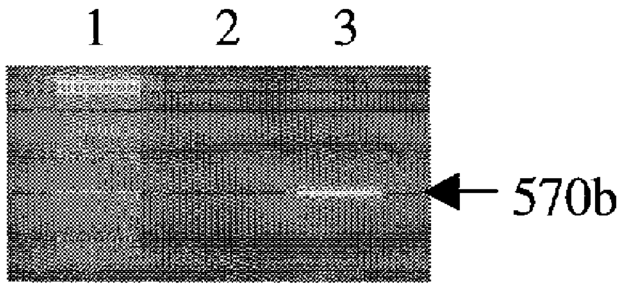
FIG. 20 presents exemplary results of PCR screening CYP3A4-luc Tg mice.

FIG. 20 presents exemplary results of PCR screening CYP3A4-luc Tg mice. In the figure: Lane 1, DNA ladder; Lane 2, negative littermate; Lane 3, positive littermate. The results demonstrate the identification of CYP3A4-luc Tg mice.

(ii) Southern Hybridization Analysis

Figure 21:
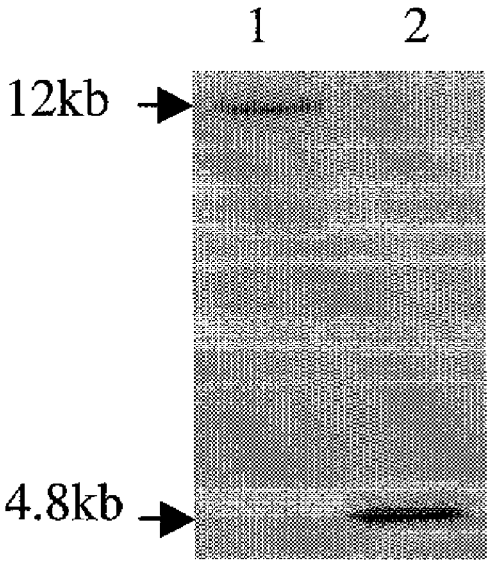
FIG. 21 presents exemplary Southern hybridization analysis data for FVB/N-TgN(CYP3A4-luc).

The 1.8 kb HindIII/XbaI fragment from pGL3-Basic containing the entire luciferase cDNA (Promega Corp.) was used as probe for Southern hybridization. Ten μg of heterozygous genomic DNA was digested with BamHI and 17 pg of pGL3-Basic was loaded as a positive control (FIG. 21). The expected size of transgene was 12 kb. The results of an exemplary hybridization analysis are shown in FIG. 21. In the figure: Exemplary screening results of FVB/N-TgN (CYP3A4-luc) mice by Southern hybridization are presented in FIG. 21. In the figure: Lane 1, 10 μg of CYP3A4-luc Tg genomic DNA; Lane 2, 17 pg of pGL3-Basic positive control. These results demonstrate the presence of the transgene in the transgenic mice.

D. Phenotyping Data as Applied to Selection Criteria

General methods for evaluating the animal lines were as follows. Tg founders were bred to wild-type FvB mice to generate F1 mice. A female transgenic founder was bred to a wild-type FvB male and a male transgenic founder was bred to a few wild-type FvB females.

A Luciferin stock solution of 30 mg/ml was prepared in sterile PBS. Luciferin was purchased as D-Luciferin Potassium Salt, as Cat #XR-1001, from Lot #14021/2 from Biosynth A G, Switzerland.

Dexamethasone (Cat #D1756), rifampicin (Cat #R3501), pregnenolone (Cat #P9129), clotrimazole (Cat #C6019). Nifedipine (Cat #N7634), 5-Pregnen-3b-OL-20-ONE-16a-Carbonitrile (Cat #P0534), and phenobarbital (Cat #P3761) were all purchased from Sigma (St. Louis, Mo.). Phenobarbital was prepared in PBS buffer and others in DMSO.

The route of administration for the drugs and for luciferin was IP. The dose of reagent administration of luciferin substrate and drugs was as follows. Dose of luciferin: 150 mg/kg of a 30 mg/ml luciferin stock was injected IP five minutes before imaging in the IVIS™ (Xenogen Corporation, Alameda, Calif.) system. Dose of chemicals: All drugs, with the exception of phenobarbital, were prepared in DMSO and were injected IP at a dose of 50 mg/kg (phenobarbital was prepared in PBS at 100 mg/Kg). DMSO was administrated as a vehicle control. The duration of treatment was typically for 2-3 days.

Following luciferin administration the animals were anesthetized using gas anesthesia (Isoflurane) and placed in an IVIS™ box (Xenogen Corporation, Alameda, Calif.) for imaging. All animals were imaged before and after chemical administration, and imaged at high resolution (binning 2) for 10 seconds or 1 minute, for males and females, respectively.

Induction of CYP3A4-luc by typical CYP3A4 inducers Dexamethasone (50 mg/kg body weight) and Rifampicin (50 mg/kg body weight) was evaluated in the animals. F1 mice from each founder (i.e., mice PCR positive for the presence of the transgene) were imaged at T=0 (pretreatment) and at T=3 hours and T=6 hours following administration of DMSO, Dexamethasone (Dex), or Rifampicin (Rif). This was performed on groups of three mice (including both genders) from nine of 18 founder lines. Primary screening results from Dex and Rif treatments are described below:

(a) Lines #75, 195, 230, and 240 showed induction in the intestine region, with higher intestinal basal expression than liver basal expression.

(b) Line #225 showed induction by Dex and Rif in liver and intestine, but had higher intestinal basal expression than liver basal expression.

(c) Line #233 showed strong induction in intestine and slight induction in liver region by Dex and Rif. This line had high intestinal basal expression.

(d) Line #221 showed no induction by either drug and had very low level of basal expression.

(e) Line #82 and 208 showed stronger induction by Dex and Rif in liver than in other regions, and basal expression in liver was greater than basal expression in intestine; males responded stronger than females.

The data were evaluated against the selection criteria described earlier in the specification; (i) induction of gene expression in the liver—Lines #225, #233, #82 and #208 satisfied this criterion; (ii) greater induction in the liver region than in other regions (e.g., intestine)—Lines #82 and #208 satisfied this criterion; and (iii) basal expression in liver that is greater than or equal to basal expression in other parts of the body (e.g., intestine)—Lines #82 and #208 satisfied this criterion.

Mice satisfying the above criteria were typically selected for subsequent analysis. Because Lines #82 and #208 showed strong induction by Dex and Rif in liver and had higher basal luciferase levels in the male liver region, they were selected for secondary screening.

Secondary Screening:

Lines #82 and #208 met the first set of criteria, in particular, transgene (CYP3A4-luc) expression was induced in liver region by Dex as well as Rif, and transgene expression in the animals showed higher liver basal expression, at least in males. These two lines looked almost identical in primary screening. Line #82 was further characterization with seven compounds believed to induce CYP3A4 expression, including pregnenolone (Preg), phenobarbitol (Phenob), rifampicin (Rif), nifedipine (Nif), 5-pregnene-3b-OL-20-ONE-16a-Carbonitrile (PCN), dexamethasone (Dex) and clotrimazole (Clotrim). Expression was evaluated in both genders. Exemplary results are presented in FIG. 22, panels A-D, described below. Line #82 responded most of CYP3A4 inducers in liver, this line was chosen as final line designated as FVB/N-TgN(CYP3A4-luc).

The results of an exemplary analysis of induction of CYP3A4-luc transgene in Tg mice are presented in FIG. 22, panels A-D. In the figure, mice were imaged at T=0 (pretreatment) and T=6 hours following administration of DMSO, pregnenolone (Preg), phenobarbitol (Phenob), rifampicin (Rif), nifedipine (Nif), 5-pregnene-3b-OL-20-ONE-16a-Carbonitrile (PCN), dexamethasone (Dex) and clotrimazole (Clotrim). NT is the non-treated control. Before each imaging session, mice were injected i.p. with 150 mg/kg luciferin. Panel A presents exemplary induction data for nine male mice, each mouse treated with the compound shown in the legend at the bottom of Panel C. Panel C presents exemplary induction data for nine female mice, each mouse treated with the compound shown in the legend at the bottom of Panel C. Panel B presents a bar graph showing similar induction experiments where the results are presented for each treatment (shown at the bottom of Panel D) as applied to a group of three male mice. Measurements on each mouse were performed as described above. Associated error bars are shown. Panel D presents a bar graph showing similar induction experiments where the results are presented for each treatment (shown at the bottom of Panel D) as applied to a group of three female mice. Measurements on each mouse were performed as described above. Associated error bars are shown.

The results of this analysis demonstrate that CYP3A4-luc Tg mice having desirable phenotypes, as outlined in the above criteria, can be identified by the methods taught herein.

As is apparent to one of skill in the art, various modification and variations of the above embodiments can be made without departing from the spirit and scope of this invention. These modifications and variations are within the scope of this invention.

What is claimed is:

1. An expression cassette that activates expression of a reporter sequence in mouse liver cells, the expression cassette comprising a reporter sequence; and a polynucleotide comprising an inducible transcriptional control element and having at least 95% identity to nucleotides 1-11,002 of SEQ ID NO:12, wherein the polynucleotide is operably linked to the reporter sequence such that when expression of the polynucleotide is induced by a compound that activates expression of the reporter sequence, the reporter sequence is expressed in liver cells.

2. The expression cassette of claim 1, wherein the reporter sequence encodes a light-generating protein.

3. The expression cassette of claim 2, wherein the light-generating protein is a bioluminescent protein or a fluorescent protein.

4. The expression cassette of claim 3, wherein the bioluminescent protein is luciferase.

5. The expression cassette of claim 3, wherein the fluorescent protein is selected from the group consisting of blue fluorescent protein, cyan fluorescent protein, green fluorescent protein, yellow fluorescent protein, and red fluorescent protein.

6. A vector comprising (a) the expression cassette of claim 1; and (b) a vector backbone.

7. The vector of claim 6, wherein said vector backbone further comprises a selectable marker.

8. A mouse liver cell comprising the expression cassette of claim 1.

9. A mouse liver cell comprising a vector of claim 6.

10. A transgenic mouse comprising liver cells, wherein the liver cells comprise the expression cassette of claim 1.

11. A method for identifying an analyte that modulates expression of a sequence encoding a light-generating protein, in a living mouse, said method comprising intravenously administering to a living mouse via the tail vein a vector mixture comprising the expression cassette of claim 2 such that hepatocytes of the mouse express the light-generating protein in the presence of a compound that activates expression of the sequence encoding the light-generating protein, administering to said mouse said analyte; and monitoring expression of said light-generating protein, wherein expression of the light-generating protein indicates that the analyte modulates expression of the reporter sequence.

12. A method for monitoring expression of a reporter sequence in an isolated mouse liver cell, said method comprising:

monitoring, in the presence of a compound that activates expression of the reporter sequence, the expression of a reporter sequence in an isolated mouse liver cell, said cell comprising the expression cassette of claim 1.

* * * * *

SEQUENCE LISTING

```
<160> NUMBER OF SEQ ID NOS: 19

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence:
      Cyp3A11TopEcoRI.primer

<400> SEQUENCE: 1

gttgaattcc agctaatgag ggcaaagttc tcag                              34


<210> SEQ ID NO 2
<211> LENGTH: 34
<212> TYPE: DNA
<213> ORGANISM: Artificial Sequence
<220> FEATURE:
<223> OTHER INFORMATION: Description of Artificial Sequence:
      Cyp3A11Bot XhoI.primer

<400> SEQUENCE: 2

atcctcgagc ttctctgtgt tctccctaca actg                              34


<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence:
      Cyp3A11F1.primer

<400> SEQUENCE: 3

ggtatgtggt gcttgtgtat gcatac                                       26


<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence:
      Cyp3A11R2.primer

<400> SEQUENCE: 4

cagataggat tgagtgagcc agagg                                        25


<210> SEQ ID NO 5
```

-continued

<211> LENGTH: 34
<212> TYPE: DNA
<213> ORGANISM: Artificial Sequence
<220> FEATURE:
<223> OTHER INFORMATION: Description of Artificial Sequence: Intron Top
BglII.primer

<400> SEQUENCE: 5
tcgagatctt gcggccgctt aactgcagaa gttg 34

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Intron Bot
HindIII.Primer

<400> SEQUENCE: 6
gccaagcttg cggccgctta agagctg 27

<210> SEQ ID NO 7
<211> LENGTH: 34
<212> TYPE: DNA
<213> ORGANISM: Artificial Sequence
<220> FEATURE:
<223> OTHER INFORMATION: Description of Artificial Sequence:
Cyp3A11TopKpnI.primer

<400> SEQUENCE: 7
gttggtaccc agctaatgag ggcaaagttc tcag 34

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence: Cyp3A11Bot
HindIII.primer

<400> SEQUENCE: 8
atcaagcttc ttctctgtgt tctccctaca actg 34

<210> SEQ ID NO 9
<211> LENGTH: 35
<212> TYPE: DNA
<213> ORGANISM: Artificial Sequence
<220> FEATURE:
<223> OTHER INFORMATION: Description of Artificial Sequence: primer
3A4Top

<400> SEQUENCE: 9
gttggtaccc tgcagtgacc actgccccat cattg 35

<210> SEQ ID NO 10
<211> LENGTH: 35
<212> TYPE: DNA
<213> ORGANISM: Artificial Sequence
<220> FEATURE:
<223> OTHER INFORMATION: Description of Artificial Sequence: 3A4Bot
Primer

<400> SEQUENCE: 10
atcaagcttc ctttcagctc tgtgttgctc tttgc 35

<210> SEQ ID NO 11
<211> LENGTH: 24

-continued

<212> TYPE: DNA
<213> ORGANISM: Artificial Sequence
<220> FEATURE:
<223> OTHER INFORMATION: Description of Artificial Sequence: primer
      lucF1

<400> SEQUENCE: 11
gccattctat ccgctggaag atgg 24

<210> SEQ ID NO 12
<211> LENGTH: 12275
<212> TYPE: DNA
<213> ORGANISM: Artificial Sequence
<220> FEATURE:
<223> OTHER INFORMATION: Description of Artificial Sequence: mouse
      Cyp3A11 gene locus
<220> FEATURE:
<221> NAME/KEY: misc_feature
<222> LOCATION: (5319)
<223> OTHER INFORMATION: 'n' = a, c, g or t
<220> FEATURE:
<221> NAME/KEY: misc_feature
<222> LOCATION: (5931)
<223> OTHER INFORMATION: 'n' = a, c, g or t
<220> FEATURE:
<221> NAME/KEY: misc_feature
<222> LOCATION: (7038)
<223> OTHER INFORMATION: 'n' = a, c, g or t

<400> SEQUENCE: 12
ggtacctggt atctgtccag aaattcatcc atttcatcca ggttttccag ttttgttgag 60
tatagctttt tgtagaagga tctgatggtg ttttggattt cttcaggatc tgttgttatg 120
tctccctttt catttctgat tttgttaatt aggatgttgt ccctgtgccc tctagtgagt 180
ctagctaagg gtttatctat cttgttgatt ttctcaaaga accaactcct cgtttggtta 240
attcttttaa tagttcttct tgtttccact tggttgattt cacccctgag tttgattatt 300
tcctgctgtc tactcctctt gggtgaattt tcttcctttt ttttctagag cttttagatg 360
tgttgtcaag ctgctagtgt atgccctctc cagtttcttc ttggaggcac tcagagctat 420
gagtttccct cttagaaatg ctttcattgt gtcccatagg tttgggtatg ttgtggcttc 480
gttttcatta aactctaaaa agtctttaat ttctttcttt attccttcct tgaccaaggt 540
atcattgaga agagtgttgt tcagtttcca tttgaatgtt tgctttccat tatttaatgt 600
tgccttagtc catggtggtc tgtgtcttag tcagggtttc ttttcctgca caaacatcat 660
gaccaagaaa caagttgggg atgaaagggt ttattcagct tacacttcca tgctgctgtt 720
catcaccaaa ggaagtcagg actggaactc aaacagatca gggagcagga gctgatgcag 780
aggccatgga gggatgttct ttactggctt gccttccctg gcttgctcag cctgctctct 840
tatagaatcc aagactacca gcccagagat ggcaccaccc acaaggggcc tttcccccctt 900 gatcactaat tgagaaaatg ccttacagtt ggatctcatg gaggcatttc ctcaactgaa 960
gctcctttct ctgtgatatc tccagctgtg tcaagttgac acaaaactag ccagtacaat 1020 tgacccccttg tcaacttgac acacaaacac atcactagta accctcaacc cttacattct 1080
tattcatccc caagatctaa ataactttaa aagtcccaca gtctttacat attcttaaaa 1140
tttcaatctc tttaaaatat ccatctcttt taaaatccaa agtcttttta caattaaaac 1200
tctcttaact atggcctcca ctaaaacagt ttcttccttc aagagggaaa atatcagggc 1260
acagtcaaag caaaaatcaa tctccaacca tccaatgtct gggatccaac tcacaatctt 1320
ctggactcct ccaagggctt gtgtcacttc tccagccatg ccctttgtag cacaggtgtc 1380

-continued atcctctagg ttccagatgc ctgtactcca ctgatgctgc tgctcttggt ggtcatctca 1440
tggtactggc atctccaaaa cactgcatgg ccccttcagt cctgggcctt caattgcaac 1500
tgaggctgca ccgtcaccaa tggccttcca tgccctctca cagtgccgag cctcagctgc 1560
tgtgcatgac cccttcatgc cttcaaaacc agtaccacct gggtgaccct tatacattac 1620
caagtcccac tgcagcagga gtacaacctt ggctatctct ggaacacagc ctctttgtgc 1680
tttcagaaaa cacttcccag aagatgtcac ctcaacgacg ctggtctctt cttaatcacc 1740
gataatttct tagctccagc taaccagcat caatagtcat agtaatgcaa ggttttgctt 1800
tagtagttct ggtatcttgt taatcacagt tgattcttca gccccagcta accagaacta 1860
cagaattttc acaatcaaaa cagcaatggc cctgaaaaga gtctttaatt ttccctctga 1920
aatttcacaa gccagacctc catcttctgc actgttctca acattatctt ctaagctcct 1980
acacaacatc tgacagagct cttaacaatg aacggatctt caagccgaaa gttccaaagt 2040
ccttccacag tcctccccaa aacatggtca ggttgtcaca ggaatacccc actcctggta 2100
ccaatttgtc ttagtcaggg tttctattcc tgcacaaaca tcatggccaa gaaacaagtt 2160
ggggaggaaa gggtttattt agcttacact tccatgctgc tgttcatcac caaaggaagt 2220
caggactgga actcaaacag gtcagggagc aggagctgat gcagaggcca tggagggatg 2280
ttctttactg gcttgccttc cctggcttgc tcagcctgca ctcttataga atccaagact 2340
accagcccag agatggcacc acccacaagg ggcctttccc ccttgatcac taattgagaa 2400
aatgccttac agttggatct catggaggca tttcctcaac tgaagctcct ttctctgtga 2460
tatctccagc tgtgtcaagt tgacacaaaa ctagccagta cagtctgata ggatgcatgg 2520
gacaatttca atatttttgt atctgttgag gcctgttttg tgaccaatta tatggttaat 2580
tttggagaag gttccgtgag gtgctgagaa gtatatcatt ttgttttagg ataaaatgtt 2640
ctgtagatat ctgtcaaatc catttgtttc atcacttctg ttagtttcac tgtgtcctgt 2700
ttagtttctg ttttcatgat ctgtccactg atgaaagtgg tgtgttgaag tctcccacta 2760
ttattgtgtg aggtgcaatg tgtgctttga gctttactaa agtgtcttta atgaatgtgg 2820
ctgcccttgc atttggagca tagatattca aaattgagag ttcctcttgg aggattttac 2880
ctttgatgag tatgaagtgt ccctccttgt cttttttgat aactttggtt tggaagttga 2940
ttttatttga tattagaatg gctaccccag cttgtttctt cagaccattt gcttggaaaa 3000
ttgttttcca gcctttcact ctgaggtagt gtctgtcttt ttccctgaga tgggtttcct 3060
gtaagcagca gaatgttggg tcctgtttgt gtagccagtc tgttagtcta tgtcttttta 3120
ttggggaatt gagtccattg atattaagag atattaagga aaagtaattg ttgcttccta 3180
ttatttttgt tgttagagtt ggcattctgt tcttttggct gtcttctttt tggcttgttg 3240
aggaattact ttcttgcttt ttctagggcg tgatatctgt ccttgtattt ttttttctgt 3300
tattatcctt tgaagggctg gattctggaa agataatgtg tgaatttggt tttgtcatgg 3360
aatactttgg tttctccatc tatggtaatt gagagtttgg ccgggtatag tagcctgggc 3420
tggctttttt ttgttctctt agtgtctgta taacatctgt ccaggctctt ctggctttca 3480
tagtctctgg tgaaaagtct ggtgtaattc tgataggcct gcctttatat gttacttgac 3540
ctttctcccg tactgctttt aatattctct ctttatttag tgcatttgtt gttctgatta 3600
ttgtgtgttg ggaggaatct cttttctggt ccagtctata tggagttctg taggcttctt 3660
gtatgttcat gggcatgtca ttctttaggt tcgggaagtt ttcttctata attttgttga 3720
aaatatttgc tggccccttta agttgaaaat cttcattctc atcaactcct attatctgta 3780

-continued

```
ggtttggtct tctcattgtg tcctggattt cctggatgtt ttgagttagg acctttttgt   3840
gttttgtatt atctttgatt gttgtcctga tgttctctat ggaatcttct gcacctgaga   3900
ttctctcttc catcttttgt atcctgttgc tgatgctcac gtctatggtt ccagatttct   3960
ttcctagagt ttctatctcc agcgttgcct cactttgggt tttctttatt gtgtctactt   4020
cccttttag gtctagtatg gctttgttca tttccatcac ctgtttggat gtgtttgcct   4080
gtttttctat gaggacttct acctgtttgg ttgtgttttc ctgctattct ttaaggattt   4140
gtaactcttt agcagtggtc tcctgtattt ctttaagtga gttattaaag tccttcttga   4200
tgtcctctac catcatcatg agatatgctt ttaaatacag gtctaccttt acggttgtgt   4260
tggggtgccc aggactaggt ggggtgggag tgctgcattc tgatgatggt gagtggtctt   4320
gatttctgtt agtaggattc ttacgttttc cttttgccat ctggtaatct ctggagttat   4380
ttgttatagt agtctctggt tagagcttgt tcctcaggtg attctgttat gctctatcag   4440
cagacctggg agactagctc tatccttagt ttcagtggtc agagtactct ctgcaggcaa   4500
gctctcctct tgcagggaag gtgcccagat atctggtgtt tgaacctgcc tcctggcaga   4560
agttgtgttc tactcaccat aggtcttaag atcccatggt tggtcctgtg tggttccttg   4620
cgtgtgtccg gagactcccc gggccagggt ccctggtgat tggaagggac ttgtgcaccg   4680
gatcaggcca ggttatctga ttccttaatt aatgcagtct caggtcccgt gcgattgaat   4740
tggagcaggc gctgtgttcc actcaccaga ggtcttagga tcctgtggag gatcctgtgt   4800
gggtccttgc gggtgtctgc agactccccg ggccagggac catggtgctg cagtgggccg   4860
gaagggactt gagccctgga tcatgccgga ttatctgctt ccttaattaa tgcagtctca   4920
ggtcctggcg attggattgg agcaggcgct gtgttccact caccagaggc cttagaatcc   4980
cgtggcggat cctgtgtggg tccttatggg tgtccgcaga ctccccgggg ctagggacca   5040
cggtgctcca gtgggccgga agggacttga gccccggatc aggccggatt atctgcttcc   5100
ttaattcctg atagtctttt aaaagtaaac ttatagttag acactgtaca caggtatata   5160
atacatttta aatattctct cactatgcca ggtggtatca tataagaact tttgaatata   5220
tttcttaaag attaatttta atattttatg ctcttatact atgcttaatt cccaaagaat   5280
attttgtatg ttttgaaaca atttactctt caacattana tataggattc acagttatag   5340
atagtattaa atgtccatta atgatatttt tagggtataa aaggatatga atataaaagt   5400
tgaacaaaaa agaggggatg ggccataaag aatatattca tatgtatata tatatgtgaa   5460
taattcaaag aataaataaa tataatttta aaaagcagca ggtatccccc ccaaaataca   5520
gttgttgaag tgccttgtga tagaaccttg tcaaatgata aaccaaagaa ataccaacta   5580
cccacccagc cacccaagag atggattaga gtcagtggat tattcagggt gtgggagcct   5640
gaggataaaa aatcagaacc ccagaccccc taaaaaaggt atgcagaccg tacagccatt   5700
ttatagtttt gtgttgagct tcattcagcg ggactctggg tacacatggc ttgtgtgggg   5760
gtgtgttgac aacctgcaag tgttcattcc taagctgata tacacacaag cacataagta   5820
gcactaaatg gtctgtgacc ttgctttggg tgggggacaa gtatgtttgg caggggctaa   5880
atgatagaac cactaagttt agggctgtgg gagagacaga gataataaat ngatagggcc   5940
cacatttcag gcagtataca tttgtgccaa gcagtgtgaa tagaggcaag ttctaatggt   6000
attggcgaag tgcttgcata ttttatccat ggattcgaaa gtgttgggag tgggatggta   6060
acttgatccc tccaggagca aaggagggta gaaaaggaga ccaggagtgg gatggttgtg   6120
```

-continued

```
acagatccca gggaaaagcc aggtggaaca gaagggagct gggagaggtc agagtccgtg   6180
caatagctcc tgggcaaggc agaatgtgct tataaaacta cagagacaaa gtttggagct   6240
gtgacgaaag gatggaccat ctagagactg ccatatccag gggatccatc ccataatcag   6300
cttctaaacg ctgacaccat tgcatacact agcaagattt tgctgaaagg acccagatat   6360
agttgtctct atatgtgaga ctatgctggg gcctagcaaa cacagaagtg gatgctcaca   6420
gtcagctatt ggatggatca cagggctccc aatggaggag ctagagatag tacccaagga   6480
gctaaaggga tctgcaatcc tataggtgga acaacattat gaactaacca gtaccccgga   6540
gctcttgact ctagctgcat atgtatcaaa agatggccta gtagaccatc actggaaaga   6600
gaggcccatt ggacacgcaa actttatatt ccccagtaca ggggaacgcc agggccaaaa   6660
aaacaaaaaa caaaaaaaaa tgggaatggg tgggtaggga agtgtggggg agggtatggg   6720
ggacttttgg gatagcattg gaaatgtaat tgaggaaaat acgtaataaa aaatattaaa   6780
aaaaaaccta cataggacag acaggcaacc attttaggac aacccttgct ccagttgtta   6840
ggggacccat atgaagatat acctttatat ttgttacata tctgtgggtg ttggaggatc   6900
taagtccagc ccatctattc tctttggttg gtggctccat gagagctccc acggttctag   6960
gttatttgac tgttggtctc cctgtggagt tcctacccag tttggggccc tcaaaatttt   7020
tctcagtttt cttctcanag cttctgaact ccatccagtt tttggctgtg aatatctgca   7080
tcttcctgag taagcttttg gatagagcct cttagaggac aaccatacta ggctcttgtc   7140
tccaagttta aatgtatcat taatagtgtc agagattgat gcttgcccat gggattggtg   7200
tcaagttgga ccagttaatg gttgatcatt ccctcagtct ctgcttcatc tttgtccctg   7260
catttcttat aaacagacca atttttgttt caaaagtttt atgagtgggt tggtgttttt   7320
atacctccat tggggatcct gcctgatcct ggggagatgg cctcttcagg ttccatatcc   7380
cctttactat gattctctac taaggtcatt tacattgata tcggaggtct ttctttattc   7440
tgggtctctg gcttctccta gagatgcccc aatccctcac tcctagcagc tgtagatttc   7500
tattcactct cctggccctc tggctttcac tcctgtctct tccctcacca catcctgaac   7560
ccccatactc ccttcctcca cattcatggg tacatttttt aaatcccaga acacagaagg   7620
cagaagcagg cagatctcta caagttttag gcaagcctgg tctatagagc aaatttcagg   7680
atggccaggg ctacacagtg aaactctatc ttaaaaaaca aaaaaacaaa ataagttatt   7740
tattacatat ttacttgttt atatgtaagc atatatgtgt gggggctgaa gagaccagaa   7800
gacaagttgt ggaaattcat tcttctgttc catcacatag atgctgggaa ttaaaatcag   7860
gttgtcgggt ttggagacag gtgactttgt tgtctgagct tccttgagag cctataagtt   7920
tttctttcat tgttagtgtg ctagctgata tccacattgt tttctgtgct aggtatcctg   7980
aattccagtt gagtccacat gtcatggaat gtcctcttac aacctctgcc actgggtttt   8040
gtttcctact atttaactta ggactttttt tttggtagtg attcttacaa gaaaggtaca   8100
catacatttt tctttttga gtttgatttg gatcaagtta taatcgtgca agtcatggtg   8160
cccttcttac taagtctcta ggttgctatg gctttgtgaa aacttttgga ttttatccta   8220
aaaaaataat aattaaaaaa aaatccagta acaatcactt tgtgcacatt tattcctaag   8280
ctataagttt ccacttctgt aacgtaggta tttgagattg aagaagaaat ctttatgtgt   8340
atgggtgtct tgctggcatg catatccttg cactatgtgt atatctgggt gcctgtgaag   8400
gccaaattat gactacaaaa acccaggagc tggagctaaa gaccattgtg agccaccaga   8460
agggtactgg gaattgaatc caggtccttt acagcagtgg acaatagatg ttaactgctg   8520
```

-continued

```
agccatatct ttagctctaa catggggaca atagcttact tatccctagg acttatcatg   8580
aggaccccaa agagagtgaa aagtacttat aagatatgat gtcttatcct ctagagcaag   8640
aaagccagag aggaaatcct gctttatttt tttttagta ctcattgtca gcttgctggt   8700
ctcccttact ttgtccctgc ttagagggat gagtgtgggg tttttattac ccattggggg   8760
aacatcccaa ttggaatgag gtgctggttt ctcgactaat cctgtatgac accaaagaag   8820
tatgaatctg ttaaaggtga aaattttgcc atcaacaacc caaccttcat acttaagtct   8880
cagagaatac agaggaagag ggccagtaat atattaagag ttagaggact aggaattctg   8940
ctctcagatg gtgtctccaa gaaatggagg caggaccaga cacattaaat atcaacaatc   9000
tatacaagat acaatgaaat ctcaaatagg catggtaaag aatatatata tatataacac   9060
aataataata atcgcaaaga agccatgaat ttgataggga gttgcgagat gggaagaact   9120
ggagggagga gatgaaagaa gatgatctaa tttcattgta gttaataatt ttaaaagatg   9180
aagaacttga actttagaac aacatggtct cttggatcct ggtttcatta aggatttatt   9240
atgtaacctt gattgaatca gttatcattt ggggtatggt ttgttcactt gtgacagagt   9300
tatccctcac aacattgcag ggtagatgat atcagctaat gagggcaaag ttctcaggac   9360
tgtaaatatt agcaatcatt ctgtgatgta atcttggtgg gtatgtggtg cttgtgtatg   9420
catacacctg tggttgtatg gcactttgta ctctggagtt tcagttgaga aacaatgaat   9480
ttttagactt caaggccaca gtgttgtttt ctaaaatcca tcttcttttt ttttcagtat   9540
tctgtcctac actcagtaac cattgcatcc tggttgggct tggagacttt gttgtttttt   9600
tctacttaat cttttttca aaaaaaaaaa tatatttggt agcagcaaca cctgcctcct   9660
atcctcccag tcccagcctc acaaatccct ctcccattac tctctcccat tcttttcaga   9720
gaaggtgaag cccctctttg agtatctttc ctgggacacc aagtctcagc agaactaggt   9780
atatcctctc ccactgaggc catcctgggt agtccagata tgggaagggg atcttatggc   9840
atgcaaaagt cagagacagt ccctgcttca attgttgggg gaccattatg aagaccaagc   9900
tgtgcatctg ttatataagt ttaggggccc taggtccagc cccttcatac tgtttggttg   9960
gtggttcagt ttttgtcagt cccatagttt caggtttgtt gactgtagat tttcctgtgg  10020
tgtccttgac ccctctggct cactcaatcc tatctgtcac cgttccacaa gaatccttgg  10080
gcttcctgtg aagtttgact gtggctggct acattccata gctaattttt aaattcaatc  10140
tctctctctc tctctctctc tctctctctc tctctctctc tctctctctc tctgtgtgtg  10200
tgtgtgtgtg tctgacaact gtatgtgtgt atagaatgca ttctgattaa attttcccca  10260
ctctcttacc ctatccctat cagcctctgt ccttcccata ttcatgactt gttttgtgtt  10320
ctgaagactt tagtgccatc tgtgtgactg tgggtttgga actatccact agagcctgtg  10380
ggtcaccagt caccagggga tcacaactga gtacaatacc tccttctttc tcagcagtga  10440
gtggcagggc ttgtttcttc ctcactgaca caattgtcaa gggatggcag gtgttggatt  10500
tttgtggata gatgtagtag agtatttttt gagacatgta ctcccttatc caatgcttgt  10560
ctcaaacact attttgcttt gaactttgtc tgtgaacttc tgattcccct gcttctactg  10620
tctgagtgta tttttgaatg aagccagcct tggtgagagg gtatttgttg ttgaatttgc  10680
ttgaatttct tataaaaacc aagaactttt acccatctgg cactgttgtt tactgatgcc  10740
acacagaatg ttagctcaaa gtaggtcaag ttgggctgtg gatgaactat acgaactgcc  10800
tagagaagag agtaccaaag tccagtgatg caaaggtgat ccatctactg gcttgatccc  10860
```

-continued

```
tggtgccgcc cattctccca gcatataatt actgcaggct gtcctcagtg cagcagagtg  10920

ggcagaggga agcattgagg aggatcacac acacagttgt agggagaaca cagagaagta  10980

aattgctgac aaacaagcag ggatggacct ggtttcagct ctctcactgg aaacctgggt  11040

gctcctagca atcagcttgg tgctcctcta ccggtaagtg atctttacat ttccttccca  11100

taccatgtct tgaggatcag ggtgatactc agacatctat tctgttatta ttgggaggct  11160

caaaatgatt atcagaacca gcagctggag agccgatggc tcagtggtta aggtcacttg  11220

ctgctctttc agagtactca agttttaagc ccaacatcca caagcagctc agaatcatct  11280

gtaactatag ctccagggaa tctgacacct tccacaggca tagttagtat ggtatttaat  11340

ggtggtagct tttgtaacct ggctagctcc taaataattg ggacagagac ctattaagtt  11400

tattagcaat ttttaagcac tatgattggg caggttcaaa gctgttttag cccacaaagc  11460

tatctacatc ccagctatag gctcagtttt acttgcactg tgactgtttc cctggcttgc  11520

tctgctccat gtgtgtcctc atggtgagct cctttgatga ctccttccca tgtctgacct  11580

catgggaacc ttcttcttcc tccaccttct tctggccctt ctgctcctag accctcatgg  11640

gccttgtggc caacaacttc tcttctgccc agtcatttga tcttcagttt attatccacc  11700

aatcagagat aattggggaa cattctttat accacattga tataggagat tcctcattag  11760

tcatgacaat acagtccaga ctgtatcgat gtctcaggtt acagaaacca gcatctgaat  11820

acacagagtg aaagaccctc ctccaacaga gagcagaagt tgaaattaag tcttgcaaaa  11880

agttttcgaa atttcatgtt tttatttatt gtggttaggg acagcgcatg tgagtgtgtg  11940

tgtgtgtgtg tgtgtgtgtg tgtgtgtgtg tgtgtgtatt tgtgtatgca ggtcagagga  12000

caacttttca gagagttctc tcctctcatg ttggtcctga agaccaaact cagattatca  12060

acattatcca tcaatgcctt tacttgtgga gtcatctcaa aggtccaaga tgaaatgagg  12120

actgagttaa ttttgcattt taatgttttg gcagtatgga ggatcaagtc agagtttata  12180

tatgctaggc acactcttca cttcttagct atattcccag tggtactaac tcttattaaa  12240

gctcatactg atgttctgca gatcttttgg gtacc                            12275
```

<210> SEQ ID NO 13
<211> LENGTH: 9330
<212> TYPE: DNA
<213> ORGANISM: Artificial Sequence
<220> FEATURE:
<223> OTHER INFORMATION: Description of Artificial Sequence: 9.3 kb region of the Cyp3A11 gene
<220> FEATURE:
<221> NAME/KEY: misc_feature
<222> LOCATION: (5319)
<223> OTHER INFORMATION: 'n' = a, c, g or t
<220> FEATURE:
<221> NAME/KEY: misc_feature
<222> LOCATION: (5931)
<223> OTHER INFORMATION: 'n' = a, c, g or t
<220> FEATURE:
<221> NAME/KEY: misc_feature
<222> LOCATION: (7038)
<223> OTHER INFORMATION: 'n' = a, c, g or t

<400> SEQUENCE: 13

```
ggtacctggt atctgtccag aaattcatcc atttcatcca ggttttccag ttttgttgag     60

tatagctttt tgtagaagga tctgatggtg ttttggattt cttcaggatc tgttgttatg    120

tctccctttt catttctgat tttgttaatt aggatgttgt ccctgtgccc tctagtgagt    180

ctagctaagg gtttatctat cttgttgatt ttctcaaaga accaactcct cgtttggtta    240
```

-continued

```
attcttttaa tagttcttct tgtttccact tggttgattt caccccctgag tttgattatt    300
tcctgctgtc tactcctctt gggtgaattt tcttcctttt ttttctagag cttttagatg    360
tgttgtcaag ctgctagtgt atgccctctc cagtttcttc ttggaggcac tcagagctat    420
gagtttccct cttagaaatg ctttcattgt gtcccatagg tttgggtatg ttgtggcttc    480
gttttcatta aactctaaaa agtctttaat ttctttcttt attccttcct tgaccaaggt    540
atcattgaga agagtgttgt tcagtttcca tttgaatgtt tgctttccat tatttaatgt    600
tgccttagtc catggtggtc tgtgtcttag tcagggtttc ttttcctgca caaacatcat    660
gaccaagaaa caagttgggg atgaaagggt ttattcagct tacacttcca tgctgctgtt    720
catcaccaaa ggaagtcagg actggaactc aaacagatca gggagcagga gctgatgcag    780
aggccatgga gggatgttct ttactggctt gccttccctg gcttgctcag cctgctctct    840
tatagaatcc aagactacca gcccagagat ggcaccaccc acaaggggcc tttccccctt    900
gatcactaat tgagaaaatg ccttacagtt ggatctcatg gaggcatttc ctcaactgaa    960
gctcctttct ctgtgatatc tccagctgtg tcaagttgac acaaaactag ccagtacaat   1020
tgacccccttg tcaacttgac acacaaacac atcactagta accctcaacc cttacattct   1080
tattcatccc caagatctaa ataactttaa aagtcccaca gtctttacat attcttaaaa   1140
tttcaatctc tttaaaatat ccatctcttt taaaatccaa agtcttttta caattaaaac   1200
tctcttaact atggcctcca ctaaaacagt ttcttccttc aagagggaaa atatcagggc   1260
acagtcaaag caaaaatcaa tctccaacca tccaatgtct gggatccaac tcacaatctt   1320
ctggactcct ccaagggctt gtgtcacttc tccagccatg ccctttgtag cacaggtgtc   1380
atcctctagg ttccagatgc ctgtactcca ctgatgctgc tgctcttggt ggtcatctca   1440
tggtactggc atctccaaaa cactgcatgg ccccttcagt cctgggcctt caattgcaac   1500
tgaggctgca ccgtcaccaa tggccttcca tgccctctca cagtgccgag cctcagctgc   1560
tgtgcatgac cccttcatgc cttcaaaacc agtaccacct gggtgaccct tatacattac   1620
caagtcccac tgcagcagga gtacaacctt ggctatctct ggaacacagc ctctttgtgc   1680
tttcagaaaa cacttcccag aagatgtcac ctcaacgacg ctggtctctt cttaatcacc   1740
gataatttct tagctccagc taaccagcat caatagtcat agtaatgcaa ggttttgctt   1800
tagtagttct ggtatcttgt taatcacagt tgattcttca gccccagcta accagaacta   1860
cagaatttc acaatcaaaa cagcaatggc cctgaaaaga gtctttaatt ttccctctga   1920
aatttcacaa gccagacctc catcttctgc actgttctca acattatctt ctaagctcct   1980
acacaacatc tgacagagct cttaacaatg aacggatctt caagccgaaa gttccaaagt   2040
ccttccacag tcctccccaa aacatggtca ggttgtcaca ggaatacccc actcctggta   2100
ccaatttgtc ttagtcaggg tttctattcc tgcacaaaca tcatggccaa gaaacaagtt   2160
ggggaggaaa gggtttattt agcttacact tccatgctgc tgttcatcac caaaggaagt   2220
caggactgga actcaaacag gtcagggagc aggagctgat gcagaggcca tggagggatg   2280
ttctttactg gcttgccttc cctggcttgc tcagcctgca ctcttataga atccaagact   2340
accagcccag agatggcacc acccacaagg ggcctttccc ccttgatcac taattgagaa   2400
aatgccttac agttggatct catggaggca tttcctcaac tgaagctcct ttctctgtga   2460
tatctccagc tgtgtcaagt tgacacaaaa ctagccagta cagtctgata ggatgcatgg   2520
gacaatttca atatttttgt atctgttgag gcctgttttg tgaccaatta tatggttaat   2580
tttggagaag gttccgtgag gtgctgagaa gtatatcatt ttgttttagg ataaaatgtt   2640
```

-continued

```
ctgtagatat ctgtcaaatc catttgtttc atcacttctg ttagtttcac tgtgtcctgt   2700
ttagtttctg ttttcatgat ctgtccactg atgaaagtgg tgtgttgaag tctcccacta   2760
ttattgtgtg aggtgcaatg tgtgctttga gctttactaa agtgtcttta atgaatgtgg   2820
ctgcccttgc atttggagca tagatattca aaattgagag ttcctcttgg aggattttac   2880
ctttgatgag tatgaagtgt ccctccttgt ctttttttgat aactttggtt tggaagttga   2940
ttttatttga tattagaatg gctaccccag cttgtttctt cagaccattt gcttggaaaa   3000
ttgttttcca gcctttcact ctgaggtagt gtctgtcttt ttccctgaga tgggtttcct   3060
gtaagcagca gaatgttggg tcctgtttgt gtagccagtc tgttagtcta tgtcttttta   3120
ttggggaatt gagtccattg atattaagag atattaagga aaagtaattg ttgcttccta   3180
ttatttttgt tgttagagtt ggcattctgt tcttttggct gtcttctttt tggcttgttg   3240
aggaattact ttcttgcttt ttctagggcg tgatatctgt ccttgtattt tttttctgt   3300
tattatcctt tgaagggctg gattctggaa agataatgtg tgaatttggt tttgtcatgg   3360
aatactttgg tttctccatc tatggtaatt gagagtttgg ccgggtatag tagcctgggc   3420
tggctttttt ttgttctctt agtgtctgta taacatctgt ccaggctctt ctggctttca   3480
tagtctctgg tgaaaagtct ggtgtaattc tgataggcct gcctttatat gttacttgac   3540
ctttctcccg tactgctttt aatattctct ctttatttag tgcatttgtt gttctgatta   3600
ttgtgtgttg ggaggaatct cttttctggt ccagtctata tggagttctg taggcttctt   3660
gtatgttcat gggcatgtca ttctttaggt tcgggaagtt ttcttctata attttgttga   3720
aaatatttgc tggcccttta agttgaaaat cttcattctc atcaactcct attatctgta   3780
ggtttggtct tctcattgtg tcctggattt cctggatgtt ttgagttagg accttttgt   3840
gttttgtatt atctttgatt gttgtcctga tgttctctat ggaatcttct gcacctgaga   3900
ttctctcttc catcttttgt atcctgttgc tgatgctcac gtctatggtt ccagatttct   3960
ttcctagagt ttctatctcc agcgttgcct cactttgggt tttctttatt gtgtctactt   4020
cccttttag gtctagtatg gctttgttca tttccatcac ctgtttggat gtgtttgcct   4080
gtttttctat gaggacttct acctgtttgg ttgtgttttc ctgctattct ttaaggattt   4140
gtaactcttt agcagtggtc tcctgtattt ctttaagtga gttattaaag tccttcttga   4200
tgtcctctac catcatcatg agatatgctt ttaaatacag gtctaccttt acggttgtgt   4260
tggggtgccc aggactaggt ggggtgggag tgctgcattc tgatgatggt gagtggtctt   4320
gatttctgtt agtaggattc ttacgttttc cttttgccat ctggtaatct ctggagttat   4380
ttgttatagt agtctctggt tagagcttgt tcctcaggtg attctgttat gctctatcag   4440
cagacctggg agactagctc tatccttagt ttcagtggtc agagtactct ctgcaggcaa   4500
gctctcctct tgcagggaag gtgcccagat atctggtgtt tgaacctgcc tcctggcaga   4560
agttgtgttc tactcaccat aggtcttaag atcccatggt tggtcctgtg tggttccttg   4620
cgtgtgtccg gagactcccc gggccagggt ccctggtgat tggaagggac ttgtgcaccg   4680
gatcaggcca ggttatctga ttccttaatt aatgcagtct caggtcccgt gcgattgaat   4740
tggagcaggc gctgtgttcc actcaccaga ggtcttagga tcctgtggag gatcctgtgt   4800
gggtccttgc gggtgtctgc agactccccg ggccagggac catggtgctg cagtgggccg   4860
gaagggactt gagccctgga tcatgccgga ttatctgctt ccttaattaa tgcagtctca   4920
ggtcctggcg attggattgg agcaggcgct gtgttccact caccagaggc cttagaatcc   4980
```

-continued

```
cgtggcggat cctgtgtggg tccttatggg tgtccgcaga ctccccgggg ctagggacca   5040
cggtgctcca gtgggccgga agggacttga gccccggatc aggccggatt atctgcttcc   5100
ttaattcctg atagtctttt aaaagtaaac ttatagttag acactgtaca caggtatata   5160
atacatttta aatattctct cactatgcca ggtggtatca tataagaact tttgaatata   5220
tttcttaaag attaatttta atattttatg ctcttatact atgcttaatt cccaaagaat   5280
attttgtatg ttttgaaaca atttactctt caacattana tataggattc acagttatag   5340
atagtattaa atgtccatta atgatatttt tagggtataa aaggatatga atataaaagt   5400
tgaacaaaaa agaggggatg ggccataaag aatatattca tatgtatata tatatgtgaa   5460
taattcaaag aataaataaa tataatttta aaaagcagca ggtatccccc ccaaaataca   5520
gttgttgaag tgccttgtga tagaaccttg tcaaatgata aaccaaagaa ataccaacta   5580
cccacccagc cacccaagag atggattaga gtcagtggat tattcagggt gtgggagcct   5640
gaggataaaa aatcagaacc ccagaccccc taaaaaaggt atgcagaccg tacagccatt   5700
ttatagtttt gtgttgagct tcattcagcg ggactctggg tacacatggc ttgtgtgggg   5760
gtgtgttgac aacctgcaag tgttcattcc taagctgata tacacacaag cacataagta   5820
gcactaaatg gtctgtgacc ttgctttggg tgggggacaa gtatgtttgg caggggctaa   5880
atgatagaac cactaagttt agggctgtgg gagagacaga gataataaat ngatagggcc   5940
cacatttcag gcagtataca tttgtgccaa gcagtgtgaa tagaggcaag ttctaatggt   6000
attggcgaag tgcttgcata ttttatccat ggattcgaaa gtgttgggag tgggatggta   6060
acttgatccc tccaggagca aaggagggta gaaaaggaga ccaggagtgg gatggttgtg   6120
acagatccca gggaaaagcc aggtggaaca gaagggagct gggagaggtc agagtccgtg   6180
caatagctcc tgggcaaggc agaatgtgct tataaaacta cagagacaaa gtttggagct   6240
gtgacgaaag gatggaccat ctagagactg ccatatccag gggatccatc ccataatcag   6300
cttctaaacg ctgacaccat tgcatacact agcaagattt tgctgaaagg acccagatat   6360
agttgtctct atatgtgaga ctatgctggg gcctagcaaa cacagaagtg gatgctcaca   6420
gtcagctatt ggatggatca cagggctccc aatggaggag ctagagatag tacccaagga   6480
gctaaaggga tctgcaatcc tataggtgga acaacattat gaactaacca gtaccccgga   6540
gctcttgact ctagctgcat atgtatcaaa agatggccta gtagaccatc actggaaaga   6600
gaggcccatt ggacacgcaa actttatatt ccccagtaca ggggaacgcc agggccaaaa   6660
aaacaaaaaa caaaaaaaaa tgggaatggg tgggtaggga agtgtgggggg agggtatggg   6720
ggacttttgg gatagcattg gaaatgtaat tgaggaaaat acgtaataaa aaatattaaa   6780
aaaaaaccta cataggacag acaggcaacc attttaggac aacccttgct ccagttgtta   6840
ggggacccat atgaagatat acctttatat ttgttacata tctgtgggtg ttggaggatc   6900
taagtccagc ccatctattc tctttggttg gtggctccat gagagctccc acggttctag   6960
gttatttgac tgttggtctc cctgtggagt tcctacccag tttggggccc tcaaaatttt   7020
tctcagtttt cttctcanag cttctgaact ccatccagtt tttggctgtg aatatctgca   7080
tcttcctgag taagcttttg gatagagcct cttagaggac aaccatacta ggctcttgtc   7140
tccaagttta aatgtatcat taatagtgtc agagattgat gcttgcccat gggattggtg   7200
tcaagttgga ccagttaatg gttgatcatt ccctcagtct ctgcttcatc tttgtccctg   7260
catttcttat aaacagacca atttttgttt caaaagtttt atgagtgggt tggtgttttt   7320
atacctccat tggggatcct gcctgatcct ggggagatgg cctcttcagg ttccatatcc   7380
```

-continued

```
cctttactat gattctctac taaggtcatt tacattgata tcggaggtct ttctttattc   7440

tgggtctctg gcttctccta gagatgcccc aatccctcac tcctagcagc tgtagatttc   7500

tattcactct cctggccctc tggctttcac tcctgtctct tccctcacca catcctgaac   7560

ccccatactc ccttcctcca cattcatggg tacatttttt aaatcccaga acacagaagg   7620

cagaagcagg cagatctcta caagttttag gcaagcctgg tctatagagc aaatttcagg   7680

atggccaggg ctacacagtg aaactctatc ttaaaaaaca aaaaaacaaa ataagttatt   7740

tattacatat ttacttgttt atatgtaagc atatatgtgt gggggctgaa gagaccagaa   7800

gacaagttgt ggaaattcat tcttctgttc catcacatag atgctgggaa ttaaaatcag   7860

gttgtcgggt ttggagacag gtgactttgt tgtctgagct tccttgagag cctataagtt   7920

tttctttcat tgttagtgtg ctagctgata tccacattgt tttctgtgct aggtatcctg   7980

aattccagtt gagtccacat gtcatggaat gtcctcttac aacctctgcc actgggtttt   8040

gtttcctact atttaactta ggactttttt tttggtagtg attcttacaa gaaaggtaca   8100

catacatttt tctttttgga gtttgatttg gatcaagtta taatcgtgca agtcatggtg   8160

cccttcttac taagtctcta ggttgctatg gctttgtgaa aacttttgga ttttatccta   8220

aaaaaataat aattaaaaaa aaatccagta acaatcactt tgtgcacatt tattcctaag   8280

ctataagttt ccacttctgt aacgtaggta tttgagattg aagaagaaat ctttatgtgt   8340

atgggtgtct tgctggcatg catatccttg cactatgtgt atatctgggt gcctgtgaag   8400

gccaaattat gactacaaaa acccaggagc tggagctaaa gaccattgtg agccaccaga   8460

agggtactgg gaattgaatc caggtccttt acagcagtgg acaatagatg ttaactgctg   8520

agccatatct ttagctctaa catggggaca atagcttact tatccctagg acttatcatg   8580

aggaccccaa agagagtgaa aagtacttat aagatatgat gtcttatcct ctagagcaag   8640

aaagccagag aggaaatcct gctttatttt ttttttagta ctcattgtca gcttgctggt   8700

ctcccttact ttgtccctgc ttagagggat gagtgtgggg tttttattac ccattggggg   8760

aacatcccaa ttggaatgag gtgctggttt ctcgactaat cctgtatgac accaaagaag   8820

tatgaatctg ttaaaggtga aaattttgcc atcaacaacc caaccttcat acttaagtct   8880

cagagaatac agaggaagag ggccagtaat atattaagag ttagaggact aggaattctg   8940

ctctcagatg gtgtctccaa gaaatggagg caggaccaga cacattaaat atcaacaatc   9000

tatacaagat acaatgaaat ctcaaatagg catggtaaag aatatatata tatataacac   9060

aataataata atcgcaaaga agccatgaat ttgataggga gttgcgagat gggaagaact   9120

ggagggagga gatgaaagaa gatgatctaa tttcattgta gttaataatt ttaaaagatg   9180

aagaacttga actttagaac aacatggtct cttggatcct ggtttcatta aggatttatt   9240

atgtaacctt gattgaatca gttatcattt ggggtatggt ttgttcactt gtgacagagt   9300

tatccctcac aacattgcag ggtagatgat                                     9330
```

<210> SEQ ID NO 14
<211> LENGTH: 13035
<212> TYPE: DNA
<213> ORGANISM: Artificial Sequence
<220> FEATURE:
<223> OTHER INFORMATION: Description of Artificial Sequence: human
CYP3A4 gene locus

<400> SEQUENCE: 14

```
ggtacctggt tatctattgg gactggttgg acaagagggt gcagcccacg gagggtgagc     60
```

-continued

```
caagcagggt ggggcgtcgc ctcacctggg aagcacaagg ggtcgtggaa ttttctcccc    120
tacccaagga aagccataag ggactgagcc tgaggaactg tgcactctgg cccagatact    180
gcacttttcc catggtcttt gcaacccgca gaccaggaga ttccctccgg tgcctatgcc    240
accagggccc tgggtttcaa gcacaaaact gggcagccat ttgggcagac accgaactag    300
ctgcaggagt tttttttttt tttttccata ccccattggc acctggaacg ccagtgagac    360
agaaccgttc actcccctgg aaagggggct gaaaccaggg atccaagtgg tctggctcgg    420
tgggccccac ccccatggag cccagcaaac aaagattcac ttggcttgaa attcttgctg    480
ccagcacagc agcagtctga gattgacctg ggaccctcga acttggttgg gtgctgtggg    540
ggggcatctt ccattgctga ggcttgagta ggtggtttta ccttcgcggt gtaaacaaag    600
ctgctgggaa gtttgaactg ggtggagctc accacagctc agtaaggcca ctgtggccag    660
actgcctctc tggatttctc ctctctggga aggatatctc tgaaaaaaag gcagcagccc    720
cagtcaggga cttatagatg aaacccccat ctccctggga cagagcccct cggggaagag    780
gtggcttcca ccattgtgga agactgtgtg gcaattcctc acggatttag aactagagat    840
accatttgac ccagcaatcc cattactggg tgtataccca taggattata aatcattcta    900
ctataaagac acatgcacac ttatgtttat tgtaacacta tttacaatag caatgacctg    960
gaaccaatcc aaaagcccat caatgataga ctgaataaag aaaatgtggc acatatacac   1020
tgtggaatac tatgcagcca taaaaaagga tgagttcatg tcctttgcag agacatggat   1080
gaagctggaa accatcattc tcagcaaact agcacaataa cagaaaacca aacactgcat   1140
gttgtcactc ataagtggga gttaaacaat gagaacacat ggacacaggg aggggaacgt   1200
cacacactgg ggcatgtcgg ggagtggggg cctacgggag ggatagcatt agcagaaata   1260
cctaatgtag gtgacgggtt gatgggtgca gcaaaccacc atggcacata tacacctatg   1320
taataaaact gcacgttctg cacatgtacc ccagaactta aagtataatt aataataata   1380
ataatttctg ggcatgtaag tagctgtctt tcaggttcta ctttgataca tattctgaga   1440
gaattaaacc tgtcaaagaa accttgactt tcaatggcag gcactggaat tgaccctaat   1500
aatgtgtttt ggggtaagcc tactcatatt ctcaacctgt ctgcagtagt cgttagaatc   1560
tgaacttcct gaagttcatg tgcaaagttg agttaattgt ttaatattca acaaggatta   1620
tgccagtaag atggtaggaa aatattagat atgtgtcatc actgctggta ttatttaaac   1680
tgcaacatat tttagctggc tgctgatctc agccaccatg cctgcatttt atctctgtct   1740
cgtggtctgc aaccttggaa gctttgaact tagctcatag aatcctgggc atcaagaaca   1800
tgtggttcta atggctagat agggaatgag agtaaaagga ttttgcccac ggtcacgtga   1860
gtaaacaaca gatttggagg ggtctggact actgtgatga cttcattctg acaatatgtt   1920
ccagttgtcc tttcatttcc tcctaatcac atgtttggtc tgatttggct gtttcccacc   1980
ttccaattcc tgccttctcc aatgctccct tccgtaggtc actctgtggc tcagagaccc   2040
tgcttagcaa gcgcccaacc tttcaattat ttgttcagta aaacttgaac tcatgtctcc   2100
ccttcttgat aaaaagaaaa tacgttatgt aatgtcgggt tactctataa ctcttgtcct   2160
gtctctcggc aactagtgaa ctaactgttt tcatattgag caaacgttta tggaaggact   2220
gccaagagtc aggtactagg cttggtaata ttccccgttc tctctagtca aagccaacac   2280
cagccagact tgcagatcta ggtcccaagc ccactgcaga tcacaggcca gggtctggtc   2340
tcctctgagc tcctttggga gggaaagaca gaattattaa cacccatttt gtagattagg   2400
```

-continued

```
caactgaggc tgaggaagtt taaataactc agacagggcc tgcacgtcag tcatattcca   2460
aggatcccta ctcactgtct tctctctaca gaacgagatg tctctggagt ccatagaaag   2520
cccaggagcc tggctgggca cggtggctcc tgcctgtaat cccagcactt tgggaggccg   2580
aggcaggcag atcacctgag ctcaggagtt caagaccagc ctgggcaaca tggcaaaacc   2640
ccatctctac taaaaataca aaaaattagc tgggcgtggt ggtgcatgcc tctaatccca   2700
gctacttggg aggctgaggc acaagaattg cttgagccca ggaggcagca gttgcagtga   2760
gctgagattg tgccagtgca ctccagcctg ggcaacagag caagattcca tttcaaaaac   2820
aaaaacaaac acaaacaaac aaacaaaaat agaaagccca gggaccacct gcgtcaggtt   2880
cccagccaca cctttttctt gtcctcctct gtctctggca tcttctcaca ggttcctaat   2940
tgtttgtggt tgcacaaatt caaaatccca gaaaaattac cacttcacac ccactcagat   3000
ggctattttt tttttgaagg aagataacaa gtgttgacaa gaacatggag aaattggaat   3060
tctcacccat tgctggtgag aatgtaatac ggtgctgctg ctatggaaaa cagcttggag   3120
tttcctcaaa aagttcaaca gaatttcaat gtgacccagc aattcccctc taagttatag   3180
atctgagagg attaaaaaca gttactaaaa tacacggact cacatatttc taacagtcca   3240
attcacaagg gccaaaaggt gctaatagcc cacatgtcca tcgatggatg gataaataaa   3300
ttgtggtcta tccatacaat ggaatattat tcggccataa atggaatgaa gtactgacgc   3360
atgctacaga atggatgaac cgcaaaaaaa atggatgaac acatgctaca gaatggatag   3420
cctcacttta ctatgaagtg aaggccagaa acgaagtcca tatattgcat catacaaaat   3480
atccagaaga gggaagccca cagagacaga atgtgcaatg gtggatgcca gggtctgggg   3540
agaggggaga gtggggagaa actgctcaac tggtacaggc tttattttgg aatgatggga   3600
acattttgca actagataga ggtagtgatt gcagaacaca gaatgtactg aattccactg   3660
atttttttca ccttaaaatg gttaattttc agtcctgaga ttggataatc ataaaaaaat   3720
ggttaatttt atgttatgtg aatttcatcc ctatacatat tttaaacctc agaaatatac   3780
actagcaggc atggaacagg tcactgtggt gcctgccaag cccggtgatg ttatctgggg   3840
tccccggcca gccttaagcc tcttgctgac cggtggaggg cagaaccttt gccctaaaag   3900
tataatatcc acatgctggc atgattcctg gccagatggc ttctttatta gcagtaattg   3960
aaactgcctc gatacagaca ctgtaccttg caaccaaaaa atgactcaac aatgataata   4020
agggttaagc tgggcctttc tctctttgcc agttaaatta tatttattat agcttgacat   4080
gaaaaacaaa gcaactccaa caggtatcac aagggcaaag gacatgaaca ttttatcaaa   4140
gaagaaatgc agctgtcaaa aatacagaaa tattcaacct tgttcataat aaagtggctg   4200
ggctcagtgg ttcatgcctg taatcccagt gctttgcaag gctgagacag gaggatcatt   4260
tgaagccaga agttcaagac catcctaggc aagtcagttc aataccagac ttcatgtcta   4320
caaaacatca aaaaattagc caggcatggt gatgcatgcc tgttgtccca gctactcagg   4380
aggctgaggc aggagaattg cttgagcctg ggaggctgcg gtggcggtga gccatgattg   4440
tgccattgta ctccagcctg ggcaatgcag caagactgtc taaataacaa aaataatagt   4500
aaagaaaagg attgggatgc catttacttg cgtattcaat acacagagtt aaaagtaatt   4560
tctacgtttt ctattttttt attactaaaa aaagctggac cattctcaca gcctgaaatg   4620
cttctcactt tcccttcttc tgtccaaaca cttctctatg ataatgcaaa cagtcactcc   4680
tttaggaaga cttcacccca ggtagttcca gatcccctta tctctgcctt cccagaactc   4740
ctggtgtctc tccagttccc tccgtgtggt gaagtaccct acctagggtt tcagtatggc   4800
```

-continued

```
tctgtctgca aaggtcttgt tcacaccttc ccttatggtt ctgttgccct gtgttgtgtc   4860
atagcacagg gcacagtgga gaacccattc acactgatag agagggcccc atggtcctgg   4920
agataaccat gtaaccgatc agaataaggc attgagggct gggtgtcagg cgtgggctgc   4980
acttgggtgg gcaggtcccc tggaaagtca ctgggtttgg caagcttcct agtaacatgt   5040
ctctctgggg tccccttgg aacttcatgc aaaaatgctg gttgctggtt tattctagag   5100
agatggttca ttcctttcat ttgattatca aagaaactca tgtcccaatt aaaggtcata   5160
aagcccagtt tgtaaactga gatgatctca gctgaatgaa cttgctgacc ctctgctttc   5220
ctccagcctc tcggtgccct tgaaatcatg tcggttcaag cagcctcatg aggcattaca   5280
aagtttaatt atttcagtga ttattaaacc ttgtcctgtg ttgaccccag gtgaatcaca   5340
agctgaactt ctgacaagaa caagctatca tattcttttc aattacagaa aaaagtaagt   5400
taattgatag gatttttttt gtttaaaaaa aatgttacta gttttgaaaa ggtaatatgt   5460
gcacatggta aacactaaga aggtataaga gcataatgct tttatactac taagaataat   5520
gttttctcta agtttttttt ggtagatgct ttcatcagat taagaaaatt ccctgctatt   5580
agttgttgaa ggtttttata tcataaatga aagttgaata ttattatcat atattattaa   5640
tatattgtta ttgaactatc aaagcctttt cctaaaacca ttgagatgat cttataacca   5700
ttctccttta acctgttgac gagatcattg gtatttatac tatttctctg ttaaccattc   5760
ttgagtctca ggtttaaatt caacttggtc atggtgtgtc atctttgatc attgctgtct   5820
gtggcttgct actgttttgt ttaggatttt tgcactgatg ctcatcaatg agactggcat   5880
gccatcttcc tttgcagtcc tgattttttt ctgatttgga tcatgtggtt atggccctca   5940
tggaatgagt tgggcatgat gccttttttt catgtctctg gattgatggg acactttgga   6000
ttctctccag atggccctca atggtccctg cctcctcatt gttaggcccc tgggcaagcc   6060
cttctcattt ctggtaggcc caggaacctg tgggggtttt gtttgtttgt ttgtttcttg   6120
agtcggagtc tcactctgtc acccaggctg gagttggagt gcaatggccc gatcttggct   6180
cactgcaacc tccacctccc agattcaagc aattctcctg cctcagcctc ctgagtagct   6240
ggaattacag gcacccaccg acacaccctg ctaatttttg tatttttagt acagatgggg   6300
tttcacaata ttggccaagc tggtctcgaa ctcctgatct catgatctgc ccggcttggc   6360
ctcccaaagt gttgagatta caagcatgag ccaccacacc cagtgaacct gtggttttta   6420
gaagctcccc atgcatgtga atgctgtgag catcccagga tgacagccac tgtgtgttca   6480
gctgttggaa ctgtgagaaa gcaccagtgg gaccttctcc agcacctgcc tgctgagttc   6540
atggaagagg cttgttgggg agatgatgcc ctggctgact cctgaaggat ggttaggaat   6600
gcaccagatg gaagctgggt tggacccact ctatgctgaa gaacagcttg tgtggacaca   6660
aggagacacg gatatgtcat ttttgtagag cctgaggagt gtccaatcac accatttgct   6720
taaaacatca tgcacacttg gaaaagtgga ctgagaccga atgaagaagc taacagtggc   6780
cagatcagaa agggtcttgt gttacttcct agagatactt agattttatc ctgtgggtga   6840
taggagcagt tggagggact gaagacaagg aaagaaacat gtttcaagat ctatgttttt   6900
caagacgctt ttctggtggc tgagtaggga attccctgga taagtcctgc ccagggtcag   6960
gcaaaacaag ttagggggtt actgaaataa ggagtatgag aaatggtgta ggttgtgctg   7020
acgttttgta acacatctca tgatgatctt catttccttc actaatttcc tgtttcatta   7080
attcccttcc acgtgctctt ctgaaatttg cctcacattc tctgatttct cttttacctg   7140
```

-continued

```
ttggtttcat caccttttac tttttgcttt cctggaaaca caaatgattc tgattgtgac   7200
atgtcagaat tatttgcaac atttgccttt ctgctgaaac catgagttca ctgaatacac   7260
aatttagtaa agtgtaggat gcacatgtcg ttttcgtggt cacaaccagc tctgtagcat   7320
tttataacta cactggcagt gtgctgggag gtgtagagag aaatatttat cacatgtgtg   7380
gctgacacaa cctgccaagt tattttagga gcctccttgg aatcccagca agaatgctac   7440
cggcacaatt tgtaatcaca gcatcctgct ccatgccttg gcttcatggc atagtcactt   7500
ctgcaagtct ctttccagct gtctgttccc atgtctataa agtatgagtt aaatcatcct   7560
aacactactc atcttacaaa gttttcttgc tgatgttaag agagttggga aagaactgta   7620
taaactgtga agtgccatgg agatgttagt ggttacttta tcaagaaata gacactctag   7680
aatggagtag aaagccaaca gttatgattg agtcctcctc ctcttcttct ttttattaat   7740
ttataaagaa aagaggttta attgactcac agttccatat ggctggggag gcctcgggaa   7800
actctcagtc atagcaggag gcaaagggga agaaggcacc ttcttcacaa ggcggcagga   7860
gagagagagc tcctgttctt ttttgtcata aagtctacag aagtgcttat acttcaggac   7920
aagggcaggc agagagaagg aaggacattg cttcacccca gccctcactg acgagtttgc   7980
taggggacct cactttgtcc cagagtaggg cagaactctg gccactaccc attcagaagg   8040
cctgggctgc actgctagtt cctcactaac tctgtgtggc cttgggcaag gttgggcctg   8100
tgttaacaga ttatgaccct gggctctcaa gctagaggat ctaaatttga atcctggctc   8160
tgctaaagca attagtgatg taaactttaa tgggtcagtt aaccttcctg tggcttagtt   8220
tgctcatctg taaaataggg atcataacag tatcaatacc acatgattgt tggacagatt   8280
gaatcagtta atgcagggga agtacttagc atgacacgta ttcactatca tttcctggag   8340
taagagctgt gtgtgagtgg gtgtgagcat gtgtgaaacc ttttctctgc aatctcagtt   8400
aagaaaccaa tccagaattt aaagttcagg gcctaaatgg gtggttatct tctcccagtt   8460
ccatcctatc ccacctttgc tcttcctccc gcccacagga gctgttggtc cttgattggg   8520
ctggaagacc tggtggaccc taagtgatct ataagaggag aatagagaac agggaatgtc   8580
ttcaaaaatc tagagggaca cagaggctga gaggcaggca gtcctgcagg gtcttctgat   8640
tgggacaagg agaaccttgg tcttcacagg ccaattctgg tcagtttccc ccatggacag   8700
atgaggaaac aggcccagga atatccaagg tctcacactt cccatctgtc aagtcttgtt   8760
gattctgttg tattcatgtc tctcaaaggg agatagagtt tagggaagaa agaaggatca   8820
actgtgtctg ataccactgg gagcttaagt aaagggttct tttacttcat agcatttatc   8880
ccaatttgta attcagtatt atttgtgtgg ctgtttggtg tctctttctc ctatatgagt   8940
gctagcttca taagggcaag gattttgatt ctttaatatt tagtgcttgc cacatgccct   9000
gaacacagca ggcatacagg ctaaccaaca tacagtggca tgaaagtcat gaaagtgaga   9060
cacctacctc ctccagtgcc aagagagcat aaccatgcac ctgtcactct cctcaacacc   9120
acccccaagc atgaggccca aaagcattag ctaatcccct cctccagcca ctaaaactta   9180
aaggccaggt gtggtggctc ccatctgaaa tcccagaact tcaggagaca gcagcaggag   9240
gatcacttga ggccaggagt ttgagatcag cctgggcaac atagctaggt cccatctgta   9300
ctaaaaatta gctgggcgtt gttgcatgcc tgtagtccca gctactaagg aggctgaggt   9360
gggaggatca cttgagccca ggaggtggaa acaacagtaa gctataatca cagcactgaa   9420
ctctagcctg ggcaacagag tgacaccctg cctcaaaaca attttaaaaa taaataagag   9480
caaaacttag ataccacgtg gtcaccccaa catgcaaaat caagttttcc cctactgaga   9540
```

-continued

```
agaatgggga cttgacagct gagttacaga gagataatct tcttcttctt tttttttttt   9600
tggtttacat cctcaagatc atgacttgtg aaatttgaat cgaatacaca tgtaattcca   9660
gagcaatgtt gcctccgcat accatcagca attcacttgg ctactggaag tcaggataag   9720
cttcccagaa gagaggtacc acttgggcta ccaatataaa aggatgaaaa tatcagagtg   9780
atggtgttct ttacaacgtt gagtccctgg acagcctgtc cactgatgct gatatctgag   9840
cctaatgctt ctctgaatgt tgagattgaa ctttgatcca atgaaactag aacgagaaag   9900
aagataagtc tttcattgtt gataaggaca ttatgtttct catacttgta tgattatttt   9960
tccttagctg tactataatt atctgcttat ttgtctctgc tctatgtgct tagggtacaa  10020
agttgaccaa gaccaacttt ggttggaagc atagtactaa gagcacagta ctgagagcac  10080
agtattgaga gcacagcttt aaaaaacatg atgaaggctt taatacagga aatgagcagg  10140
ggagaggcat gtggtggttg gatgtatctt ccttgacaca gtcagtgcag ctctcagtag  10200
tcaagtccct acatgttaga agatgttacc ttctgtggaa ttaagtggca gaacttgcct  10260
tcaattattt tcctttgcag aacaacacca actgcattag ttaggacaca gtgctggctg  10320
catttaagtc ccaagcgatg attagtctct cactgttggt atagattcaa accaatcaga  10380
ccacctccta aagtttgtag ggcaggtaaa tcctcatctt agaataaaaa tcatcttacc  10440
aagtatgtgt tttagaggca agaagaaaac atatttgttt ctgtaagagt tttgtttaaa  10500
aaaaatataa gaaaggctct cggtttaggt gaggtaatga agttgttgat agttatcaga  10560
tgacactgga atctttactt ctctgaacgt gttctgtgca tctctcagtg tgggaacata  10620
gagagggaga tcctccagca atgccactga tatggtcaga aactgcatct ttctttctcc  10680
ctgctgagat gagatggagt cctttgttct agaagaccca tggtggtgcc gctgggagta  10740
acccttgaga caggaacaca aatcccaacc aatttgtggt tgcagccttg agtctcacta  10800
tttcccatag tgatgcgtag cagggaatgg caggtgcacc agagcaggag aggacctaat  10860
atctcccttc ctgttagctt tttataaagt tttattgtga tcagtagcag ttgggaagct  10920
acttgcagtc actgagcctc agtttctaca tctgtaaact ggggatagta gcatggcccc  10980
tacttaatgt gctcagcaaa gccactgaaa ggagacagaa atgtatctaa attaccctgg  11040
acttttatcc tacctctctt ggggattgtc accaccttcc catgtttgtc ctttttggtt  11100
tgatgcttgc tgtcacttct ttccttaggt gcctctctgt acggctcttt tatcccaggg  11160
attccagagt tacagcacat gcataccacc atccaagcat gtttatttgt ctcctgcttc  11220
actaggctgt ccccaaggaa catgtggctc ccggcacaca cctggcacaa cactgcacat  11280
gacattcacc cacttggcct tgaatctgac aaggaatctg gcatgatgtt cacccactca  11340
ggccaggtgc cgagcagccc tggaggctta ggggccagag ggatgggaaa aggtgtcttt  11400
ctggggtgag tatcagtttc tgcaggaggg ctgaatgtga gaaagaataa agagagaagg  11460
aagcgaacaa gcacagctta aacatcgcct atttctattg agttttaaga acgctgtgat  11520
tttgtttgtc atgcaatcca ttcatcaggc caggcagaca cagaacttgg gtgtgagtga  11580
cgataatgag ctgatataat tttcacaccc tcatcactga gatctctccc atcaggaatg  11640
ggtcagggag ctcacaggtg gcagcaactg ctattacagg cctcatctct accagctcct  11700
ggggcctgcc ctcctcccat tagaaaatcc tccacttgtc aaaaaggaag ccatttgctt  11760
tgaactccaa ttccaccccc aagaggctgg gaccatctta ctggagtcct tgatgctgtg  11820
tgacctgcag tgaccactgc cccatcattg ctggctgagg tggttggggt ccatctggct  11880
```

-continued atctgggcag ctgttctctt ctctcctttc tctcctgttt ccagacatgc agtatttcca 11940
gagagaaggg gccactcttt ggcaaagaac ctgtctaact tgctatctat ggcaggacct 12000
ttgaagggtt cacaggaagc agcacaaatt gatactattc caccaagcca tcagctccat 12060
ctcatccatg ccctgtctct cctttagggg tccccttgcc aacagaatca cagaggacca 12120
gcctgaaagt gcagagacag cagctgaggc acagccaaga gctctggctg tattaatgac 12180
ctaagaagtc accagaaagt cagaagggat gacatgcaga ggcccagcaa tctcagctaa 12240
gtcaactcca ccagcctttc tagttgccca ctgtgtgtac agcaccctgg tagggaccag 12300
agccatgaca gggaataaga ctagactatg cccttgagga gctcacctct gttcagggaa 12360
acaggcgtgg aaacacaatg gtggtaaaga ggaaagagga caataggatt gcatgaaggg 12420
gatggaaggt gcccagggga ggaaatggtt acatctgtgt gaggagtttg gtgaggaaag 12480
actctaagag aaggctctgt ctgtctgggt ttggaaggat gtgtaggagt cttctagggg 12540
gcacaggcac actccaggca taggtaaaga tctgtaggtg tggcttgttg ggatgaattt 12600
caagtatttt ggaatgagga cagccataga gacaagggca agagagaggc gatttaatag 12660
attttatgcc aatggctcca cttgagtttc tgataagaac ccagaaccct tggactcccc 12720
agtaacattg attgagttgt ttatgatacc tcatagaata tgaactcaaa ggaggtcagt 12780
gagtggtgtg tgtgtgattc tttgccaact tccaaggtgg agaagcctct tccaactgca 12840
ggcagagcac aggtggccct gctactggct gcagctccag ccctgcctcc ttctctagca 12900
tataaacaat ccaacagcct cactgaatca ctgctgtgca gggcaggaaa gctccatgca 12960
catagcccag caaagagcaa cacagagctg aaaggaagac tcagaggaga gagataagta 13020
aggaaagtag tgatg 13035

<210> SEQ ID NO 15
<211> LENGTH: 2461
<212> TYPE: DNA
<213> ORGANISM: Artificial Sequence
<220> FEATURE:
<223> OTHER INFORMATION: Description of Artificial Sequence: 2.5 kb region of the CYP3A4 gene

<400> SEQUENCE: 15
ggtacctggt tatctattgg gactggttgg acaagagggt gcagcccacg gagggtgagc 60
caagcagggt ggggcgtcgc ctcacctggg aagcacaagg ggtcgtggaa ttttctcccc 120
tacccaagga aagccataag ggactgagcc tgaggaactg tgcactctgg cccagatact 180
gcacttttcc catggtcttt gcaacccgca gaccaggaga ttccctccgg tgcctatgcc 240
accagggccc tgggtttcaa gcacaaaact gggcagccat ttgggcagac accgaactag 300
ctgcaggagt tttttttttt tttttccata ccccattggc acctggaacg ccagtgagac 360
agaaccgttc actcccctgg aaagggggct gaaaccaggg atccaagtgg tctggctcgg 420
tgggccccac ccccatggag cccagcaaac aaagattcac ttggcttgaa attcttgctg 480
ccagcacagc agcagtctga gattgacctg ggaccctcga acttggttgg gtgctgtggg 540
ggggcatctt ccattgctga ggcttgagta ggtggtttta ccttcgcggt gtaaacaaag 600
ctgctgggaa gtttgaactg ggtggagctc accacagctc agtaaggcca ctgtggccag 660
actgcctctc tggatttctc ctctctggga aggatatctc tgaaaaaaag gcagcagccc 720
cagtcaggga cttatagatg aaacccccat ctccctggga cagagcccct cggggaagag 780
gtggcttcca ccattgtgga agactgtgtg gcaattcctc acggatttag aactagagat 840

-continued

```
accatttgac ccagcaatcc cattactggg tgtataccca taggattata aatcattcta    900

ctataaagac acatgcacac ttatgtttat tgtaacacta tttacaatag caatgacctg    960

gaaccaatcc aaaagcccat caatgataga ctgaataaag aaaatgtggc acatatacac   1020

tgtggaatac tatgcagcca taaaaaagga tgagttcatg tcctttgcag agacatggat   1080

gaagctggaa accatcattc tcagcaaact agcacaataa cagaaaacca aacactgcat   1140

gttgtcactc ataagtggga gttaaacaat gagaacacat ggacacaggg aggggaacgt   1200

cacacactgg ggcatgtcgg ggagtggggg cctacgggag ggatagcatt agcagaaata   1260

cctaatgtag gtgacgggtt gatgggtgca gcaaaccacc atggcacata tacacctatg   1320

taataaaact gcacgttctg cacatgtacc ccagaactta aagtataatt aataataata   1380

ataatttctg ggcatgtaag tagctgtctt tcaggttcta ctttgataca tattctgaga   1440

gaattaaacc tgtcaaagaa accttgactt tcaatggcag gcactggaat tgaccctaat   1500

aatgtgtttt ggggtaagcc tactcatatt ctcaacctgt ctgcagtagt cgttagaatc   1560

tgaacttcct gaagttcatg tgcaaagttg agttaattgt ttaatattca acaaggatta   1620

tgccagtaag atggtaggaa aatattagat atgtgtcatc actgctggta ttatttaaac   1680

tgcaacatat tttagctggc tgctgatctc agccaccatg cctgcatttt atctctgtct   1740

cgtggtctgc aaccttggaa gctttgaact tagctcatag aatcctgggc atcaagaaca   1800

tgtggttcta atggctagat agggaatgag agtaaaagga ttttgcccac ggtcacgtga   1860

gtaaacaaca gatttggagg ggtctggact actgtgatga cttcattctg acaatatgtt   1920

ccagttgtcc tttcatttcc tcctaatcac atgtttggtc tgatttggct gtttcccacc   1980

ttccaattcc tgccttctcc aatgctccct tccgtaggtc actctgtggc tcagagaccc   2040

tgcttagcaa gcgcccaacc tttcaattat ttgttcagta aaacttgaac tcatgtctcc   2100

ccttcttgat aaaaagaaaa tacgttatgt aatgtcgggt tactctataa ctcttgtcct   2160

gtctctcggc aactagtgaa ctaactgttt tcatattgag caaacgttta tggaaggact   2220

gccaagagtc aggtactagg cttggtaata ttccccgttc tctctagtca aagccaacac   2280

cagccagact tgcagatcta ggtcccaagc ccactgcaga tcacaggcca gggtctggtc   2340

tcctctgagc tcctttggga gggaaagaca gaattattaa cacccatttt gtagattagg   2400

caactgaggc tgaggaagtt taaataactc agacagggcc tgcacgtcag tcatattcca   2460

a                                                                   2461
```

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence: primer lucR4

<400> SEQUENCE: 16

```
cgattttacc acatttgtag aggttttact tgc                                  33
```

<210> SEQ ID NO 17
<211> LENGTH: 15185
<212> TYPE: DNA
<213> ORGANISM: Artificial Sequence
<220> FEATURE:
<223> OTHER INFORMATION: Description of Artificial Sequence: CYP3A4-luc transgene

<400> SEQUENCE: 17

-continued ggtacctggt tatctattgg gactggttgg acaagagggt gcagcccacg gagggtgagc 60
caagcagggt ggggcgtcgc ctcacctggg aagcacaagg ggtcgtggaa ttttctcccc 120
tacccaagga aagccataag ggactgagcc tgaggaactg tgcactctgg cccagatact 180
gcacttttcc catggtcttt gcaacccgca gaccaggaga ttccctccgg tgcctatgcc 240
accagggccc tgggtttcaa gcacaaaact gggcagccat ttgggcagac accgaactag 300
ctgcaggagt tttttttttt tttttccata ccccattggc acctggaacg ccagtgagac 360
agaaccgttc actcccctgg aaagggggct gaaaccaggg atccaagtgg tctggctcgg 420
tgggccccac cccca tggag cccagcaaac aaagattcac ttggcttgaa attcttgctg 480
ccagcacagc agcagtctga gattgacctg ggaccctcga acttggttgg gtgctgtggg 540
ggggcatctt ccattgctga ggcttgagta ggtggtttta ccttcgcggt gtaaacaaag 600
ctgctgggaa gtttgaactg ggtggagctc accacagctc agtaaggcca ctgtggccag 660
actgcctctc tggatttctc ctctctggga aggatatctc tgaaaaaaag gcagcagccc 720
cagtcaggga cttatagatg aaacccccat ctccctggga cagagcccct cggggaagag 780
gtggcttcca ccattgtgga agactgtgtg gcaattcctc acggatttag aactagagat 840
accatttgac ccagcaatcc cattactggg tgtataccca taggattata aatcattcta 900
ctataaagac acatgcacac ttatgtttat tgtaacacta tttacaatag caatgacctg 960
gaaccaatcc aaaagcccat caatgataga ctgaataaag aaaatgtggc acatatacac 1020
tgtggaatac tatgcagcca taaaaaagga tgagttcatg tcctttgcag agacatggat 1080
gaagctggaa accatcattc tcagcaaact agcacaataa cagaaaacca aacactgcat 1140
gttgtcactc ataagtggga gttaaacaat gagaacacat ggacacaggg aggggaacgt 1200
cacacactgg ggcatgtcgg ggagtggggg cctacgggag ggatagcatt agcagaaata 1260
cctaatgtag gtgacgggtt gatgggtgca gcaaaccacc atggcacata tacacctatg 1320
taataaaact gcacgttctg cacatgtacc ccagaactta aagtataatt aataataata 1380
ataatttctg ggcatgtaag tagctgtctt tcaggttcta ctttgataca tattctgaga 1440
gaattaaacc tgtcaaagaa accttgactt tcaatggcag gcactggaat tgaccctaat 1500
aatgtgtttt ggggtaagcc tactcatatt ctcaacctgt ctgcagtagt cgttagaatc 1560
tgaacttcct gaagttcatg tgcaaagttg agttaattgt ttaatattca acaaggatta 1620
tgccagtaag atggtaggaa aatattagat atgtgtcatc actgctggta ttatttaaac 1680
tgcaacatat tttagctggc tgctgatctc agccaccatg cctgcatttt atctctgtct 1740
cgtggtctgc aaccttggaa gctttgaact tagctcatag aatcctgggc atcaagaaca 1800
tgtggttcta atggctagat agggaatgag agtaaaagga ttttgcccac ggtcacgtga 1860
gtaaacaaca gatttggagg ggtctggact actgtgatga cttcattctg acaatatgtt 1920
ccagttgtcc tttcatttcc tcctaatcac atgtttggtc tgatttggct gtttcccacc 1980
ttccaattcc tgccttctcc aatgctccct tccgtaggtc actctgtggc tcagagaccc 2040
tgcttagcaa gcgcccaacc tttcaattat ttgttcagta aaacttgaac tcatgtctcc 2100
ccttcttgat aaaaagaaaa tacgttatgt aatgtcgggt tactctataa ctcttgtcct 2160
gtctctcggc aactagtgaa ctaactgttt tcatattgag caaacgttta tggaaggact 2220
gccaagagtc aggtactagg cttggtaata ttccccgttc tctctagtca aagccaacac 2280
cagccagact tgcagatcta ggtcccaagc ccactgcaga tcacaggcca gggtctggtc 2340

-continued

```
tcctctgagc tcctttggga gggaaagaca gaattattaa cacccatttt gtagattagg   2400
caactgaggc tgaggaagtt taaataactc agacagggcc tgcacgtcag tcatattcca   2460
aggatcccta ctcactgtct tctctctaca gaacgagatg tctctggagt ccatagaaag   2520
cccaggagcc tggctgggca cggtggctcc tgcctgtaat cccagcactt tgggaggccg   2580
aggcaggcag atcacctgag ctcaggagtt caagaccagc ctgggcaaca tggcaaaacc   2640
ccatctctac taaaaataca aaaaattagc tgggcgtggt ggtgcatgcc tctaatccca   2700
gctacttggg aggctgaggc acaagaattg cttgagccca ggaggcagca gttgcagtga   2760
gctgagattg tgccagtgca ctccagcctg ggcaacagag caagattcca tttcaaaaac   2820
aaaaacaaac acaaacaaac aaacaaaaat agaaagccca gggaccacct gcgtcaggtt   2880
cccagccaca ccttttcttt gtcctcctct gtctctggca tcttctcaca ggttcctaat   2940
tgtttgtggt tgcacaaatt caaaatccca gaaaaattac cacttcacac ccactcagat   3000
ggctattttt tttttgaagg aagataacaa gtgttgacaa gaacatggag aaattggaat   3060
tctcacccat tgctggtgag aatgtaatac ggtgctgctg ctatggaaaa cagcttggag   3120
tttcctcaaa aagttcaaca gaatttcaat gtgacccagc aattcccctc taagttatag   3180
atctgagagg attaaaaaca gttactaaaa tacacggact cacatatttc taacagtcca   3240
attcacaagg gccaaaaggt gctaatagcc cacatgtcca tcgatggatg gataaataaa   3300
ttgtggtcta tccatacaat ggaatattat tcggccataa atggaatgaa gtactgacgc   3360
atgctacaga atggatgaac cgcaaaaaaa atggatgaac acatgctaca gaatggatag   3420
cctcacttta ctatgaagtg aaggccagaa acgaagtcca tatattgcat catacaaaat   3480
atccagaaga gggaagccca cagagacaga atgtgcaatg gtggatgcca gggtctgggg   3540
agaggggaga gtggggagaa actgctcaac tggtacaggc tttattttgg aatgatggga   3600
acattttgca actagataga ggtagtgatt gcagaacaca gaatgtactg aattccactg   3660
atttttttca ccttaaaatg gttaattttc agtcctgaga ttggataatc ataaaaaaat   3720
ggttaatttt atgttatgtg aatttcatcc ctatacatat tttaaacctc agaaatatac   3780
actagcaggc atggaacagg tcactgtggt gcctgccaag cccggtgatg ttatctgggg   3840
tccccggcca gccttaagcc tcttgctgac cggtggaggg cagaaccttt gccctaaaag   3900
tataatatcc acatgctggc atgattcctg gccagatggc ttctttatta gcagtaattg   3960
aaactgcctc gatacagaca ctgtaccttg caaccaaaaa atgactcaac aatgataata   4020
agggttaagc tgggcctttc tctctttgcc agttaaatta tatttattat agcttgacat   4080
gaaaaacaaa gcaactccaa caggtatcac aagggcaaag gacatgaaca ttttatcaaa   4140
gaagaaatgc agctgtcaaa aatacagaaa tattcaacct tgttcataat aaagtggctg   4200
ggctcagtgg ttcatgcctg taatcccagt gctttgcaag gctgagacag gaggatcatt   4260
tgaagccaga agttcaagac catcctaggc aagtcagttc aataccagac ttcatgtcta   4320
caaaacatca aaaaattagc caggcatggt gatgcatgcc tgttgtccca gctactcagg   4380
aggctgaggc aggagaattg cttgagcctg ggaggctgcg gtggcggtga gccatgattg   4440
tgccattgta ctccagcctg ggcaatgcag caagactgtc taaataacaa aaataatagt   4500
aaagaaaagg attgggatgc catttacttg cgtattcaat acacagagtt aaaagtaatt   4560
tctacgtttt ctattttttt attactaaaa aaagctggac cattctcaca gcctgaaatg   4620
cttctcactt tcccttcttc tgtccaaaca cttctctatg ataatgcaaa cagtcactcc   4680
tttaggaaga cttcacccca ggtagttcca gatcccctta tctctgcctt cccagaactc   4740
```

-continued

```
ctggtgtctc tccagttccc tccgtgtggt gaagtaccct acctagggtt tcagtatggc   4800
tctgtctgca aaggtcttgt tcacaccttc ccttatggtt ctgttgccct gtgttgtgtc   4860
atagcacagg gcacagtgga gaacccattc acactgatag agagggcccc atggtcctgg   4920
agataaccat gtaaccgatc agaataaggc attgagggct gggtgtcagg cgtgggctgc   4980
acttgggtgg gcaggtcccc tggaaagtca ctgggtttgg caagcttcct agtaacatgt   5040
ctctctgggg tccccccttgg aacttcatgc aaaaatgctg gttgctggtt tattctagag   5100
agatggttca ttcctttcat ttgattatca aagaaactca tgtcccaatt aaaggtcata   5160
aagcccagtt tgtaaactga gatgatctca gctgaatgaa cttgctgacc ctctgctttc   5220
ctccagcctc tcggtgccct tgaaatcatg tcggttcaag cagcctcatg aggcattaca   5280
aagtttaatt atttcagtga ttattaaacc ttgtcctgtg ttgaccccag gtgaatcaca   5340
agctgaactt ctgacaagaa caagctatca tattcttttc aattacagaa aaaagtaagt   5400
taattgatag gatttttttt gtttaaaaaa aatgttacta gttttgaaaa ggtaatatgt   5460
gcacatggta aacactaaga aggtataaga gcataatgct tttatactac taagaataat   5520
gttttctcta agtttttttt ggtagatgct ttcatcagat taagaaaatt ccctgctatt   5580
agttgttgaa ggtttttata tcataaatga aagttgaata ttattatcat atattattaa   5640
tatattgtta ttgaactatc aaagcctttt cctaaaacca ttgagatgat cttataacca   5700
ttctccttta acctgttgac gagatcattg gtatttatac tatttctctg ttaaccattc   5760
ttgagtctca ggtttaaatt caacttggtc atggtgtgtc atctttgatc attgctgtct   5820
gtggcttgct actgttttgt ttaggatttt tgcactgatg ctcatcaatg agactggcat   5880
gccatcttcc tttgcagtcc tgattttttt ctgatttgga tcatgtggtt atggccctca   5940
tggaatgagt tgggcatgat gccttttttt catgtctctg gattgatggg acactttgga   6000
ttctctccag atggccctca atggtccctg cctcctcatt gttaggcccc tgggcaagcc   6060
cttctcattt ctggtaggcc caggaacctg tgggggtttt gtttgtttgt ttgtttcttg   6120
agtcggagtc tcactctgtc acccaggctg gagttggagt gcaatggccc gatcttggct   6180
cactgcaacc tccacctccc agattcaagc aattctcctg cctcagcctc ctgagtagct   6240
ggaattacag gcacccaccg acacaccctg ctaatttttg tatttttagt acagatgggg   6300
tttcacaata ttggccaagc tggtctcgaa ctcctgatct catgatctgc ccggcttggc   6360
ctcccaaagt gttgagatta caagcatgag ccaccacacc cagtgaacct gtggttttta   6420
gaagctcccc atgcatgtga atgctgtgag catcccagga tgacagccac tgtgtgttca   6480
gctgttggaa ctgtgagaaa gcaccagtgg gaccttctcc agcacctgcc tgctgagttc   6540
atggaagagg cttgttgggg agatgatgcc ctggctgact cctgaaggat ggttaggaat   6600
gcaccagatg gaagctgggt tggacccact ctatgctgaa gaacagcttg tgtggacaca   6660
aggagacacg gatatgtcat ttttgtagag cctgaggagt gtccaatcac accatttgct   6720
taaaacatca tgcacacttg gaaaagtgga ctgagaccga atgaagaagc taacagtggc   6780
cagatcagaa agggtcttgt gttacttcct agagatactt agattttatc ctgtgggtga   6840
taggagcagt tggagggact gaagacaagg aaagaaacat gtttcaagat ctatgttttt   6900
caagacgctt ttctggtggc tgagtaggga attccctgga taagtcctgc ccagggtcag   6960
gcaaaacaag ttagggggtt actgaaataa ggagtatgag aaatggtgta ggttgtgctg   7020
acgttttgta acacatctca tgatgatctt catttccttc actaatttcc tgtttcatta   7080
```

-continued

```
attcccttcc acgtgctctt ctgaaatttg cctcacattc tctgatttct cttttacctg   7140
ttggtttcat cacctttttac tttttgcttt cctggaaaca caaatgattc tgattgtgac   7200
atgtcagaat tatttgcaac atttgccttt ctgctgaaac catgagttca ctgaatacac   7260
aatttagtaa agtgtaggat gcacatgtcg ttttcgtggt cacaaccagc tctgtagcat   7320
tttataacta cactggcagt gtgctgggag gtgtagagag aaatatttat cacatgtgtg   7380
gctgacacaa cctgccaagt tattttagga gcctccttgg aatcccagca agaatgctac   7440
cggcacaatt tgtaatcaca gcatcctgct ccatgccttg gcttcatggc atagtcactt   7500
ctgcaagtct ctttccagct gtctgttccc atgtctataa agtatgagtt aaatcatcct   7560
aacactactc atcttacaaa gttttcttgc tgatgttaag agagttggga aagaactgta   7620
taaactgtga agtgccatgg agatgttagt ggttacttta tcaagaaata gacactctag   7680
aatggagtag aaagccaaca gttatgattg agtcctcctc ctcttcttct ttttattaat   7740
ttataaagaa aagaggttta attgactcac agttccatat ggctggggag gcctcgggaa   7800
actctcagtc atagcaggag gcaaagggga agaaggcacc ttcttcacaa ggcggcagga   7860
gagagagagc tcctgttctt ttttgtcata aagtctacag aagtgcttat acttcaggac   7920
aagggcaggc agagagaagg aaggacattg cttcacccca gccctcactg acgagtttgc   7980
taggggacct cactttgtcc cagagtaggg cagaactctg gccactaccc attcagaagg   8040
cctgggctgc actgctagtt cctcactaac tctgtgtggc cttgggcaag gttgggcctg   8100
tgttaacaga ttatgaccct gggctctcaa gctagaggat ctaaatttga atcctggctc   8160
tgctaaagca attagtgatg taaactttaa tgggtcagtt aaccttcctg tggcttagtt   8220
tgctcatctg taaaataggg atcataacag tatcaatacc acatgattgt tggacagatt   8280
gaatcagtta atgcagggga agtacttagc atgacacgta ttcactatca tttcctggag   8340
taagagctgt gtgtgagtgg gtgtgagcat gtgtgaaacc ttttctctgc aatctcagtt   8400
aagaaaccaa tccagaattt aaagttcagg gcctaaatgg gtggttatct tctcccagtt   8460
ccatcctatc ccacctttgc tcttcctccc gcccacagga gctgttggtc cttgattggg   8520
ctggaagacc tggtggaccc taagtgatct ataagaggag aatagagaac agggaatgtc   8580
ttcaaaaatc tagagggaca cagaggctga gaggcaggca gtcctgcagg gtcttctgat   8640
tgggacaagg agaaccttgg tcttcacagg ccaattctgg tcagtttccc ccatggacag   8700
atgaggaaac aggcccagga atatccaagg tctcacactt cccatctgtc aagtcttgtt   8760
gattctgttg tattcatgtc tctcaaaggg agatagagtt tagggaagaa agaaggatca   8820
actgtgtctg ataccactgg gagcttaagt aaagggttct tttacttcat agcatttatc   8880
ccaatttgta attcagtatt atttgtgtgg ctgtttggtg tctctttctc ctatatgagt   8940
gctagcttca taagggcaag gattttgatt ctttaatatt tagtgcttgc cacatgccct   9000
gaacacagca ggcatacagg ctaaccaaca tacagtggca tgaaagtcat gaaagtgaga   9060
cacctacctc ctccagtgcc aagagagcat aaccatgcac ctgtcactct cctcaacacc   9120
acccccaagc atgaggccca aaagcattag ctaatcccct cctccagcca ctaaaactta   9180
aaggccaggt gtggtggctc ccatctgaaa tcccagaact tcaggagaca gcagcaggag   9240
gatcacttga ggccaggagt ttgagatcag cctgggcaac atagctaggt cccatctgta   9300
ctaaaaatta gctgggcgtt gttgcatgcc tgtagtccca gctactaagg aggctgaggt   9360
gggaggatca cttgagccca ggaggtggaa acaacagtaa gctataatca cagcactgaa   9420
ctctagcctg ggcaacagag tgacaccctg cctcaaaaca attttaaaaa taaataagag   9480
```

-continued

```
caaaacttag ataccacgtg gtcaccccaa catgcaaaat caagttttcc cctactgaga   9540
agaatgggga cttgacagct gagttacaga gagataatct tcttcttctt tttttttttt   9600
tggtttacat cctcaagatc atgacttgtg aaatttgaat cgaatacaca tgtaattcca   9660
gagcaatgtt gcctccgcat accatcagca attcacttgg ctactggaag tcaggataag   9720
cttcccagaa gagaggtacc acttgggcta ccaatataaa aggatgaaaa tatcagagtg   9780
atggtgttct ttacaacgtt gagtccctgg acagcctgtc cactgatgct gatatctgag   9840
cctaatgctt ctctgaatgt tgagattgaa ctttgatcca atgaaactag aacgagaaag   9900
aagataagtc tttcattgtt gataaggaca ttatgtttct catacttgta tgattatttt   9960
tccttagctg tactataatt atctgcttat ttgtctctgc tctatgtgct tagggtacaa  10020
agttgaccaa gaccaacttt ggttggaagc atagtactaa gagcacagta ctgagagcac  10080
agtattgaga gcacagcttt aaaaaacatg atgaaggctt taatacagga aatgagcagg  10140
ggagaggcat gtggtggttg gatgtatctt ccttgacaca gtcagtgcag ctctcagtag  10200
tcaagtccct acatgttaga agatgttacc ttctgtggaa ttaagtggca gaacttgcct  10260
tcaattattt tcctttgcag aacaacacca actgcattag ttaggacaca gtgctggctg  10320
catttaagtc ccaagcgatg attagtctct cactgttggt atagattcaa accaatcaga  10380
ccacctccta aagtttgtag ggcaggtaaa tcctcatctt agaataaaaa tcatcttacc  10440
aagtatgtgt tttagaggca agaagaaaac atatttgttt ctgtaagagt tttgtttaaa  10500
aaaaatataa gaaaggctct cggtttaggt gaggtaatga agttgttgat agttatcaga  10560
tgacactgga atctttactt ctctgaacgt gttctgtgca tctctcagtg tgggaacata  10620
gagagggaga tcctccagca atgccactga tatggtcaga aactgcatct ttctttctcc  10680
ctgctgagat gagatggagt cctttgttct agaagaccca tggtggtgcc gctgggagta  10740
acccttgaga caggaacaca aatcccaacc aatttgtggt tgcagccttg agtctcacta  10800
tttcccatag tgatgcgtag cagggaatgg caggtgcacc agagcaggag aggacctaat  10860
atctcccttc ctgttagctt tttataaagt tttattgtga tcagtagcag ttgggaagct  10920
acttgcagtc actgagcctc agtttctaca tctgtaaact ggggatagta gcatggcccc  10980
tacttaatgt gctcagcaaa gccactgaaa ggagacagaa atgtatctaa attaccctgg  11040
acttttatcc tacctctctt ggggattgtc accaccttcc catgtttgtc ctttttggtt  11100
tgatgcttgc tgtcacttct ttccttaggt gcctctctgt acggctcttt tatcccaggg  11160
attccagagt tacagcacat gcataccacc atccaagcat gtttatttgt ctcctgcttc  11220
actaggctgt ccccaaggaa catgtggctc ccggcacaca cctggcacaa cactgcacat  11280
gacattcacc cacttggcct tgaatctgac aaggaatctg gcatgatgtt cacccactca  11340
ggccaggtgc cgagcagccc tggaggctta ggggccagag ggatgggaaa aggtgtcttt  11400
ctggggtgag tatcagtttc tgcaggaggg ctgaatgtga gaaagaataa agagagaagg  11460
aagcgaacaa gcacagctta aacatcgcct atttctattg agttttaaga acgctgtgat  11520
tttgtttgtc atgcaatcca ttcatcaggc caggcagaca cagaacttgg gtgtgagtga  11580
cgataatgag ctgatataat tttcacaccc tcatcactga gatctctccc atcaggaatg  11640
ggtcagggag ctcacaggtg gcagcaactg ctattacagg cctcatctct accagctcct  11700
ggggcctgcc ctcctcccat tagaaaatcc tccacttgtc aaaaaggaag ccatttgctt  11760
tgaactccaa ttccaccccc aagaggctgg gaccatctta ctggagtcct tgatgctgtg  11820
```

-continued

```
tgacctgcag tgaccactgc cccatcattg ctggctgagg tggttggggt ccatctggct  11880
atctgggcag ctgttctctt ctctcctttc tctcctgttt ccagacatgc agtatttcca  11940
gagagaaggg gccactcttt ggcaaagaac ctgtctaact tgctatctat ggcaggacct  12000
ttgaagggtt cacaggaagc agcacaaatt gatactattc caccaagcca tcagctccat  12060
ctcatccatg ccctgtctct cctttagggg tccccttgcc aacagaatca cagaggacca  12120
gcctgaaagt gcagagacag cagctgaggc acagccaaga gctctggctg tattaatgac  12180
ctaagaagtc accagaaagt cagaagggat gacatgcaga ggcccagcaa tctcagctaa  12240
gtcaactcca ccagcctttc tagttgccca ctgtgtgtac agcaccctgg tagggaccag  12300
agccatgaca gggaataaga ctagactatg cccttgagga gctcacctct gttcagggaa  12360
acaggcgtgg aaacacaatg gtggtaaaga ggaaagagga caataggatt gcatgaaggg  12420
gatggaaggt gcccagggga ggaaatggtt acatctgtgt gaggagtttg gtgaggaaag  12480
actctaagag aaggctctgt ctgtctgggt ttggaaggat gtgtaggagt cttctagggg  12540
gcacaggcac actccaggca taggtaaaga tctgtaggtg tggcttgttg ggatgaattt  12600
caagtatttt ggaatgagga cagccataga gacaagggca agagagaggc gatttaatag  12660
attttatgcc aatggctcca cttgagtttc tgataagaac ccagaaccct tggactcccc  12720
agtaacattg attgagttgt ttatgatacc tcatagaata tgaactcaaa ggaggtcagt  12780
gagtggtgtg tgtgtgattc tttgccaact tccaaggtgg agaagcctct tccaactgca  12840
ggcagagcac aggtggccct gctactggct gcagctccag ccctgcctcc ttctctagca  12900
tataaacaat ccaacagcct cactgaatca ctgctgtgca gggcaggaaa gctccatgca  12960
catagcccag caaagagcaa cacagagctg aaaggaagct tgcggccgct taactgcaga  13020
agttggtcgt gaggcactgg gcaggtaagt atcaaggtta caagacaggt ttaaggagac  13080
caatagaaac tgggcttgtc gagacagaga agactcttgc gtttctgata ggcacctatt  13140
ggtcttactg acatccactt tgcctttctc tccacaggtg tccactccca ggttcaatta  13200
cagctcttaa gcggccgcaa gcttggcatt ccggtactgt tggtaaagcc accatggaag  13260
acgccaaaaa cataaagaaa ggcccggcgc cattctatcc gctggaagat ggaaccgctg  13320
gagagcaact gcataaggct atgaagagat acgccctggt tcctggaaca attgctttta  13380
cagatgcaca tatcgaggtg gacatcactt acgctgagta cttcgaaatg tccgttcggt  13440
tggcagaagc tatgaaacga tatgggctga atacaaatca cagaatcgtc gtatgcagtg  13500
aaaactctct tcaattcttt atgccggtgt tgggcgcgtt atttatcgga gttgcagttg  13560
cgcccgcgaa cgacatttat aatgaacgtg aattgctcaa cagtatgggc atttcgcagc  13620
ctaccgtggt gttcgtttcc aaaaaggggt tgcaaaaaat tttgaacgtg caaaaaaagc  13680
tcccaatcat ccaaaaaatt attatcatgg attctaaaac ggattaccag ggatttcagt  13740
cgatgtacac gttcgtcaca tctcatctac ctcccggttt taatgaatac gattttgtgc  13800
cagagtcctt cgatagggac aagacaattg cactgatcat gaactcctct ggatctactg  13860
gtctgcctaa aggtgtcgct ctgcctcata gaactgcctg cgtgagattc tcgcatgcca  13920
gagatcctat ttttggcaat caaatcattc cggatactgc gattttaagt gttgttccat  13980
tccatcacgg ttttggaatg tttactacac tcggatattt gatatgtgga tttcgagtcg  14040
tcttaatgta tagatttgaa gaagagctgt ttctgaggag ccttcaggat tacaagattc  14100
aaagtgcgct gctggtgcca accctattct ccttcttcgc caaaagcact ctgattgaca  14160
aatacgattt atctaattta cacgaaattg cttctggtgg cgctcccctc tctaaggaag  14220
```

-continued

```
tcggggaagc ggttgccaag aggttccatc tgccaggtat caggcaagga tatgggctca  14280

ctgagactac atcagctatt ctgattacac ccgaggggga tgataaaccg ggcgcggtcg  14340

gtaaagttgt tccatttttt gaagcgaagg ttgtggatct ggataccggg aaaacgctgg  14400

gcgttaatca aagaggcgaa ctgtgtgtga gaggtcctat gattatgtcc ggttatgtaa  14460

acaatccgga agcgaccaac gccttgattg acaaggatgg atggctacat tctggagaca  14520

tagcttactg ggacgaagac gaacacttct tcatcgttga ccgcctgaag tctctgatta  14580

agtacaaagg ctatcaggtg gctcccgctg aattggaatc catcttgctc caacacccca  14640

acatcttcga cgcaggtgtc gcaggtcttc ccgacgatga cgccggtgaa cttcccgccg  14700

ccgttgttgt tttggagcac ggaaagacga tgacggaaaa agagatcgtg gattacgtcg  14760

ccagtcaagt aacaaccgcg aaaaagttgc gcggaggagt tgtgtttgtg gacgaagtac  14820

cgaaaggtct taccggaaaa ctcgacgcaa gaaaaatcag agagatcctc ataaaggcca  14880

agaagggcgg aaagatcgcc gtgtaattct agagtcgggg cggccggccg cttcgagcag  14940

acatgataag atacattgat gagtttggac aaaccacaac tagaatgcag tgaaaaaaat  15000

gctttatttg tgaaatttgt gatgctattg ctttatttgt aaccattata agctgcaata  15060

aacaagttaa caacaacaat tgcattcatt ttatgtttca ggttcagggg gaggtgtggg  15120

aggtttttta aagcaagtaa aacctctaca aatgtggtaa aatcgataag gatcgatccg  15180

tcgac                                                              15185


<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence: Luc 3
      primer

<400> SEQUENCE: 18

gaaatgtccg ttcggttggc agaagc                                          26


<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Luc 4
      primer

<400> SEQUENCE: 19

ccaaaaccgt gatggaatgg aacaaca                                         27
```